(12) United States Patent
Geiss et al.

(10) Patent No.: US 8,415,102 B2
(45) Date of Patent: Apr. 9, 2013

(54) METHODS AND COMPUTER SYSTEMS FOR IDENTIFYING TARGET-SPECIFIC SEQUENCES FOR USE IN NANOREPORTERS

(75) Inventors: Gary K. Geiss, Seattle, WA (US); Tim Dahl, Seattle, WA (US); Craig E. Dahl, legal representative, Juneau, AK (US); Eric Davidson, Pasadena, CA (US)

(73) Assignee: NanoString Technologies, Inc., Seattle, WA (US)

( * ) Notice: Subject to any disclaimer, the term of this patent is extended or adjusted under 35 U.S.C. 154(b) by 454 days.

(21) Appl. No.: 12/100,990

(22) Filed: Apr. 10, 2008

(65) Prior Publication Data
US 2010/0112710 A1 May 6, 2010

Related U.S. Application Data

(60) Provisional application No. 61/029,220, filed on Feb. 15, 2008, provisional application No. 60/922,817, filed on Apr. 10, 2007.

(51) Int. Cl.
| | |
|---|---|
| C12Q 1/68 | (2006.01) |
| C12P 19/34 | (2006.01) |
| C12M 1/36 | (2006.01) |
| C12M 1/38 | (2006.01) |
| C12M 3/00 | (2006.01) |
| C12M 1/34 | (2006.01) |
| C07H 21/02 | (2006.01) |
| C07H 21/04 | (2006.01) |

(52) U.S. Cl. .... 435/6.11; 435/6.1; 435/91.1; 435/287.2; 536/23.1; 536/24.3

(58) Field of Classification Search ............ 436/94, 436/93, 91; 435/6.1, 6.11, 91.1, 287.2; 536/23.11, 536/24.3
See application file for complete search history.

(56) References Cited

U.S. PATENT DOCUMENTS

| | | |
|---|---|---|
| 5,137,819 A | 8/1992 | Kilburn et al. |
| 5,202,247 A | 4/1993 | Kilburn et al. |

(Continued)

FOREIGN PATENT DOCUMENTS

| | | |
|---|---|---|
| WO | WO-02/29379 A2 | 4/2002 |
| WO | WO 03003810 A2 * | 1/2003 |

(Continued)

OTHER PUBLICATIONS

Li et al., Selection of optimal DNA oligos for gene expression arrays, Bioinformatics, 2001, 11, 1067-1076.*

(Continued)

*Primary Examiner* — Robert T Crow
*Assistant Examiner* — Joseph G Dauner
(74) *Attorney, Agent, or Firm* — Mintz Levin Cohn Ferris Glovsky and Popep, P.C.; Ivor R. Elrifi; Matthew Pavao

(57) ABSTRACT

The present invention relates to compositions and methods for detection and quantification of individual target molecules in biomolecular samples. In particular, the invention relates to coded, labeled probes that are capable of binding to and identifying target molecules based on the probes' label codes. Methods, computers, and computer program products for identifying target-specific sequences for inclusion in the probes are also provided, as are methods of making and using such probes. The probes can be used in diagnostic, prognostic, quality control and screening applications.

10 Claims, 38 Drawing Sheets

U.S. PATENT DOCUMENTS

| | | | |
|---|---|---|---|
| 5,293,050 | A | 3/1994 | Chapple-Sokol et al. |
| 5,354,707 | A | 10/1994 | Chapple-Sokol et al. |
| 5,496,934 | A | 3/1996 | Shoseyov et al. |
| 5,556,749 | A * | 9/1996 | Mitsuhashi et al. ......... 435/6.18 |
| 5,840,862 | A | 11/1998 | Bensimon et al. |
| 5,843,650 | A * | 12/1998 | Segev ............................ 435/6.1 |
| 6,001,983 | A | 12/1999 | Benner |
| 6,054,327 | A | 4/2000 | Bensimon et al. |
| 6,225,055 | B1 | 5/2001 | Bensimon et al. |
| 6,265,153 | B1 | 7/2001 | Bensimon et al. |
| 6,303,296 | B1 | 10/2001 | Bensimon et al. |
| 6,344,319 | B1 | 2/2002 | Bensimon et al. |
| 6,548,255 | B2 | 4/2003 | Bensimon et al. |
| 2003/0104378 | A1* | 6/2003 | Allawi et al. ...................... 435/6 |
| 2003/0232382 | A1* | 12/2003 | Brennan et al. ................... 435/6 |
| 2004/0166498 | A1* | 8/2004 | Peterson ........................... 435/6 |
| 2006/0068378 | A1* | 3/2006 | Mirkin et al. ..................... 435/5 |
| 2006/0110744 | A1* | 5/2006 | Sampas et al. .................... 435/6 |
| 2010/0261026 | A1 | 10/2010 | Ferree et al. |

FOREIGN PATENT DOCUMENTS

| | | |
|---|---|---|
| WO | WO-2004/099443 A2 | 11/2004 |
| WO | WO-2007/076132 A2 | 7/2007 |
| WO | WO-2007139766 A2 | 12/2007 |

OTHER PUBLICATIONS

Bridges. CABIOS. 1990. 6(2): 124-125.*
Maizel et al. PNAS. 1981. 78(12): 7665-7669.*
Burpo (Biochemistry 218. 2001; retrieved on Jan. 25, 2012 from the internet: <url: http://web.archive.org/web/20050429073014/http://biochem.stanford.edu/biochem218/Projects%202001/Burpo.pdf>).*
He et al. Applied and Environmental Microbiology. 2005. 71(7): 3753-3760.*
Erdtmann-Vourliotis et al. Brain Research Protocols. 1999. 4: 82-91.*
Altschul et al., "Basic local alignment search tool", *J. Mol. Biol.*, 215:403-410 (1990).
Asbury et al., "Trapping of DNA by dielectrophoresis", *Electrophoresis*, 23(16):2658-2666 (2002).
Asbury et al., "Trapping of DNA in Nonuniform Oscillating Electric Fields", *Biophys. J*, 74:1024-1030 (1998).
Ashkin et al., "Observation of a single-beam gradient force optical trap for dielectric particles", *Opt. Lett.*, 11(5):288-290 (1986).
Ashkin et al., "Optical trapping and manipulation of single cells using infrared laser beams", *Nature*, 330:769-771 (1987).
Ashkin et al., "Optical Trapping and Manipulation of Viruses and Bacteria", *Science*, 235:1517-1520 (1987).
Atkinson et al., "Solid Phase Synthesis of Oligodeoxyribonucleotides by the Phosphite Triester Method", *Oligonucleotide Synthesis: A Practical Approach*, pp. 45-49 (1984).
Baldino et al., "High-resolution in situ hybridization histochemistry", *Methods in Enzymol.*, 168:761-777 (1989).
Bensimon et al., "Alignment and Sensitive Detection of DNA by a Moving Interface", *Science*, 265:2096-2098 (1994).
Blanchard et al., "Sequence to array: Probing the genome's secrets", *Nature Biotech.*, 14:1649 (1996).
Block et al., "Bead movement by single kinesin molecules studied with optical tweezers", *Nature*, 348:348-352 (1990).
Brazma et al., "ArrayExpress-a public repository for microarray gene expression data at the EBI", *Nucl. Acids Res.*, 31:68-71 (2003).
Breslauer et al., "Predicting DNA duplex stability from the base sequence", *Proc. Natl. Acad. Sci. U.S.A.*, 83:3746-3750 (1986).
Britten et al., "Analysis of Repeating DNA Sequences by Reassociation", *Meth. Enzymol.*, 29E:363-406 (1974).
Brody et al., "Surface Treatment", *Wiley Encyclopedia of Packaging Technology, 2nd Ed.*, pp. 867-874 (1997).
Canales et al., "Evaluation of DNA microarray results with quantitative gene expression platforms", *Nat. Biotechnol*, 24:1115-1122 (2006).
*CRC Practical Handbook of Biochemistry and Molecular Biology*, pp. 385-392 (1985).

Egholm et al., "Peptide Nucleic Acids (PNA). Oligonucleotide Analogues with an Achiral Peptide Backbone", *J. Am. Chem. Soc.*, 114:1895-1897 (1992).
Ferree et al., "Electrokinetic Stretching of Tethered DNA", *Biophys. J.*, 85(4):2539-2546 (2003).
Ferree et al., "The Hydrodynamics of DNA Electrophoretic Stretch and Relaxation in a Polymer Solution", *Biophys. J.*, 87(1):468-475 (2004).
Geiss et al., "Direct multiplexed measurement of gene expression with color-coded probe pairs", *Nature Biotech.*, 26(3):317-325 (2008).
GenBank Accession No. AY058560.1, dated Oct. 16, 2001.
GenBank Accession No. DQ412624, dated Dec. 14, 2006.
GenBank Accession No., AY058658.1, dated Aug. 27, 2005.
Gentleman et al., "Bioconductor: open software development for computational biology and bioinformatics", *Genome Biol.*, 5:R80 (2004).
Golub et al., "Molecular Classification of Cancer: Class Discovery and Class Prediction by Gene Expression Monitoring", *Science*, 286:431-537 (1999).
Goodchild, J., "Conjugates of Oligonucleotides and Modified Oligonucleotides: A Review of Their Synthesis and Properties", *Bioconjugate Chem.*, 1(3):165-187 (1990).
Grier, D. G., "A revolution in optical manipulation", *Nature*, 424:21-27 (2003).
Gryaznov et al., "Oligodeoxyribonucleotide N3'→P5' Phosphoramidates: Synthesis and Hybridization Properties", *J. Am. Chem. Soc.*, 116:3143-3144 (1994).
Guan et al., "Vectors that facilitate the expression and purification of foreign peptides in *Escherichia coli* by fusion to maltose-binding protein", *Gene*, 67:21-30 (1988).
Gustafsson, "Nonlinear structured-illumination microscopy: widefield fluorescence imaging with theoretically unlimited resolution", *Proc. Natl. Acad. ScL U.S.A.*, 102(37):13081-13086 (2005).
Hastie et al., "The expression of three abundance classes of messenger RNA ion mouse tissues", *Cell*, 9:761-774 (1976).
He et al., "Empirical establishment of oligonucleotide probe design criteria", *Appl. Environ. Microbiol.*, 71(7):3753-3760 (2005).
Henegariu et al., "Rapid DNA Fiber Technique for Size Measurements of Linear and Circular DNA Probes", *BioTech.*, 31(2):246-250 (2001).
Hyrup et al., "Peptide nucleic acids (PNA): synthesis, properties and potential applications", *Bioorg. Med. Chem.*, 4(1):5-23 (1996).
Inoue,S. and K.R. Spring. *Video Microscopy: The Fundamentals.* $2^{nd}$ edition. p. 30. Plenum Press, New York, NY. (1997).
Kabata et al., "Visualization of Single Molecules of RNA Polymerase Sliding along DNA", *Science*, 262(5139):1561-1563 (1993).
Kane et al., "Assessment of the sensitivity and specificity of oligonucleotide (50mer) microarrays", *Nucl. Acids Res.*, 28:4552-4557 (2000).
Kraus et al., "High-resolution comparative hybridization to combed DNA fibers", *Human Genet.*, 99:374-380 (1997).
Kuo et al., "A sequence-oriented comparison of gene expression measurements across different hybridization-based technologies", *Nat. Biotechnol.*, 24:832-840 (2006).
Li et al., "Selection of optimal oligonucleotide probes for microarrays using multiple criteria, global alignment and parameter estimation", *Nucl. Acids Res.*, 33:6114-6123 (2005).
Lockhart et al., "Expression monitoring by hybridization to high-density oligonucleotide arrays", *Nature Biotech.*, 14:1675-1680 (1996).
Mathews et al., "Expanded sequence dependence of thermodynamic parameters improves prediction of RNA secondary structure", *J. Mol. Biol.*, 288:911-940 (1999).
Matsuura et al., "One-End Immobilization of Individual DNA Molecules on a Functional Hydrophobic Glass Surface", *J. Biomol. Struct. Dyn.*, 20(3):429-436 (2002).
Matsuura et al., "Real-time observation of a single DNA digestion by λ exonuclease under a fluorescence microscope field", *Nucl. Acids Res.*, 29(16):E79 (2001).
Michalet et al., "Dynamic Molecular Combing: Stretching the Whole Human Genome for High- Resolution Studies", *Science*, 277:1518-1523 (1997).

Oliveri et al., "A regulatory gene network that directs micromere specification in the sea urchin embryo", *Dev. Biol.*, 246:209-228 (2002).

Otobe et al., "Behavior of DNA fibers stretched by precise meniscus motion control", *Nucl. Acids Res.*, 29(22):E109 (2001).

Patterson et al., "Performance comparison of one-colore and two-color platforms within the MicroArray Quality Control (MACQ) project", *Nat. Biotechnol.*, 24:1140-1150 (2006).

Pease et al., "Light-generated oligonucleotide arrays for rapid DNA sequence analysis", *Proc. Natl. Acad. Sci. U.S.A.*, 91:5022-5026 (1994).

Perkins et al., "Relaxation of a Single DNA Molecule Observed by Optical Microscopy", *Science*, 264:822-826 (1994).

Perry-O'Keefe et al., "Peptide nucleic acid pre-gel hybridization: an alternative to southern hybridization", *Proc. Natl. Acad. Sci. U.S.A.*, 93:14670-14675 (1996).

Pruitt et al., "NCBI Reference Sequence (RefSeq): a curated non-redundant sequence database of genomes, transcripts and proteins", *Nucl. Acids Res.*, 33:D501-D504 (2005).

Rast et al., "Recovery of developmentally defined gene sets from high-density cDNA macroarrays", *Dev. Biol.*, 228:270-286 (2000).

Schena et al., "Quantitative Monitoring of Gene Expression Patterns with a Complementary DNA Microarray", *Science*, 270:467-470 (1995).

Shi et al., "The MicroArray Quality Control (MAQC) project shows inter-and intraplatform reproducibility of gene expression measurements", *Nat. Biotechnol.*, 24:1151-1161 (2006).

Simmons et al., "Quantitative Measurements of Force and Displacement Using an Optical Trap", *Biophys. J.*, 70:1813-1822 (1996).

Simon et al., "Roadmap for developing and validating therapeutically relevant genomic classifiers", *J. Clin. Oncol.*, 23:7332-7341 (2005).

Smith, D. B., "Purification of Glutathione S-Transferase Fusion Proteins", *Meth. Mol. Cell Biol.*, 4:220-229 (1993).

Stigter et al., "Theory for the Hydrodynamic and Electrophoretic Stretch of Tethered B-DNA", *Biophys. J.*, 75(3):1197-1210 (1998).

Thomann et al., "Automatic fluorescent tag localization II: improvement in super-resolution by relative tracking", *J. Microsc.*, 211:230-248 (2002).

Tomme et al., "An internal cellulose-binding domain mediates adsorption of an engineered bifunctional xylanase/cellulase", *Protein Eng.*, 7(1):117-123 (1994).

Uhlman et al., "Antisense Oligonucleotides: A New Therapeutic Principle", *Chem. Rev.*, 90(4):544-584 (1990).

van 't Veer et al., "Gene expression profiling predicts clinical outcome of breast cancer", *Nature*, 415:530-536 (2002).

van de Vijver et al., "A gene-expression signature as a predictor of survival in breast cancer", *N. Engl. J. Med.*, 347:1999-2009 (2002).

Velculescu et al., "Analysis of human transcriptomes", *Nat. Genet*, 23:387-388 (1999).

Williams et al., *Chemical Approaches to the Synthesis of Peptides and Protiens*, Chapter 2 (1997).

Yokota et al., "A new method for straightening DNA molecules for optical restriction mapping", *Nucl. Acids Res.*, 25(5):1064-1070 (1997).

Zimmermann et al., "DNA stretching on functionalized gold surfaces", *Nucl. Acids Res.*, 22(3):492-497 (1994).

Zuker, M., "Mfold web server for nucleic acid folding and hybridization prediction", *Nucl. Acids Res.*, 31(13):3406-3415 (2003).

Marti et al. "Pyrene Binary Probes for Unambiguous Detection of mRNA Using Time-Resolved Fluorscence Spectroscopy." *Nucl. Acids Res.* 34.10(2006):3161-3168.

Santangelo et al. "Dual FRET Molecular Beacons for mRNA Detection in Living Cells." *Nucl. Acids Res.* 32.6(2004):357.

\* cited by examiner

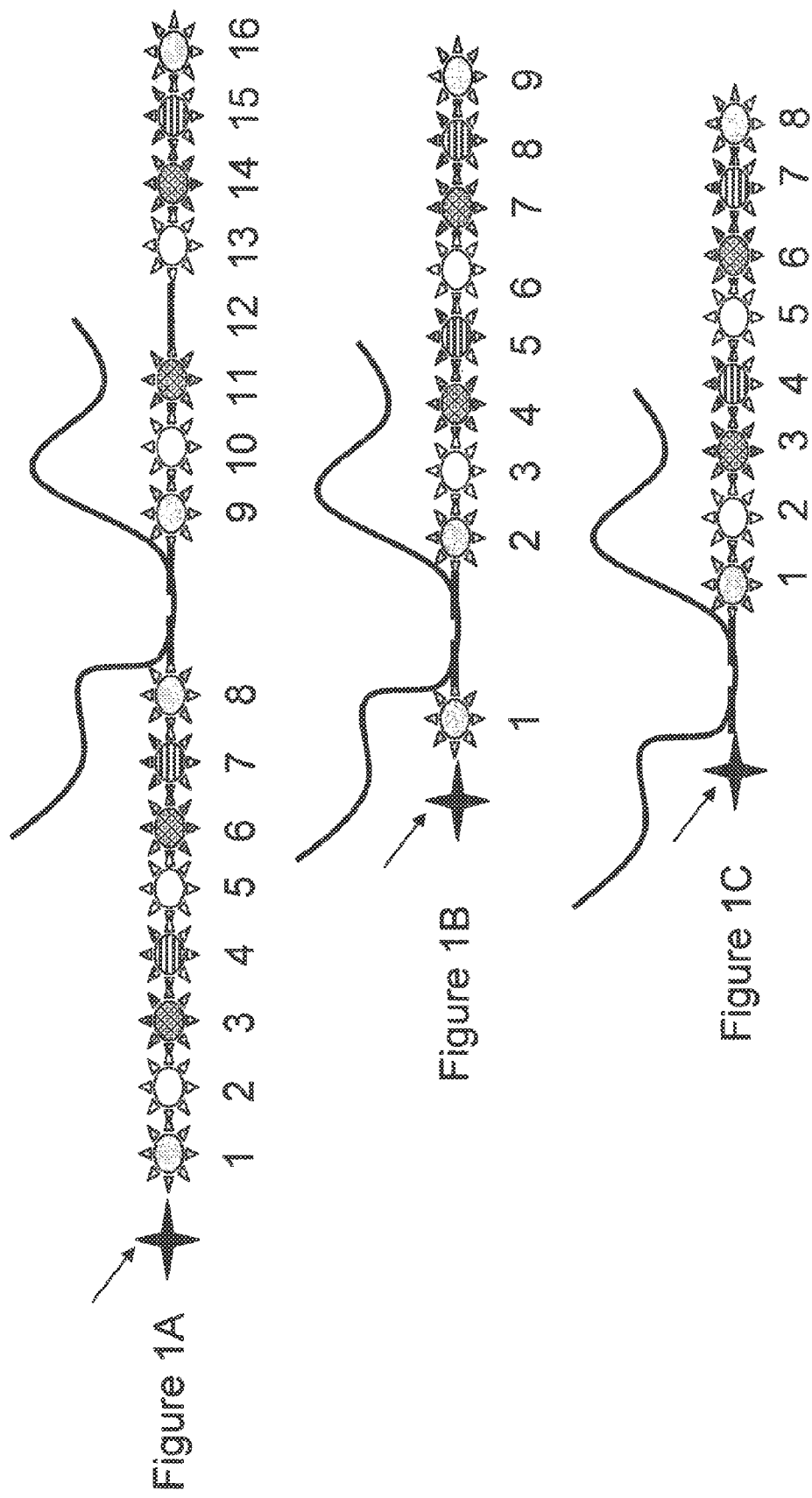

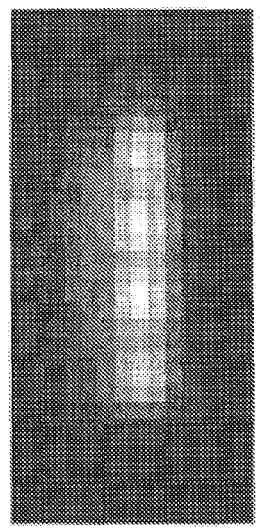
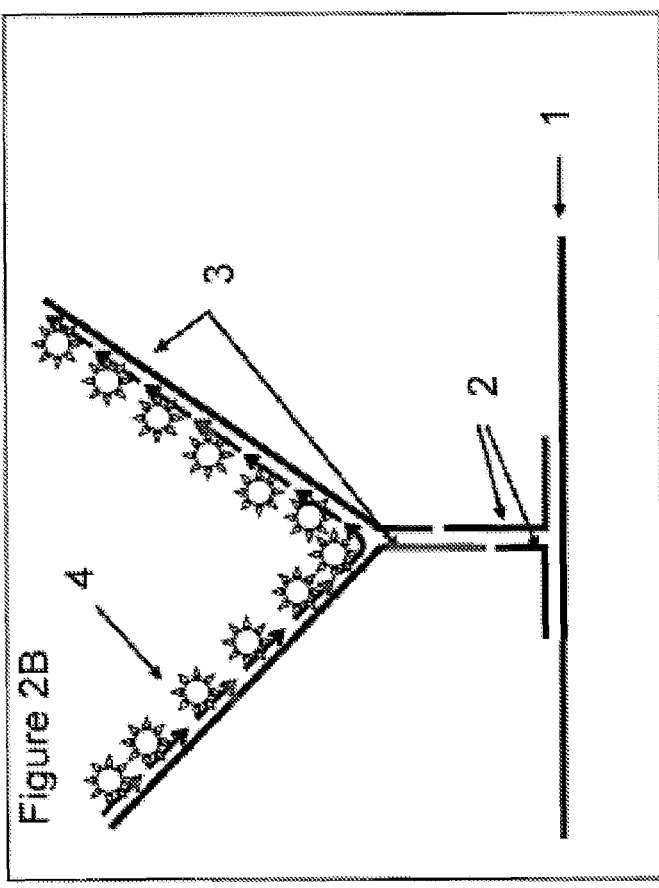
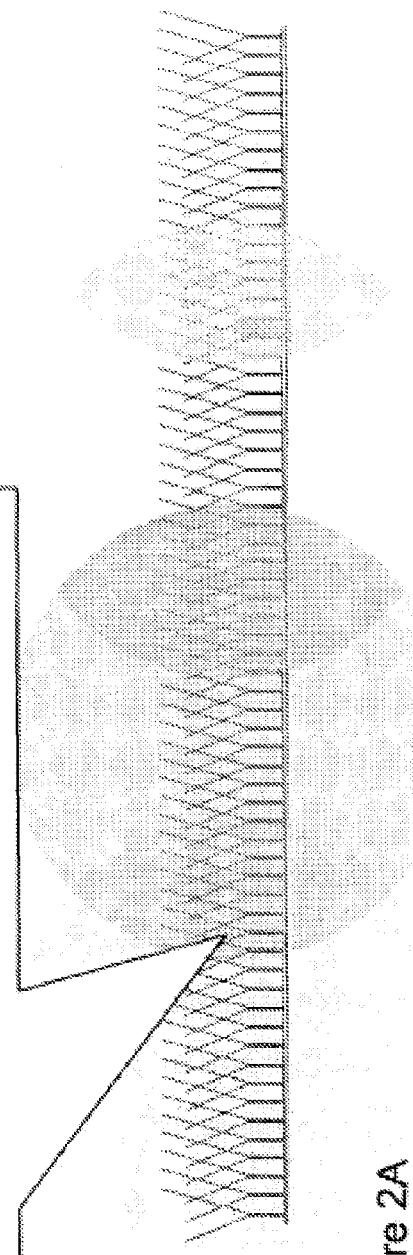
Figure 2C
Figure 2B
Figure 2A

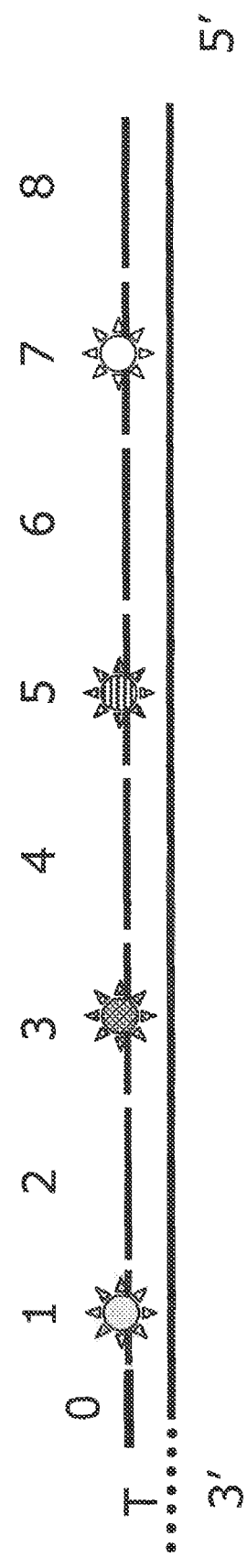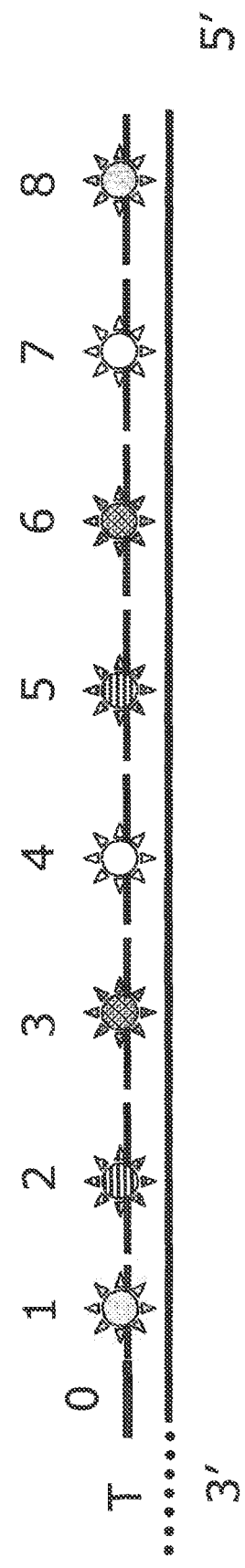

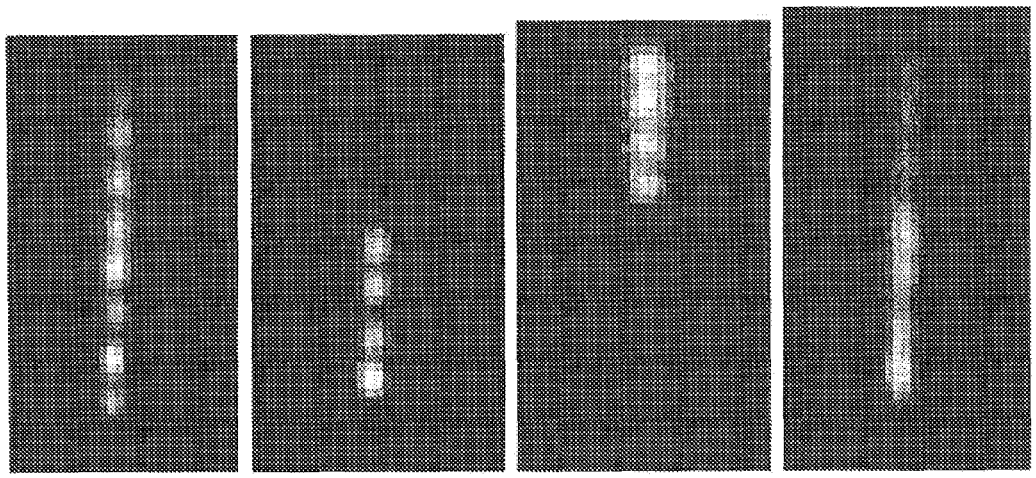
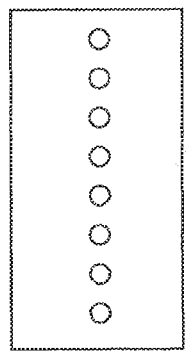
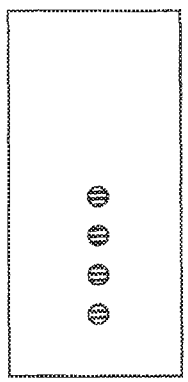
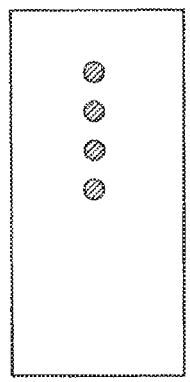
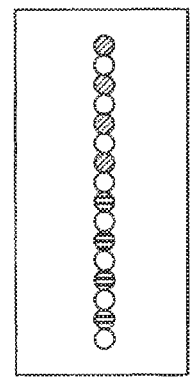
Figure 5A  Figure 5B  Figure 5C  Figure 5D

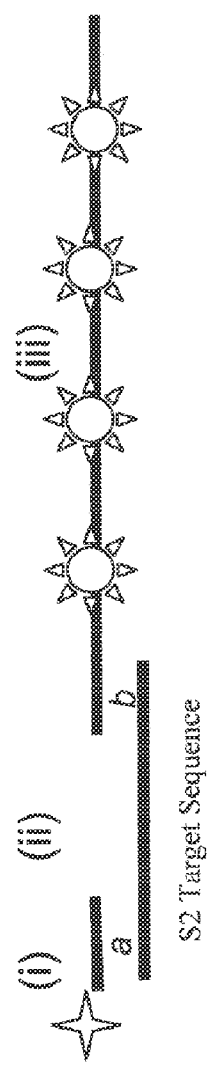
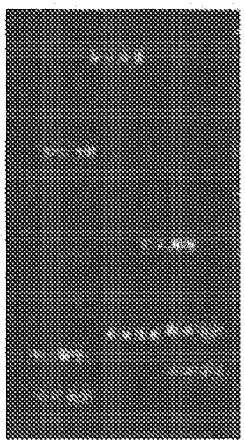
Figure 6A
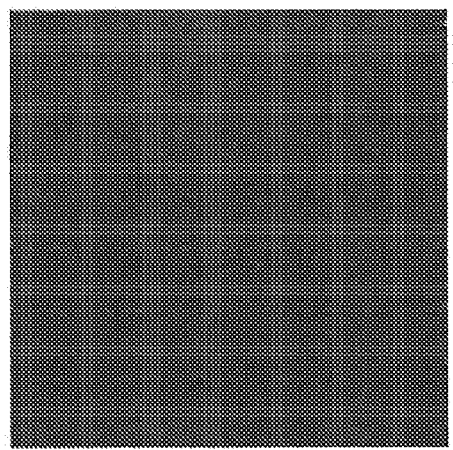
Figure 6E
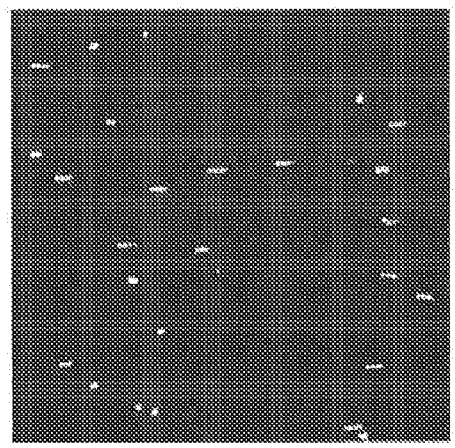
Figure 6D
Figure 6B 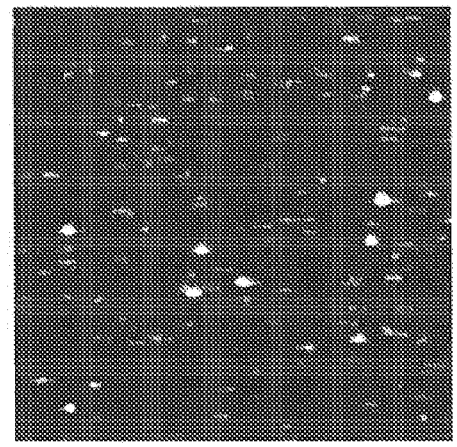 Figure 6C

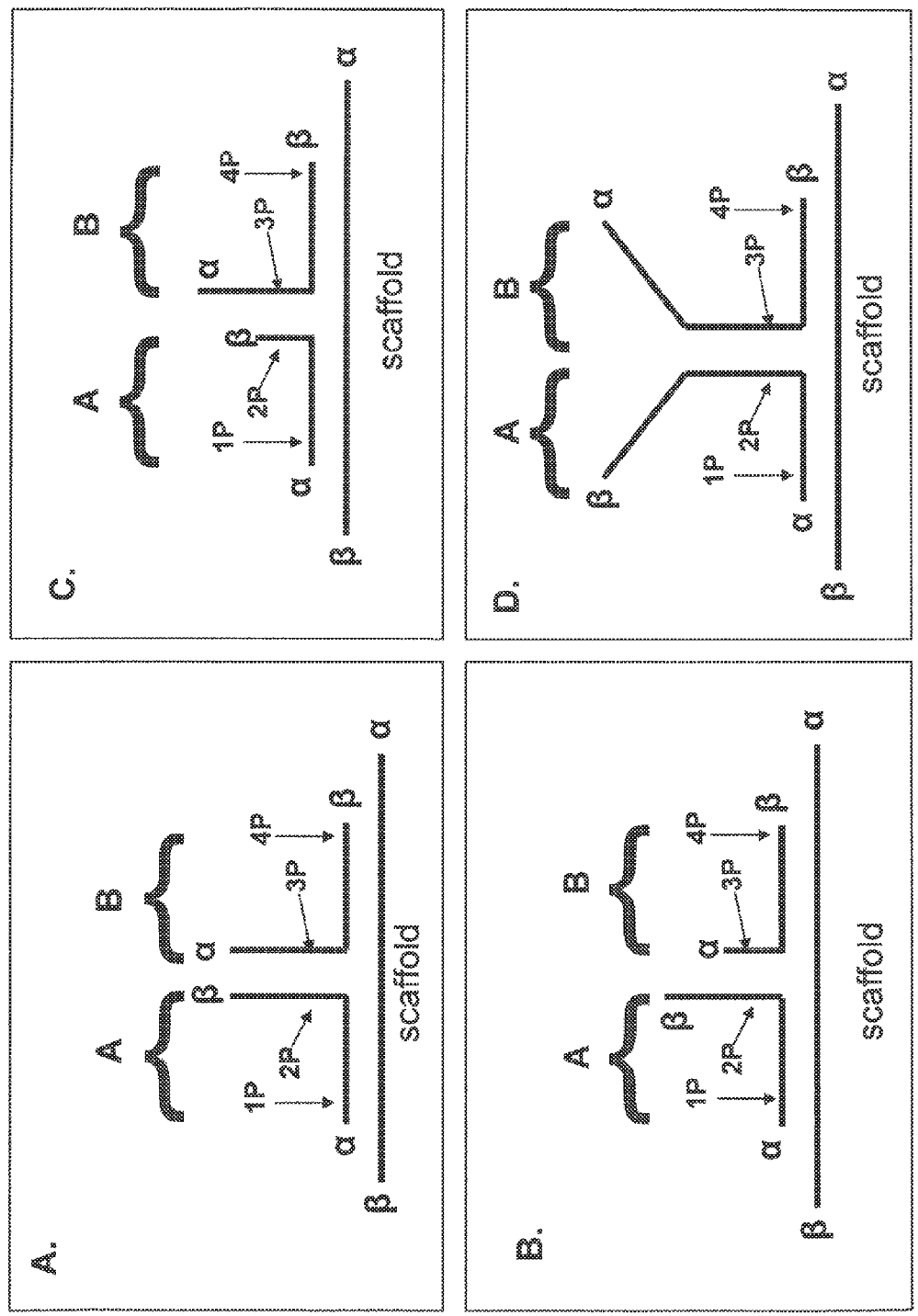
FIGURE 7A-D

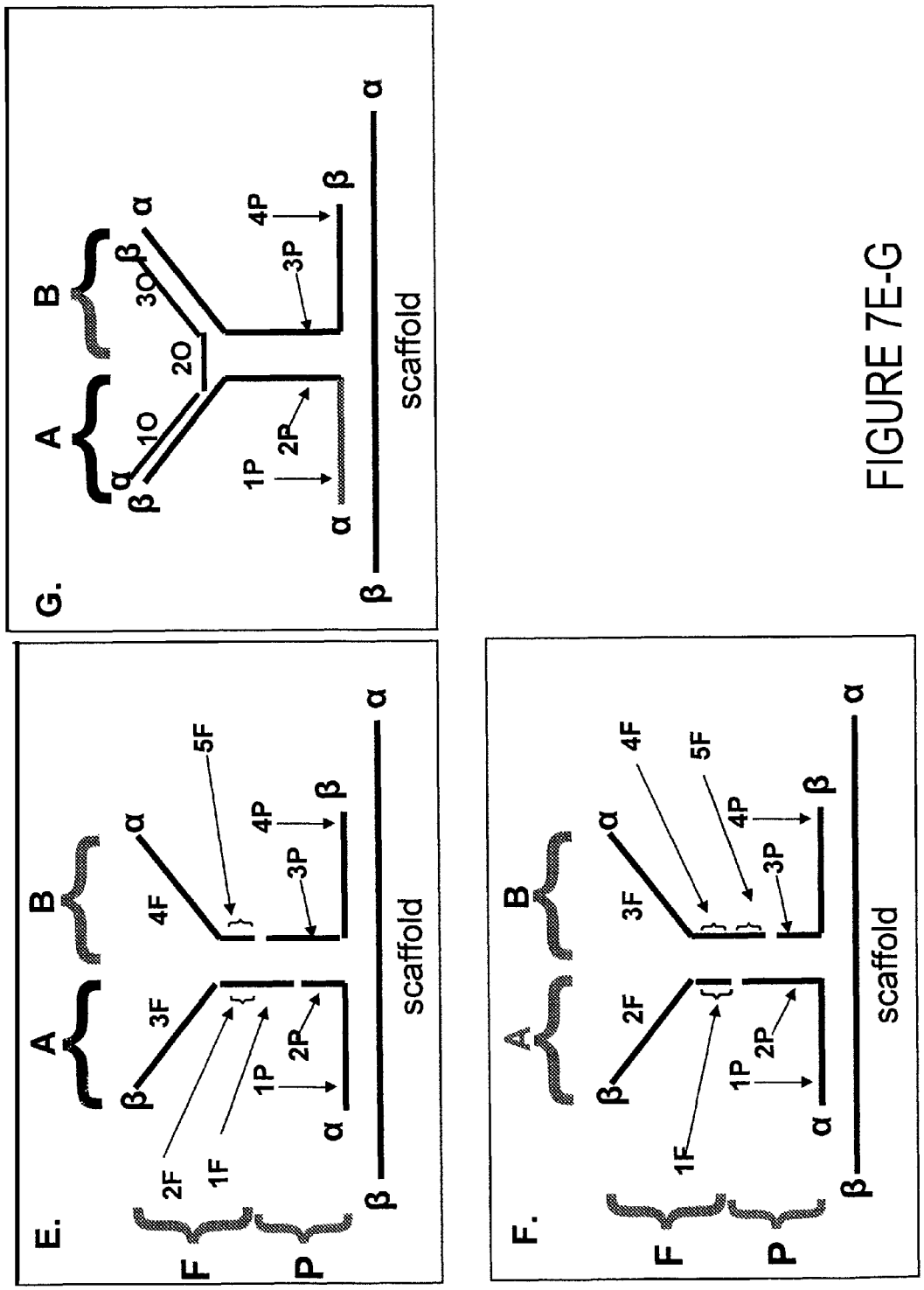
FIGURE 7E-G

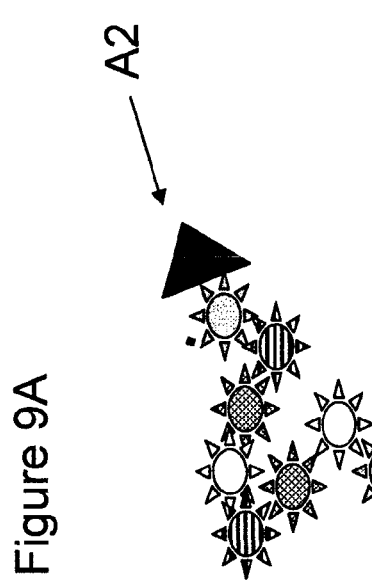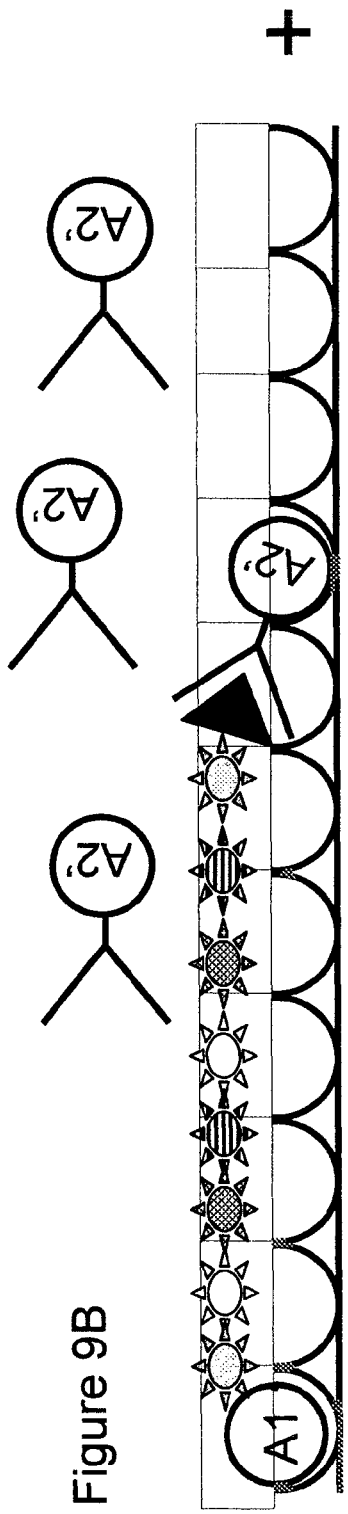

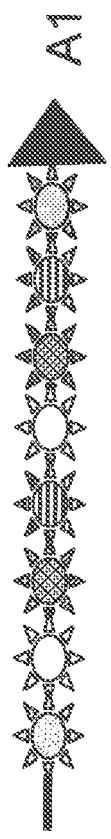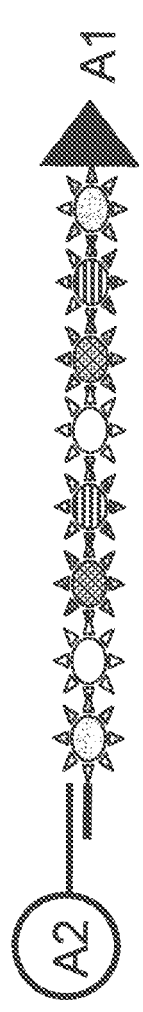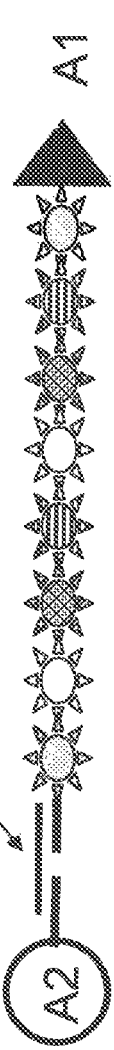
Figure 10A
Figure 10B
Figure 10C

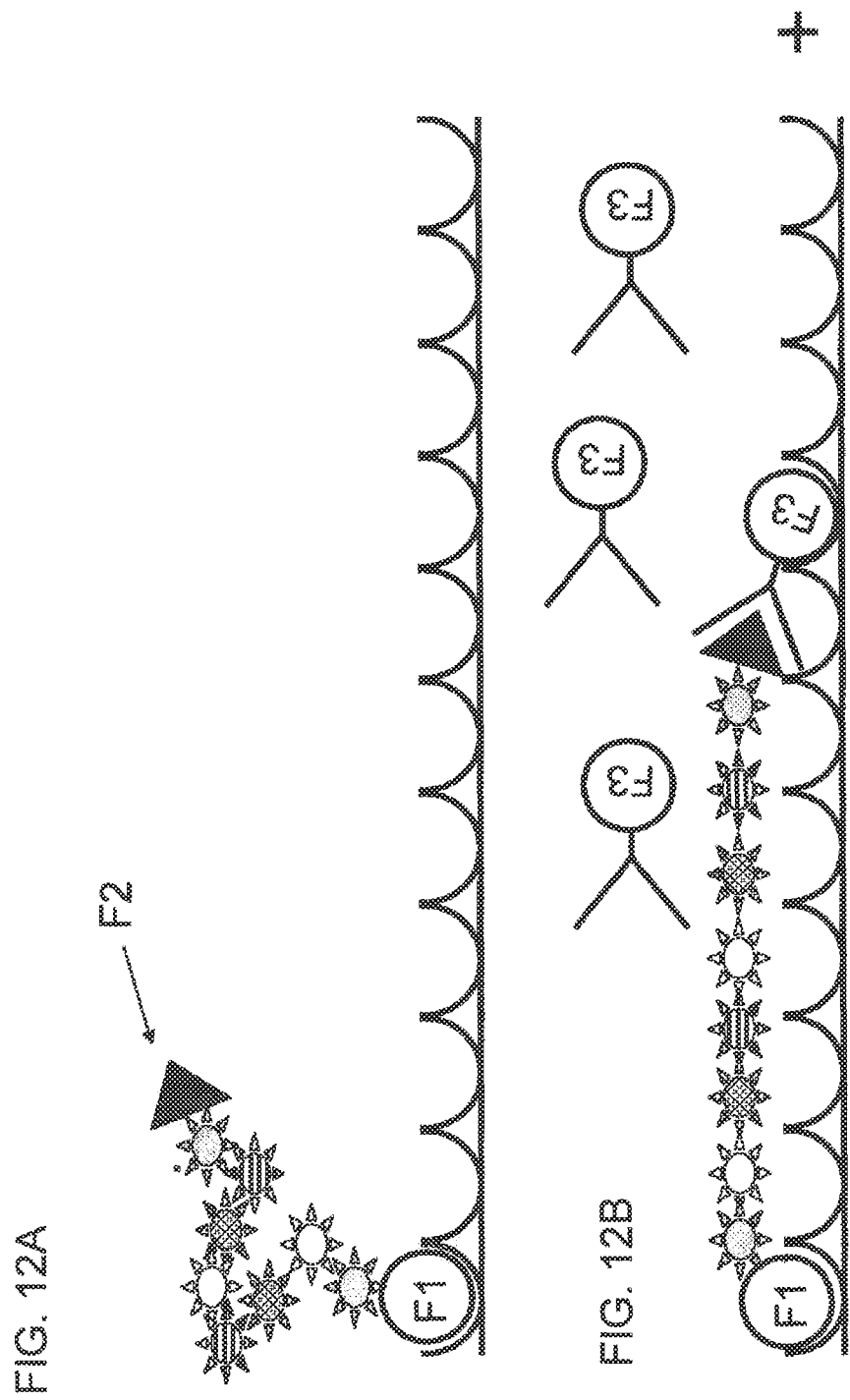

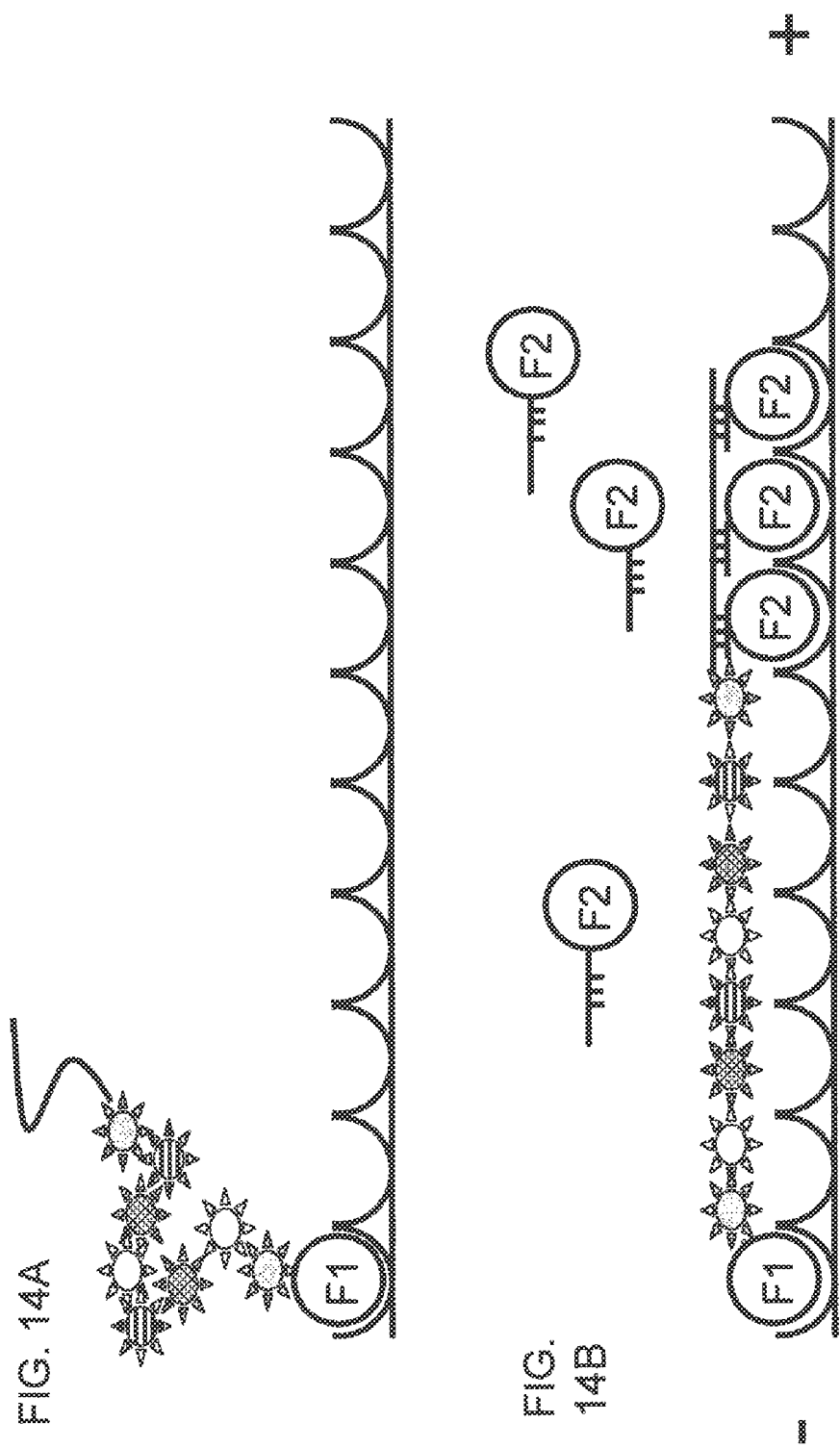

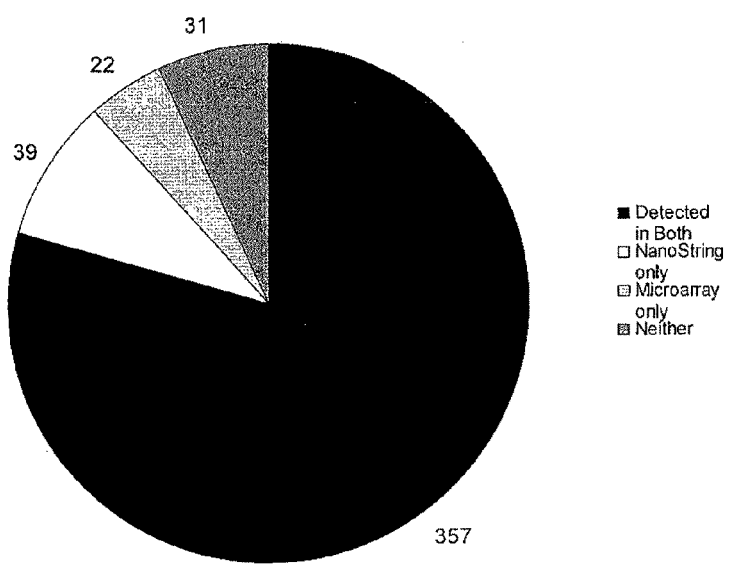
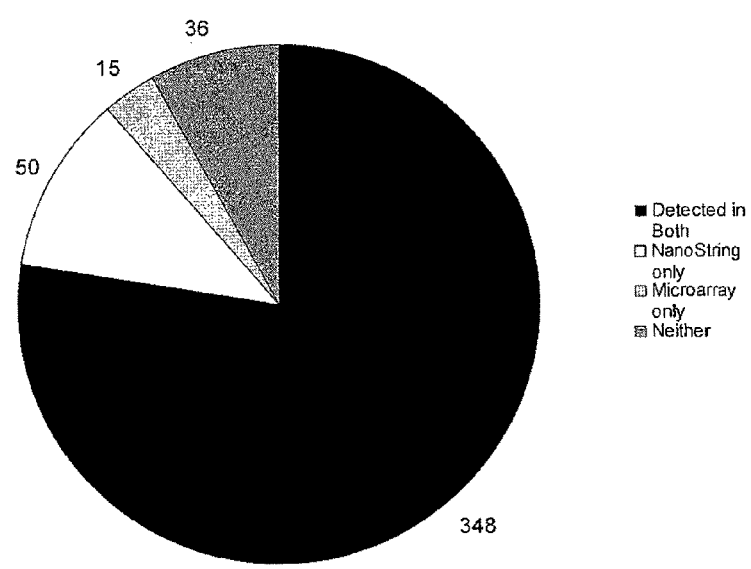
Figure 25

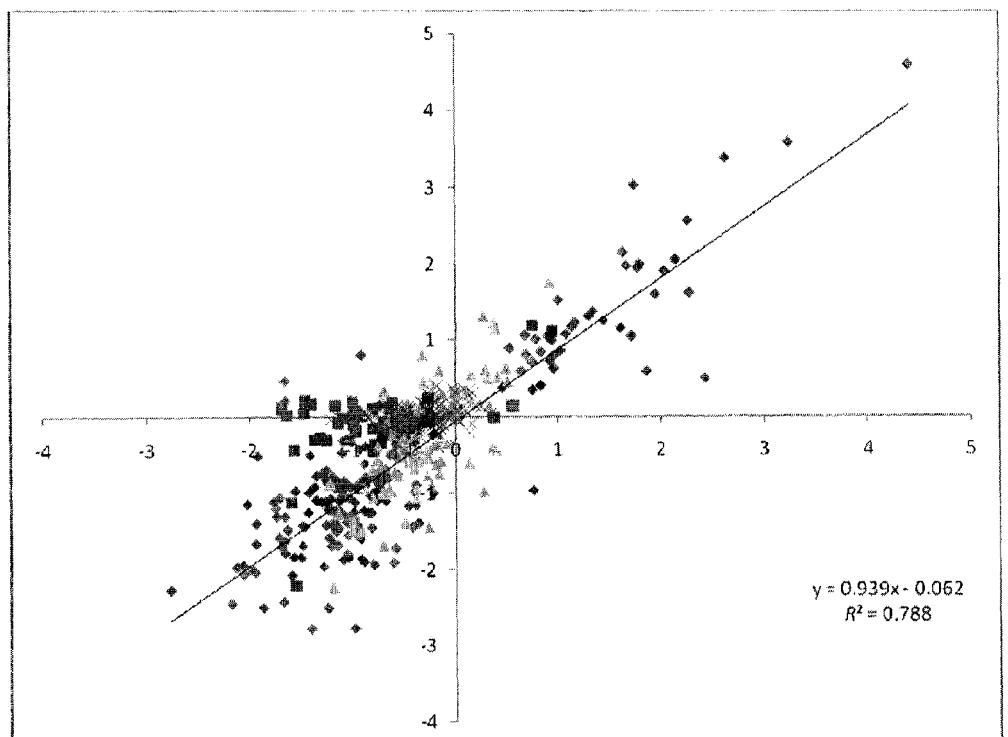

Supplementary Figure 1: *Comparison of fold change results for all 509 genes*

Scatter plot of log2 fold change for 317 genes that were measured by both NanoString and Affymetrix platforms. Genes are color-coded based on the significance of their fold change values (P≤0.05) in either both platforms (♦), NanoString platform only (■), Affymetrix platform only (▲), or neither platform (X). The $R2$ value shown represents the correlation of fold changes of genes that were found to be significant in both NanoString and microarray platforms.

FIGURE 27

METHODS AND COMPUTER SYSTEMS FOR IDENTIFYING TARGET-SPECIFIC SEQUENCES FOR USE IN NANOREPORTERS

CROSS-REFERENCES TO RELATED APPLICATIONS

This application claims the benefit under 35 U.S.C. §119 (e) of U.S. Provisional Patent Application No. 61/029,220, filed Feb. 15, 2008 and U.S. Provisional Patent Application No. 60/922,817, filed Apr. 10, 2007; where these provisional applications are incorporated herein by reference in their entireties.

FIELD OF THE INVENTION

The present invention relates to compositions and methods for detection and quantification of individual target molecules in biomolecular samples. In particular, the invention relates to coded, labeled reporter molecules, referred to herein as labeled "nanoreporters," that are capable of binding individual target molecules. Through the nanoreporters' label codes, the binding of the nanoreporters to target molecules results in the identification of the target molecules. Methods of making and using such nanoreporters are also provided. The nanoreporters can be used in diagnostic, prognostic, quality control and screening applications.

BACKGROUND OF THE INVENTION

This invention relates generally to the field of detection, identification, and quantification of target molecules in mixtures.

Although all cells in the human body contain the same genetic material, the same genes are not active in all of those cells. Alterations in gene expression patterns can have profound effects on biological functions. These variations in gene expression are at the core of altered physiologic and pathologic processes. Therefore, identifying and quantifying the expression of genes in normal cells compared to diseased cells can aid the discovery of new drug and diagnostic targets.

Nucleic acids can be detected and quantified based on their specific polynucleotide sequences. The basic principle underlying existing methods of detection and quantification is the hybridization of a labeled complementary probe sequence to a target sequence of interest in a sample. The formation of a duplex indicates the presence of the target sequence in the sample and the degree of duplex formation, as measured by the amount of label incorporated in it, is proportional to the amount of the target sequence.

This technique, called molecular hybridization, has been a useful tool for identifying and analyzing specific nucleic acid sequences in complex mixtures. This technique has been used in diagnostics, for example, to detect nucleic acid sequences of various microbes in biological samples. In addition, hybridization techniques have been used to map genetic differences or polymorphisms between individuals. Furthermore, these techniques have been used to monitor changes in gene expression in different populations of cells or in cells treated with different agents.

In the past, only a few genes could be detected in a complex sample at one time. Within the past decade, several technologies have made it possible to monitor the expression level of a large number of transcripts within a cell at any one time (see, e.g., Schena et al., 1995, Science 270: 467-470; Lockhart et al., 1996, Nature Biotechnology 14: 1675-1680; Blanchard et al., 1996, Nature Biotechnology 14:1649). In organisms for which most or all of the genome is known, it is possible to analyze the transcripts of large numbers of the genes within the cell. Most of these technologies employ, DNA microarrays, devices that consist of thousands of immobilized DNA sequences present on a miniaturized surface that have made this process more efficient. Using a microarray, it is possible in a single experiment to detect the presence or absence of thousands of genes in a biological sample. This allows researchers to simultaneously perform several diagnostic tests on one sample, or to observe expression level changes in thousands of genes in one experiment. Generally, microarrays are prepared by binding DNA sequences to a surface such as a nylon membrane or glass slide at precisely defined locations on a grid. Then nucleic acids in a biological sample are labeled and hybridized to the array. The labeled sample DNA marks the exact position on the array where hybridization occurs, allowing automatic detection.

Unfortunately, despite the miniaturization of array formats, this method still requires significant amounts of the biological sample. However, in several cases, such as biopsies of diseased tissues or samples of a discrete cell type, the biological sample is in limited supply. In addition, the kinetics of hybridization on the surface of a microarray is less efficient than hybridization in small amounts of aqueous solution. Moreover, while methods exist to estimate the amount of nucleic acid present in a sample based on microarray hybridization result, microarray technology thus far does not allow for detection of target molecules on an individual level, nor are there microarray-based methods for directly quantifying the amount of target molecule in a given sample.

Thus, there exists a need for accurate and sensitive detection, identification and quantification of target molecules in complex mixtures.

Discussion or citation of a reference herein shall not be construed as an admission that such reference is prior art to the present invention.

SUMMARY OF THE INVENTION

One aspect of the present invention provides a computer program product comprising a computer readable storage medium and a computer program mechanism embedded therein. The computer program mechanism is for identifying and selecting target-specific sequences useful in the probes of the invention. The computer program mechanism comprises a data storage module and a sequence selection module. The data storage module comprises one or more sequence databases. The sequence selection module comprises instructions for assessing the suitability of a sequence for use as a target-specific sequence in the probes of the invention and/or for selecting target-specific sequences for use in the probes of the invention. The sequence selection module can be a single-tiered or multi-tiered program that identifies useful target-specific sequences.

Each of the methods, computer program products, and computers disclosed herein optionally further comprise a step of, or instructions for, outputting a result (for example, to a monitor, to a user, to computer readable media, e.g., storage media or to a remote computer). Here the result is any result obtained by the methods, computer program products, and computers disclosed herein.

In certain aspects, the present invention provides a method (reflected in FIG. 20A-C) for identifying a pair of adjacent target-specific sequences for use in a probe pair hybridizable to a target mRNA, comprising the steps of: (a) generating a first pool of candidate nucleotide sequences of a first predetermined length or lengths that are reverse complements of a target mRNA sequence, wherein each candidate nucleotide sequence can be divided into two adjacent nucleotide sequences of equal length consisting of a 5' candidate sequence and a 3' candidate sequence; (b) deleting from said first pool one or more candidate nucleotide sequences that meet at least two of the following criteria: (i) contain inverted repeats of greater than a predetermined length of consecutive nucleotides; (ii) contain direct repeats of greater than a predetermined length of consecutive nucleotides; (iii) whose 5' candidate sequence and/or 3' candidate sequence have a GC content outside a predetermined range; (iv) whose 5' candidate sequence and/or 3' candidate sequence contain contiguous stretches of C residues of greater than a predetermined length; and (v) whose 5' candidate sequence and/or 3' candidate sequence have melting temperatures that are outside a first predetermined melting temperature range; thereby generating a second pool of candidate nucleotide sequences; (c) deleting from said second pool one or more candidate nucleotide sequences whose 5' candidate sequence and/or 3' candidate sequence has a cross-hybridization potential to non-specific sequences that is higher than a predetermined threshold, thereby generating a third pool of candidate nucleotide sequences; (d) deleting from said third pool one or more candidate nucleotide sequences whose 5' candidate sequence and/or 3' candidate sequence has a melting temperature outside a second predetermined temperature range, wherein the second predetermined melting temperature range is within the first predetermined melting temperature range; (e) determining the melting temperature for a modified 5' candidate sequence or a modified 3' candidate sequence, wherein the modified 5' candidate sequence or a modified 3' candidate sequence is a modified form of a 5' candidate sequence or a 3' candidate sequence, respectively, of a candidate nucleotide sequence deleted in step (d) because its 5' candidate sequence and/or 3' candidate sequence has a melting temperature above the second predetermined range, wherein the modified 5' candidate sequence has been modified by trimming at least one nucleotide from the 5' end of the corresponding 5' candidate sequence, and wherein the modified 3' candidate sequence has been modified by trimming at least one nucleotide from the 3' end of the corresponding 3' candidate sequence; (f) in the event that: (A) the modified 5' or modified 3' candidate sequence, and (B) a 3' or 5', respectively, candidate sequence or the modified form thereof, each have a melting temperature within the second predetermined melting temperature range and both are derived from the same candidate nucleotide sequence; adding to the third pool a modified candidate nucleotide sequence composed of (A) and (B), thereby generating a fourth pool of candidate nucleotide sequences; (g) in the event that the length of the modified 5' or modified 3' candidate sequence is greater than a second predetermined length, repeating step (e) one or more times wherein the modified 5' candidate sequence or modified 3' candidate sequence, respectively, has been trimmed by a greater number of nucleotides than in step (e) each time, until the length of the modified 5' or modified 3' candidate sequence is the earlier of (i) equal to, or (ii) lower than, the second predetermined length; (h) for each modified 5' or modified 3' candidate sequence of step (g) wherein: (C) said modified 5' or modified 3' candidate sequence, and (D) a 3' or 5', respectively, candidate sequence or the modified form thereof, each have a melting temperature within the second predetermined melting temperature range and both are derived from the same candidate nucleotide sequence; adding to the third pool a modified candidate sequence composed of (C) and (D), thereby generating a fifth pool of candidate nucleotide sequences; and (i) optionally repeating steps (e)-(h) for one or more different candidate nucleotide sequences deleted in step (d), thereby generating a sixth pool of candidate nucleotide sequences, whereby the fourth, fifth and sixth pools consist of candidate nucleotide sequences composed of pairs of adjacent target-specific sequences for use in a probe pair hybridizable to the target mRNA. Optionally, the method further comprises the step of outputting to a user interface device, a computer readable storage medium, or a local or remote computer system, or displaying, one or a plurality of candidate nucleotide sequences and/or modified candidate nucleotide sequences in the fourth, fifth and/or sixth pools and/or the 5' candidate sequences or modified 5' candidate sequences and/or 3' candidate sequences or modified 3' candidate sequences contained therein. Moreover, the candidate nucleotide sequences and/or modified candidate nucleotide sequences are optionally outputted as pairs of adjacent target-specific nucleotide sequences derived from said candidate nucleotide sequences and/or modified candidate nucleotide sequences, respectively.

In certain aspects of the foregoing methods for identifying a pair of adjacent target-specific sequences for use in a probe pair hybridizable to a target mRNA, the method comprises in step (b) deleting one or more candidate nucleotide sequences that at least 3 (e.g., 3, 4 or all 5) criteria of step (b) from the first pool.

According to the above methods, in step (c) a 5' candidate sequence or 3' candidate sequence can, in certain embodiments, be deemed to have a cross-hybridization potential to non-specific sequences that is higher than said predetermined threshold if said 5' candidate sequence or 3' candidate sequence has (i) a sequence percentage identity with a first sequence (hereinafter "first non-target sequence") or its complement that is equal to or greater than a first predetermined cutoff, said first non-target sequence being other than the complement of the target mRNA and, optionally, other than the complements of one or more alternatively spliced mRNAs corresponding to the same gene as the target mRNA, and said first non-target sequence being present in a database comprising cellular mRNA sequences or cDNA sequences derived therefrom; and (ii) a contiguous block of sequence identity with a second sequence (hereinafter "second non-target sequence") or its complement that is equal to or greater than a second predetermined cutoff, said second non-target sequence being other than the complement of the target mRNA and, optionally, other than the complements of one or more alternatively spliced mRNAs corresponding to the same gene as the target mRNA, and said second non-target sequence being present in the database. The first non-target sequence and the second non-target sequence can be the same or they can be different.

According to the foregoing methods for identifying a pair of adjacent target-specific sequences for use in a probe pair hybridizable to a target mRNA, a plurality of candidate nucleotide sequences and/or modified candidate nucleotide sequences in the fourth, fifth and/or sixth pools and/or the 5' candidate sequences or modified 5' candidate sequences and 3' candidate sequences or modified 3' candidate sequences contained therein are, in certain embodiments, outputted or displayed in a ranked order based on a weighted score of the cross-hybridization potentials and the melting temperatures of said 5' candidate sequences or modified 5' candidate sequences and 3' candidate sequences or modified 3' candidate sequences. In a specific embodiment, the weighted score is calculated according to the formula:

(Tm score*WFa)+(MCB score*WFb)+(PID score*WFc)

where:

Tm score is a melting temperature score calculated according to the formula:

(differential score+general score)/3 where the differential score is calculated according to the following formula:

1−|(TmA−TmB)|/(TmHco−TmLco)

where the general score is calculated according to the following formula:

(((TmI−|(TmA−TmI)|)/TmI)+(((TmI−|(TmB−TmI)/TmI)))

where TmA is the melting temperature of the 5' candidate sequence or modified 5' candidate sequence in a pair of adjacent target-specific sequences, TmB is the melting temperature of the 3' candidate sequence or modified 3' candidate sequence in said pair of adjacent target-specific sequences, TmHco is the upper limit of the second predetermined temperature range; TmLco is the lower limit of the second predetermined temperature range; and TmI is a predetermined ideal melting temperature;

where:

MCB score is a maximum contiguous block score calculated according to the formula:

1−(MCB/MCBco);

where MCB is the greater of (i) and (ii) below, where (i) and (ii) are respectively:

(i) the maximum contiguous block of identity between (A) and (B) below:
  (A) a first target-specific nucleotide sequence in said pair of adjacent target-specific sequences; and
  (B) a sequence in the database other than the complement of the target mRNA and, optionally, other than the complements of one or more alternatively spliced mRNAs corresponding to the same gene as the target mRNA;
  and
(ii) the maximum contiguous block of identity between (A) and (B) below:
  (A) a second target-specific nucleotide sequence in said pair of adjacent target-specific sequences; and
  (B) a sequence in the database other than the complement of the target mRNA and, optionally, other than the complements of one or more alternatively spliced mRNAs corresponding to the same gene as the target mRNA,
  and wherein MCBco is the first predetermined cutoff;

where:

PID score is a percent identity score calculated according to the formula:

1−(PID/PIDco));

where PID is the greater of (i) and (ii) below, where (i) and (ii) are respectively:

(i) the greatest percentage sequence identity between (A) and (B) below:
  (A) a first target-specific nucleotide sequence in said pair of adjacent target-specific sequences; and
  (B) a sequence in the database other than the complement of the target mRNA and, optionally, other than the complements of one or more alternatively spliced mRNAs corresponding to the same gene as the target mRNA; below:
  and
(ii) the greatest percentage sequence identity between (A) and (B)
  (A) a second target-specific nucleotide sequence in said pair of adjacent target-specific sequences; and
  (B) a sequence in the database other than the complement of the target mRNA and, optionally, other than the complements of one or more alternatively spliced mRNAs corresponding to the same gene as the target mRNA,
  and wherein PIDco is the second predetermined cutoff,
  and where WFa, WFb, and WFc are each independently a weighting factor, each of which is a real number.

In certain specific embodiments, the present invention provides a method for identifying a pair of adjacent target-specific sequences for use in a probe pair hybridizable to a target mRNA, comprising the steps of: (a) generating a first pool of candidate nucleotide sequences of 100 nucleotides that are reverse complements of a target mRNA sequence, wherein each candidate nucleotide sequence can be divided into two adjacent nucleotide sequences of 50 nucleotides each, said adjacent nucleotide sequences consisting of a 5' candidate sequence and a 3' candidate sequence; (b) deleting from said first pool one or more candidate nucleotide sequences that meet the following criteria: (i) contain inverted repeats that are 6 consecutive nucleotides in length or greater; (ii) contain direct repeats that are 9 consecutive nucleotides in length or greater; (iii) whose 5' candidate sequence and/or 3' candidate sequence have a GC content outside 40-70%; (iv) whose 5' candidate sequence and/or 3' candidate sequence contain contiguous stretches of 3 C residues or greater; and (v) whose 5' candidate sequence and/or 3' candidate sequence have melting temperatures that are outside a range of (A) 60-90° C. or (B) 65-85° C.; thereby generating a second pool of candidate nucleotide sequences; (c) deleting from said second pool one or more candidate nucleotide sequences whose 5' candidate sequence and/or 3' candidate sequence has (i) a sequence percentage identity of 85% or greater with a first sequence (hereinafter "first non-target sequence") or its complement, said first non-target sequence being other than the complement of the target mRNA and, optionally, other than the complements of one or more alternatively spliced mRNAs corresponding to the same gene as the target mRNA, and said first non-target sequence being present in a database comprising cellular mRNA sequences or cDNA sequences derived therefrom; and (ii) a contiguous block of sequence identity of 15 nucleotides or greater with a second sequence (hereinafter "second non-target sequence") or its complement, said second non-target sequence being other than the complement of the target mRNA and, optionally, other than the complements of one or more alternatively spliced mRNAs corresponding to the same gene as the target mRNA, and said second non-target sequence being present in the database; thereby generating a third pool of candidate nucleotide sequences; (d) deleting from said third pool one or more candidate nucleotide sequences whose 5' candidate sequence and/or 3' candidate sequence has a melting temperature outside the range of 78-83° C.; (e) determining the melting temperature for a modified 5' candidate sequence or a modified 3' candidate sequence, wherein the modified 5' candidate sequence or a modified 3' candidate sequence is a modified form of a 5' candidate sequence or a 3' candidate sequence, respectively, of a candidate nucleotide sequence deleted in step (d) because its 5' candidate sequence and/or 3' candidate sequence has a melting temperature above 83° C., wherein the modified 5' candidate sequence has been modified by trimming at least one nucleotide from the 5' end of the corresponding 5' candidate sequence, and wherein the modified 3' candidate sequence has been modified by trimming at least one nucleotide from the 3' end of the corresponding 3' candidate sequence; (f) in the event that: (A) the modified 5' or modified 3' candidate sequence, and (B) a 3' or 5', respectively, candidate sequence or the modified form thereof, each have a melting temperature within the range of 78-83° C. and both are derived from the same candidate nucleotide sequence, adding to the third pool a modified candidate nucleotide sequence composed of (A) and (B); thereby generating a fourth pool of candidate nucleotide sequences; (g) in the event that the length of the modified 5' or modified 3' candidate sequence is greater than 35 nucleotides, repeating step (e) one or more times wherein the modified 5' candidate sequence or modified 3' candidate sequence, respectively, has been trimmed by a greater number of nucleotides than in step (e) each time, until the length of the modified 5' or modified 3' candidate sequence is the earlier of (i) equal to, or (ii) lower than, 35 nucleotides; (h) for each modified 5' or modified 3' candidate sequence of step (g) wherein: (C) the modified 5' or modified 3' candidate sequence, and (D) a 3' or 5', respectively, candidate sequence or modified candidate sequence; each have a melting temperature in the range of 78-83° C. and both are derived from the same candidate nucleotide sequence, adding to the third pool a modified candidate sequence composed of (C) and (D); thereby generating a fifth pool of candidate nucleotide sequences; and (i) optionally repeating steps (e)-(h) for one or more different candidate nucleotide sequences deleted in step (d), thereby generating a sixth pool of candidate nucleotide sequences, whereby the fourth, fifth and sixth pools consist of candidate nucleotide sequences composed of pairs of adjacent target-specific sequences for use in a probe pair hybridizable to the target mRNA. The first non-target sequence and the second non-target sequence can be the same or they can be different.

Optionally, the method further comprises the step of outputting to a user interface device, a computer readable storage medium, or a local or remote computer system, or displaying, one or a plurality of candidate nucleotide sequences and/or modified candidate nucleotide sequences in the fourth, fifth and/or sixth pools and/or the 5' candidate sequences or modified 5' candidate sequences and/or 3' candidate sequences or modified 3' candidate sequences contained therein. Moreover, the candidate nucleotide sequences and/or modified candidate nucleotide sequences are optionally outputted as a pair of adjacent target-specific nucleotide sequences derived from said candidate nucleotide sequences and/or modified candidate nucleotide sequences, respectively.

In certain embodiments of the foregoing method, a plurality of candidate nucleotide sequences and/or modified candidate nucleotide sequences in the fourth, fifth and/or sixth pools and/or the 5' candidate sequences or modified 5' candidate sequences and 3' candidate sequences or modified 3' candidate sequences contained therein are outputted or displayed in a ranked order based on a weighted score of the cross-hybridization potentials and the melting temperatures of said 5' candidate sequences or modified 5' candidate sequences and 3' candidate sequences or modified 3' candidate sequences. In a specific embodiment, the weighted score is calculated according to the formula:

(Tm score*WFa)+(MCB score*WFb)+(PID score*WFc)

where:
Tm score is a melting temperature score calculated according to the formula:

(differential score+general score)/3 where the differential score is calculated according to the following formula:

1−|(TmA−TmB)|/5 where the general score is calculated according to the following formula:

(((80.5−|(TmA−80.5)|)/80.5)+(((80.5−|(TmB−80.5)|)/80.5)))

where TmA is the melting temperature of the 5' candidate sequence or modified 5' candidate sequence of a pair of adjacent target-specific sequences and TmB is the melting temperature of the 3' candidate sequence or modified 3' candidate sequence of said pair of adjacent target-specific sequences;
where:
MCB score is a maximum contiguous block score calculated according to the formula:

1−(MCB/15);

where MCB is the greater of (i) and (ii) below, where (i) and (ii) are respectively:
(i) the maximum contiguous block of identity between (A) and (B) below:
  (A) a first target-specific nucleotide sequence in said pair of adjacent target-specific sequences; and
  (B) a sequence in the database other than the complement of the target mRNA and, optionally, other than the complements of one or more alternatively spliced mRNAs corresponding to the same gene as the target mRNA;
and
(ii) the maximum contiguous block of identity between (A) and (B) below:
  (A) a second target-specific nucleotide sequence in said pair of adjacent target-specific sequences; and
  (B) a sequence in the database other than the complement of the target mRNA and, optionally, other than the complements of one or more alternatively spliced mRNAs corresponding to the same gene as the target mRNA;
where:
PID score is a percent identity score calculated according to the formula:

1−(PID/85%);

where PID is the greater of (i) and (ii) below, wherein (i) and (ii) are respectively:
(i) the greatest percentage sequence identity between (A) and (B) below:
  (A) a first target-specific nucleotide sequence in said pair of adjacent target-specific sequences; and
  (B) a sequence in the database other than the complement of the target mRNA and, optionally, other than the complements of one or more alternatively spliced mRNAs corresponding to the same gene as the target mRNA;
and
(ii) the greatest percentage sequence identity between (A) and (B) below:
  (A) a second target-specific nucleotide sequence in said pair of adjacent target-specific sequences; and
  (B) a sequence in the database other than the complement of the target mRNA and, optionally, other than the complements of one or more alternatively spliced mRNAs corresponding to the same gene as the target mRNA,
and wherein PIDco is the second predetermined cutoff, and where WFa, WFb, and WFc are each independently a weighting factor, each of which is a real number.

The foregoing methods for identifying a pair of adjacent target-specific sequences for use in a probe pair hybridizable to a target mRNA can be utilized for identifying a plurality of pairs of adjacent target-specific sequences for use in a respective plurality of probe pairs, each probe pair being hybridizable to a different target mRNA, comprising, for each target mRNA: identifying a pair of adjacent target-specific sequences according to any embodiment of the foregoing methods.

The present invention yet further provides a method (reflected in FIG. 21A-C) for identifying a target-specific nucleotide sequence for use in a probe hybridizable to a target mRNA, comprising the steps of: (a) generating a first pool of candidate nucleotide sequences of a first predetermined length or lengths that are reverse complements of a target mRNA sequence; (b) deleting from said first pool one or more candidate nucleotide sequences that meet at least two of the following criteria: (i) contains inverted repeats of greater than a predetermined length of consecutive nucleotides; (ii) contains direct repeats of greater than a predetermined length of consecutive nucleotides; (iii) has a GC content outside a predetermined range; (iv) contains a contiguous stretch of C residues of greater than a predetermined length; and (v) has a melting temperature that is outside a first predetermined melting temperature range; thereby generating a second pool of candidate nucleotide sequences; (c) deleting from said second pool one or more candidate nucleotide sequences that have a cross-hybridization potential to non-specific sequences that is higher than a predetermined threshold, thereby generating a third pool of candidate nucleotide sequences; (d) deleting from said third pool one or more candidate nucleotide sequences that have a melting temperature outside a second predetermined temperature range, wherein the second predetermined melting temperature range is within the first predetermined melting temperature range; (e) determining the melting temperature for a modified candidate nucleotide sequence, wherein the modified candidate nucleotide sequence is a modified form of a candidate nucleotide sequence deleted in step (d) because it has a melting temperature above the second predetermined range, wherein the modified candidate nucleotide sequence has been modified by trimming at least one nucleotide from the 5' end or the 3' end of said candidate nucleotide sequence; (f) in the event that the modified candidate nucleotide sequence has a melting temperature within the second predetermined melting temperature range, adding to the third pool the modified candidate nucleotide sequence, thereby generating a fourth pool of candidate nucleotide sequences; (g) in the event that the length of the modified candidate nucleotide sequence is greater than a second predetermined length, repeating step (e) one or more times wherein the modified candidate nucleotide sequence has been trimmed by a greater number of nucleotides than in step (e) each time, until the length of the modified candidate nucleotide sequence is the earlier of (i) equal to, or (ii) lower than, the second predetermined length; (h) adding to the third pool each modified candidate nucleotide sequence of step (g) which has a melting temperature within the second predetermined melting temperature range; thereby generating a fourth pool of candidate nucleotide sequences; and (i) optionally repeating steps (e)-(h) for one or more different candidate nucleotide sequences deleted in step (d), thereby generating a sixth pool of candidate nucleotide sequences, whereby the fourth, fifth and sixth pools consist of target-specific nucleotide sequences for use in a probe hybridizable to a target mRNA. The method optionally further comprises the step of outputting to a user interface device, a computer readable storage medium, or a local or remote computer system, or displaying, one or a plurality of candidate nucleotide sequences and/or modified candidate nucleotide sequences in the fourth, fifth and/or sixth pools.

According to the foregoing method for identifying a target-specific nucleotide sequence for use in a probe hybridizable to a target mRNA, in step (c) a candidate target-specific sequence can, in certain embodiments, be deemed to have a cross-hybridization potential to non-specific sequences that is higher than said predetermined threshold if said candidate target-specific sequence has (i) a sequence percentage identity with a first sequence (hereinafter "first non-target sequence") or its complement that is equal to or greater than a first predetermined cutoff, said first non-target sequence being other than the complement of the target mRNA and, optionally, other than the complements of one or more alternatively spliced mRNAs corresponding to the same gene as the target mRNA, and said first non-target sequence being present in a database comprising cellular mRNA sequences or cDNA sequences derived therefrom; and (ii) a contiguous block of sequence identity with a second sequence (hereinafter "second non-target sequence") or its complement that is equal to or greater than a second predetermined cutoff, said second non-target sequence being other than the complement of the target mRNA and, optionally, other than the complements of one or more alternatively spliced mRNAs corresponding to the same gene as the target mRNA, and said second non-target sequence being present in the database. The first non-target sequence and the second non-target sequence can be the same or they can be different.

In the foregoing method for identifying a target-specific nucleotide sequence for use in a probe hybridizable to a target mRNA, a plurality of candidate nucleotide sequences and/or modified candidate nucleotide sequences in the fourth, fifth and/or sixth pools are optionally outputted or displayed in a ranked order based on a weighted score of the cross-hybridization potentials and the melting temperatures of said candidate nucleotide sequences and/or modified candidate nucleotide sequences.

The foregoing methods for identifying a target-specific nucleotide sequence for use in a probe hybridizable to a target mRNA can be utilized for identifying a plurality of target-specific sequences for use in a respective plurality of probes, each probe being hybridizable to a different target mRNA, comprising, for each target mRNA: identifying a target-specific sequence according to any embodiment of the foregoing method.

In certain aspects of the foregoing methods for identifying a target-specific nucleotide sequence for use in a probe hybridizable to a target mRNA, one or more candidate nucleotide sequences that meet 3 or more, e.g., 3, 4 or all 5, criteria of step (b) are deleted from the first pool in step (b).

In any of the foregoing methods for identifying a target-specific nucleotide sequence and/or identifying a pair of adjacent target-specific sequences, if the fourth, fifth and/or sixth pools contains no candidate nucleotide sequences, the method may further comprise repeating steps (b) to (i), wherein step (b) is performed under more relaxed criteria (e.g., with an increased predetermined length of direct and/or inverted repeats and/or a broader range of GC content and/or a broader range of melting temperatures and/or a greater predetermined length of contiguous C residues).

In specific embodiments of the foregoing methods for identifying a target-specific nucleotide sequence and/or identifying a pair of adjacent target-specific sequences, each repetition of the trimming step (e) can be performed in increments of 1 nucleotide, 2 nucleotides, 3 nucleotides, 4 nucleotides, or more.

In specific embodiments of the foregoing methods for identifying a pair of adjacent target-specific sequences, wherein the first predetermined length can be selected from the range of 70 to 120 nucleotides, and/or the second predetermined length can be selected from the range of 30 to 45 nucleotides. In a specific embodiment, the second predetermined length is selected from the range of 35-40 nucleotides.

In specific embodiments of the foregoing methods for identifying a target-specific nucleotide sequence, the first predetermined length can be selected from the range of 35 to 60 nucleotides and/or the second predetermined length can selected from the range of 30 to 45 nucleotides. In a specific embodiment, the second predetermined length is selected from the range of 35-40 nucleotides.

In certain embodiments of the foregoing methods for identifying a target-specific nucleotide sequence and/or identifying a pair of adjacent target-specific sequences, the predetermined length of the inverted repeats of step (b)(i) can be selected from the range of 5 to 7 consecutive nucleotides and/or the predetermined length of the direct repeats of step (b)(ii) can be selected from the range of 7 to 9 consecutive nucleotides and/or the predetermined range of GC content of step (b)(iii) can be from 35-45% at the lower limit to 65-80% at the upper limit. In a specific embodiment, the predetermined range of GC content of step (b)(iii) is 40-70%.

In certain embodiments of the foregoing methods for identifying a target-specific nucleotide sequence and/or identifying a pair of adjacent target-specific sequences, the predetermined length in step (b)(iv) is preferably 3.

In certain embodiments of the foregoing methods for identifying a target-specific nucleotide sequence and/or identifying a pair of adjacent target-specific sequences, the highest and lowest temperatures of the first predetermined melting temperature range preferably differ by 15° C. to 30° C., and most preferably by 20° C. to 25° C. In specific embodiments, the first predetermined melting temperature range is from 60° C. to 90° C., from 65° C. to 85° C., or from 65° C. to 90° C.

In aspects of the present methods that entail the use of a first predetermined cutoff for cross-hybridization potential determination, the first predetermined cutoff is preferably selected from the range of 70-95% sequence identity, more preferably selected from the range of 80-90% sequence identity. In a specific embodiment, the first predetermined cutoff is 85% sequence identity.

In aspects of the present methods that entail the use of a second predetermined cutoff for cross-hybridization potential determination, wherein the second predetermined cutoff is preferably selected from the range of 10-18 contiguous nucleotides, and more preferably from the range of 14-16 contiguous nucleotides.

In certain embodiments of the foregoing methods for identifying a target-specific nucleotide sequence and/or identifying a pair of adjacent target-specific sequences, the highest and lowest temperatures of the second predetermined melting temperature range preferably differ by 4° C. to 8° C. In specific embodiments, the second predetermined melting temperature range is from 78° C. to 83° C.

In certain embodiments, the foregoing methods for identifying a target-specific nucleotide sequence and/or identifying a pair of adjacent target-specific sequences further comprises the step of deleting from the fourth, fifth and/or sixth pools candidate nucleotide sequences that have a cross-hybridization potential to sequences present in other components of the probe or in a preparation step for the probe.

In certain embodiments of the foregoing methods for identifying a target-specific nucleotide sequence and/or identifying a pair of adjacent target-specific sequences, the target mRNA is an alternatively spliced mRNA. In such embodiment, the methods may further comprise the step of determining whether one or more candidate nucleotide sequences are unique to one splice form or common to more than one splice form of the target mRNA. Alternatively, the first pool of candidate nucleotide sequences is designed to contain only candidate nucleotide sequences unique to one splice form or only candidate nucleotide sequences common to multiple splice forms.

Any of the foregoing methods for identifying a target-specific nucleotide sequence and/or identifying a pair of adjacent target-specific sequences can be a computer implemented method The present invention further provides a computer system for identifying a pair of adjacent target-specific sequences, for use in a probe pair hybridizable to a target mRNA, comprising a processor and a memory coupled with the processor comprising a plurality of machine instructions that cause the processor to perform the method of any one of the foregoing methods for identifying a pair of adjacent target-specific sequences. The present invention yet further provides computer system for identifying a target-specific nucleotide sequence for use in a probe hybridizable to a target mRNA, comprising: a processor and a memory coupled with the processor, the memory storing a plurality of machine instructions that cause the processor to perform any one of the foregoing methods for identifying a target-specific sequence.

The present invention yet further provides a computer system for identifying a plurality of pairs of adjacent target-specific sequences for use in a respective plurality of probe pairs, each probe pair being hybridizable to a different target mRNA, comprising: a processor and a memory coupled with the processor, the memory storing a plurality of machine instructions that cause the processor to perform any of the foregoing methods for identifying a plurality of pairs of adjacent target-specific sequences.

The present invention yet further provides a computer system for identifying a plurality of target-specific sequences for use in a respective plurality of probes, each probe being hybridizable to a different target mRNA, each probe being specific sequences for use in a respective plurality of probes, comprising: a processor and a memory coupled with the processor, the memory storing a plurality of machine instructions that cause the processor to perform any one of the foregoing methods for identifying a target-specific sequence.

The present invention further provides computer system comprising: a processor and a memory coupled with the processor, the memory storing a plurality of machine instructions that cause the processor to perform anone of the foregoing method for identifying a target-specific sequence.

The present invention yet further provides a computer program product for use in conjunction with a computer system, the computer program product comprising a computer readable storage medium and a computer program mechanism embedded therein, the computer program mechanism comprising instructions for performing any of the foregoing methods for identifying a target-specific nucleotide sequence (or a plurality thereof) and/or identifying a pair of adjacent target-specific sequences (or a plurality thereof).

BRIEF DESCRIPTION OF THE FIGURES

FIG. 1A-1F: FIG. 1A illustrates a dual nanoreporter with a 16-position nanoreporter code, using two 8-position nanoreporter components. FIG. 1B illustrates a dual nanoreporter with a 9-position nanoreporter code, using one 8-position nanoreporter component and one single-position nanoreporter component. FIG. 1C illustrates a dual nanoreporter with an 8-position nanoreporter code, using one ghost probe and one 8-position nanoreporter component. FIG. 1D illustrates a single nanoreporter with an 8-position nanoreporter code. In FIGS. 1A-1D, the star shape (depicted with an arrow) is illustrative of an affinity tag, which can be used to purify the nanoreporter or immobilize the nanoreporter (or nanoreporter-target molecule complex) for the purpose of imaging. The numbered regions in FIG. 1A-1D refer to separate label attachment regions. All except for position 12 of FIG. 1A are labeled with one of four types of label monomers, depicted as grey, white, hatched or stripe "sun" diagrams. Position 12 of FIG. 1A is an unlabeled "dark spot." FIGS. 1E and 1F represent variations on the nanoreporters of FIGS. 1B and 1D, respectively, in which the target molecule to which the nanoreporters are bound comprises biotin moieties (shown as small asterisks), for example biotin-modified nucleotides randomly incorporated into a target nucleic acid. The nanoreporters themselves further optionally comprise an affinity tag (not shown).

FIG. 2A-2C: FIG. 2A shows an illustration of a label unit of a nanoreporter, containing a scaffold with patch units and corresponding split flaps disposed along its length. FIG. 2B illustrates the components of a single patch pair and its corresponding flap, containing: 1: a portion of a nanoreporter scaffold (e.g., M13 single-stranded DNA); 2: A patch pair; 3: a split flap pair; and 4: labeled oligonucleotides, each with a label monomer incorporated, hybridized to the split flap. FIG. 2C shows a nanoreporter with 4 "spots," each spot designed to contain 9 patch pairs of 60-65 nucleotides, each attached to a split flap pair of 95-100 nucleotides. Each split flap pair had binding site for 12 oligonucleotides each attached to a single label monomer. Each spot therefore had binding sites for 108 label monomers.

FIG. 3: A nanoreporter in which the patches are RNA segments can be used with (FIG. 3A) and without registers (FIG. 3B). Both FIGS. 3A and 3B depict a (1) nanoreporter scaffold (heavy black line) to which are attached (2) 8 RNA segments (heavy grey lines 1-8), (3) a target-specific sequence (dotted line "T") and (4) an oligonucleotide (checkered line "O") that is partly complementary to the nanoreporter scaffold and partly complementary to the target-specific sequence. This oligonucleotide is referred to as a "ligator" oligonucleotide. In FIG. 3A, only one register, i.e., every alternate RNA segment is labeled. The second register positions serve as "spacers," making it possible to generate a nanoreporter code in which consecutive positions in the code are the same "color," or spectrally indistinguishable. In FIG. 3B, both registers, i.e., adjacent RNA segments with no intervening spacers, are labeled, with no nearest neighbor of the same "color."

FIG. 5A-5D: This figure illustrates the various components of the dual nanoreporters shown in FIG. 4. FIG. 5A illustrates one color (here, Alexa 488, depicted in the left column as open circles), which is spectrally distinguishable from Cy3 (shown in FIG. 5B, depicted in the left column as vertically striped circles) and Alexa 647 (shown in FIG. 5C as diagonally striped circles). The images obtained from each were superimposed to generate FIG. 5D.

FIG. 6A-6E: FIG. 6A is a schematic illustration of the experiment shown in FIGS. 6B and 6C. In this case, the star represents biotin that was used to attach the complex by one end to the surface prior to stretching. FIGS. 6B and 6C show images from experiments in which S2-A ghost probe, S2-B labeled nanoreporter and S2 target DNA (FIG. 6B) or S2 target RNA (FIG. 6C) were hybridized. FIG. 6E shows a close-up of a nanoreporter complexes from FIG. 6B, each containing S2-A ghost probe, S2-B labeled nanoreporter and S2 target DNA. FIG. 6D shows an image of a negative control experiment, in which S2-A ghost probe, S2-B labeled nanoreporter and no S2 target RNA were hybridized.

FIG. 7A-G. FIGS. 7A, 7B, 7C and 7D depict different permutations of patches on a nanoreporter scaffold, FIGS. 7E and 7F depict different permutations of split flaps on a nanoreporter scaffold, optionally hybridized to one or more oligonucleotides, as in FIG. 7G. In FIG. 7A-G, α refers to a 5' or 3' molecule or end of a molecule, and 13 refers to a corresponding 3' or 5' molecule or end of a molecule.

FIG. 8 depicts a scheme in which single-stranded M13 phage is linearized for use as a nanoreporter scaffold. The circular M13 phage is annealed to a five-fold excess of BamH1 cutter oligonucleotide (hatched lines) (1), and the resulting partially double-stranded M13 digested with the restriction endonuclease BamH1 (2), resulting in a linearized M13 in which BamH1 cutter oligonucleotide is still attached (3). This M13-oligonucleotide complex is heated in the presence of an excess oligonucleotide complementary to the BamH1 cutter oligonucleotide (an "anti-BamH1 oligonucleotide") (grey lines) (4). The BamH1 cutter oligonucleotide anneals to the excess of anti-BamH1 oligonucleotide, and the M13 molecule is purified from the oligonucleotide, for example by using size exclusion columns, to yield M13 scaffold.

FIG. 9A-9B: Shows a labeled nanoreporter with an affinity tag at each end, A1 and A2. In FIG. 9, the labeled nanoreporter is immobilized through the binding of A1 to an immobilized affinity partner. In the absence of an affinity binding partner for A2, the A2 end of the nanoreporter remains in solution (FIG. 9A), but in the presence of an affinity binding partner (A2'), the A2 end of the nanoreporter is also immobilized (FIG. 9B). Upon immobilization, the nanoreporter can be stretched, or "elongated" as depicted in FIG. 9B, for example by electrostretching, for separation of the label attachment regions in a manner that permits detection of the nanoreporter code.

FIG. 10A-10C: FIG. 10A shows a labeled nanoreporter containing a single affinity tag, A1. Another affinity tag, A2, can be attached to the nanoreporter by direct binding of the nanoreporter to a molecule containing A2 (e.g., if the nanoreporter is or comprises a nucleic acid, it can hybridize directly with another nucleic acid to which A2 is attached), as depicted in FIG. 10B. Alternatively, the second affinity tag, A2, can be attached to the labeled nanoreporter via a bridging molecule, such as the bridging nucleic acid ("X") depicted in FIG. 10C.

In FIG. 11, the labeled nanoreporter is immobilized through the binding of A1 to an immobilized affinity partner. The other end of the nanoreporter is in solution (FIG. 11A), but can be immobilized by hybridization to a complementary oligonucleotide which contains another affinity tag (A2) used to immobilize the nanoreporter (FIG. 11B). A1 and A2 can be the same, for example biotin, for immobilization on an avidin- or streptavidin-coated surface. Upon immobilization of A1, the nanoreporter can be stretched, or "elongated" as depicted in FIG. 11, for example by electrostretching, for separation of the label attachment regions in a manner that permits detection of the nanoreporter code. Optionally, while the nanoreporter is in an elongated state, A2 is introduced and binds the end of the nanoreporter that is complementary to A2 down to the surface.

FIG. 12A-12B. FIG. 12A provides an illustration of a nanoreporter comprising an immobilized first portion F1; and FIG. 12B provides an illustration of a nanoreporter extended in an electrical field and comprising immobilized first portion F1 and immobilized second portion F2, wherein F2 is immobilized via a complex with molecule F3.

FIG. 13A provides an illustration of a three-member complex for immobilization of an extended nanoreporter; FIG. 13B provides an illustration of a two-member complex for immobilization of an extended nanoreporter; and FIG. 13C provides an illustration of an incomplete complex for immobilization of an extended nanoreporter.

FIG. 14A-14D. FIG. 14A provides an illustration of a nanoreporter comprising an immobilized first portion F1; FIG. 14B provides an illustration of an extended nanoreporter immobilized at first portion F1 and at a second portion via complexes with F2; FIG. 14C provides an illustration of a nanoreporter comprising a first portion immobilized to an avidin surface via biotin; and FIG. 14D provides an illustration of an extended nanoreporter immobilized at a first portion and at a second portion via selective binding of biotin to an avidin surface.

FIG. 15A illustrates immobilization of one terminus of a DNA molecule in a microfluidic device; FIG. 15B illustrates extension of the DNA in an electric field; and FIG. 15C illustrates selective immobilization of a second terminus of the extended DNA molecule.

FIG. 22a shows the capture probe and reporter probe hybridized to a complementary target mRNA in solution via the gene-specific sequences. After hybridization, the tripartite molecule is affinity-purified first by the 3'-repeat sequence and then by the 5'-repeat sequence to remove excess reporter and capture probes, respectively. FIG. 22b provides a schematic representation of binding, electrophoresis, and immobilization. (i) The purified complexes are attached to a streptavidin-coated slide via biotinylated capture probes. (ii) Voltage is applied to elongate and align the molecules. Biotinylated anti-5' oligonucleotides that hybridize to the 5'-repeat sequence are added. (iii) The stretched reporters are immobilized by the binding of the anti-5' oligonucleotides to the slide surface via the biotin. Voltage is turned off and the immobilized reporters are prepared for imaging and counting. FIG. 22c shows false-color image of immobilized reporter probes.

FIG. 23a shows signal (counts) on a log scale vs. concentration of the spike on a log scale. Each of three replicate measurements for each spike in Mock- and PV-infected RNA is shown. At this scale, the replicate measurements lie essentially on top of each other except at the lowest spike-in concentration. FIG. 23b provides average signal vs. concentration on a linear scale for spikes in both mock- and PV-infected samples. The correlation coefficients ($R^2$ values) of a linear fit to the average signal are 0.9988 and 0.9992 for mock and PV-infected samples respectively. The normalized counts used to construct both graphs are available in Table 6.

FIG. 24a is a scatter plot of normalized signal for all 509 genes assayed shown in log scale for technical replicates. Genes were not filtered based on detection. The $R^2$ value of a linear fit to this data is 0.9999+/−0.0002. The $R^2$ value for all pairwise comparisons of technical replicates for both NanoString and Affymetrix are shown in Table 6. FIG. 24b is a scatter plot of mock-infected vs. PV-infected counts for 509 genes. The normalized average counts for the triplicate assays are shown. The top and bottom lines represent 2-fold increase and decrease in expression levels, respectively. All 509 data points are shown without filtering.

FIG. 25 shows a comparison of detected/undetected calls for the NanoString and Affymetrix assays. A set of 449 RefSeq mRNAs that had corresponding Affymetrix probe sets was used in this analysis. FIG. 25a depicts mock-infected and FIG. 25b depicts PV-infected samples. For the NanoString assay a gene was considered detected if the average normalized signal for the three replicates was significantly above that of the negative controls ($P \leq 0.05$). For Affymetrix assay, a gene was considered detected if any one of the three replicates was called "Present" or "Marginal" based on MAS 5.0 analysis.

FIG. 26a provides $\log_2$ (PV-infected/mock-infected) ratios as measured by NanoString assay (x-axis) and Affymetrix arrays (y-axis). Genes were considered differentially regulated if the P-value in a Student's T-test performed on replicate data was $\leq 0.05$ (n=3). Affymetrix ratios were based on RMA normalized data. A linear fit to the ratios that are deemed statistically significant in both assays (♦) yields a correlation coefficient of 0.79. Genes were not filtered based on the magnitude of fold-change or the detected/undetected calls for this analysis. A set of 14 genes whose expression levels were discordant between the two platforms and were selected for real-time PCR analysis are also shown (♦). Genes were selected based on criteria outlined in the Examples. FIG. 26b demonstrates that the discordant 14 genes shown in FIG. 26a as analyzed by TaqMan® real-time PCR performed in triplicate on 100 ng of the same mock and PV-infected samples. The bar graph shows $\log_2$ ratios (PV-infected/mock-infected) for the NanoString (■), TaqMan® (■) and Affymetrix (■) platforms in triplicate. The root mean square deviation of $\log_2$ ratios between NanoString to TaqMan® was 0.34, DNA microarray to TaqMan® was 1.20. FIG. 26c shows the results obtained when a library of probe pairs to 35 RefSeq mRNAs that overlapped with the published MAQC consortium study was hybridized to commercially-available reference RNAs. Data was filtered to remove genes that were not detected in all samples (see Methods). The Affymetrix data shown here was downloaded from the MAQC study and represents data from a single site (site 1, Affymetrix). TaqMan® real-time PCR data was performed at Applied Biosystems Inc. The $R^2$ values for 27 NanoString genes (♦) and 18 Affymetrix genes (■) that met the selection criteria were 0.95 and 0.83, respectively. The overall correlation of Affymetrix data for 469 genes (site 1) in the original study was 0.92.

FIG. 27 is a graph depicting a comparison of the fold change results for all 509 genes examined. This graph is a scatter plot of log 2 fold change for 317 genes that were measured by both NanoString and Affymetrix platforms. Genes are coded based upon the significance of their fold change values (P<0.05) in either both platforms (♦), NanoString platform only (■), Affymetrix platform only (▲), or neither platform (X). The $R^2$ value shown represents the correlation of fold changes of genes that were found to be significant in both NanoString and microarray platforms.

DETAILED DESCRIPTION OF THE INVENTION

Figure 1D:
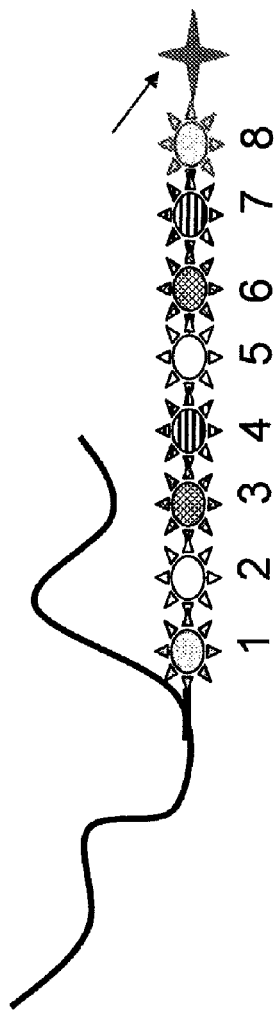
Figure 1E:
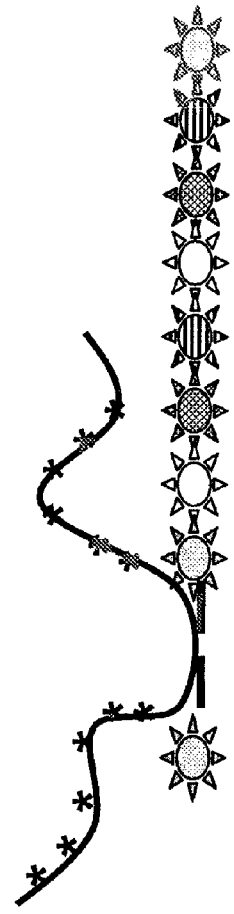
Figure 1F:
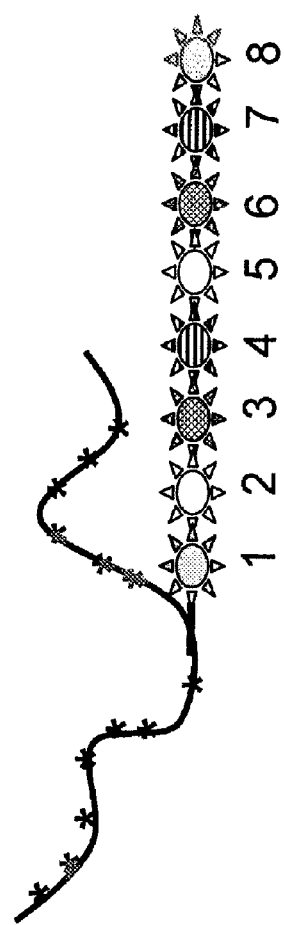

The present invention pertains to nanoreporters, and their manufacture and use. A fully assembled and labeled nanoreporter comprises two main portions, a target-specific sequence that is capable of binding to a target molecule, and a labeled region which emits a "code" of signals (the "nanoreporter code") associated with the target-specific sequence. Upon binding of the nanoreporter to the target molecule, the nanoreporter code identifies the target molecule to which the nanoreporter is bound.

Nanoreporters are modular structures. Generally, a nanoreporter is a molecular entity containing three basic elements: a scaffold containing two or more label attachment regions, one or more patches attached to the scaffold, and a target-specific sequence, also attached to the scaffold. The elements of a nanoreporter can be found in a single molecular entity (a "singular" nanoreporter), or two distinct molecular entities (a "dual" nanoreporter). Each molecular entity may be composed of one molecule or more than one molecule attached to one another by covalent or non-covalent means. Generally, each component of a dual nanoreporter has a target-specific sequence that binds to a different site on the same target molecule. This allows for smaller nanoreporter components with more efficient kinetics of binding of the nanoreporter to the target molecule and better signal:noise ratios resulting from the greater binding specificity.

The patches attached to a nanoreporter scaffold serve to attach label monomers to a nanoreporter scaffold. Patches may be directly labeled, for example by covalent incorporation of one or more label monomers into nucleic acid patches. Alternatively, patches may be attached to flaps, which may be labeled directly, for example by covalent incorporation of one or more label monomers into a nucleic acid flap, or indirectly, for example by hybridization of a nucleic acid flap to an oligonucleotide which is covalently attached to one or more label monomers. Where the label monomers attached to a label attachment region are not directly incorporated into a patch or flap, the patch or flap serves as a "bridge" between the label monomer and the label attachment region, and may be referred to as a "bridging molecule," e.g., a bridging nucleic acid.

Additionally, nanoreporters may have affinity tags for purification and/or for immobilization (for example to a solid surface). Nanoreporters, or nanoreporter-target molecule complexes, are preferably purified in two or more affinity selection steps. For example, in a dual nanoreporter, one probe can comprise a first affinity tag and the other probe can comprise a second (different) affinity tag. The probes are mixed with target molecules, and complexes comprising the two probes of the dual nanoreporter are separated from unbound materials (e.g., the target or the individual probes of the nanoreporter) by affinity purification against one or both individual affinity tags. In the first step, the mixture can be bound to an affinity reagent for the first affinity tag, so that only probes comprising the first affinity tag and the desired complexes are purified. The bound materials are released from the first affinity reagent and optionally bound to an affinity reagent for the second affinity tag, allowing the separation of complexes from probes comprising the first affinity tag. At this point only full complexes would be bound. The complexes are finally released from the affinity reagent for the second affinity tag and then preferably stretched and imaged. The affinity reagent can be any solid surface coated with a binding partner for the affinity tag, such as a column, bead (e.g., latex or magnetic bead) or slide coated with the binding partner Immobilizing and stretching nanoreporters using affinity reagents is fully described in U.S. Patent Publication No. 2010/0261026, which is incorporated by reference herein in its entirety.

Nanoreporter and nanoreporter-target complexes which are or comprise nucleic acids may be affinity-purified or immobilized using a nucleic acid, such as an oligonucleotide, that is complementary to at least part of the nanoreporter or target. In a specific application where the target includes a poly A or poly dA stretch, the nanoreporter-target complex can be purified or immobilized by an affinity reagent coated with a poly dT oligonucleotide.

The sequence of signals emitted by the label monomers associated with the various label attachment regions of the scaffold of a given nanoreporter allows for the unique identification of the nanoreporter. A nanoreporter having a unique identity or unique spectral signature is associated with a target-specific sequence that recognizes a specific target molecule or a portion thereof. When a nanoreporter is exposed to a mixture containing the target molecule under conditions that permit binding of the target-specific sequence(s) of the nanoreporter to the target molecule, the target-specific sequence(s) preferentially bind(s) to the target molecule. Detection of the spectral code associated with the nanoreporter allows detection of the presence of the target molecule in the mixture (qualitative analysis). Counting all the label monomers associated with a given spectral code or signature allows the counting of all the molecules in the mixture associated with the target-specific sequence coupled to the nanoreporter (quantitative analysis). Nanoreporters are thus useful for the diagnosis or prognosis of different biological states (e.g., disease vs. healthy) by quantitative analysis of known biological markers. Moreover, the exquisite sensitivity of single molecule detection and quantification provided by the nanoreporters of the invention allows for the identification of new diagnostic and prognostic markers, including those whose fluctuations among the different biological states is too slight detect a correlation with a particular biological state using traditional molecular methods. The sensitivity of nanoreporter-based molecular detection permits detailed pharmacokinetic analysis of therapeutic and diagnostic agents in small biological samples.

Many nanoreporters, referred to as singular nanoreporters, are composed of one molecular entity, as depicted in FIG. 1D. However, to increase the specificity of a nanoreporter and/or to improve the kinetics of its binding to a target molecule, a preferred nanoreporter is a dual nanoreporter composed of two molecular entities, each containing a different target-specific sequence that binds to a different region of the same target molecule. Various embodiments of dual nanoreporters are depicted in FIGS. 1A-1C. In a dual nanoreporter, at least one of the two molecular entities is labeled. The other molecular entity is not necessarily labeled. Such unlabeled components of dual nanoreporters are referred to herein as "ghost probes" (see FIG. 1C) and often have affinity tags attached, which are useful to immobilize and/or stretch the complex containing the dual nanoreporter and the target molecule to allow visualization and/or imaging of the complex.

Because of their modular structures, nanoreporters may be assembled and labeled in a variety of different ways. For example, a nanoreporter scaffold can be attached to a target-specific sequence (for example by hybridization and, optionally, ligation), and the structure comprising the scaffold and target-specific sequence attached to one or more patches and, where desired, flaps. Alternatively, the nanoreporter scaffold can first be attached to one or more patches (and, optionally, flaps), and the scaffold/patch structure then attached to a target specific sequence. Thus, unless stated otherwise, a discussion or listing of steps in nanoreporter assembly does not imply that a specific route of assembly must be followed.

Nanoreporter assembly and use is exemplified herein largely by way of description of a variety of nucleic acid-based nanoreporters; however, one of skill in the art would recognize that the methods described herein are applicable to an amino acid-based (or hybrid nucleic acid-/amino acid-based) nanoreporter. Illustrative embodiments of partially and fully assembled nanoreporters are listed below.

At its simplest, the invention provides a scaffold having at least two label attachment regions capable of being labeled and resolved. The scaffold can be any molecular entity that allows the formation of label attachment regions on the scaffold that can be separately labeled and resolved. The number of label attachment regions to be formed on a scaffold is based on the length and nature of the scaffold, the means of labeling the nanoreporter, as well as the type of label monomers emitting a signal to be attached to the label attachment regions of the scaffold. A nanoreporter according to the invention may have a scaffold including two or more label attachment regions. Suitable scaffold structures include DNA-based scaffolds.

The invention also provides labeled nanoreporters wherein one or more label attachment regions are attached to corresponding label monomers, each label monomer emitting a signal. For example a labeled nanoreporter according to the invention is obtained when at least two label monomers are attached to two corresponding label attachment regions of the scaffold such that these labeled label attachment regions, or "spots," are distinguishable. Label monomers emitting a signal associated with different label attachment regions of the scaffold can emit signals that are spectrally indistinguishable under the detections conditions ("like" signals), or can emit signals that are spectrally distinguishable, at least under the detection conditions (e.g., when the nanoreporter is immobilized, stretched and observed under a microscope).

The invention also provides a nanoreporter wherein two or more label monomers are attached to a label attachment region. The signal emitted by the label monomers associated with said label attachment region produces an aggregate signal that is detected. The aggregate signal produced may be made up of like signals or made up of at least two spectrally distinguishable signals.

In one embodiment, the invention provides a nanoreporter wherein at least two label monomers emitting like signals are attached to two corresponding label attachment regions of the scaffold and said two label monomers are spatially distinguishable. In another embodiment, the invention provides a nanoreporter wherein at least two label monomers emitting two distinguishable signals are attached to two neighboring label attachment regions, for example two adjacent label attachment regions, whereby said at least two label monomers are spectrally distinguishable.

The invention provides a nanoreporter wherein two spots emitting like signals are separated by a spacer region, whereby interposing the spacer region allows resolution or better resolution of said like signals emitted by label monomers attached to said two spots. In one embodiment, the spacer regions have a length determined by the resolution of an instrument employed in detecting the nanoreporter.

The invention provides a nanoreporter with one or more "double spots." Each double spot contains two or more (e.g., three, four or five) adjacent spots that emit like signals without being separated by a spacer region. Double spots can be identified by their sizes.

A label monomer emitting a signal according to the invention may be attached covalently or non-covalently (e.g., via hybridization) to a patch that is attached to the label attachment region. The label monomers may also be attached covalently or non-covalently (e.g., via hybridization) to a flap attached to a patch that is in turn attached to the scaffold. The flap can be formed by one molecule or two or more molecules ("flap pieces") that form a split flap.

The invention also provides a nanoreporter associated with a spectral code determined by the sequence of signals emitted by the label monomers attached (e.g., indirectly via a patch) to label attachment regions on the scaffold of the nanoreporter, whereby detection of the spectral code allows identification of the nanoreporter.

In one embodiment, the invention provides a nanoreporter further comprising an affinity tag attached to the nanoreporter scaffold, such that attachment of the affinity tag to a support allows scaffold stretching and resolution of signals emitted by label monomers corresponding to different label attachment regions on the scaffold. Nanoreporter stretching may involve any stretching means known in the art including but not limited to, means involving physical, hydrodynamic or electrical means.

In yet another embodiment, the invention provides a nanoreporter further comprising flaps attached to label attachment regions of the scaffold, wherein a flap attached to a label attachment region of the scaffold attaches the label monomer corresponding to said label attachment region, thereby indirectly attaching label monomers to corresponding label attachment regions on said scaffold. In a further embodiment, each label monomer comprises a signal emitting portion and an oligonucleotide portion of a predetermined sequence, and the flaps comprise repeats of a flap sequence complementary to the oligonucleotide portion of a corresponding label, whereby one or more label monomers attach to a corresponding label attachment region through hybridization of said oligonucleotide portions of said label monomers to said repeats of said flap sequence thereby producing a labeled nanoreporter.

A nanoreporter according to the invention can further include a target-specific sequence coupled to the scaffold. The target-specific sequence is selected to allow the nanoreporter to recognize, bind or attach to a target molecule. The nanoreporters of the invention are suitable for identification of target molecules of all types. For example, appropriate target-specific sequences can be coupled to the scaffold of the nanoreporter to allow detection of a target molecule. Preferably the target molecule is DNA (including cDNA), RNA (including mRNA and cRNA), a peptide, a polypeptide, or a protein.

One embodiment of the invention provides increased flexibility in target molecule detection with label monomers according to the invention. In this embodiment, a dual nanoreporter comprising two different molecular entities, each with a separate target-specific region, at least one of which is labeled, bind to the same target molecule. Thus, the target-specific sequences of the two components of the dual nanoreporter bind to different portions of a selected target molecule, whereby detection of the spectral code associated with the dual nanoreporter provides detection of the selected target molecule in a biomolecular sample contacted with said dual nanoreporter.

The invention also provides a method of detecting the presence of a specific target molecule in a biomolecular sample comprising: (i) contacting said sample with a dual nanoreporter under conditions that allow binding of the target-specific sequences in the dual nanoreporter to the target molecule and (ii) detecting the spectral code associated with the dual nanoreporter. Depending on the nanoreporter architecture, the dual nanoreporter may be labeled before or after binding to the target molecule.

In certain embodiments, the methods of detection are performed in multiplex assays, whereby a plurality of target molecules are detected in the same assay (a single reaction mixture). In a preferred embodiment, the assay is a hybridization assay in which the plurality of target molecules are detected simultaneously. In certain embodiments, the plurality of target molecules detected in the same assay is at least 5 different target molecules, at least 10 different target molecules, at least 20 different target molecules, at least 50 different target molecules, at least 75 different target molecules, at least 100 different target molecules, at least 200 different target molecules, at least 500 different target molecules, or at least 750 different target molecules, or at least 1000 different target molecules. In other embodiments, the plurality of target molecules detected in the same assay is up to 50 different target molecules, up to 100 different target molecules, up to 150 different target molecules, up to 200 different target molecules, up to 300 different target molecules, up to 500 different target molecules, up to 750 different target molecules, up to 1000 different target molecules, up to 2000 different target molecules, or up to 5000 different target molecules. In yet other embodiments, the plurality of target molecules detected is any range in between the foregoing numbers of different target molecules, such as, but not limited to, from 20 to 50 different target molecules, from 50 to 200 different target molecules, from 100 to 1000 different target molecules, from 500 to 5000 different target molecules, and so on and so forth.

In certain embodiments, the invention is directed to detecting different splice forms of the same RNA. The different splice forms can be detected using a plurality of nanoreporter probes, each with a different target-specific sequence complementary to a different exon of the same gene.

Structural stability of a nanoreporter can be increased through ligation of the patches and, optionally, ligation of the split flaps and/or the labeled oligonucleotides hybridized to the split flaps.

In addition to the qualitative analytical capabilities provided by the nanoreporters of the invention and the analytical techniques based thereon, the nanoreporters of the invention are uniquely suitable for conducting quantitative analyses. By providing a one to one binding between the nanoreporters (whether singular or dual nanoreporters) of the invention and their target molecules in a biomolecular sample, all or a representative portion of the target molecules present in the sample can be identified and counted. This individual counting of the various molecular species provides an accurate and direct method for determining the absolute or relative concentration of the target molecule in the biomolecular sample. Moreover, the ability to address each molecule in a mixture individually leverages benefits of miniaturization including high sensitivity, minimal sample quantity requirements, high reaction rates which are afforded by solution phase kinetics in a small volume, and ultimately very low reagent costs.

As will be appreciated from the description and examples provided below, the present invention provides numerous advantages. For example, the complex modularity in forming nanoreporters according to the invention allows for systematic creation of libraries of unique nanoreporters having a very high degree of diversity (e.g., millions of uniquely recognizable nanoreporters). This modularity allows flexibility in customizing nanoreporter populations to specific applications which in turn provides significant manufacturing efficiencies. Another advantage that will be appreciated through the following description stems from the flexibility in assembling the nanoreporters of the invention. That is, due to their modular structure, the nanoreporters of the invention can be assembled prior to shipment to a point of use or assembled at the point of use.

Nanoreporter Nomenclature

NANOREPORTER: The term "nanoreporter" refers to a molecular entity that has (i) a molecule ("scaffold") containing at least two label attachment regions; (ii) at least one patch attached to at least one label attachment region; and (iii) a target-specific sequence. As described in detail below, nanoreporters can be singular nanoreporters (all components being in a single molecular entity) or dual nanoreporters (all the components being in two separate molecular entities). Nanoreporters are preferably synthetic, i.e., non-naturally-occurring molecules, for example are chimeric molecules made by joining two or more manmade and/or naturally occurring sequences that normally exist on more than one molecule (e.g., plasmid, chromosome, viral genome, protein, etc.).

LABELED NANOREPORTER: A labeled nanoreporter is a nanoreporter in which at least one patch of the nanoreporter is attached to one or more label monomers that generate(s) a signal that forms at least part of the nanoreporter code.

LABEL UNIT: The term "label unit" refers to the non-target-specific portions of a labeled nanoreporter.

PROBE: This refers to a molecule that has a target-specific sequence. In the context of a singular nanoreporter, the term "probe" refers to the nanoreporter itself; in the context of a dual nanoreporter, the term "probe" refers to one or both of the two components of the nanoreporter.

PROBE PAIR: This refers to a dual nanoreporter.

PATCH: The term "patch" refers to a molecular entity attached to the label attachment region of the nanoreporter scaffold, generally for the purpose of labeling the nanoreporter. The patch can have one or more label monomers either directly (covalently or noncovalently) or indirectly attached to it, either prior to or after its attachment to the scaffold.

FLAP: The term "flap" as used herein refers to a molecular entity attached to a patch or patch pair attached to a label attachment region. The flap is one or more molecule containing label monomers or capable of binding one or more molecules containing label monomers. By providing indirect labeling of the regions, the flaps provide more flexibility in controlling the number of signal emitting monomers associated with a region as well as the nature of those monomers. Flaps may be formed by a single molecular piece or several molecular pieces (e.g., two pieces) forming a "split flap" (see, e.g., FIG. 7)

TARGET-SPECIFIC SEQUENCE: The term "target-specific sequence" refers to a molecular entity that is capable of binding a target molecule. In the context of a nanoreporter, the target-specific sequence is attached to the nanoreporter scaffold. The target molecule is preferably (but not necessarily) a naturally occurring molecule or a cDNA of a naturally occurring molecule or the complement of said cDNA.

GHOST PROBE: A molecule comprising a target-specific sequence, but which is not labeled with a label monomer that emits a signal that contributes to the nanoreporter code.

REPORTER PROBE: A molecule comprising a target-specific sequence that is labeled with at least one label monomer that emits a signal that contributes to the nanoreporter code. A singular nanoreporter is a reporter probe, as is a labeled component of a dual nanoreporter.

F-HOOK and G-HOOK: In the context of a dual nanoreporter, F- and G-hooks are each an affinity tag that is capable of being selectively bound to one of the probes. In preferred embodiments, the F-hook and G-hook are biotinylated oligonucleotides that are hybridizable to respective complementary sequences present in (e.g., via ligation) or attached to (e.g., via hybridization) the respective nanoreporter probes in a dual nanoreporter. Thus, the F-hooks and G-hooks can be used for purification, immobilization and stretching of the nanoreporter. Generally, where a dual nanoreporter contains one reporter probe and one ghost probe, the G-hook becomes attached to the reporter probe and the F-hook becomes attached to the ghost probe. F-hooks and G-hooks can be biotinylated on either end or internally. They can also be amine-modified to allow for attachment to a solid substrate for affinity purification.

F-TAG and G-TAG: Tandemly-repeated sequences of about 10 to about 25 nucleotides that are complementary to the F-hook and G-hook, respectively. G-tags and F-tags are attached to the nanoreporter probes. Generally, an F-tag is present in or attached to a ghost probe via a ligator sequence and a G-tag is present in or attached the reporter probe scaffold via a ligator sequence.

SPOT: A spot, in the context of nanoreporter detection, is the aggregate signal detected from the label monomers attached to a single label attachment site on a nanoreporter, and which, depending on the size of the label attachment region and the nature (e.g., primary emission wavelength) of the label monomer, may appear as a single point source of light when visualized under a microscope. Spots from a nanoreporter may be overlapping or non-overlapping. The nanoreporter code that identifies that target molecule can comprise any permutation of the length of a spot, its position relative to other spots, and/or the nature (e.g., primary emission wavelength(s)) of its signal. Generally, for each probe or probe pair of the invention, adjacent label attachment regions are non-overlapping, and/or the spots from adjacent label attachment regions are spatially and/or spectrally distinguishable, at least under the detection conditions (e.g., when the nanoreporter is immobilized, stretched and observed under a microscope, as described herein).

Occasionally, reference is made to a spot "size" as a certain number of bases or nucleotides. As would be readily understood by one of skill in the art, this refers to the number of bases or nucleotides in the corresponding label attachment region.

NANOREPORTER CODE: The order and nature (e.g., primary emission wavelength(s), optionally also length) of spots from a nanoreporter serve as a nanoreporter code that identifies the target molecule capable of being bound by the nanoreporter through the nanoreporter's target specific sequence(s). When the nanoreporter is bound to a target molecule, the nanoreporter code also identifies the target molecule. Optionally, the length of a spot can be a component of the nanoreporter code.

DARK SPOT: The term "dark spot" refers to a lack of signal, or "spot," from a label attachment site on a nanoreporter. Dark spots can be incorporated into the nanoreporter code to add more coding permutations and generate greater nanoreporter diversity in a nanoreporter population.

REGISTER: The term "register" refers to a set of alternating label attachment regions.

The Nanoreporter Scaffold

The nanoreporter scaffold can be any molecular entity, more preferably a nucleic acid molecule, containing label attachment regions to which label monomers can be directly or indirectly attached. In one embodiment, the nanoreporter scaffold is a protein scaffold; in a preferred embodiment, the nanoreporter scaffold is a nucleic acid scaffold in which the label attachment regions are single-stranded regions to which other nucleic acids, such as oligonucleotide patches, RNA patches, or DNA patches, can attach by hybridization. In specific embodiments, the nanoreporter scaffold is a nucleic acid molecule.

There are no particular limitations on the types of scaffolds that are suitable for forming the nanoreporters of the invention. A scaffold according to the invention can essentially have any structure including, for example, single stranded linear scaffold, double stranded linear scaffold, single stranded circular scaffold or double stranded circular scaffold. Examples of scaffold structures include, for example, a scaffold made of one molecular entity such as polypeptides, nucleic acids or carbohydrates. A scaffold may also include a combination of structures, for example, a scaffold may be made of one or more polypeptide stretches coupled to one or more carbohydrate stretches.

Suitable molecular entities for scaffolds according to the invention include polymeric structures particularly nucleic acid based polymeric structures such as DNA. DNA based structures offer numerous advantages in the context of the present invention due at least in part to the vast universe of existing techniques and methodologies that allow manipulation of DNA constructs.

As indicated above, the scaffold may be single stranded or double stranded.

Double stranded scaffold can be either conventional double stranded DNA or a double strand that is composed of a linear single stranded stretch of nucleic acid with patch units or flat-patches attached.

A scaffold can have 1, 2, 3, 4, 5, 6, 7, 8, 9, 10, 11, 12, 13, 14, 15, 16, 17, 18, 19, 20, 21-100 label attachment regions or more.

The label attachment regions of a nanoreporter scaffold will vary in size depending on the method of labeling. In various embodiments, a label attachment region can have a length anywhere from 10 nm to 10,000 nm, but is more preferably from 50 nm to 5,000 nm, and is more preferably from 100 nm to 1,000 nm. In various embodiments, the label attachment region is from about 100 nm to about 500 nm, from about 150 nm to about 450 nm, from about 200 nm to about 400 nm, or from 250 to about 350 nm. In a preferred embodiment, the label attachment region corresponds closely to the size of a diffraction-limited spot, i.e., the smallest spot that can be detected with standard optics, which is about 300 nm.

Where the scaffold is a nucleic acid, 1 nm corresponds to approximately 3 nucleotides; thus, an approximately 300 nm-label attachment region corresponds to approximately 900 bases. In other preferred embodiments, the label attachment region is from about 300 nucleotides to about 1.5 kb, from about 450 nucleotides to about 1.35 kb, from about 0.6 kb to about 1.2 kb, or from 0.75 kb to about 1.05 kb.

An illustrative example of a molecular entity for a nanoreporter scaffold according to the invention is M13 DNA, which is single-stranded. In one embodiment, the nanoreporter scaffold is circular at least partially single stranded DNA, such as circular M13. In a more preferred embodiment, the nanoreporter scaffold is linear at least partially single stranded DNA, such as linear M13. In a specific embodiment, the M13 single-stranded DNA obtained by operating a cut at the BamH1 site of circular M13 DNA.

It should be noted that within the context of the present invention, linear DNA provides additional advantages compared to circular DNA. One advantage of using linear DNA in forming a scaffold according to the invention relates to the significantly reduced torsional stress associated with linear DNA. The added torsional stress associated with circular DNA may interfere with the structural integrity of the scaffold upon the addition to the scaffold of other components of the nanoreporter, such as patch units. Severe torsional stress may lead to the breaking of the structure of the scaffold. It should be noted however that the nanoreporters where only a few, short label attachment sites are labeled, circular DNA may be suitable.

Novel Synthetic Nanoreporter Scaffold Sequences

The present invention provides nanoreporter scaffold that are artificial nucleic acid molecules (DNA, RNA, or DNA/RNA hybrids) designed to have features that optimize labeling and detection of the nanoreporter. In these aspects of the invention, a nanoreporter scaffold is an artificial nucleic acids comprising one or more synthetic sequences from 50 to 50,000 bases long. Accordingly, the nanoreporter scaffold, which is preferably a DNA, is designed to have one or more Regions, useful as label attachment regions, comprising a regular pattern of a particular base (the "regularly-repeated base"). In such regions, the regularly-repeated base occurs with a periodicity of every nth residue, where n is any number, and preferably from 4 to 25.

Preferably, not more than 25% of the regularly-repeated base in a Region appears at other than said regular intervals. For example, if in a Region of 100 nucleotides there are 12 thymidine bases, and thymidine is the regularly-repeated base, in this aspect of the invention not more than 25% of these, i.e., 3 thymidine bases, appear outside the regular pattern of thymidines. In specific embodiments, not more than 20%, not more than 15%, not more than 10%, not more than 9%, not more than 8%, not more than 7%, not more than 6%, not more than 5%, not more than 4%, not more than 3%, not more than 2% or not more than 1% of said base appears at other than said regular intervals in said region.

The regularly-repeated base in the Regions in a nanoreporter scaffold, or its complementary regularly-repeated base in an annealed patch (or segment) can be used to attach label monomers, preferably light emitting label monomers, to the nanoreporter in a regular, evenly spaced pattern for better distribution of the nanoreporter signal. Preferably, where a Region is labeled, at least 50%, at least 60%, at least 70%, at least 80%, at least 90%, at least 95% or at least 98% of occurrences of the regularly-repeated base is attached to at least one light-emitting label monomer, either by covalent attachment of a label monomer to a base, or by hybridization to a nucleic acid in which the complements of the regularly-repeated base are so-labeled.

This percentage of occurrences can be measured by any means known in the art. In one method, the amount of nucleic acid produced in a labeling reaction is purified (for example, RNA can be purified using a Qiagen RNeasy kit) and subjected to UV spectrophotometry. The absorbance ("A") at the appropriate wavelengths is measured for each of the nucleic acid (260 nm) and the label monomer whose occurrence is to be measured (e.g., 495 nm for ALEXA Fluor™ 488; 590 nm for ALEXA Fluor™ 594; 650 for ALEXA Fluor™ 647; and 550 nm for Cy3). The absorbance of the nucleic acid is corrected by adjusting the value of the absorbance at 260 nm ("A260") to remove the "noise" contribution from the label monomer by subtracting the absorbance at the peak wavelength for the label monomer ($A_{LM}$) minus the correction factor for that label monomer. Where the nucleic acid is RNA, the number of label monomers per one thousand nucleotides is calculated according to the formula:

$$\frac{\text{no. of label monomers}}{1000 \text{ nucleotides}} = \frac{A260}{A_{LM}} \times \frac{9010}{EC_{LM}} \times 1000$$

where $EC_{LM}$ is the extinction coefficient for the label monomer. From this formula, the percentage of occurrences of the regularly-repeated base that are attached to a light-emitting label monomer can be calculated.

Generally, the preferred regularly-repeating base in a label attachment region is thymidine, so that the region can be labeled by hybridization to one or more complementary patches (e.g., RNA segments) in which the regularly-repeated base is uridine. This permits the use of amino-allyl-modified UTPs, which are readily commercially available, as label monomer attachment sites, in an otherwise random sequence. Preferably, in addition to the regular periodicity of the Regions, the regions (and the nucleic acid comprising them) contain minimal secondary structure. The overall GC-content is preferably maintained close to 50%, and is preferably consistent over relatively short stretches to make local Tm's similar.

The artificial nucleic acids of the invention, or at least the Regions therein, preferably do not have direct or inverted repeats that are greater than 12 bases in length. In other embodiments, the artificial nucleic acids and/or Regions do not have direct or inverted repeats that are greater than about 11, about 10 or about 9 bases in length.

In an exemplary Region in which the regularly-repeated nucleotide is a thymidine and a GC content of approximately 50%, excess adenines would make up the loss in abundance of T's. To generate the selected sequence, random sequences with fixed patterns of T's ranging from every 4th base to every 25th base are created and screened to minimize the presence of inverted and direct repeats.

Sequences are also screened preferably to avoid common six-base-cutter restriction enzyme recognition sites. Selected sequences are additionally subjected to predicted secondary structure analysis, and those with the least secondary structure are chosen for further evaluation. Any program known in the art can be used to predict secondary structure, such as the MFOLD program (Zuker, 2003, Nucleic Acids Res. 31 (13): 3406-15; Mathews et al., 1999, J. Mol. Biol. 288:911-940).

An appropriate sequence is divided into label attachment regions ranging from 50 bases to 2 kilobases long (could be longer). Each label attachment region is a unique sequence, but contains a consistent number and spacing of T's in relation to the other label attachment regions in a given reporter sequence. These label attachment regions can interspersed with other regions whose sequence does not matter. The synthetic label attachment regions in a nanoreporter scaffold can be of different lengths and/or have different regularly-repeated bases. An optimized start sequence for transcription by RNA polymerase T7, T3, or SP6 (beginning at position +1 of the transcript) can be added to the 5' end of each label attachment region. Restriction sites are optionally added at the boundaries of each label attachment region to allow specific addition or deletion of individual label attachment regions to the sequence using conventional cloning techniques. The number of synthetic label attachment regions in a nanoreporter preferably ranges from 1 to 50. In yet other embodiments, the number of synthetic label attachment regions in a nanoreporter ranges from 1, 2, 3, 4, 5, 6, 7, 8, 9, or 10 synthetic label attachment regions to 15, 20, 30, 40, or 50 synthetic label attachment regions, or any range in between.

An example of such a novel synthetic label attachment region is given below. In this sequence, shown 5' to 3', the T's are placed in every 8th position and the region is bounded by a 5' Sac I restriction site and a 3' Kpn I restriction site. An optimized transcript start site for T7 polymerase (GGGAGA) is included at the 5' end of the region, downstream of the 5' restriction site. The complement of this sequence, when generated as a single-stranded molecule, forms the scaffold for the RNA molecule transcribed from this label attachment region.

(SEQ ID NO: 1)
GAGCTCGGGAGATGGCGAGCTGGAAGCATCAGAAAGTAGGAAGATGACAA

AATAGGGCCATAGAAGCATGAAGAACTGAACGCATGAGACAATAGGAAGC

TACGCCACTAGGGACCTGAGAAGCTGAGCGGCTCAGCGGGTCCGAGCGTC

AAAAAATAAAGAGTGAAACAATAGACGAATGACGCGGTAAAACCATCCA

GAAGTAAACGGGTACAAACATACAGAGATAGCCACCTGGACCAATAGGCA

-continued

CGTACAAACGTACAAGCCTGGCGCGATGAGGCAATCCACACGTGCAGAGC

TGGAACAATGGAAAGATGCAAGAATAAACCGATACCGGGATCGAGGGCTC

AGCGAATAAAGCAGTCAACAACTGGAAAGATCCACACATACCGGCGTAAC

CGAGTCCAAACATACAGACCTGCAAGACTCGCGACATGGGACGGTAAAAC

CATCCGACCGTAAACCGGTAACCAGGTAGCCGGGTAAAAACATAGCAGGG

TGGAGACCTCAGAACGTAAAGACGTCCAAGGGTCGCCGGATAGCGAACTA

CGCGCATCGCCCAATGGGCCAATCAACAGATAAACGAGTAGAAAAGTCAG

AAAATAAGAAACTAACGAAATACGAGGGTCCAAGGATGCAAGACTGAGGC

CCTAAGGAGATAAGGAAATAGGCCGATGCAGACCTGAAACGATGCACCGA

TCCGACGGTAAAACACTAGACACGTAGCCGGATCAGGGCCTGGGAGGCTG

GAACCGTGAGCACATAGCAAAGTCGCAGCGTCGGCAGATGCGCCGGTAAA

AAAGTAGAGGCATGACCGGATGGGCAAATAGCGACGTACAGCAGTGAAGC

ACTAAAAGCATCCAAGGGTAGGAGACTAGGCGCCTCGACGGGTAGGTACC

The synthetic nucleic acids of the present invention can be chemically synthesized using naturally occurring nucleotides or variously modified nucleotides designed to increase the biological stability of the molecules or to increase the physical stability of the duplex formed between the label attachment region and the annealed patches or segments, e.g., phosphorothioate derivatives and acridine substituted nucleotides can be used. Examples of modified nucleotides which can be used to generate the synthetic nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)$_w$, and 2,6-diaminopurine.

Alternatively, the synthetic nucleic acid can be produced biologically using a vector into which a nucleic acid has been subcloned.

In various embodiments, the synthetic nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, Bioorganic & Medicinal Chemistry 4(1): 5-23; Perry-O'Keefe et al., 1996, Proc. Natl. Acad. Sci. USA 93: 14670-675.

In an exemplary embodiment, the selected novel synthetic sequence can be constructed synthetically as double-stranded DNA by a commercial gene synthesis company and cloned in an oriented fashion into a "phagemid", a plasmid vector containing an M13 or f1 phage intergenic (IG) region which contains the cis-acting sequences necessary for DNA replication and phage encapsidation, such as pUC119. The appropriate orientation of the cloned insert relative to the phage origin of replication allows for the generation of a single-stranded DNA scaffold which is the reverse complement of the RNA molecules generated by in vitro transcription for each label attachment region.

In order to generate the single-stranded DNA scaffold of the novel reporter, the phagemid is transformed into an *E. coli* strain containing an F' episome. Subsequent infection of the transformed bacteria with a helper phage such as the M13 mutant K07 results in the secretion of the phagemid carrying the novel reporter sequence as a single-stranded, packaged phage from which the circular, single-stranded DNA is prepared using a standard protocol. This DNA is linearized and the vector portion is excised by annealing short, complementary oligonucleotides to either end of the novel reporter sequence to generate double-stranded restriction sites, followed by treatment with the appropriate restriction enzymes.

To make the RNA molecules (patches or "segments") for each label attachment region, polymerase chain reaction ("PCR") primers are designed to generate a double-stranded template beginning with an RNA polymerase promoter (T7, T3, or SP6) directly upstream (5') of the transcription start site and ending following the 3' restriction enzyme site. Using this template, in vitro transcription of RNA molecules is performed in the presence of amino-allyl modified regularly-repeated base in the RNA (e.g., UTP) and unmodified other bases (e.g., ATP, CTP and GTP). This leads to an RNA product in which every regularly-repeated base (e.g., U) is modified to allow covalent coupling of a label monomer at that position in the RNA molecule.

Coupling of light-emitting label monomers to the RNA molecules and annealing of the labeled RNA molecules to the scaffold are carried out as described below.

Some design considerations for the de novo sequence are listed in Table 1 below.

| Feature Of Synthetic Scaffold | Advantages |
|---|---|
| Novel synthetic sequence | Can be of any length and be designed to incorporate any desired sequence feature including but not limited to those listed in this table. |
| Minimal secondary structure (select against inverted repeats) | Allows for consistent transcription of full-length RNA molecules. Allows for consistent annealing of RNA molecules to scaffold at predictable temperatures. Minimizes self-annealing and/or cross-annealing between RNA molecules or scaffolds. |
| Minimal repeated sequences | Avoids mis-annealing between RNA molecules and inappropriate regions of the scaffold. |
| Unique restriction sites at borders of label attachment regions | Allows addition and deletion of individual label attachment regions using standard molecular cloning techniques. |
| Defined, even spacing of T's and transcription with amino-allyl-modified UTP (no unmodified UTP) | Controls number of coupling sites for monomers in each label attachment region, allowing for consistent brightness of individual labeled RNA molecules. Controls distance between monomers: spacing can be optimized to avoid stearic hindrance and fluorescence quenching. |
| Optimized start sequence for transcription by RNA polymerase T7, T3, or SP6 | Promotes efficient in vitro transcription of each label attachment region. |

Patches

Label monomers that emit signals which constitute all or part of the nanoreporter code are attached to label attachment region(s) of the nanoreporter scaffold through a structure referred to herein as a "patch." The label monomers can be directly (e.g., covalently or noncovalently) attached to a patch, or indirectly attached to a patch (e.g., through hybridization).

Nucleic acid patches can by anywhere from 25 nucleotides to several kilobases (e.g., 5 kb) in length, and are preferably 50 nucleotides to 2 kb in length. In specific embodiments, nucleic acid patches are approximately 25 to 250, 50 to 200, 50 to 150, or 50 to 100 nucleotides in length. In other embodiments, nucleic acid patches are approximately 500 to 2,000, 500 to 1,500, 500 to 1,000, 750 to 1,250, or 750 to 1,000 nucleotides in length. Nucleic acid patches can be RNA patches or DNA patches.

A label monomer can be covalently attached to a patch before or after the patch is attached to the label attachment region of a nanoreporter scaffold. For example, where the patch is a nucleic acid molecule, the label can be covalently attached by incorporation of a nucleotide containing a label monomer into the nucleic acid during its synthesis but before it is attached, e.g., via hybridization, to the label attachment region of the scaffold. Alternatively, during the synthesis of a nucleic acid patch, a nucleotide containing a label monomer acceptor group can be included, and the label monomer added to the nucleic acid patch after its synthesis, either before or after it is attached to the label attachment region of the scaffold. Alternatively, the label monomer can be indirectly attached to the patch, for example by hybridization of the patch to a "flap" that serves as a basis for attachment of the label monomer to the nanoreporter.

Thus, where a patch is a nucleic acid, it can range anywhere from 20 nucleotides to more than 5 kb in length, depending on the method of assembly of the nanoreporter.

For example, where a patch has covalently incorporated into it one or more label monomers that emit signals that are part of the nanoreporter code in the context of the labeled nanoreporter, the patch is preferably about 100 to about 10,000 bases, more preferably 200 to about 2000 bases, and yet more preferably 700 to about 1200 nucleotides in length, and is generally referred to herein as a "segment," a "dark segment" being the patch prior to the incorporation of the label monomer (but, in a preferred embodiment, containing label monomer acceptor sites, such as amino allyl nucleotides), and a "colored" segment being one containing the desired label monomer or label monomers. The Tm of a segment when hybridized to its label attachment region preferably is >80° C., more preferably >90° C., in 825 mM Na$^+$ (5×SSC).

Where a patch merely serves as a template for flap attachment to the nanoreporter, then it is preferably smaller in size, for example about 25-250 nucleotides in length, and is most preferably about 50-100 nucleotides in length. Such patches are referred to herein as "oligonucleotide patches." As detailed in Section below, an oligonucleotide is preferably partially complimentary in sequence to a scaffold, such that when it is annealed to the scaffold, an overhang is generated that is complementary to all or a portion of a flap.

The terms "segment" and "oligonucleotide patch" are used herein merely for convenience of description; however, there is no size cutoff to distinguish a "segment" from an "oligonucleotide patch." The purpose of both types of structures is to maximize the labeling—and thus signal intensity—from the nanoreporter, thereby allowing for single target molecule detection by a nanoreporter.

In certain aspects, the present invention provides a synthetic molecule, whose configuration is illustrated by reference to FIG. 7A, comprising a strand of a nucleic acid (scaffold) and a plurality of patch pairs hybridized to said strand, wherein each patch pair comprises an "A" patch and a "B" patch, wherein, for each patch pair, (a) each "A" patch is an oligonucleotide comprising a first region (1P) and a second region (2P), said first region being (i) at the alpha end of said "A" patch, and (ii) hybridized to a first portion of said strand, said second region being (ii) at the beta end of said "A" patch; (b) each "B" patch is an oligonucleotide comprising a third region (3P) and a fourth region (4P), said third region being (i) at the alpha end of said "B" patch, and (ii) hybridized to said second region of said "A" patch, said fourth region being (i) at the beta end of said "B" patch and (ii) hybridized to a second portion of said strand, said second portion of said strand being to the beta end of said first portion of said strand, wherein said second region or said third region further comprises at its beta end or alpha end, respectively, a hybridizable region that is not hybridized to said "B" patch or "A" patch, respectively.

In the synthetic molecule of FIG. 7A, the second region may further comprise at its beta end a hybridizable region that is not hybridized to said "B" patch, as depicted in FIG. 7B, or the third region further comprises at its alpha end a hybridizable region that is not hybridized to said "A" patch, as depicted in FIG. 7C.

The present invention further provides a synthetic molecule, whose configuration is illustrated by reference to FIG. 7D, comprising a strand of a nucleic acid (scaffold) and a plurality of patch pairs hybridized to said strand, wherein each patch pair comprises an "A" patch and a "B" patch, wherein, for each patch pair, (a) each "A" patch is an oligonucleotide comprising a first region (1P) and a second region (2P), said first region being (i) at the alpha end of said "A" patch, and (ii) hybridized to a first portion of said strand, said second region being (ii) at the beta end of said "A" patch; (b) each "B" patch is an oligonucleotide comprising a third region (3P) and a fourth region (4P), said third region being (i) at the alpha end of said "B" patch, and (ii) hybridized to said second region of said "A" patch, said fourth region being (i) at the beta end of said "B" patch and (ii) hybridized to a second portion of said strand, said second portion of said strand being to the first of said first portion of said strand, wherein said second region further comprises at its beta end a first hybridizable region that is not hybridized to said "B" patch, and wherein said third region further comprises at its alpha end a second hybridizable region that is not hybridized to said "A" patch.

In the synthetic molecule of FIG. 7B, each patch pair can be attached to a flap pair, as depicted in FIG. 7F, wherein each flap pair comprises an "A" flap and a "B" flap, wherein, for each flap pair, (a) each "A" flap is an oligonucleotide comprising a first flap region (1F) and a second flap region (2F); said first flap region being at the alpha end of said "A" flap; said second flap region (i) being at the beta end of said "A" flap and (ii) comprising at its beta end a hybridizable region that is not hybridized to said "A" patch, "B" patch or "B" flap; and (b) each "B" flap is an oligonucleotide comprising a third flap region (3F), a fourth flap region (4F), and a fifth flap region (5F); said third flap region (i) being at the alpha end of said "B" flap and (ii) comprising at its alpha end a hybridizable region that is not hybridized to said "A" patch, "B" patch or "A" flap; said fourth flap region (i) being between the third flap region and the fifth flap region and (ii) hybridized to said first flap region of said "A" flap; said fifth flap region being (i) at the beta end of said "B" flap, and (ii) hybridized to said hybridizable region of said second region of said "A" patch.

In the synthetic molecule of FIG. 7C, each patch pair can be attached to a flap pair, as depicted in FIG. 7E, wherein each flap pair comprises an "A" flap and a "B" flap, wherein, for each flap pair, (a) each "A" flap is an oligonucleotide comprising a first flap region (1F), a second flap region (2F), and a third flap region (3F); said "A" flap region being (i) at the alpha end of said "A" flap and (ii) hybridized to said hybridizable region of said third region of said "B" patch; said second flap region being between the first flap region and the third flap region; said third flap region (i) being at the beta end of said "A" flap and (ii) comprising at its beta end a hybridizable region that is not hybridized to said "A" patch, "B" patch or "B" flap, and (b) each "B" flap is an oligonucleotide comprising a fourth flap region (4F) and a fifth flap region (5F); said fourth flap region being (i) being at the alpha end of said "B" flap and (ii) comprising at its alpha end a hybridizable region that is not hybridized to said "A" patch, "B" patch or "A" flap; said fifth flap region being (i) at the beta end of said "B" flap, and (ii) hybridized to said second flap region of said "A" flap.

In the synthetic molecule of FIGS. 7D and 7E, the split flaps can be attached one (e.g., (1O)), or more (e.g., (2O) and (3O)) oligonucleotides, as depicted in FIG. 7G. Thus, the one or more oligonucleotides can be attached to the all or a portion of the "A" flap individually (e.g., (1O)), the "B" flap individually (e.g., (3O)), or span all or a portion of each of the "A" flap and "B" flap (e.g., (2O)). Such oligonucleotides are preferably covalently bound to one or more label monomers.

The hybridizable regions of said synthetic molecules may be hybridized to a plurality of oligonucleotides, each bound, preferably covalently bound, to at least one label monomer, more preferably to at least five label monomers. In certain embodiments, all the oligonucleotides attached to a single patch pair comprise the same label monomers, e.g., comprise label monomers that emit light at the same wavelength(s); in specific embodiments, all the oligonucleotides attached to at least two, or at least four, adjacent patch pairs preferably comprise the same label monomers. One or more of the oligonucleotides may be bound to at least one affinity tag.

In certain preferred embodiments, the label monomers are fluorophores or quantum dots.

In the synthetic molecule described above, alpha can refers to either 5' or 3', and the corresponding beta to either 3' or 5', respectively.

The region of complementary in each patch pair, or between a given patch and corresponding flap, is preferably about 20 to 5,000 nucleotides. In certain embodiments, the region of complementary is about 20 to 100 nucleotides, or about 5 to 50 nucleotides.

In the synthetic molecules described above, each flap is preferably about 50 to 5,000 nucleotides in length. In certain embodiments, each flap is about 50 to 150 nucleotides.

The synthetic molecules described above may further comprise a target-specific region which binds to a target molecule. The target-specific region can be attached to the beta or alpha end of said strand.

In certain embodiments, the synthetic molecule described above may comprise at least ten patch pairs, or at least fifty patch pairs.

In the synthetic molecules described above, the strand, or scaffold, can be a linearized vector, such as linearized M13.

The synthetic molecule described above may further comprise (a) a first label attachment region to which are attached (directly or indirectly) one or more label monomers that emit light constituting a first signal; (b) a second label attachment region, which is non-overlapping with the first label attachment region, to which is attached one or more label monomers that emit light constituting a second signal; (c) a third label attachment region, which is non-overlapping with the first and second label attachment regions, to which is attached one or more label monomers that emit light constituting a third signal; wherein each attachment region comprises a plurality of patch pairs; wherein the first and second signals are spectrally distinguishable; wherein the second and third signals are spectrally distinguishable; wherein the first and second signals are not spatially resolvable under conditions that can be used to detect said first, second and third signals; wherein the second and third signals are not spatially resolvable under conditions that can be used to detect said first, second and third signals; wherein the first and third signals are spatially resolvable under conditions that can be used to detect said first, second and third signals; and wherein the identities of the first, second and third signals and the locations of the first and third signal relative to each other constitute at least part of a code that identifies the target molecule.

Label Monomers

The nanoreporters of the present invention can be labeled with any of a variety of label monomers, such as a radioisotope, fluorochrome, dye, enzyme, nanoparticle, chemiluminescent marker, biotin, or other monomer known in the art that can be detected directly (e.g., by light emission) or indirectly (e.g., by binding of a fluorescently-labeled antibody). Generally, one or more of the label attachment regions in the nanoreporter is labeled with one or more label monomers, and the signals emitted by the label monomers attached to the label attachment regions of a nanoreporter constitute a code that identifies the target to which the target-specific region of the nanoreporter binds. In certain embodiments, the lack of a given signal from the label attachment region (i.e., a "dark" spot) can also constitute part of the nanoreporter code. An example of a dark spot is depicted at position 12 of the nanoreporter in FIG. 1A.

Radioisotopes are an example of label monomers that can be utilized by the invention. Several radioisotopes can be used as label monomers for labeling nucleotides or proteins, including, for example, $^{32}P$, $^{33}P$, $^{35}S$, $^{3}H$, and $^{125}I$. These radioisotopes have different half-lives, types of decay, and levels of energy which can be tailored to match the needs of a particular experiment. For example, $^{3}H$ is a low energy emitter which results in low background levels, however this low energy also results in long time periods for autoradiography. Radioactively labeled ribonucleotides, deoxyribonucleotides and amino acids are commercially available. Nucleotides are available that are radioactively labeled at the first, or $\alpha$, phosphate group, or the third, or $\gamma$, phosphate group. For example, both [$\alpha$-$^{32}P$] dATP and [$\gamma$-$^{32}P$] dATP are commercially available. In addition, different specific activities for radioactively labeled nucleotides are also available commercially and can be tailored for different experiments.

Another example of label monomers that can be utilized by the invention are fluorophores. Several fluorophores can be used as label monomers for labeling nucleotides including, for example, fluorescein, tetramethylrhodamine, and Texas Red. Several different fluorophores are known, and more continue to be produced, that span the entire spectrum. Also, different formulations of the same fluorophore have been produced for different applications. For example, fluorescein, can be used in its isothiocynanate form (FITC), as mixed isomer or single isomer forms of carboxyfluorescein succinimidyl ester (FAM), or as isomeric dichlorotriazine forms of fluorescein (DTAF). These monomers are chemically distinct, but all emit light with a peak between 515-520 nm, thereby generating a similar signal. In addition to the chemical modifications of fluorescein, completely different fluorophores have been synthesized that have the same or very similar emission peaks as fluorescein. For example, the Oregon Green dye has virtually superimposable excitation and emission spectra compared to fluorescein. Other fluorophores such as Rhodol Green and Rhodamine Green are only slightly shifted in their emission peaks and so also serve functionally as substitutes for fluorescein. In addition, different formulations or related dyes have been developed around other fluorophores that emit light in other parts of the spectrum.

Non-radioactive and non-fluorescent label monomers are also available. For example, biotin can be attached directly to nucleotides and detected by specific and high affinity binding to avidin or streptavidin which has been chemically coupled to an enzyme catalyzing a colorimetric reaction (such as phosphatase, luciferase, or peroxidase). Digoxigenin labeled nucleotides can also similarly be used for non-isotopic detection of nucleic acids. Biotinylated and digoxigenin-labeled nucleotides are commercially available.

Very small particles, termed nanoparticles, also can be used as label monomers to label nucleic acids. These particles range from 1-1000 nm in size and include diverse chemical structures such as gold and silver particles and quantum dots.

When irradiated with angled incident white light, silver or gold nanoparticles ranging from 40-120 nm will scatter monochromatic light with high intensity. The wavelength of the scattered light is dependent on the size of the particle. Four to five different particles in close proximity will each scatter monochromatic light which when superimposed will give a specific, unique color. The particles are being manufactured by companies such as Genicon Sciences. Derivatized silver or gold particles can be attached to a broad array of molecules including, proteins, antibodies, small molecules, receptor ligands, and nucleic acids. For example, the surface of the particle can be chemically derivatized to allow attachment to a nucleotide.

Another type of nanoparticle that can be used as a label monomer are quantum dots. Quantum dots are fluorescing crystals 1-5 nm in diameter that are excitable by a large range of wavelengths of light. These crystals emit light, such as monochromatic light, with a wavelength dependent on their chemical composition and size. Quantum dots such as CdSe, ZnSe, InP, or InAs possess unique optical properties.

Many dozens of classes of particles can be created according to the number of size classes of the quantum dot crystals. The size classes of the crystals are created either 1) by tight control of crystal formation parameters to create each desired size class of particle, or 2) by creation of batches of crystals under loosely controlled crystal formation parameters, followed by sorting according to desired size and/or emission wavelengths. Use of quantum dots for labeling particles, in the context of the present invention, is new, but is old in the art of semiconductors. Two examples of earlier references in which quantum dots are embedded within intrinsic silicon epitaxial layers of semiconductor light emitting/detecting devices are U.S. Pat. Nos. 5,293,050 and 5,354,707 to Chapple Sokol, et al.

In specific embodiments, one or more of the label attachments regions in the nanoreporter is labeled with one or more light-emitting dyes, each label attachment region containing, directly or indirectly, one or more label monomers. The light emitted by the dyes can be visible light or invisible light, such as ultraviolet or infrared light. In exemplary embodiments, the dye is a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-($\epsilon$-carboxypentyl)-3'-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4', 5'-dichloro-2',7'-dimethoxyfluorescein (JOE); ALEXA Fluor™; Cy2; Texas Red and Rhodamine Red; 6- carboxy-2',4,7,7'-tetrachlorofluorescein (TET); 6-carboxy-2', 4, 4', 5', 7, 7'-hexachlorofluorescein (HEX); 5-carboxy-2', 4', 5', 7'-tetrachlorofluorescein (ZOE); NAN; NED; Cy3; Cy3.5; Cy5; Cy5.5; Cy7; and Cy7.5; ALEXA Fluor™ 350; ALEXA Fluor™ 488; ALEXA Fluor™ 532; ALEXA Fluor™ 546; ALEXA Fluor™ 568; ALEXA Fluor™ 594; or ALEXA Fluor™ 647.

The label monomers can be incorporated into a nanoreporter at different stages of its assembly, or into a component (e.g., a "flap" or of the nanoreporter prior to its assembly into the nanoreporter).

A label monomer can be directly attached to a nucleotide using methods well known in the art. Nucleotides can also be chemically modified or derivatized in order to attach a label monomer. For example, a fluorescent monomer such as a fluorescein molecule can be attached to dUTP (deoxyuridine-triphosphate) using a four-atom aminoalkynyl group. Each label monomer is attached to a nucleotide making a label monomer: nucleotide complex.

This label monomer: nucleotide complex can be incorporated into nucleic acids (for example, a DNA patch or a detection oligonucleotide) in a variety of ways. For example, a label monomer: nucleotide complex can be incorporated at only one location within a nucleic acid or at two or more locations within a nucleic acid.

Amine-reactive and thiol-reactive fluorophores are available and used for labeling nucleotides and biomolecules. Generally, nucleotides are fluorescently labeled during chemical synthesis, for example, incorporation of amines or thiols during nucleotide synthesis permit addition of fluorophores. Fluorescently labeled nucleotides are commercially available. For example, uridine and deoxyuridine triphosphates are available that are conjugated to ten different fluorophores that cover the spectrum.

A nucleotide can be attached to a label monomer first and then be incorporated into a nucleic acid. Alternatively, an existing nucleic acid can be labeled by attaching a label monomer to a nucleotide within the nucleic acid. For example aminoallyl-("AA-") modified UTP nucleotides can be incorporated into the RNA product during transcription. In various embodiments, 20% or more of UTP nucleotides in a transcription reaction to generate RNA patches are AA modified. In various embodiments, about 20% to 100%, 20% to 80%, 30% to 80%, 40% to 60% or 50% to 75% of UTPs in a transcription reaction are AA-modified, in a preferred embodiment, approximately 50% of UTPs in a transcription reaction are AA-modified.

In addition, for example, different types of label monomer: nucleotide complexes can be incorporated into a single acid nucleic acid, where one component of the nanoreporter code comprises more than one type of signal.

Fluorescent dyes that can be bound directly to nucleotides can also be utilized as label monomers. For example, FAM, JOE, TAMRA, and ROX are amine reactive fluorescent dyes that have been attached to nucleotides and are used in automated DNA sequencing. These fluorescently labeled nucleotides, for example, ROX-ddATP, ROX-ddCTP, ROX-ddGTP and ROX-ddUTP, are commercially available.

Other types of label monomers that may be used to label a nanoreporter are quantum dots. Due to their very small size the quantum dots can be coupled into oligonucleotides directly without affecting the solubility or use of the oligonucleotide. In a preferred embodiment, only one oligonucleotide molecule is coupled to each nanoparticle. To synthesize an oligonucleotide-nanoparticle complex in a 1:1 ratio by conventional batch chemistry, both the oligonucleotide and the nanoparticle require a single reactive group of different kinds that can be reacted with each other. For example, if an oligonucleotide has an amino group and a nanoparticle has an aldehyde group, these groups can react to form a Schiff base. An oligonucleotide can be derivatized to attach a single amino or other functional group using chemistry well known in the art. However, when a nanoparticle is derivatized, it is covered with a chemical reagent which results in coating the entire surface of the nanoparticle with several functional groups.

The invention provides a method of coupling one oligonucleotide to one nanoparticle by chemically coupling the oligonucleotide on a solid surface such as the glass support used for the oligonucleotide synthesis.

For example, commercially available resins for oligonucleotide synthesis such as long chain alkylamino controlled pore glass (1 caa CPG) can be used.

Alternatively, a flat surface such as a derivatized microscope slide can be used. The surface density of the nascent oligonucleotide chains should be lower than the diameter of the nanoparticle. This can be achieved by either choosing a glass support with low surface density of the reactive groups, or by using diluted reagent for the first step of the oligonucleotide synthesis so that the surface is not saturated. Another point of consideration when using the standard glass matrices for oligonucleotide synthesis is to use a pore diameter higher than the nanoparticle diameter to ensure the flow of the reagents. For example, an oligonucleotide can be synthesized on a diluted basis relative to the solid support, for example one tenth of a nominal synthesis, to ensure good spacing of the oligonucleotides on the glass support. After the oligonucleotide is synthesized with a reactive functional group, for example, an amino group, derivatized nanoparticles are passed over the glass support to react with the oligonucleotides. A sufficiently large pore size of the glass support can be chosen to prevent clogging with nanoparticles. For example, a pore size of about 200 nm can be used. After the reaction is complete, un-reacted groups on the nanoparticle can be blocked and the complexes can be uncoupled from the glass support.

The Nanoreporter Code

Dual Nanoreporters

A nanoreporter whose components exist in two molecular entities is referred to as a dual nanoreporter. In a dual nanoreporter, generally each component contains a target-specific sequence, which improves the specificity of and binding kinetics of the nanoreporter to its target. The two different target-specific sequences are designed or selected such that each recognizes a different portion of a target molecule.

FIGS. 1A-1C illustrate embodiments of the invention involving dual nanoreporters. In FIGS. 1A and 1B, each of the two components of the nanoreporter is labeled, such that the nanoreporter's spectral code is formed only when the two components of the nanoreporter come together upon binding of the dual nanoreporter to its target molecule. However, in a dual nanoreporter, it is not necessary that both components are labeled. For example, as depicted in FIG. 1C, one component of a dual nanoreporter is labeled with the nanoreporter code, and the other component attached to an affinity tag (arrow) that is useful to immobilize the nanoreporter for stretching a visualization.

Registers

The term "register" refers to a set of alternating (every other) label attachment regions. Registers are useful where it is desirable to label adjacent label attachment regions without a spacer region, and where the signal emanating from adjacent label attachment regions cannot be spatially resolved using the desired method of detection. Thus, the signals detected with use of a register is that form by the alternating, rather than adjacent, label attachment regions. Signals detected from a plurality of registers (e.g., that together are all the label attachment regions) can be combined to form a nanoregister code. Generally when using registers, adjacent label attachment regions are labeled with spectrally distinguishable label monomers.

Examples of registers are depicted in FIGS. 3 and 5. For example, in FIGS. 3A-3B, there are 8 label attachment regions 1-8. Alternating label attachment regions 1, 3, 5 and 7 form one register, and label attachment regions 2, 4, 6 and 8 form another register. In FIG. 3A, only one of the registers (1, 3, 5 and 7) is labeled; in FIG. 3B, both registers are labeled.

Affinity Tags

A variety of affinity tags known in the art may be used to purify and/or immobilize nanoreporters.

Where an affinity tag is used to immobilize a nanoreporter for the purpose of detection or imaging, it may be referred to herein as an "anchor." In a preferred embodiment, a biotin anchor is attached to the nanoreporter, allowing immobilization of the nanoreporter on a streptavidin coated slide.

An affinity tag that can be used for attachment to beads or other matrixes for a variety of useful applications including but not limited to purification.

Non-limiting examples of suitable affinity tags are provided below. It should be understood that most affinity tags could serve dual purposes: both as anchors for immobilization of the nanoreporters and tags for purification of the nanoreporters (whether fully or only partially assembled) or their components.

In certain embodiments, the affinity tag is a protein monomer. Examples of protein monomers include, but are not limited to, the immunoglobulin constant regions (see Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell. Bio. 4:220-229), the *E. coli* maltose binding protein (Guan et al., 1987, Gene 67:21-30), and various cellulose binding domains (U.S. Pat. Nos. 5,496,934; 5,202,247; 5,137,819; Tomme et al., 1994, Protein Eng. 7:117-123), etc. Other affinity tags are recognized by specific binding partners and thus facilitate isolation and immobilization by affinity binding to the binding partner, which can be immobilized onto a solid support. For example, the affinity tag can be an epitope, and the binding partner an antibody. Examples of such epitopes include, but are not limited to, the FLAG epitope, the myc epitope at amino acids 408-439, the influenza virus hemagglutinin (HA) epitope, or digoxigenin ("DIG"). In other embodiments, the affinity tag is a protein or amino acid sequence that is recognized by another protein or amino acid, for example the avidin/streptavidin and biotin.

In certain aspects of the invention, the affinity tag is a nucleotide sequence. A large variety of sequences of about 8 to about 30 bases, more preferably of about 10 to about 20 bases, can be used for purification and immobilization of nanoreporters, and the sequence can be tandemly repeated (e.g., from 1 to 10 tandem repeats). Such a sequence is preferably not widely represented (that is, present in fewer than 5% of the genes, more preferably, present in fewer than 3% of the genes, and, most preferably, present in fewer than 1% of the genes) in the sample being assayed (for example, where the nanoreporter is used for detection of human cellular RNA, the sequence is preferably not widely represented in the human genome); have little or no secondary structure or self-complementarity either internally or with copies of itself when multimerized (that is, all secondary structures of the multimerized tag preferably have a Tm less than 25° C. at 1 M NaCl); have no significant identity or complementarity with scaffold or segment sequences (that is, the Tm of complementary sequences is preferably less than 25° C. at 0.2 M NaCl); and have a Tm of about 35-65° C., more preferably about 40-50° C., in 50 mM Na$^+$.

In certain embodiments, different sequences are used as purification and immobilization tags. In this case, for example, the purification tag can be as described above, but the immobilization tag can be in the range of 10 to 100 bases, with a Tm up to 95° C. in 50 mM Na$^+$. An alternative embodiment would be to have the purification tag nested within the immobilization tag (e.g., the affinity tag would comprise a 25-base sequence of which 15 bases are used as a purification tag and the entire 25 bases are used as the immobilization tag).

In certain instances, the affinity tag can be used for labeling a nanoreporter in addition to purifying or immobilizing the nanoreporter.

As will be appreciated by those skilled in the art, many methods can be used to obtain the coding region of the affinity tags, including but not limited to, DNA cloning, DNA amplification, and synthetic methods. Some of the affinity tags and reagents for their detection and isolation are available commercially.

Target-Specific Sequences

The term "target-specific sequence" refers to a molecular entity that is capable of binding a target molecule. In the context of a nanoreporter, the target-specific sequence is attached to the nanoreporter scaffold.

The target specific sequence is generally an amino acid sequence (i.e., a polypeptide or peptide sequence) or a nucleic acid sequence.

In specific embodiments, where the target-specific sequence is an amino acid sequence, the target-specific sequence is an antibody fragment, such as an antibody Fab' fragment, a single chain FY antibody.

The target-specific sequence is preferably a nucleic acid sequence, and is most preferably within an oligonucleotide that is either covalently attached (e.g., by ligation) or noncovalently attached (e.g., by hybridization) to the nanoreporter scaffold. A target-specific nucleic acid sequence is preferably at least 15 nucleotides in length, and more preferably is at least 20 nucleotides in length. In specific embodiments, the target-specific sequence is approximately 10 to 500, 20 to 400, 30 to 300, 40 to 200, or 50 to 100 nucleotides in length. In other embodiments, the target-specific sequence is approximately 30 to 70, 40 to 80, 50 to 90, or 60 to 100, 30 to 120, 40 to 140, or 50 to 150 nucleotides in length.

A target-specific nucleotide sequence preferably has a Tm of about 65-90° C. for each probe in 825 mM $Na^+$ (5×SSC), most preferably about 78-83° C.

In certain preferred embodiments, the target specific sequence of each probe of a dual nanoreporter is about 35 to 100 nucleotides (for a total target sequence of about 70 to 200 nucleotides, covered by 2 probes), most preferably about 40 to 50 nucleotides for each probe (for a total of about 80 to 100 nucleotides).

Computer Programs for Selection of Target-Specific Sequences

The invention provides methods, and computer systems and computer program products that may be used to automate the methods of the invention, for selecting target-specific sequences for use in nanoreporters. The invention provides methods, and various computer systems which run one or more programs described below (e.g., target-specific sequence selection module 50), as well as computer program products that comprise computer-readable media and computer-program mechanisms embedded therein which comprise instructions for carrying out the methods of the invention, i.e., running one or more programs described below.

Figure 19:
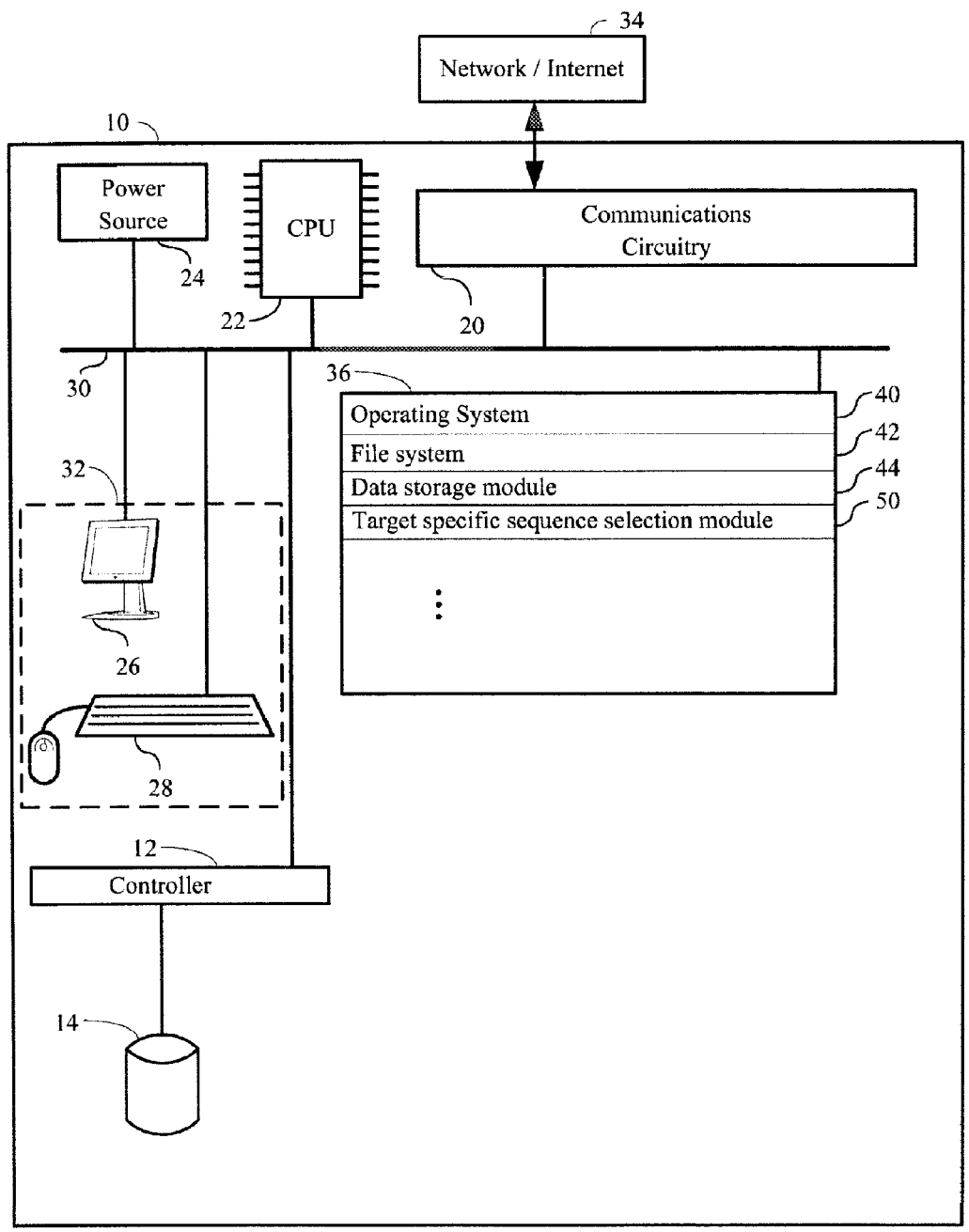
FIG. 19 illustrates a computer system in accordance with an embodiment of the present invention.

FIG. 19 details an exemplary system that supports the functionality described herein. The system is preferably a computer system 10 having:

a central processing unit 22;
a main non-volatile storage unit 14, for example, a hard disk drive, for storing software and data, the storage unit 14 controlled by controller 12;
a system memory 36, preferably high speed random-access memory (RAM), for storing system control programs, data, and application programs, comprising programs and data loaded from non-volatile storage unit 14; system memory 36 may also include read-only memory (ROM);
a user interface 32, comprising one or more input devices (e.g., keyboard 28) and a display 26 or other output device;
a network interface card 20 or other communication circuitry for connecting to detector 72 and, optionally, any wired or wireless communication network 34 (e.g., the Internet or any other wide area network);
an internal bus 30 for interconnecting the aforementioned elements of the system; and
a power source 24 to power the aforementioned elements.

Operation of computer system 10 is controlled primarily by operating system 40, which is executed by central processing unit 22. Operating system 40 can be stored in system memory 36. In addition to operating system 40, in a typical implementation, system memory 36 can include one or more of the following:

file system 42 for controlling access to the various files and data structures used by the present invention;
a data storage module 44 comprising instructions for storing a plurality of sequences; and
a target-specific sequence selection module 50 for identifying a plurality of target-specific sequences.

As illustrated in FIG. 19, computer system 10 comprises software program modules and data structures. The data structures stored in computer system 10 include, for example, sequence databases of interest and sequences present in the nanoreporter structure (these are protocol- and fabrication-specific sequences). Each of these data structures can comprise any form of data storage including, but not limited to, a flat ASCII or binary file, an Excel spreadsheet, a relational database (SQL), an on-line analytical processing (OLAP) database (MDX and/or variants thereof), or a comma separated value file. In some embodiments, the data structures and software modules depicted in FIG. 19 are not housed on computer system 10, but rather are housed on a computer or other type of storage device that is in electrical communication with computer system 10 across network 34.

One aspect of the present invention provides a computer program product comprising a computer readable storage medium (e.g., memory 36, storage unit 14, and/or other computer readable storage media) and a computer program mechanism embedded therein. The computer program mechanism is for identifying suitable target-specific sequences for use in nanoreporters. The computer program mechanism comprises data storage module 44 and the target-specific sequence identification module 50.

Data storage module 44. Data storage module 44 comprises sequence databases, for example, for use as reference sequences. For example, human reference sequences can be acquired from refseq database for mRNA sequences (Pruitt et al., 2005, Nucleic Acids Res. 33(1):D501-D504).

In addition, the data storage module can comprise sequences of relevance to the user of the program, for example sequences used in nanoreporter assemblies that can be used as reference sequences in the Higher-Resolution Context Sensitive Structural Filter of the third selection tier of the target-specific sequence selection program (described below).

Target-Specific Sequence Identification Module 50.

Figure 21A:
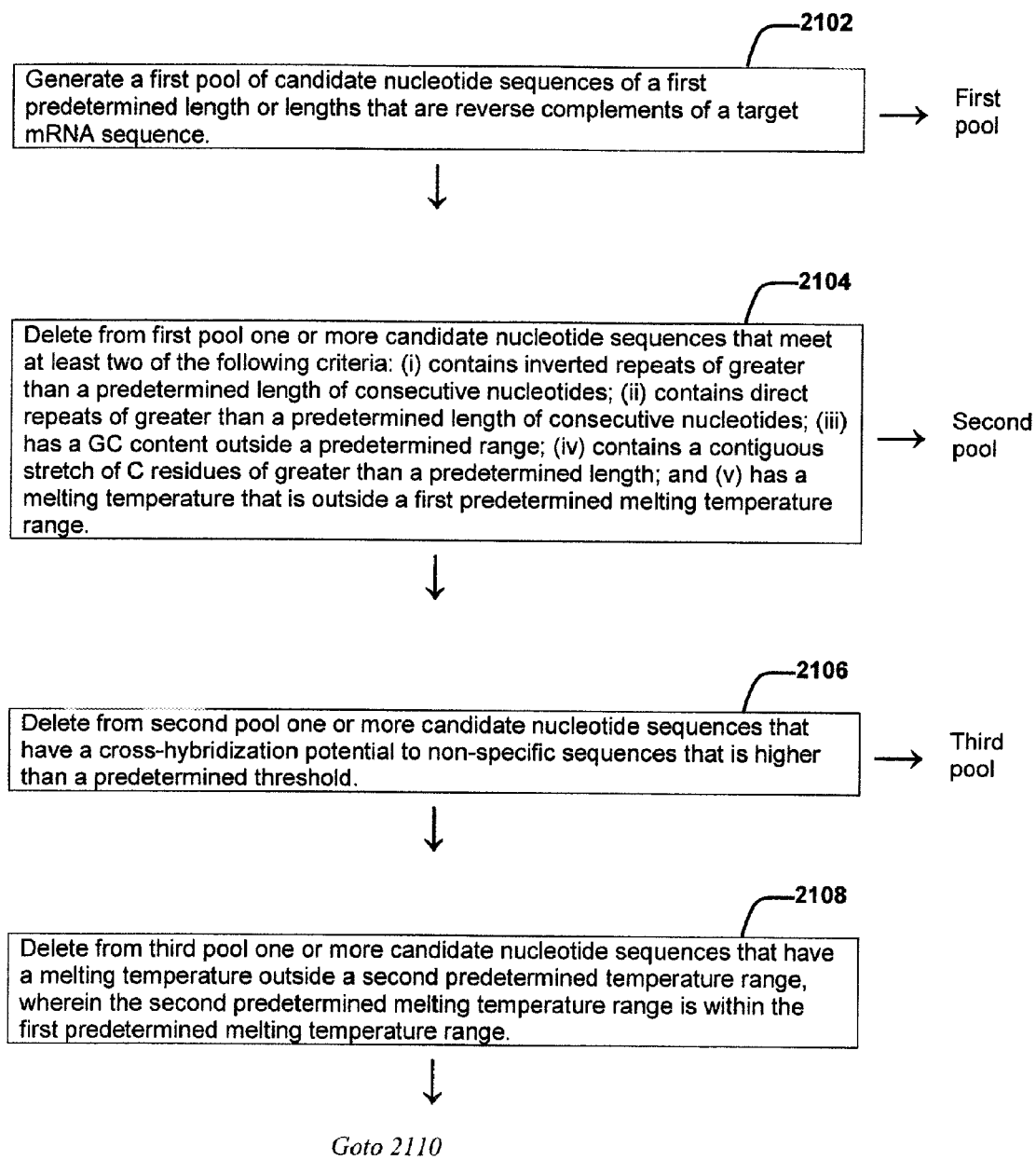
FIG. 21A-21C illustrates the steps of an exemplary method for the identification of a target-specific sequence, which can be used in a probe hybridizable to a target mRNA.
Figure 21B:
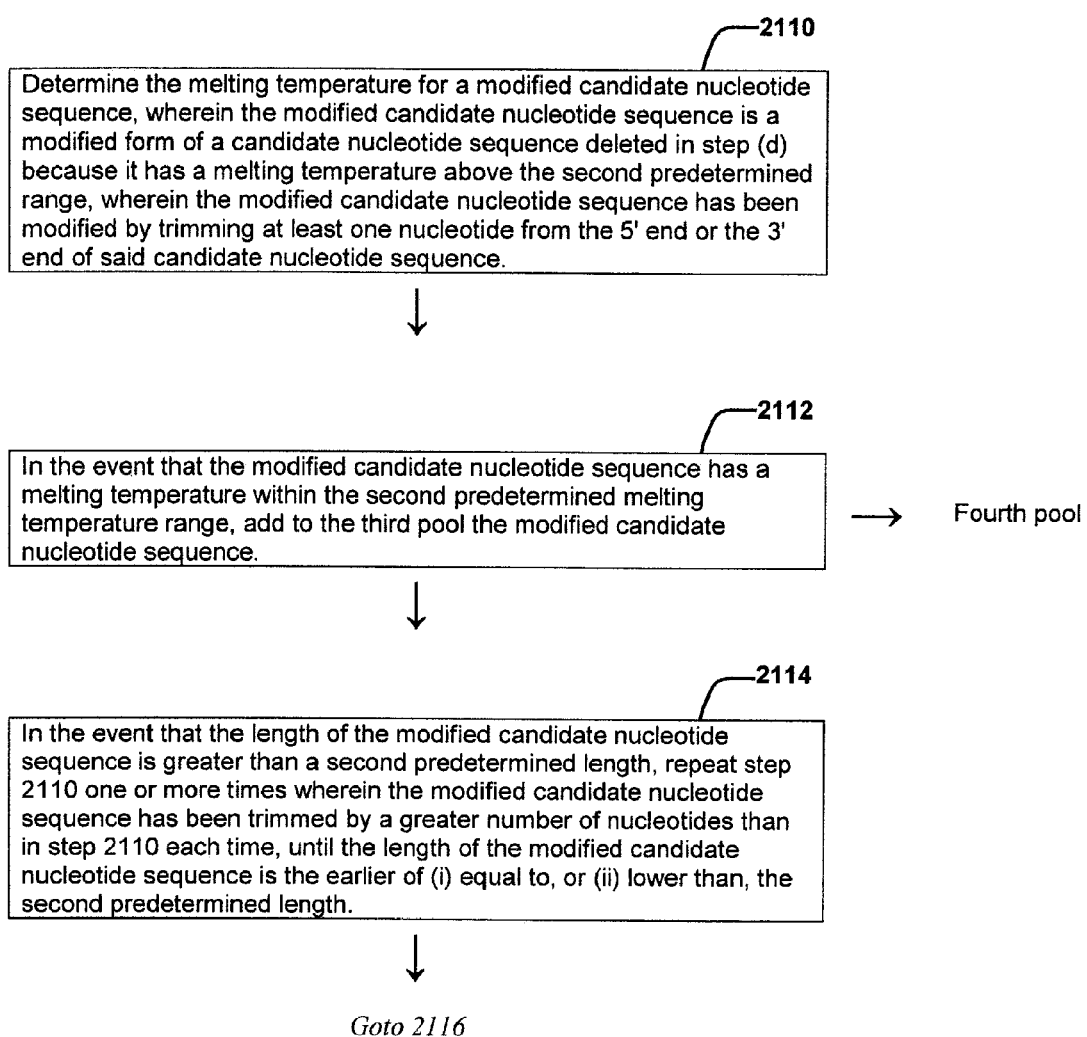
Figure 21C:
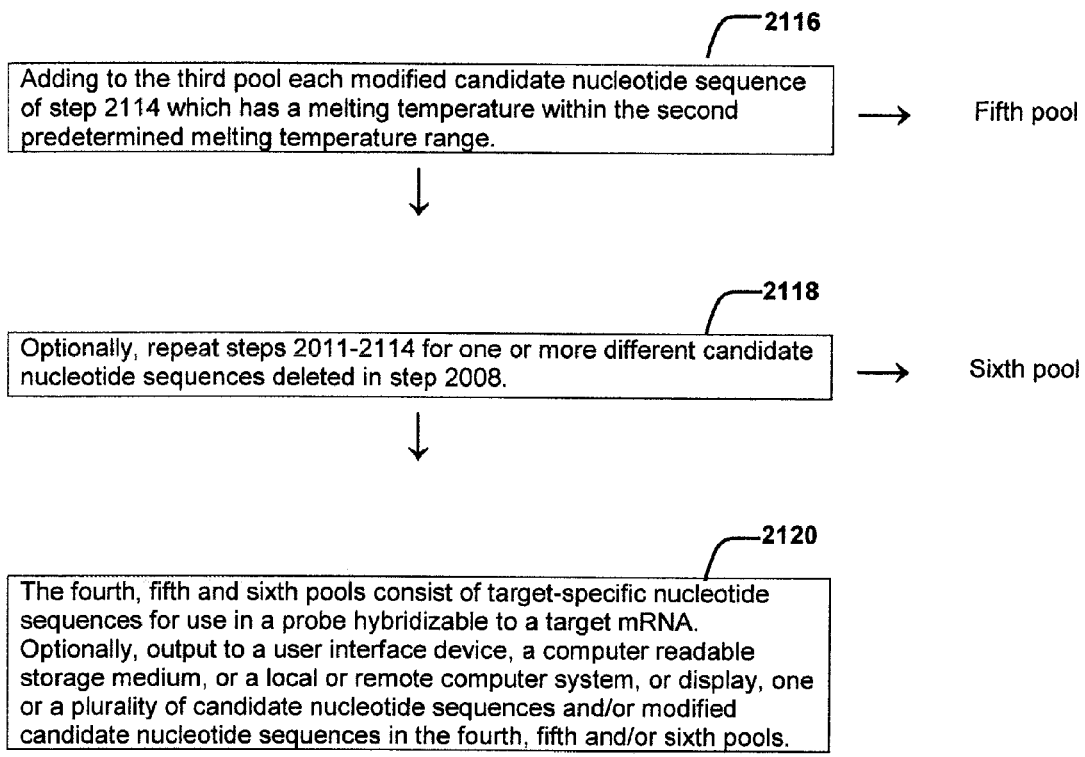

This module is illustrated in FIGS. 21 and 22 for dual nanoreporter and single nanoreporter target-specific sequence selection, respectively. However, the methods described herein are useful for identifying target-specific sequences (or pairs thereof) for use in any other probe system, for example for use in gene expression analysis by RT-PCR or microarrays.

First Selection Tier

Figure 20A:
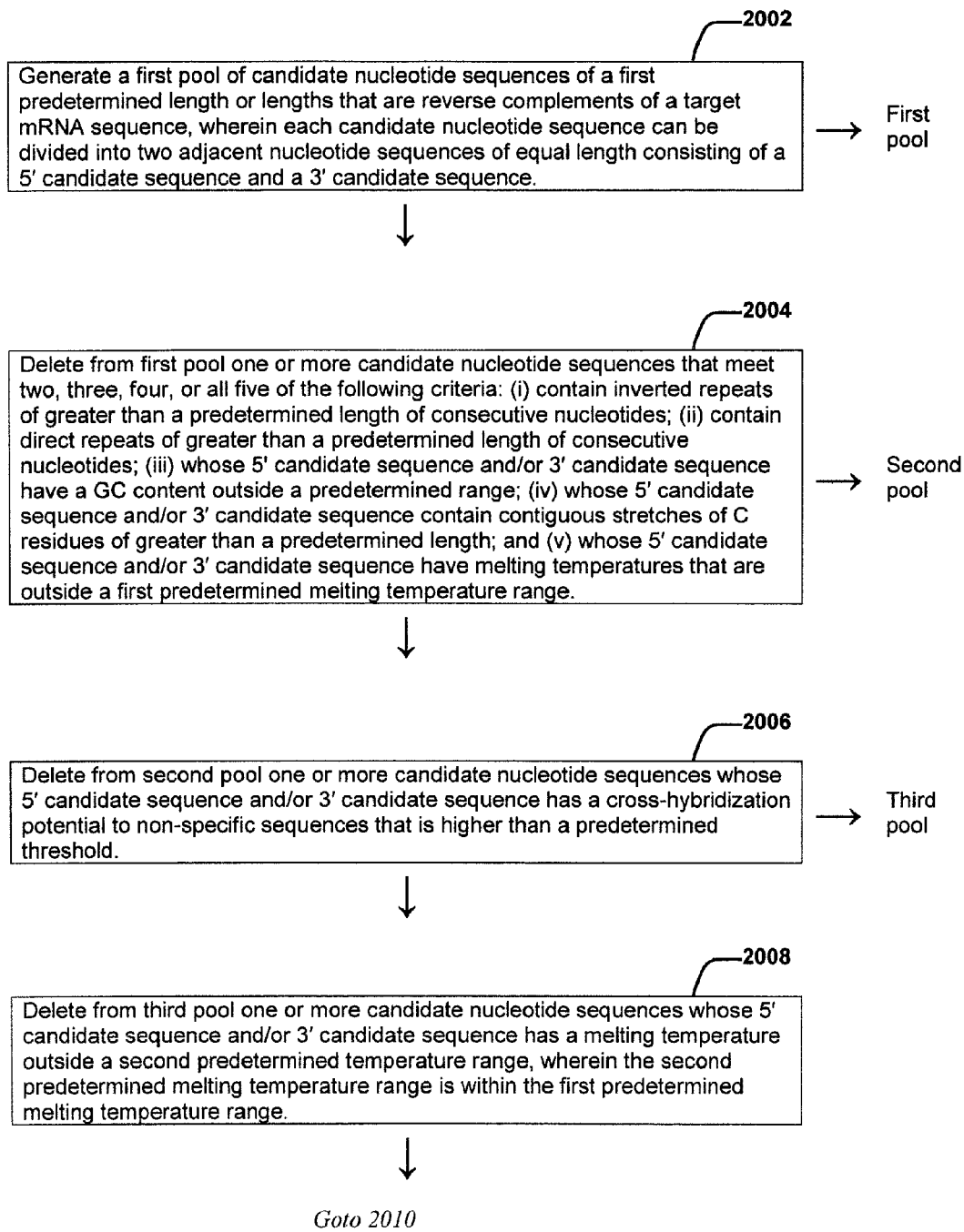
FIG. 20A-20C illustrates the steps of an exemplary method for the identification of a pair of adjacent target-specific sequences, which can be used in a probe pair hybridizable to a target mRNA.
Figure 20B:
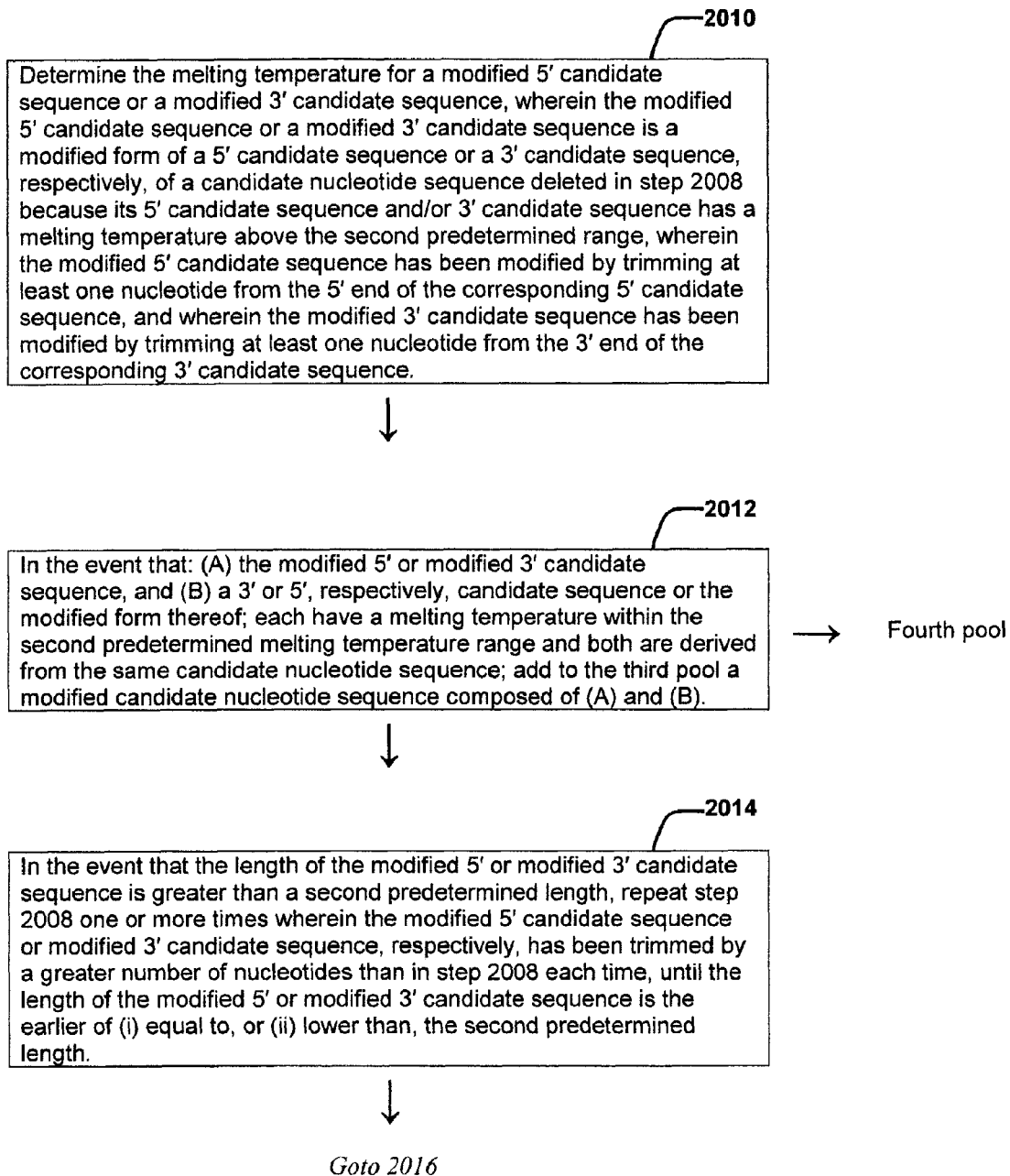
Figure 20C:
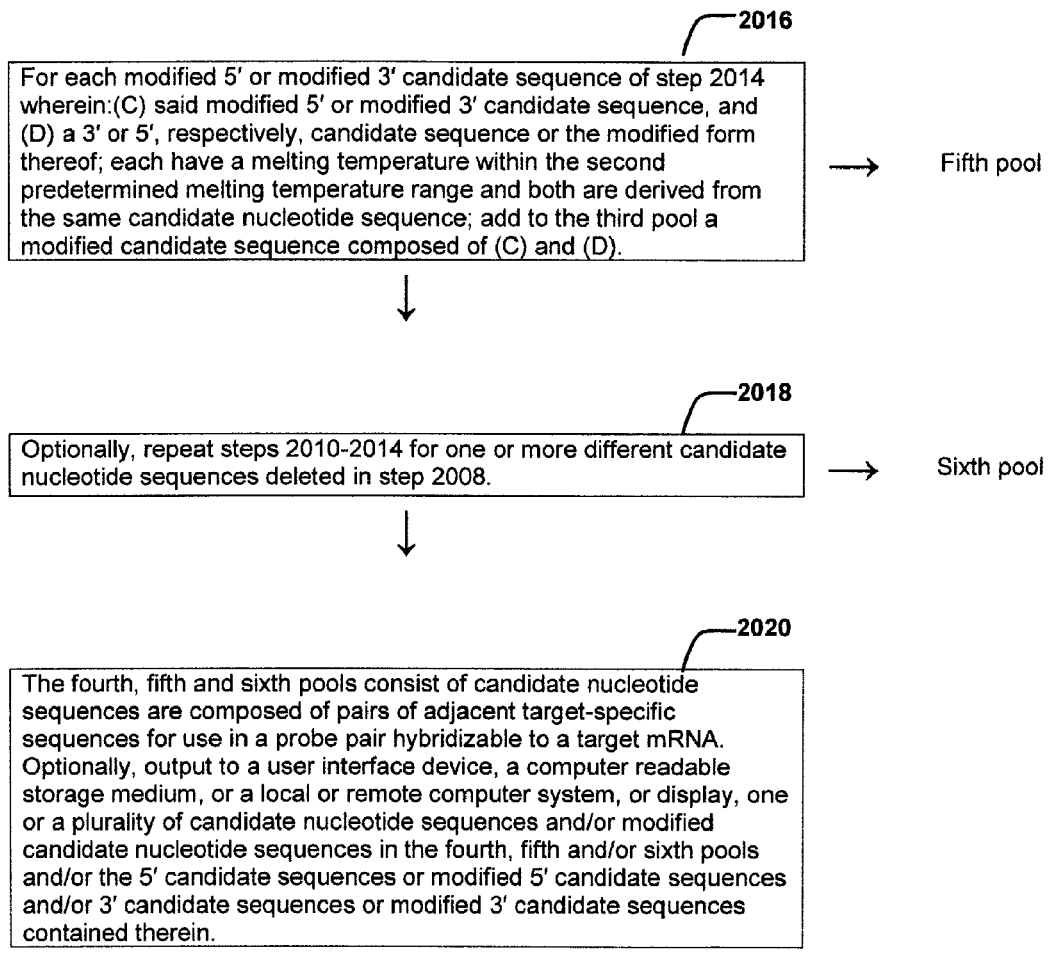

In a single-tiered program or in a first tier of a multi-tiered program, the program generates candidate target-specific sequences of a given size (e.g., 100 bases) from each target mRNA. In FIGS. 20 and 21, this step is illustrated as step 2002 and 2202, respectively.

In various embodiments, target-specific sequences are selected for any where from 1 to 10,000 target mRNAs, for example from 1 to 20 target mRNAs, from 5 to 100 target mRNAs, from 20 to 250 target mRNAs, from 100 to 500 target mRNAs, from 200 to 1,000 target mRNAs, from 500 to 2,000 target mRNAs, from 1,000 to 10,000 mRNAs, or any range in between (e.g., from 5 to 250 target mRNAs). In specific embodiments, target-specific sequences are selected for at least 10 target mRNAs, at least 25 target mRNAs, at least 50 target mRNAs, at least 100 mRNAs, at least 200 target mRNAs, or at least 500 target mRNAs.

Candidate target-specific sequences are preferably 30-160 bases long. Candidate target-specific sequences for use in a single nanoreporters probe are preferably 30-80, more preferably 35-70, and most preferably 40-55 bases in length. Candidate target-specific sequences for use in two nanoreporter probes, the candidate target-specific sequences are preferably 60-160, more preferably 70-150, and most preferably 80-110 bases in length.

For each target molecule, the pool of candidate target-specific sequences may be all possible target-specific sequences of a selected size against the target molecule. The pool of target-specific sequences can be generated using a sliding window such that each candidate target-specific sequence will be adjacent to or overlap with the adjacent candidate target-specific sequence. In embodiments where the sliding window covers overlapping candidate target-specific sequences, the overlap can be of a step size of 1 to up to 1 base less than the length of the candidate target-specific sequence (e.g., for a 100-base target-specific sequence, the step size can be anywhere from 1 to 99 bases, wherein a 1-base step size results in a 99-base overlap between adjacent candidate target-specific sequences and a 99-base step size results in a 1-base overlap between adjacent candidate target-specific sequences). In a preferred embodiment, the step size is not a multiple of 3. In other preferred embodiments, the step size is 2-20 bases less than the window size, most preferably 4-10 bases less than the window size. Where the candidate target-specific sequence will be divided into two target-specific sequences for use in two nanoreporter probes (e.g., the two components of a dual nanoreporter), the step size is preferably less than half the window size (for example, for a 100-base target-specific sequence which will form the basis of two 50-base target-specific regions of a dual nanoreporter, the window size is preferably less than 50).

In some embodiments, each candidate target-specific sequence is assessed on any combination of two or more, preferably three or more, and more preferably four or all four of the following criteria (this step is reflected as step 2004 of FIG. 20 and step 2104 of FIG. 21, respectively):

(1) the candidate target-specific sequence has no inverted repeats of a predetermined length or greater, e.g., five or more, preferably six or more, consecutive bases (this criterion prevents inter-probe interactions);

(2) the candidate target-specific sequence has no direct repeats of a predetermined length or greater, e.g., five or more consecutive bases, more preferably six, seven or eight or more consecutive bases, and most preferably nine or more consecutive bases (this criterion prevents inter-probe interactions);

(3) each target-specific sequence (or each of the 5' half and the 3' half of the candidate target-specific sequence where the target-specific sequence will be the basis of the two target-specific sequences of a dual nanoreporter) has a GC content in a preferred range, e.g., of 25-85%, more preferably 30-80%, yet more preferably 35-75% GC, and yet most preferably 40-70%, or any range in between (e.g., 32%-76% or 38%-68%) (this criterion is used for identifying/selecting target-specific regions of dual nanoreporters and avoids skew in the hybridization properties of the two components of the dual nanoreporters); and (4) the candidate target-specific sequence has no contiguous stretches of Cs longer than a predetermined length, e.g., longer than three, longer than four, or longer than five (this criterion avoids complications in probe synthesis); and (5) the candidate target-specific sequence has a melting temperature in a predetermined range, preferably from 60-75° C. at its lower end to 80-90° C. at its upper end.

In specific embodiments, mFOLD or Oligowalk (available on the Internet) may be used to predict probe folding. If for a given target molecule one or more candidate target-specific sequences that meet the predetermined combination of the foregoing criteria, the target-specific sequences can be selected for use in a nanoreporter probe of the invention (in a single-tier selection), or the candidate target-specific sequence can be subject to additional selection criteria, as described below. If, on the other hand, there are no candidate target-specific sequences against a particular target molecule that meet the predetermined combination of the foregoing four criteria (e.g., all four criteria or some predetermined subset of the four criteria), one or more of the criteria used in this selection step are relaxed and candidate target-specific sequences are selected on the basis of the less stringent criteria.

The melting temperatures of each candidate target-specific sequence are either actual melting temperatures (for example melting temperatures measured under conditions of interest) or calculated using standard algorithm and thermodynamic parameters. As used herein, a reference to a melting temperature, or Tm, refers to the melting temperature of a duplex consisting of the sequence in question (e.g., the candidate target-specific sequence (usually DNA) and the reverse complement (usually mRNA). For RNA/DNA hybrids, for example, the Dan program of the EMBOSS freeware program suite (available on the Internet) calculates the melting temperature (Tm) and the percent G+C of a nucleic acid sequence. For the melting temperature profile, free energy values calculated from nearest neighbor thermodynamics are used (Breslauer et al., Proc. Natl. Acad. Sci. USA 83:3746-3750 and Baldino et al., Methods in Enzymol. 168:761-777). The Tm information can be used to discard candidate target-specific sequences of unsuitable melting temperatures (e.g., outside the range of 65° C.-90° C.), and is used in a subsequent selection round of a multi-tiered program for further refinement of probe selection.

Many genes produce different RNAs, for example as a result of alternative splicing. The first selection tier can be used to identify specific products or all products of a particular gene, by running the first selection tier in "specific" mode or "common" mode. In "specific" mode, the sliding window only covers regions that are specific to one RNA, for example regions that are at splice junctions specific to that RNA. In "common" mode, the sliding window covers regions that are common to all products of interest of a given gene.

Either following or during the first selection round, an alignment such as a BLAST or FASTA alignment is performed on target-specific sequence (using algorithms such as NCBI BLAST, selecting dual strand BLAST with the following parameters: 'w11 q–1'). The alignment output is used in a subsequent selection round of a multi-tiered program. The alignment can be performed locally or remotely. Local alignments require that the local computer carry the alignment program (e.g., BLAST) and the sequence database against which the candidate target-specific sequences are going to be compared; for example, where the target genes are human genes whose expression will be monitored, the sequence database can be a database of expressed human genes. Optionally, the sequence database contains only sequences that are expressed in a target tissue of interest. Remote alignments require a connection to a remote site that can perform alignments, such as the NCBI web site.

Second Selection Tier

As reflected in step 2006 of FIG. 20 and step 2106 of FIG. 21, candidate sequences are eliminated from contention if they have the potential to cross-hybridize to non-specific sequences present in a biological sample of interest.

In one embodiment, the cross-hybridization potential of target-specific sequence is determined as follows. The sequence selection program performs an additional, second step of alignment output interpretation and scoring. In this step, for example, the BLAST (preferably in dual strand mode) or other alignment program results are used to calculate some basic metrics for every hit. In one embodiment, the BLAST hit coordinates (which, for 100-base candidate target-specific sequences, will range anywhere from ~12 to 100 bases when the 'w11q-1' BLAST parameter set is used) are extended to line up with the candidate target-specific sequence, and the following is calculated:

(i) Percent identity calculated between each hit and the candidate target-specific sequence; and (ii) Maximum contiguous block of identity (stretch of contiguous bases that align perfectly) between each hit and candidate target-specific sequence (or each of the 5' half and the 3' half of the candidate target-specific sequence where the target-specific sequence will be the basis of two halves of a dual nanoreporter).

Sequences are eliminated from contention when:

(1) the percentage identity between non-specific hits (i.e., those sequence hits identified by the alignment program (e.g., BLAST) that do not correspond to the gene to which the target-specific sequence corresponds) and the candidate target-specific sequence is greater than a predetermined amount; and/or (2) the longest contiguous block of sequence identity between the candidate target-specific sequence and non-specific hits.

In certain embodiments, the cutoffs above are (i) a sequence identity with a non-specific hit of 95% or greater, 90% or greater, 85% or greater, or 80% or greater and (ii) a contiguous block of sequence identity with a non-specific hit of 20 bases or greater, of 19 bases or greater, of 18 bases or greater, of 17 bases or greater, of 16 bases or greater, of 15 bases or greater, of 14 bases or greater, of 13 bases or greater, of 12 bases or greater, of 11 bases or greater or of 10 bases or greater.

Candidate target-specific sequences that meet criteria (i) and/or (ii) of the second selection tier are eliminated. This step allows the elimination of target-specific sequences that will cross-hybridize to transcripts other than the target transcript in a nanoreporter assay. In addition to criteria (i) and/or (ii) above, other criteria selected by the user may be used to score candidate eliminate target-specific sequences on the basis of their ability to cross-hybridize with non-target sequences.

The scored candidate target sequences of the second selection tier can be subject to further optional steps in a third selection tier, described below.

Third Selection Tier

This third selection tier consists of a series of various optional steps to optimize the target-specific sequence selection.

(a) Higher-Resolution Context Sensitive Structural Filter

A "Higher-Resolution Context Sensitive Structural Filter" or HRCSSF scans various parts of nanoreporters, such as the nanoreporter backbone (e.g., M13), affinity tags (e.g., G-hooks, F-hooks), and checks for inter- and intra-reporter interactions based on the context of when certain exposed sequences have potential to interact.

In certain embodiment, the HRCSSF contains two or three main features, described below:

(1) A structural check on the target-specific sequence (or pair of target-specific sequences). This is almost identical to the first two criteria of the first tier (e.g., as reflected in (i) and (ii) of step 2004 of FIG. 20 and step 2104 of FIG. 21), but allows the addition of non-target-specific sequences present in the nanoreporters or mRNA sequence adjacent to the target-specific sequences. The two primary cutoffs are Direct Repeats (DR) and Inverted repeats (IR). Preferably those target-specific sequences with DRs of a predetermined length of, e.g., 6-10 bases or longer, are eliminated. For example, target-specific sequences with DRs 10 bases or longer, at least 8 bases or longer, 6 bases or longer, are eliminated). Preferably those target-specific sequences with IRs of a predetermined length of, e.g., 4-8 bases or longer, are eliminated. For example, target-specific sequences with IRs of 4 bases or longer, 6 bases or longer, or 8 bases or longer, are eliminated.

(2) An intra-molecular check of each nanoreporter (or each component of a dual nanoreporter). Again, preferably, the two primary cutoffs are Direct Repeats (DR) and Inverted repeats (IR). Preferably, the cutoff size for each DR and IR is 8-12, such that target-specific sequences with DRs or IRs of 8 bases or longer, 10 bases or longer, or 12 bases or longer, are eliminated.

(3) Optionally, for dual nanoreporters, an inter-molecular check between the different components of the nanoreporters (for example between a ghost probe and a reporter probe). Again, the two primary cutoffs are Direct Repeats (DR) (preferably those target-specific sequences with direct repeats of 12-18 bases or longer, e.g., 17 bases or longer, 16 bases or longer, or 15 bases or longer, are eliminated) and Inverted repeats (IR) (preferably those target-specific sequences with inverted repeats of 12-18 bases or longer, e.g., 13 bases or longer, at least 15 bases or longer, or at least 17 bases or longer, are eliminated).

The algorithm contains no scoring, if a feature is found above cutoff, that a target-specific sequence (or pair of target-specific sequences) is discarded completely.

(b) Dynamic Tm Filter

To optimize the signal to noise ratio in multiplex nanoreporter detection assays (involving the detection of multiple target molecules in one experiment), it is preferable that the target-specific sequences of all reporter probes fall into a small melting temperature range, e.g., three, four, five, six, or seven degrees Celsius between 72° C. and 86° C. (e.g., from 78° C. to 83° C. or from 75° C. to 82° C.). The dynamic Tm filter takes candidate target-specific sequences that are above Tm Range and "trims" the target-specific sequences until they either fall into the range, or reach a minimum size. Preferably, the candidate target-specific sequences for dual nanoreporters are trimmed from their outside ends (i.e., the 5' end for the 5' candidate sequence and the 3' end for the 3' candidate sequence) or from either end for individual target-specific sequences. This embodiment is illustrated steps 2008, 2010, 2012, 2014, 2016, and 2018 of FIG. 20, and steps 2108, 2110, 2112, 2114, 2116, and 2118 of FIG. 21. For dual nanoreporters whose target-specific sequences are not adjacent, the opposite end can be trimmed also; however, it is preferable that each pair of target-specific sequences correspond to sequences no more than 5 nucleotides apart on the target mRNA, and more preferably no more than 3 nucleotides apart or even no more than 1 nucleotide apart on the target mRNA.

The dynamic Tm filter can be designed to also extend sequences that have too low a Tm (outside the preselected Tm range) until they fall into the range, or reach a maximum size. Preferably, the candidate target-specific sequences for dual nanoreporters are extended from their outside ends (i.e., the 5' end for the 5' candidate sequence and from the 3' end for the 3' candidate sequence) or from either end for individual target-specific sequences.

Thus, in this dynamic Tm filter step, a candidate target-specific sequence may be modified to be longer or shorter than the initial window size of the first selection tier.

(c) Transcript Specificity Check

Many genes produce different RNAs, for example as a result of alternative splicing. In certain embodiments of the invention, a transcript specificity check is performed.

For the target-specific sequence to hybridize with multiple variants of the mRNA it must have a perfect or near-perfect alignment to the variants in common. Accordingly, after identifying one or more target-specific sequences, it is possible to check whether they hybridize to multiple splice forms (or other variations such as allelic variations) of the same RNA. In practice, it is possible to check whether in the second selection tier sequences are not eliminated if they only cross-hybridize to variants of the same RNA.

As an alternative to the transcript specificity check, it is possible to include in the pool for the first selection tier only candidate sequences present in only a specific variant of an RNA of interest (so as to identify target-specific sequences hybridizable only to that variant), or candidate sequences present in multiple variants (so as to identify target-specific sequences hybridizable to the multiple variants).

Scoring

A scoring software module that calculates quality scores (the term score refers to any qualitative and quantitative values with regard to desired properties of a target-specific sequence) for candidate target-specific sequences. Scores based on the Tm values and non-specific hybridization potential of each candidate target-specific are inserted into the score sheet which is used to select "top scoring" target-specific sequence for each target molecule. Target-specific sequences (or, for dual nanoreporters, target-specific sequence pairs) passing all minimum requirements are given a score to choose the pair most likely to perform well. In an exemplary embodiment, this score is based on a weighted score of the cross-hybridization potentials and the melting temperatures of the adjacent target-specific sequences (whether unmodified or as modified by the dynamic Tm filter). In a specific embodiment, the weighted score is calculated according to the formula:

$$(Tm\ score*WFa)+(MCB\ score*WFb)+(PID\ score*WFc)$$

where:

Tm score is a melting temperature score calculated according to the formula:

$$(differential\ score+general\ score)/3$$

where the differential score is calculated according to the following formula:

$$1-|(TmA-TmB)|/(TmHco-TmLco)$$

where the general score is calculated according to the following formula:

$$(((TmI-|(TmA-TmI)|)/TmI)+(((TmI-|(TmB-TmI)|)/TmI)))$$

where TmA and TmB are the respective melting temperatures of the adjacent target-specific sequences (one or both of which is optionally modified by the dynamic Tm filter), TmHco is the upper limit of the second predetermined temperature range; TmLco is the lower limit of the second predetermined temperature range; and TmI is a predetermined ideal melting temperature;

where:

MCB score is a maximum contiguous block score calculated according to the formula:

$$1-(MCB/MCBco);$$

where MCB is the greater of (i) and (ii) below, where (i) and (ii) are respectively:

(i) the maximum contiguous block of identity between (A) and (B) below:
  (A) a first target-specific nucleotide sequence in said pair of adjacent target-specific sequences; and
  (B) a sequence in the database other than the complement of the target mRNA and, optionally, other than the complements of one or more variants, such as alternatively spliced mRNAs, corresponding to the same gene as the target mRNA;
and
(ii) the maximum contiguous block of identity between (A) and (B) below:
  (A) a second target-specific nucleotide sequence in said pair of adjacent target-specific sequences; and
  (B) a sequence in the database other than the complement of the target mRNA and, optionally, other than the complements of one or more variants, such as alternatively spliced mRNAs, corresponding to the same gene as the target mRNA,
and wherein MCBco is the first predetermined cutoff;

where:

PID score is a percent identity score calculated according to the formula:

$$1-(PID/PIDco));$$

where PID is the greater of (i) and (ii) below, where (i) and (ii) are respectively:

(i) the greatest percentage sequence identity between (A) and (B) below:
  (A) a first target-specific nucleotide sequence in said pair of adjacent target-specific sequences; and
  (B) a sequence in the database other than the complement of the target mRNA and, optionally, other than the complements of one or more variants, such as alternatively spliced mRNAs, corresponding to the same gene as the target mRNA;
and
(ii) the greatest percentage sequence identity between (A) and (B) below:
  (A) a second target-specific nucleotide sequence in said pair of adjacent target-specific sequences; and
  (B) a sequence in the database other than the complement of the target mRNA and, optionally, other than the complements of one or more variants, such as alternatively spliced mRNAs, corresponding to the same gene as the target mRNA,
and wherein PIDco is the second predetermined cutoff,
and where WFa, WFb, and WFc are each independently a weighting factor, each of which is a real number.

For dual nanoreporters, the top scoring pair of target-specific sequences are selected, which are preferably complementary to portions of the target molecule no more than 10 bases apart, more preferably complementary to portions of the target molecule no more than 5, 4, 3, 2 or 1 base(s) apart, and most preferably complementary to immediately adjacent portions of the target molecule).

In a variation of the computer program of the present invention, instead of using the five criteria of the first selection tier as cutoff points, such criteria may be factored in to the scores of the candidate target-specific sequences.

Iterative rounds of selection according to the first selection tier, with progressively more relaxed parameters (e.g., broader melting temperature range, broader % GC content range, higher cutoff for inverted and/or direct repeats), can be used to identify target-specific sequences of genes for which suitable target-specific sequences are identified under the more stringent criteria.

As will be appreciated by one of skill in the art, the present invention may be embodied as a method, computer system or program products. Accordingly, the present invention may take the form of data analysis systems, methods, analysis software, etc. Software written according to the present invention can be stored in some form of computer readable medium, such as memory, or CD-ROM, or transmitted over a network, and executed by a processor. For a description of basic computer systems and computer networks, see, e.g., Introduction to Computing Systems: From Bits and Gates to C and Beyond, by Yale N. Patt, Sanjay J. Patel, 1st edition (Jan. 15, 2000) McGraw Hill Text; ISBN: 0072376902; and Introduction to Client/Server Systems: A Practical Guide for Systems Professionals, by Paul E. Renaud, 2nd edition (June 1996), John Wiley & Sons; ISBN: 0471133337.

Each of the methods, computer program products, and computer systems disclosed herein optionally further comprise a step of, or instructions for, outputting or displaying a result (for example, to a monitor, to a user, to computer readable media, e.g., storage media or to a remote computer). Here the result is any result obtained by the methods, computer program products, and computer systems disclosed herein. Optionally, the method further comprises the step of outputting to a user interface device, a computer readable storage medium, or a local or remote computer system, or displaying, one or a plurality of candidate target-specific sequences (optionally, modified by the dynamic Tm filter). Moreover, in certain embodiments, the candidate target-specific sequences (optionally, modified by the dynamic Tm filter) may be outputted as pairs of adjacent target-specific nucleotide sequences, e.g., for use in dual nanoreporters. The candidate target-specific sequences outputted in this manner can be target-specific sequences that have undergone only the first selection tier; the first and second selection tiers; or the first selection tier, the second selection tier, and one or more embodiments of the third selection tier (such as the dynamic Tm filter and/or the HRCSSF and/or transcript specificity check). In certain specific embodiments, the candidate target-specific sequences are outputted or displayed in a ranked order based on a weighted score, for example a weighted score of the cross-hybridization potentials and the melting temperatures of the sequences (or one or both the adjacent target-specific nucleotide sequences contained therein). An example of a scoring algorithm is described above.

Computer software products may be written in any of various suitable programming languages, such as C, C++, Fortran and Java (Sun Microsystems). Preferably, the software products are written in Perl, a dynamic programming language that derives broadly from C. The computer software product may be an independent application with data input and data display modules. Alternatively, the computer software products may be classes that may be instantiated as distributed objects. The computer software products may also be component software such as Java Beans (Sun Microsystems), Enterprise Java Beans (EJB), Microsoft™ COM/DCOM, etc.

Target Molecules

The term "target molecule" is the molecule detected or measured by binding of a labeled nanoreporter whose target-specific sequence(s) recognize (are specific binding partners thereto). Preferably, a target molecule can be, but is not limited to, any of the following: DNA, cDNA, RNA, mRNA, peptide, a polypeptide/protein (e.g., a bacterial or viral protein or an antibody), a lipid, a carbohydrate, a glycoprotein, a glycolipid, a small molecule, an organic monomer, or a drug. Generally, a target molecule is a naturally occurring molecule or a cDNA of a naturally occurring molecule or the complement of said cDNA.

A target molecule can be part of a biomolecular sample that contains other components or can be the sole or major component of the sample. A target molecule can be a component of a whole cell or tissue, a cell or tissue extract, a fractionated lysate thereof or a substantially purified molecule. The target molecule can be attached in solution or solid-phase, including, for example, to a solid surface such as a chip, microarray or bead. Also the target molecule can have either a known or unknown structure or sequence.

In certain specific embodiments, that target molecule is not a chromosome. In other specific embodiments, the target molecule is no greater than 1,000 kb (or 1 mb) in size, no greater than 500 kb in size, no greater than 250 kb in size, no greater than 175 kb in size, no greater than 100 kb in size, no greater than 50 kb in size, no greater than 20 kb in size, or no greater than 10 kb in size. In yet other specific embodiments, the target molecule is isolated from its cellular milieu.

In specific, non-limiting embodiments, the target molecule is one of the following antibodies or an antigen recognized by one of the following antibodies: anti-estrogen receptor antibody, an anti-progesterone receptor antibody, an anti-p53 antibody, an anti-Her-2/neu antibody, an anti-EGFR antibody, an anti-cathepsin D antibody, an anti-Bcl-2 antibody, an anti-E-cadherin antibody, an anti-CA125 antibody, an anti-CA15-3 antibody, an anti-CA19-9 antibody, an anti-c-erbB-2 antibody, an anti-P-glycoprotein antibody, an anti-CEA antibody, an anti-retinoblastoma protein antibody, an anti-ras oncoprotein antibody, an anti-Lewis X antibody, an anti-Ki-67 antibody, an anti-PCNA antibody, an anti-CD3 antibody, an anti-CD4 antibody, an anti-CD5 antibody, an anti-CD7 antibody, an anti-CD8 antibody, an anti-CD9/p24 antibody, an anti-CD10 antibody, an anti-CD11c antibody, an anti-CD 13 antibody, an anti-CD 14 antibody, an anti-CD 15 antibody, an anti-CD19 antibody, an anti-CD20 antibody, an anti-CD22 antibody, an anti-CD23 antibody, an anti-CD30 antibody, an anti-CD31 antibody, an anti-CD33 antibody, an anti-CD34 antibody, an anti-CD35 antibody, an anti-CD38 antibody, an anti-CD41 antibody, an anti-LCA/CD45 antibody, an anti-CD45RO antibody, an anti-CD45RA antibody, an anti-CD39 antibody, an anti-CD100 antibody, an anti-CD95/Fas antibody, an anti-CD99 antibody, an anti-CD106 antibody, an anti-ubiquitin antibody, an anti-CD71 antibody, an anti-c-myc antibody, an anti-cytokeratins antibody, an anti-vimentins antibody, an anti-HPV proteins antibody, an anti-kappa light chains antibody, an anti-lambda light chain antibody, an anti-melanosome antibody, an anti-prostate specific antigen antibody, an anti-S-100 antibody, an anti-tau antigen antibody, an anti-fibrin antibody, an anti-keratins antibody, an anti-Tn-antigen antibody receptor protein, a lymphokine, an enzyme, a hormone, a growth factor, or a nucleic acid binding protein, a ligand for a cell adhesion receptor; a ligand for a signal transduction receptor; a hormone; a molecule that binds to a death domain family molecule; an antigen; a viral particle, a viral coating protein or fragment thereof, a toxic polypeptide selected from the group consisting of: (a) ricin, (b) *Pseudomonas* exotoxin (PE); (c) bryodin; (d) gelonin; (e) α-sarcin; (f) aspergillin; (g) restrictocin; (h) angiogenin; (i) saporin; (j) abrin; (k) pokeweed antiviral protein (PAP); and (l) a functional fragment of any of (a)-(k); a cytokine, or a soluble cytokine selected from the group consisting of erythropoietin, interleukins, interferons, fibroblast growth factors, transforming growth factors, tumor necrosis factors, colony stimulating factors and epidermal growth factor, Class I MHC antigens, class II MHC antigens, internalizing cell-surface receptors and/or viral receptors.

In specific, non-limiting embodiments, the target molecule is an antigen such as alpha fetoprotein, alpha-1 antitrypsin, α-2 macroglobulin, adiponectin, apoliprotein-A-1, apoliprotein-CIII, apoliprotein-H, BDNF, β-2 microglobulin, C reactive protein, calcitonin, cancer antigen 19-9, cancer antigen 125, CEA, CD 40, CD 40 ligand, complement 3, CK-MB, EGF, ENA-78, endothelin-1, enrage, eotaxin, erythropoietin, Factor VII, FABP, ferritin, FGF-basic, fibrinogen, G-CSF, GST, GM-CSF, growth hormone, haptoglobin, ICAM-1, IFN-gamma, IgA, IgE, IGF-1, IgM, IL-Iα, IL-1β, IL-1ra, IL-2, IL-3, IL-4, IL-5, IL-6, IL-7, IL-8, IL-10, IL-12 p40, IL-12 p70, IL-13, IL-15, IL-16, insulin, leptin, lipoprotein (a), lymphotactin, MCP-1, MDC, MIP-1α, MIP-1β, MMP-2, MMP-3, MMP-9, myeloperoxidase, myoglobin, PAI-1, PAP, PAPP-A, SGOT, SHBG, PSA (free), RANTES, serum amyloid P, stem cell factor, TBG, thrombopoietin, TIMP-1, tissue factor, TNF-α, TNF-β, TNF RII, TSH, VCAM-1, VEGF, or vWF.

In some embodiments, the target molecule is an autoimmune related molecule such as ASCA, β-2 glycoprotein, C1q, centromere Prot. B, collagen type 1, collagen type 2, collagen type 4, collagen type 6, Cyto P450, ds DNA, histone, histone H1, histone H2A, histone H2B, histone H3, histone H4, HSC-70, HSP-32, HSP-65, HSP-71, HSP-90α, HSP-90β, insulin, JO-1, mitochondrial, myeloperoxidase, pancreatic islet cells, PCNA, PM-1, PR3, ribosomal P, RNP-A, RNP-C, RNP, Sel-70, Smith, SSA, SSB, T3, T4, thyroglobulin, tTG, (celiac disease), or thyroid microsomal.

In some embodiments, the target molecule is a component isolated from an infectious agent, such as Cholera Toxin, Cholera Toxin β, *Campylobacter jejuni*, cytomegalovirus, Diptheria toxin, Epstein-Barr NA, Epstein-Barr EA, Epstein-Barr VCA, *Heliobacter pylori*, HBV core, HBV envelope, HBV surface (Ad), HBV surface (Ay), HCV core, HCV NS3, HCV NS4, HCV NS5, hepatitis A, hepatitis D, HEV orf2 3 KD, HEV orf2 6 KD, HEV orf3 KD, HIV-1 p24, HIV-1 gp41, HIV-1 gp120, HPV, HSV-1/2, HSV-1 gD, HSV-2 gD, HTLV-1/2, influenza A, influenza A H3N2, influenza B, *Leishmania donorani*, Lyme disease, mumps, *M. pneumonia, M. tuberculosis*, parainfluenza 1, parainfluenza 2, parainfluenza 3, polio virus, RSV, Rubella, Rubeola, Streptolysin 0, Tetanus Toxin, *T. pallidum* 15 kD, *T. pallidum* p4'7, *T. cruzi*, Toxoplasma, *Varicella zoster.*

Nanoreporter Populations

The present invention provides nanoreporter or nanoreporter label unit populations, for example nanoreporter or nanoreporter label unit libraries, that contain at least 10, at least 15, at least 20, at least 25, at least 30, at least 40, at least 50, at least 75, at least 100, at least 200, at least 300, at least 400, at least 500, at least 750, or at least 1,000 unique nanoreporters or nanoreporter label units, respectively. As used herein, "unique" when used in reference to a nanoreporter or nanoreporter label units within a population is intended to mean a nanoreporter or label unit that has a code that distinguishes it from other nanoreporters or label units in the same population.

In specific embodiments, the present invention provides nanoreporter populations with at least 5,000, at least 10,000, at least 20,000 or at least 50,000 unique nanoreporters or nanoreporter label units.

The nanoreporters in a population of nanoreporters can be singular nanoreporters, dual nanoreporters, or a combination thereof. The nanoreporters can be labeled or unlabeled.

The size of a nanoreporter population and the nature of the target-specific sequences of the nanoreporters within it will depend on the intended use of the nanoreporter. Nanoreporter populations can be made in which the target-specific sequences correspond to markers of a given cell type, including a diseased cell type. In certain embodiments, nanoreporters populations are generated in which the target-specific sequences represent at least 0.1%, at least 0.25%, at least 0.5%, at least 1%, at least 2%, at least 3%, at least 4%, at least 5%, at least 10%, at least 15%, at least 20%, at least 25%, at least 30%, at least 40%, at least 50%, at least 60%, or at least 70% of the different type of transcripts in a cell. In certain embodiments, nanoreporters populations are generated in which the target-specific sequences represent at least 0.1%, at least 0.25%, at least 0.5%, at least 1%, at least 2%, at least 3%, at least 4%, at least 5%, at least 10%, at least 15%, at least 20%, at least 25%, at least 30%, at least 40%, at least 50%, at least 60%, or at least 70% of the different genes in a cell. In yet other embodiments, nanoreporter populations are generated in which at least some of the target-specific sequences represent rare transcripts in a cell or tissue. Such nanoreporter populations preferably represent at least 5 rare transcripts. In specific embodiments, such nanoreporter populations represent at least 10, at least 20, at least 30, at least 40 or at least 50 rare transcripts.

In a specific embodiment, the cell or tissue is a mammalian cell or tissue, and more preferably is a human cell or tissue.

In certain embodiments, the nanoreporter population is a diagnostic or prognostic nanoreporter populations. For example, a diagnostic nanoreporter population can be generated that is useful for screening blood products, in which the target-specific sequences bind to the nucleic acids of contaminating viruses such as hepatitis B, hepatitis C, and the human immunodeficiency virus. Alternatively, the diagnostic nanoreporter population may contain target-specific sequences corresponding to cellular disease markers, such as tumor antigens. Prognostic nanoreporter populations generally include target-specific markers that represent different stages of a given disease such as cancer. By selecting appropriate target-specific sequences, a nanoreporter population can be used both to diagnose and prognose disease.

Biomolecular Samples

The nanoreporter systems of the invention can be used to detect target molecule in any biomolecular sample. As will be appreciated by those in the art, the sample may comprise any number of things, including, but not limited to: cells (including both primary cells and cultured cell lines), cell lysates or extracts (including but not limited to RNA extracts; purified mRNA), tissues and tissue extracts (including but not limited to RNA extracts; purified mRNA); bodily fluids (including, but not limited to, blood, urine, serum, lymph, bile, cerebrospinal fluid, interstitial fluid, aqueous or vitreous humor, colostrum, sputum, amniotic fluid, saliva, anal and vaginal secretions, perspiration and semen, a transudate, an exudate (e.g., fluid obtained from an abscess or any other site of infection or inflammation) or fluid obtained from a joint (e.g., a normal joint or a joint affected by disease such as rheumatoid arthritis, osteoarthritis, gout or septic arthritis) of virtually any organism, with mammalian samples being preferred and human samples being particularly preferred; environmental samples (including, but not limited to, air, agricultural, water and soil samples); biological warfare agent samples; research samples including extracellular fluids, extracellular supernatants from cell cultures, inclusion bodies in bacteria, cellular compartments, cellular periplasm, mitochondria compartment, etc.

The biomolecular samples can be indirectly derived from biological specimens. For example, where the target molecule of interest is a cellular transcript, e.g., a messenger RNA, the biomolecular sample of the invention can be a sample containing cDNA produced by a reverse transcription of messenger RNA. In another example, the biomolecular sample of the invention is generated by subjecting a biological specimen to fractionation, e.g., size fractionation or membrane fractionation.

The biomolecular samples of the invention may be either "native," i.e., not subject to manipulation or treatment, or "treated," which can include any number of treatments, including exposure to candidate agents including drugs, genetic engineering (e.g., the addition or deletion of a gene), etc.

Separation of Label Monomers

In addition to detecting an overall signal generated from a labeled nanoreporter, the invention provides for the determination of the spatial location of signals emanating from the label monomers (i.e., spots) on a nanoreporter, each spot representing the aggregate signal from label monomers attached to a given label attachment region. A spot may contain signals of the same wavelength or of different wavelengths. Thus, the nature of the spots on a nanoreporter and their location constitutes the nanoreporter code. Any of a variety of means can be used to "stretch" the nanoreporter to separate the individual spots. For example, a nanoreporter can be stretched using a flowstretch technique (Henegariu et al., 2001, Biotechniques 31:246-250), a receding meniscus technique (Yokota et al., 1997, Nuc. Acids Res. 25:1064-1070) or an electrostretching technique (Matsuura et al., 2001, Nuc. Acids Res. 29: E79). The use of flow-stretching, receding meniscus, or electro-stretching techniques allows for the separation of the label attachment regions within a nanoreporter so that one can determine spatially where a particular signal is positioned in the nanoreporter. Therefore, unique nanoreporters that have the same combination of label monomers and the same overall signal can be differentiated from one another based on the location of those label monomers within the nanoreporter.

This ability to locate the position of a label attachment region or spot within a nanoreporter allows for the position of the signal(s) emitted by the label monomers in each label attachment region to be used as a distinguishing characteristic when generating a set of unique nanoreporters. Hence, a complex set of nanoreporters can be generated using the same combination of starting label monomers by varying the positions of the label monomers within a nanoreporter.

Prior to stretching a nanoreporter, it is preferable to immobilize the nanoreporter to a solid surface using an affinity tag, as described in Section 5.6 above.

In certain aspects of the invention, one end of a nanoreporter is immobilized, either through specific or non-specific binding to a solid surface, the nanoreporter is stretched, and then the other end of the reporter is immobilized, also either through specific or non-specific binding to a solid surface. Accordingly, the nanoreporter is "frozen" in its stretched, or extended, state, to facilitate resolution of the nanoreporters code by detecting and/or imaging the signals emitted by the label monomers attached to a nanoreporter and their locations relative to one another. These aspects of the invention are described below in Section 5.13.

Immobilization of Stretched Nanoreporters

The present invention provides methods and compositions that facilitate the identification of primary structures of a variety of nanoreporters. In certain aspects, the present invention provides methods for the selective immobilization of nanoreporters in an extended state. According to the invention, a nanoreporter can be selectively immobilized while fully extended under whatever force is used for the extension. In addition, the methods of the invention facilitate the selective immobilization of extended nanoreporters that are oriented with respect to each other. In other words, according to the methods of the invention, a plurality of nanoreporters can readily be immobilized in the same orientation with respect to each other.

In one aspect, the present invention provides methods for selectively immobilizing a nanoreporter in an extended state. For the methods of this aspect of the invention, generally, a first portion of the nanoreporter is immobilized by any technique known to those of skill in the art. Indeed, the technique for immobilizing the first portion of the nanoreporter is not critical to many embodiments of the invention. In certain embodiments, the first portion of the nanoreporter can be immobilized selectively or non-selectively. In certain embodiments the first portion is immobilized by one or more covalent bonds. In certain embodiments, the first portion is immobilized by one or more non-covalent bonds. Exemplary immobilized first portions are described in the sections below.

With an immobilized first portion, the nanoreporter can be extended by any technique for extending a nanoreporter apparent to those of skill in the art. In certain embodiments, the technique for extending the nanoreporter is not critical for the methods of the invention. In certain embodiments, the technique for extending the nanoreporter appropriate for the class of nanoreporter according to the judgment of one of skill in the art. In certain embodiments, the nanoreporter is extended by application of a force capable of extending the nanoreporter. The force can be any force apparent to one of skill in the art for extending the nanoreporter. Exemplary forces include gravity, hydrodynamic force, electromagnetic force and combinations thereof. Specific techniques for extending the nanoreporter are described in the sections below.

The nanoreporter is in an extended state if it would be recognized as extended by one of skill in the art. In certain embodiments, the nanoreporter is in an extended state when it is in the field of a force capable of extending the nanoreporter. In certain embodiments, the nanoreporter is in an extended state when its average hydrodynamic radius is more than double the average hydrodynamic radius of the nanoreporter in its native state as recognized by those of skill in the art.

In this aspect of the invention, the methods generally comprise the step of selectively immobilizing a second portion of the nanoreporter while it is in an extended state. This can result in an immobilized nanoreporter that is extended between the first and the second portion. Remarkably, since the nanoreporter is selectively immobilized while extended, that extension can be preserved in the immobilized nanoreporter. Generally, the first portion and the second portion of the nanoreporter are not the same.

The selective immobilization can be according to any technique for selective immobilization of a portion of a nanoreporter apparent to those of skill in the art. The selective immobilization can be through, for example, the formation of one or more covalent bonds or one or more non-covalent bonds, or both. Particular examples of selective immobilization techniques are described in the sections below. In particular embodiments, one or more binding pairs are used to immobilize the second portion of the nanoreporter.

The second portion can be immobilized onto any substrate apparent to those of skill in the art. The substrate can be any substrate judged to be useful for immobilization known to those of skill in the art. In certain embodiments, the second portion can be immobilized to another molecule. Further useful substrates include surfaces, membranes, beads, porous materials, electrodes, arrays and any other substrate apparent to those of skill in the art.

In another aspect, the present invention provides a composition comprising a selectively immobilized, extended nanoreporter. The compositions generally comprise a substrate and an extended nanoreporter selectively immobilized onto the substrate. The substrate can be any substrate known to those of skill in the art. Exemplary substrates include those described in the sections below. At least two portions of the nanoreporter are immobilized onto the substrate, and the nanoreporter is in an extended state between the two portions. In certain embodiments, at least one portion of the nanoreporter is selectively immobilized onto the substrate. In certain embodiments, two or more portions of the nanoreporter are selectively immobilized onto the substrate. The nanoreporter can be extended and/or immobilized by any technique apparent to those of skill, including particularly the methods of the present invention.

In another aspect, the present invention provides methods for selectively immobilizing a nanoreporter in an oriented state. The nanoreporter can be any nanoreporter described above. In certain embodiments, the nanoreporter can be flexible, or in certain embodiments the nanoreporter can be rigid or semi-rigid. For the methods of this aspect of the invention, generally, a first portion of the nanoreporter is immobilized as described above. With an immobilized first portion, the nanoreporter can be oriented by any technique for extending a nanoreporter apparent to those of skill in the art. In certain embodiments, the technique for orienting the nanoreporter is not critical for the methods of the invention. In certain embodiments, the technique for orienting the nanoreporter appropriate for the class of nanoreporter is determined according to the judgment of one of skill in the art. In certain embodiments, the nanoreporter is oriented by application of a force capable of orienting the nanoreporter. The force can be any force apparent to one of skill in the art for orienting the nanoreporter. Exemplary forces include gravity, hydrodynamic force, electromagnetic force and combinations thereof. Specific techniques for extending the nanoreporter are described in the subsections below.

The nanoreporter is in an oriented state if it would be recognized as oriented by one of skill in the art. In certain embodiments, the nanoreporter is in an oriented state when it is in the field of a force capable of orienting the nanoreporter. In certain embodiments, the nanoreporter is in an oriented state when its termini are arranged in parallel, as recognized by those of skill in the art, with the field of a force capable of orienting the nanoreporter. In certain embodiments, a plurality of nanoreporters is in an oriented state when the termini of the nanoreporters are arranged in parallel, as recognized by those of skill in the art.

In this aspect of the invention, the methods generally comprise the step of selectively immobilizing a second portion of the nanoreporter while it is in an oriented state. This can result in an immobilized nanoreporter that is oriented between the first and the second portion. Remarkably, since the nanoreporter is selectively immobilized while extended, that orientation can be preserved in the immobilized nanoreporter. The selective immobilization can according to the methods described above.

In another aspect, the present invention provides a composition comprising a selectively immobilized, oriented nanoreporter. The compositions generally comprise a substrate and an oriented nanoreporter selectively immobilized onto the substrate. The substrate can be any substrate known to those of skill in the art. Exemplary substrates include those described in the sections below. At least two portions of the nanoreporter are immobilized onto the substrate, and the nanoreporter is in an oriented state between the two portions. In certain embodiments, at least one portion of the nanoreporter is selectively immobilized onto the substrate. In certain embodiments, both portions of the nanoreporter are selectively immobilized onto the substrate. The nanoreporter can be oriented and/or immobilized by any technique apparent to those of skill, including particularly the methods of the present invention.

The methods and compositions of the present invention can be used for any purpose apparent to those of skill in the art. For instance, the immobilized and extended and/or oriented nanoreporter can be used as a label for a substrate on which the nanoreporter is immobilized. The primary sequence of the immobilized and extended and/or oriented nanoreporter can be identified by any technique apparent to those of skill.

Advantageously, immobilization of the extended and/or oriented nanoreporter can facilitate such techniques. In certain embodiments, the immobilized and extended and/or oriented nanoreporter can be used to guide the manufacture of nanopaths, for example to create nanowires or nanocircuts. Further uses for the immobilized and extended and/or oriented nanoreporters are described in the sections below.

All terms used herein have their ordinary meanings to those of skill in the art unless indicated otherwise. The following terms shall have the following meanings.

As used herein, the term "binding pair" refers to first and second molecules or moieties that are capable of selectively binding to each other, i.e., binding to each other with greater affinity than to other components in a composition. The binding between the members of the binding pair can be covalent or non-covalent. In certain embodiments, the binding is non-covalent. Exemplary binding pairs include immunological binding pairs (e.g., any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone-hormone binding protein, receptor-receptor ligand (e.g., acetylcholine receptor-acetylcholine or an analog thereof), IgG-protein A, lectin-carbohydrate, enzyme-enzyme cofactor, enzyme-enzyme inhibitor, complementary polynucleotide pairs capable of forming nucleic acid duplexes, and the like). For instance, immunoreactive binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other binding members. Other common binding pairs include but are not limited to, biotin and avidin (or derivatives thereof), biotin and streptavidin, carbohydrates and lectins, complementary nucleotide sequences (including probe and capture nucleic acid sequences), complementary peptide sequences including those formed by recombinant methods, effector and receptor molecules, hormone and hormone binding protein, enzyme cofactors and enzymes, enzyme inhibitors and enzymes, and so forth.

"Selective binding" refers to the preferential binding of a pair of molecules or moieties for each other with respect to other molecules or moieties in a composition that would be recognized by one of skill in the art. In certain embodiments, a pair of molecules or moieties selectively binds when they preferentially bind each other compared to other molecules or moieties. Selective binding can include affinity or avidity, or both, of one molecule or moiety for another molecule or moiety. In particular embodiments, selective binding requires a dissociation constant ($K_D$) of less than about $1\times10^{-5}$ M or less than about $1\times10^{-6}$ M, $1\times10^{-7}$ M, $1\times10^{-8}$ M, $1\times10^{-9}$ M, or $1\times10^{-10}$ M. In contrast, in certain embodiments, non-selective binding has significantly less affinity, for example, a $K_D$ greater than $1\times10^{-3}$ M.

"Extended state" refers to a nanoreporter in a state that would be recognized as extended by one of skill in the art. In certain embodiments, a nanoreporter is in an extended state when it is extended relative to its native conformation in solution. In certain embodiments, a nanoreporter is in an extended state when it is in the field of a force capable of extending the nanoreporter. In certain embodiments, an extended state of a nanoreporter can be determined quantitatively. In such embodiments, those of skill in the art will recognize R as the end-to-end vector of the nanoreporter, i.e., the distance between two termini of the nanoreporter, and <R> as the average end-to-end vector such that 95% of R will be within 2<R> in a solution deemed appropriate to one of skill in the art. Exemplary solutions include, for example, a dilute solution of the nanoreporter in water or in a pH buffer. In particular embodiments, a nanoreporter is in an extended state when R is greater than 2.0<R>.

"Oriented state" refers to a nanoreporter in a state that would be recognized as oriented by one of skill in the art. In certain embodiments, a nanoreporter is in an oriented state when it is oriented relative to its native conformation in solution. In certain embodiments, the nanoreporter is oriented when it is arranged in parallel with the field of a force capable of orienting the nanoreporter. In certain embodiments, the nanoreporter is oriented when it is one of a plurality of nanoreporters that are arranged in parallel, as recognized by those of skill in the art.

Methods of Selective Immobilization

As described above, the present invention provides methods for the selective immobilization of a nanoreporter in an extended state. The nanoreporter, once selectively immobilized, can be used for any purpose apparent to those of skill in the art.

In certain embodiments, the nanoreporter is any polymer known to those of skill in the art. For instance, the nanoreporter can be a polysaccharide, a polypeptide or a polynucleotide. Useful polynucleotides include ribonucleic acids, deoxyribonucleic acids and other polynucleotides known to those of skill in the art.

The nanoreporter can be of any size that is sufficient to allow extension and immobilization of the nanoreporter according to the methods of the invention. In certain embodiments when the nanoreporter is a polynucleotide, the nanoreporter can have a length of greater than 500 bp, greater than 750 bp, greater than 1 kb, greater than 1.5 kb, greater than 2.0 kb, greater than 2.5 kb, greater than 3.0 kb, greater than 4.0 kb or greater than 5.0 kb. In certain embodiments, when the nanoreporter is a polypeptide, the nanoreporter can have a size of greater than 50 amino acids, greater than 100 amino acids, greater than 200 amino acids, greater than 300 amino acids, greater than 400 amino acids, greater than 500 amino acids, greater than 750 amino acids, greater than 1000 amino acids, greater than 1500 amino acids, greater than 2000 amino acids, greater than 2500 amino acids, greater than 3000 amino acids, greater than 4000 amino acids or greater than 5000 amino acids. In certain embodiments, when the nanoreporter is a polysaccharide, the nanoreporter can have a size of greater than 50 saccharides, greater than 100 saccharides, greater than 200 saccharides, greater than 300 saccharides, greater than 400 saccharides, greater than 500 saccharides, greater than 750 saccharides, greater than 1000 saccharides, greater than 1500 saccharides, greater than 2000 saccharides, greater than 2500 saccharides, greater than 3000 saccharides, greater than 4000 saccharides or greater than 5000 saccharides.

The nanoreporter can be a native nanoreporter as understood by those of skill in the art, or the nanoreporter can be a non-native nanoreporter. In certain embodiments, when the nanoreporter is a polypeptide, the nanoreporter can comprise only naturally occurring amino acids, or the nanoreporter can comprise naturally occurring amino acids and non-naturally occurring amino acids. The other amino acids can be any amino acids, or derivatives or analogs thereof, known to those of skill in the art. In certain embodiments, when the nanoreporter is a polynucleotide, the polynucleotide can comprise only naturally occurring nucleotides, or the polynucleotide can comprise naturally occurring nucleotides and non-naturally occurring nucleotides. In certain embodiments, when the nanoreporter is a polysaccharide, the polysaccharide can comprise only naturally occurring saccharides, or the polysaccharide can comprise naturally occurring saccharides and non-naturally occurring saccharides. In certain embodiments, the polymers can comprise only non-natural monomers. In further embodiments, the nanoreporter can comprise a plurality of classes of monomers, such as amino acids, nucleotides and/or saccharides.

Figure 13A:
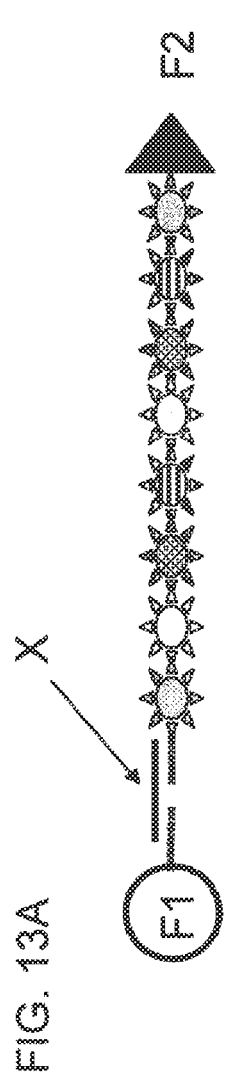
FIG. 13A-13C.

In certain embodiments, the nanoreporter comprises only one primary, covalently linked chain of monomers. For instance, when the nanoreporter is a polypeptide, in certain embodiments, the nanoreporter comprises only one primary amino acid chain. When the nanoreporter is a polynucleotide, in certain embodiments, the nanoreporter is single stranded. In further embodiments, the nanoreporter comprises two primary, covalently linked chains of monomers. For instance, when the nanoreporter is a polypeptide, in certain embodiments, the nanoreporter comprises two primary amino acid chains. When the nanoreporter is a polynucleotide, in certain embodiments, the nanoreporter comprises two polynucleotide strands; in certain embodiments, the nanoreporter can be double stranded, in part or in whole. In further embodiments, the nanoreporter comprises three or more primary, covalently linked chains of monomers. For instance, when the nanoreporter is a polypeptide, in certain embodiments, the nanoreporter comprises three primary amino acid chains. When the nanoreporter is a polynucleotide, in certain embodiments, the nanoreporter comprises three polynucleotide strands. For instance, the nanoreporter can comprise three strands F1, X and F2 where a portion of strand X is complementary to strand F1 and a portion of strand X is complementary to strand F2. An example is illustrated in FIG. 13A. In certain embodiments, the nanoreporter comprises more than three primary, covalently linked chains of monomers.

Advantageously, a nanoreporter of the invention can comprise one or more labels that facilitate the detection, imaging or identification of the nanoreporter by techniques known to those of skill in the art. The label can be any detectable moiety known to those of skill in the art. Exemplary labels for nanoreporters include detectable isotopes, radioisotopes, fluors, dyes, enzymes, ligands, receptors, antigens, antibodies, lectins, carbohydrates, nucleotide sequences, and any other detectable label apparent to those of skill in the art.

In certain embodiments, a polynucleotide is a polymer of natural (e.g., A, G, C, T, U) or synthetic nucleobases, or a combination of both. The backbone of the polynucleotide can be composed entirely of "native" phosphodiester linkages, or it may contain one or more modified linkages, such as one or more phosphorothioate, phosphorodithioate, phosphoramidate or other modified linkages. As a specific example, a polynucleotide may be a peptide nucleic acid (PNA), which contains amide interlinkages. Additional examples of synthetic bases and backbones that can be used in conjunction with the invention, as well as methods for their synthesis can be found, for example, in U.S. Pat. No. 6,001,983; Uhlman & Peyman, 1990, *Chemical Review* 90(4):544-584; Goodchild, 1990, *Bioconjugate Chem.* 1(3):165-186; Egholm et al., 1992, *J. Am. Chem. Soc.* 114:1895-1897; Gryaznov et al., *J. Am. Chem. Soc.* 116:3143-3144, as well as the references cited in all of the above. Common synthetic nucleobases of which polynucleotides may be composed include 3-methlyuracil, 5,6-dihydrouracil, 4 thiouracil, 5 bromouracil, 5-thorouracil, 5-iodouracil, 6-dimethyl aminopurine, 6-methyl aminopurine, 2-aminopurine, 2,6-diamino purine, 6-amino-8-bromopurine, inosine, 5-methylcytosine, 7-deazaadenine, and 7-deazaguanosine. Additional non-limiting examples of synthetic nucleobases of which the target nucleic acid may be composed can be found in Fasman, *CRC Practical Handbook of Biochemistry and Molecular Biology*, 1985, pp. 385-392; *Beilstein's Handbuch der Organischen Chemie*, Springer Verlag, Berlin and Chemical Abstracts, all of which provide references to publications describing the structures, properties and preparation of such nucleobases.

The nanoreporter can be prepared according to any technique apparent to those of skill in the art. Advantageously, nanoreporters according to the invention can comprise labels and/or members of binding pairs, as described in the sections below, that can be used to facilitate preparation and/or purification of the nanoreporter. In addition, certain nanoreporters of the invention are capable of forming complexes with molecules that comprise members of binding pairs, as described below. These complexes can be used to facilitate preparation and/or purification of the nanoreporter or complex.

Immobilization of First Portion

In the methods of the invention, a first portion of the nanoreporter is immobilized.

Generally, the first portion is immobilized if it would be recognized as immobilized by one of skill in the art. The first portion can be immobilized by any technique apparent to those of skill in the art. In certain embodiments, the technique for immobilization of the first portion of the nanoreporter is not critical for the methods of the invention.

The first portion of the nanoreporter can be at any location in the nanoreporter. In certain embodiments, the first portion is at a terminus of the nanoreporter. For the purposes of the invention, a portion of a nanoreporter can be "at a terminus" when it is less than five, four, three, two, one or zero monomers from a terminus of the nanoreporter. Of course, although many nanoreporters have two termini, the methods of the invention are applicable to nanoreporters having more than two termini and to nanoreporters having one or zero termini, e.g., circular nanoreporters. In certain embodiments, the first portion is not at a terminus of the nanoreporter.

The nanoreporter can be immobilized onto any substrate apparent to those of skill in the art. The substrate can be any moiety to which the nanoreporter can be immobilized without limitation. In certain embodiments, the substrate is a surface, membrane, bead, porous material, electrode or array.

In certain embodiments, the first portion of the nanoreporter can be immobilized non-selectively. In further embodiments, the first portion of the nanoreporter can be immobilized selectively. In advantageous embodiments, after the first portion of the nanoreporter is immobilized, some portion of the nanoreporter should be free to move sufficiently so that the nanoreporter can be extended in the following steps of the method. In particular, in certain embodiments, when the first portion of the nanoreporter is immobilized non-selectively, it is important that the entire nanoreporter not be immobilized non-selectively to an extent that prevents extension of any portion of the nanoreporter.

The immobilization can be by any interaction with the substrate apparent to those of skill in the art. The immobilization can be via electrostatic or ionic interaction, via one or more covalent bonds, via one or more non-covalent bonds or combinations thereof. In certain embodiments, the immobilization can be via electrostatic interaction with an electrode. In further embodiments, the immobilization is via electrostatic interaction with a substrate other than the electrode.

In certain embodiments, the first portion of the nanoreporter comprises a first member of a binding pair. The first member of the binding pair can be covalently bound to the first portion of the nanoreporter, or they can be non-covalently bound. Useful covalent bonds and non-covalent bonds will be apparent to those of skill in the art. In useful embodiments, the substrate onto which the first portion of the nanoreporter is bound will comprise a second member of the binding pair. The substrate can be covalently bound to the second member, or they can be non-covalently bound. FIG. 12A illustrates a nanoreporter that comprises a moiety F1 that is capable of selectively binding a moiety of the substrate. Moiety F1 can be, for example, biotin, capable of binding, for example, a substrate coated with avidin.

In certain embodiments, the first portion of the nanoreporter can comprise a member of a binding pair that is capable of binding with a member of a binding pair on the substrate to form one or more non-covalent bonds. Exemplary useful substrates include those that comprise a binding moiety selected from the group consisting of ligands, antigens, carbohydrates, nucleic acids, receptors, lectins, and antibodies. The first portion of the nanoreporter would comprise a binding moiety capable of binding with the binding moiety of the substrate. Exemplary useful substrates comprising reactive moieties include, but are not limited to, surfaces comprising epoxy, aldehyde, gold, hydrazide, sulfhydryl, NHS-ester, amine, thiol, carboxylate, maleimide, hydroxymethyl phosphine, imidoester, isocyanate, hydroxyl, pentafluorophenyl-ester, psoralen, pyridyl disulfide or vinyl sulfone, or mixtures thereof. Such surfaces can be obtained from commercial sources or prepared according to standard techniques.

In advantageous embodiments, the first portion of the nanoreporter can be immobilized to the substrate via an avidin-biotin binding pair. In certain embodiments, the nanoreporter can comprise a biotin moiety in its first portion. For instance, a polynucleotide nanoreporter can comprise a biotinylated nucleotide residue. Similarly, a polypeptide nanoreporter can comprise a biotinylated amino acid residue. The substrate comprising avidin can be any substrate comprising avidin known to those of skill in the art. Useful substrates comprising avidin are commercially available including TB0200 (Accelr8), SAD6, SAD20, SAD100, SAD500, SAD2000 (Xantec), SuperAvidin (Array-It), streptavidin slide (catalog #MPC 000, Xenopore) and STREPTAVIDINnslide (catalog #439003, Greiner Bio-one).

In certain embodiments, the first portion of the nanoreporter can comprise a nucleotide sequence that is capable of selectively binding a nucleotide sequence on the substrate.

In further embodiments, the first portion of the nanoreporter can comprise avidin, and the substrate can comprise biotin. Useful substrates comprising biotin are commercially available including Optiarray-biotin (Accelr8), BD6, BD20, BD100, BD500 and BD2000 (Xantec).

In further embodiments, the first portion of the nanoreporter is capable of forming a complex with one or more other molecules that, in turn, are capable of binding, covalently or non-covalently, a binding moiety of the substrate. For instance, a first portion of the nanoreporter can be capable of selectively binding another molecule that comprises, for instance, a biotin moiety that is capable of selectively binding, for instance, an avidin moiety of the substrate. FIG. 13A illustrates a nanoreporter that is capable of selectively binding a second molecule X that is capable of selectively binding a third molecule that comprises F1. F1 is capable of selectively binding a moiety on a substrate.

Figure 13B:
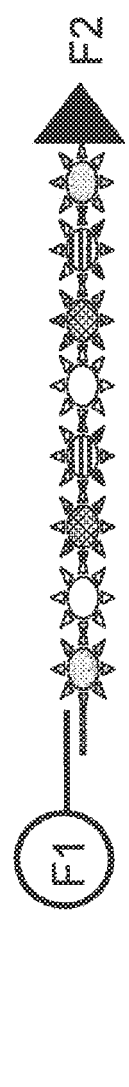
Figure 13C:
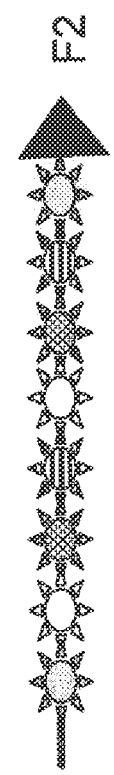

FIG. 13B illustrates a nanoreporter that is capable of selectively binding a second molecule that comprises F1, and F1 is capable of selectively binding a moiety on a substrate.

In further embodiments, the first portion of the nanoreporter can comprise a member of a binding pair that is capable of reacting with a member of a binding pair on the substrate to form one or more covalent bonds. Exemplary useful substrates comprising reactive groups include those that comprise a reactive moiety selected from the group consisting of succinamides, amines, aldehydes, epoxies and thiols. The first portion of the nanoreporter would comprise a reactive moiety capable of reacting with the reactive moiety of the substrate. Exemplary useful substrates comprising reactive moieties include, but are not limited to, OptArray-DNA NHS group (Accelr8), Nexterion Slide AL (Schott) and Nexterion Slide E (Schott).

In certain embodiments, the first portion of the nanoreporter can comprise a reactive moiety that is capable of being bound to the substrate by photoactivation. The substrate could comprise the photoreactive moiety, or the first portion of the nanoreporter could comprise the photoreactive moiety. Some examples of photoreactive moieties include aryl azides, such as N-((2-pyridyldithio)ethyl)-4-azidosalicylamide; fluorinated aryl azides, such as 4-azido-2,3,5,6-tetrafluorobenzoic acid; benzophenone-based reagents, such as the succinimidyl ester of 4-benzoylbenzoic acid; and 5-Bromo-deoxyuridine.

In further embodiments, the first portion of the nanoreporter can be immobilized to the substrate via other binding pairs apparent to those of skill in the art.

Extension of the Nanoreporter

In certain methods of the invention, the nanoreporter is in an extended state. Generally, any nanoreporter is in an extended state if it would be recognized as such by one of skill in the art.

In certain embodiments, the nanoreporter is in an extended state when it is in the field of a force capable of extending the nanoreporter under conditions suitable for extending the nanoreporter. Such forces and conditions should be apparent to those of skill in the art. For instance, many nanoreporters can be extended by hydrodynamic force or by gravity, and many charged nanoreporters can be extended by electromagnetic force. In certain embodiments, the force can be applied to the nanoreporter indirectly. For instance, the nanoreporter can comprise or can be linked, covalently or noncovalently, to a moiety capable of being moved by a force. In certain embodiments, the nanoreporter can be linked to a moiety.

In certain embodiments, the force is an electromagnetic force. For instance, when the nanoreporter is charged, such as a polynucleotide, the nanoreporter can be extended in an electric or magnetic field. The field should be strong enough to extend the nanoreporter according to the judgment of one of skill in the art. Exemplary techniques for extending a nanoreporter in an electric or magnetic field are described in Matsuura et al., 2002, *J Biomol Struct Dyn.* 20(3):429-36; Ferree & Blanch, 2003, *Biophys J.* 85(4):2539-46; Stigter & Bustamante, 1998, *Biophys J.* 1998 75(3):1197-210; Matsuura et al., 2001, *Nucleic Acids Res.* 29(16); Ferree & Blanch, 2004, *Biophys* 187(1):468-75; the contents of which are hereby incorporated by reference in their entirety.

In certain embodiments, the force is a hydrodynamic force. For instance, many nanoreporters, including polysaccharides, polypeptides, and polynucleotides, can be extended in the field of a moving fluid. The hydrodynamic force should be strong enough to extend the nanoreporter according to the judgment of one of skill in the art. Exemplary techniques for extending a nanoreporter in a hydrodynamic field are described in Bensimon et al., 1994, *Science* 265:2096-2098; Henegariu et al., 2001, *BioTechniques* 31:246-250; Kraus et al., 1997, *Human Genetics* 99:374-380; Michalet et al., 1997, *Science* 277:1518-1523; Yokota et al., 1997, *Nucleic Acids Res.* 25(5):1064-70; Otobe et al., 2001, *Nucleic Acids Research* 29:109; Zimmerman & Cox, 1994, *Nucleic Acids Res.* 22(3):492-7, and U.S. Pat. Nos. 6,548,255; 6,344,319; 6,303,296; 6,265,153; 6,225,055; 6,054,327; and 5,840,862, the contents of which are hereby incorporated by reference in their entirety.

In certain embodiments, the force is gravity. In advantageous embodiments, the force of gravity can be combined with, for example, hydrodynamic force to extend the nanoreporter. In certain embodiments, the force should be strong enough to extend the nanoreporter according to the judgment of one of skill in the art. Exemplary techniques for extending a nanoreporter with gravity are described in Michalet et al., 1997, *Science* 277:1518-1523; Yokota et al., 1997, *Nucleic Acids Res.* 25(5):1064-70; Kraus et al., 1997, *Human Genetics* 99:374-380, the contents of which are hereby incorporated by reference in their entirety.

In particular embodiments, the force is applied through a moving meniscus. Those of skill in the art will recognize that a moving meniscus can apply various forces to a nanoreporter including hydrodynamic force, surface tension and any other force recognized by those of skill in the art. The meniscus can be moved by any technique apparent to those of skill in the art including evaporation and gravity. Exemplary techniques for extending a nanoreporter with a moving meniscus are described in, for example, U.S. Pat. Nos. 6,548,255; 6,344, 319; 6,303,296; 6,265,153; 6,225,055; 6,054,327; and 5,840, 862, the contents of which are hereby incorporated by reference in their entireties.

In particular embodiments, the nanoreporter can be extended by an optical trap or optical tweezers. For instance, the nanoreporter can comprise or can be linked, covalently or noncovalently, to a particle capable of being trapped or moved by an appropriate source of optical force. Useful techniques for moving particles with optical traps or optical tweezers are described in Ashkin et al., 1986, *Optics Letters* 11:288-290; Ashkin et al., 1987, *Science* 235:1517-1520; Ashkin et al., *Nature* 330:769-771; Perkins et al., 1994, *Science* 264:822-826; Simmons et al., 1996, *Biophysical Jour-* nal 70:1813-1822; Block et al., 1990, *Nature* 348:348-352; and Grier, 2003, *Nature* 424:810-816; the contents of which are hereby incorporated by reference in their entireties.

In certain embodiments, the nanoreporter can be extended by combinations of the above forces that are apparent to those of skill in the art. In the examples, below, certain nanoreporters are extended by a combination of an electric field and hydrodynamic force.

The nanoreporter is extended when it would be recognized as extended by one of skill in the art according to standard criteria for extension of a nanoreporter. In certain embodiments, the nanoreporter is extended when it loses most of its tertiary structural features as recognized by those of skill in the art. In certain embodiments, the nanoreporter is extended when it loses most of its secondary structural features as recognized by those of skill in the art. In certain embodiments, the nanoreporter is extended when its primary structural features are detectable in sequence when imaged according to standard techniques. Exemplary imaging techniques are described in the examples below.

In certain embodiments, an extended state of a nanoreporter can be recognized by comparing its hydrodynamic radius to its average hydrodynamic radius when free in dilute solution. For instance, in certain embodiments, a nanoreporter, or portion thereof, is extended when its hydrodynamic radius is more than about double its average hydrodynamic radius in dilute solution. More quantitatively, R represents the hydrodynamic radius of the nanoreporter, or portion thereof, and <R> represents the average hydrodynamic radius of the nanoreporter, or portion thereof, in dilute solution. The average <R> should be calculated such that R for the nanoreporter, or portion thereof, when unbound in dilute solution is less than 2<R>95% of the time. In certain embodiments, a nanoreporter, or portion thereof, is in an extended state when R is greater than 1.5<R>, greater than 1.6<R>, greater than 1.7<R>, greater than 1.8<R>, greater than 1.9<R>, greater than 2.0<R>, greater than 2.1<R>, greater than 2.2<R>, greater than 2.3<R>, greater than 2.4<R>, greater than 2.5<R> or greater than 3.0<R>. In particular embodiments, a nanoreporter, or portion thereof, is in an extended state when R is greater than 2.0<R>.

Orientation of the Nanoreporter

In certain methods of the invention, the nanoreporter is in an oriented state. Generally, any nanoreporter is in an oriented state if it would be recognized as such by one of skill in the art.

In certain embodiments, the nanoreporter is in an oriented state when it is in the field of a force capable of orienting the nanoreporter under conditions suitable for orienting the nanoreporter. Such forces and conditions should be apparent to those of skill in the art.

In certain embodiments, the force is an electromagnetic force. For instance, when the nanoreporter is charged, such as a polynucleotide, the nanoreporter can be oriented in an electric or magnetic field. The field should be strong enough to orient the nanoreporter according to the judgment of one of skill in the art. Exemplary techniques for orienting a nanoreporter in an electric or magnetic field are described above.

In certain embodiments, the force is a hydrodynamic force. For instance, many nanoreporters, including polysaccharides, polypeptides, and polynucleotides, can be oriented in the field of a moving fluid. The hydrodynamic force should be strong enough to orient the nanoreporter according to the judgment of one of skill in the art. Exemplary techniques for orienting a nanoreporter in hydrodynamic field are described above.

In certain embodiments, the force is gravity. In advantageous embodiments, the force of gravity can be combined with, for example, hydrodynamic force to orient the nanoreporter. In certain embodiments, the force should be strong enough to orient the nanoreporter according to the judgment of one of skill in the art. Exemplary techniques for orienting a nanoreporter with gravity are described above.

In certain embodiments, the nanoreporter can be oriented by combinations of the above forces that are apparent to those of skill in the art. In the examples, below, certain nanoreporters are oriented by a combination of an electric field and hydrodynamic force.

The nanoreporter is oriented when it would be recognized as oriented by one of skill in the art according to standard criteria for orientation of a nanoreporter. In certain embodiments, the nanoreporter is oriented when it is arranged in parallel, as recognized by those of skill in the art, with the field of a force capable of orienting the nanoreporter. In certain embodiments, the nanoreporter is oriented when it is one of a plurality of nanoreporters that are arranged in parallel, as recognized by those of skill in the art. For instance, a plurality of nanoreporters can be oriented when the vector from a first terminus to a second terminus of a nanoreporter is parallel, as recognized by those of skill in the art, to the vectors between corresponding termini of other nanoreporters in the plurality.

Selective Immobilization of Second Portion of Nanoreporter

As discussed above, in the methods of the invention, a second portion of the nanoreporter is selectively immobilized. The second portion of the nanoreporter can be any portion of the nanoreporter that is not identical to the first portion of the nanoreporter.

In some embodiments, the second portion of the nanoreporter does not overlap any part of the first portion of the nanoreporter.

In certain embodiments, the present invention provides methods that comprise the single step of selectively immobilizing a second portion of a nanoreporter while the nanoreporter is in an extended or oriented state, and while a first portion of the nanoreporter is immobilized. Exemplary methods for immobilization of the first portion of the nanoreporter, and for extension or orientation of the nanoreporter are described in detail in the sections above.

In certain embodiments, the present invention provides methods that comprise the step of extending a nanoreporter, while a first portion of the nanoreporter is immobilized, and the step of selectively immobilizing a second portion of a nanoreporter while the nanoreporter is in an extended state. Exemplary methods for immobilization of the first portion of the nanoreporter, and for extension of the nanoreporter are described in detail in the sections above.

In certain embodiments, the present invention provides methods that comprise the step of immobilizing a first portion of a nanoreporter, the step of extending the nanoreporter while the first portion is immobilized and the step of selectively immobilizing a second portion of a nanoreporter while the nanoreporter is in an extended state. Exemplary methods for immobilization of the first portion of the nanoreporter, and for extension of the nanoreporter are described in detail above.

In certain embodiments, the present invention provides methods that comprise the step of orienting a nanoreporter, while a first portion of the nanoreporter is immobilized, and the step of selectively immobilizing a second portion of a nanoreporter while the nanoreporter is in an oriented state. Exemplary methods for immobilization of the first portion of the nanoreporter, and for orienting the nanoreporter are described in detail in the sections above.

In certain embodiments, the present invention provides methods that comprise the step of immobilizing a first portion of a nanoreporter, the step of orienting the nanoreporter while the first portion is immobilized and the step of selectively immobilizing a second portion of a nanoreporter while the nanoreporter is in an oriented state. Exemplary methods for immobilization of the first portion of the nanoreporter, and for orienting the nanoreporter are described in detail above.

The selective immobilization of the second portion of the nanoreporter can follow any technique for selective immobilization of a nanoreporter apparent to those of skill in the art. Significantly, in advantageous embodiments of the invention, the second portion of the nanoreporter is not immobilized non-selectively. Selective immobilization can allow the nanoreporter to be immobilized while in a fully extended state or nearly fully extended state. Selective immobilization can also allow the nanoreporter to be immobilized in an oriented manner. In other words, the first portion and second portion of the nanoreporter can be immobilized along the direction of the field or fields used to extend the nanoreporter, with the first portion preceding the second portion in the field. When a plurality of nanoreporters are immobilized, the plurality can be uniformly oriented along the field.

The second portion of the nanoreporter can be at any location in the nanoreporter. In certain embodiments, the second portion is at a terminus of the nanoreporter. In certain embodiments, the second portion is not at a terminus of the nanoreporter. In certain embodiments, the first portion, described in the sections above, is at one terminus of the nanoreporter, and the second portion is at another terminus of the nanoreporter.

As discussed above, the second portion of the nanoreporter is immobilized selectively. The immobilization can be by any selective interaction with the substrate apparent to those of skill in the art. The immobilization can be via electrostatic or ionic interaction, via one or more covalent bonds, via one or more non-covalent bonds or combinations thereof. In certain embodiments, the immobilization can be via electrostatic interaction with an electrode. In further embodiments, the immobilization is via electrostatic interaction with a substrate other than the electrode.

If the first portion and the second portion of the nanoreporter are selectively immobilized to the same substrate, the techniques of selective immobilization should of course be compatible with the substrate. In particular embodiments, the techniques of immobilization are the same. For instance, on a substrate coated with avidin, both the first and second portion of the nanoreporter can be immobilized selectively via biotin-avidin interactions. However, as will be apparent to those of skill in the art, the same interaction need not be used at both the first and second portions for immobilization on the same substrate. For instance, the substrate can comprise multiple moieties capable of selective binding, or the first portion can be immobilized non-selectively, or other techniques apparent to those of skill in the art.

In certain embodiments, the second portion of the nanoreporter comprises a first member of a binding pair. The second member of the binding pair can be covalently bound to the second portion of the nanoreporter, or they can be non-covalently bound. Useful covalent bonds and non-covalent bonds will be apparent to those of skill in the art.

In useful embodiments, the substrate onto which the second portion of the nanoreporter is bound will comprise a second member of the binding pair. The substrate can be covalently bound to the second member, or they can be non-covalently bound.

In certain embodiments, the second portion of the nanoreporter can comprise a member of a binding pair that is capable of binding with a member of a binding pair on the substrate to form one or more non-covalent bonds. Exemplary useful substrates include those that comprise a binding moiety selected from the group consisting of ligands, antigens, carbohydrates, nucleic acids, receptors, lectins, and antibodies such as those described in the sections above.

In advantageous embodiments, the second portion of the nanoreporter can be immobilized to the substrate via an avidin-biotin binding pair. In certain embodiments, the nanoreporter can comprise a biotin moiety in its first portion. For instance, a polynucleotide nanoreporter can comprise a biotinylated nucleotide residue. Similarly, a polypeptide nanoreporter can comprise a biotinylated amino acid residue. Useful substrates comprising avidin are described in the sections above.

In further embodiments, the second portion of the nanoreporter can comprise avidin, and the substrate can comprise biotin. Useful substrates comprising biotin are described in the sections above.

In further embodiments, the second portion of the nanoreporter can comprise a member of a binding pair that is capable of reacting with a member of a binding pair on the substrate to form one or more covalent bonds. Exemplary useful substrates comprising reactive groups are described in the sections above.

In certain embodiments, the second portion of the nanoreporter can comprise a reactive moiety that is capable of being bound to the substrate by photoactivation. The substrate could comprise the photoreactive moiety, or the second portion of the nanoreporter could comprise the photoreactive moiety. Some examples of photoreactive moieties include aryl azides, such as N-((2-pyridyldithio)ethyl)-4-azidosalicylamide; fluorinated aryl azides, such as 4-azido-2,3,5,6-tetrafluorobenzoic acid; benzophenone-based reagents, such as the succinimidyl ester of 4-benzoylbenzoic acid; and 5-Bromo-deoxyuridine.

In further embodiments, the second portion of the nanoreporter can be immobilized to the substrate via other binding pairs described in the sections above.

In further embodiments, the second portion of the nanoreporter is capable of forming a complex with one or more other molecules that, in turn, are capable of binding, covalently or non-covalently, a binding moiety of the substrate. For instance, the second portion of the nanoreporter can be capable of selectively binding another molecule that comprises, for instance, a biotin moiety that is capable of selectively binding, for instance, an avidin moiety of the substrate. FIG. 12B illustrates a nanoreporter of selectively binding a second molecule that comprises F3 that is, in turn, capable of selectively binding a moiety on a substrate. The interaction between the second portion of the nanoreporter and the molecule that comprises F3 can be mediated, for example, by an antigen-antibody interaction.

Figure 14C:
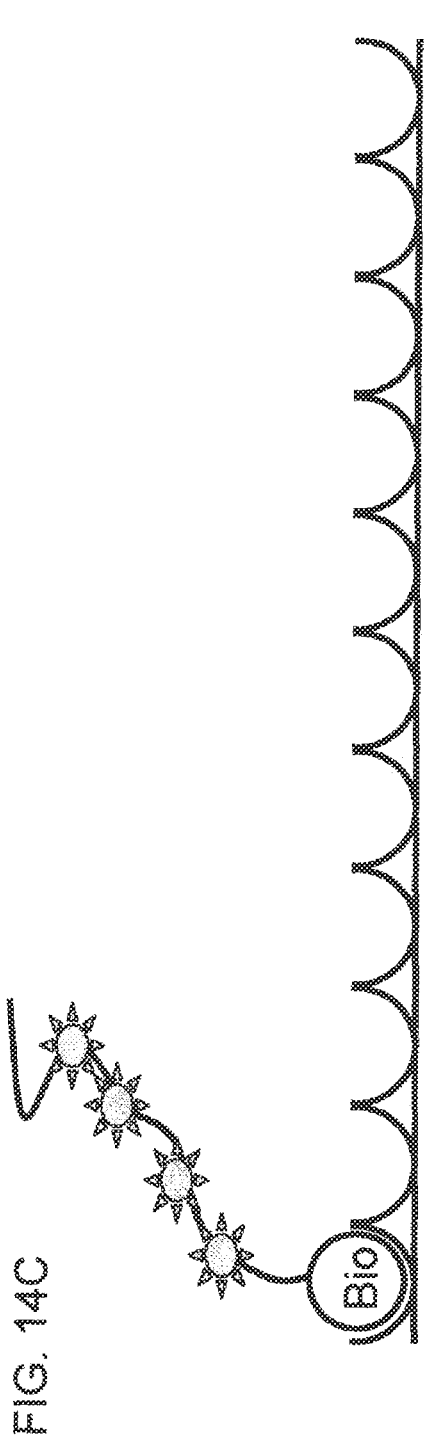
Figure 14D:
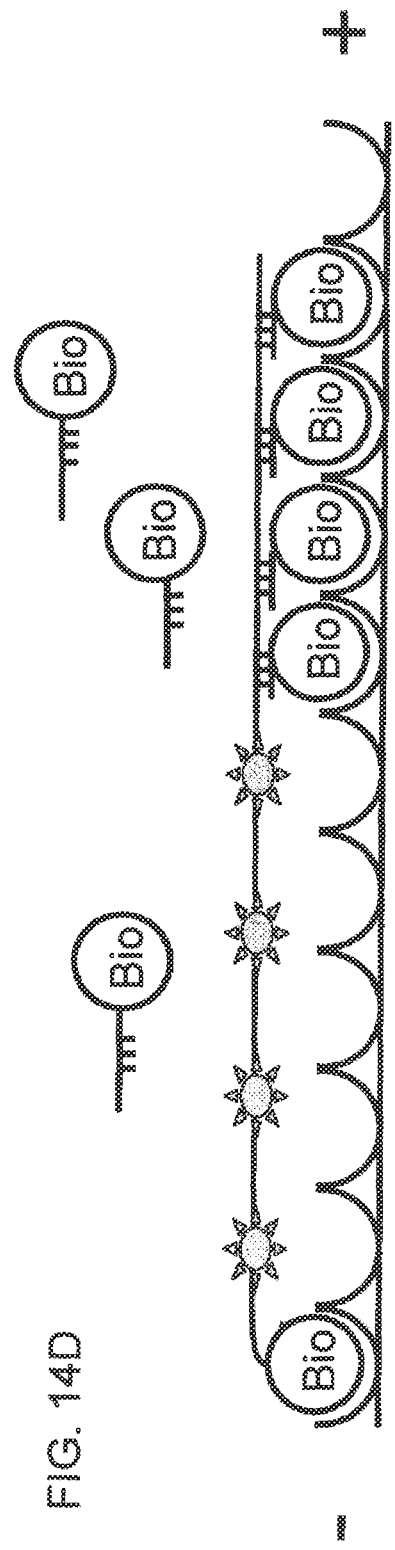
Figure 15A:
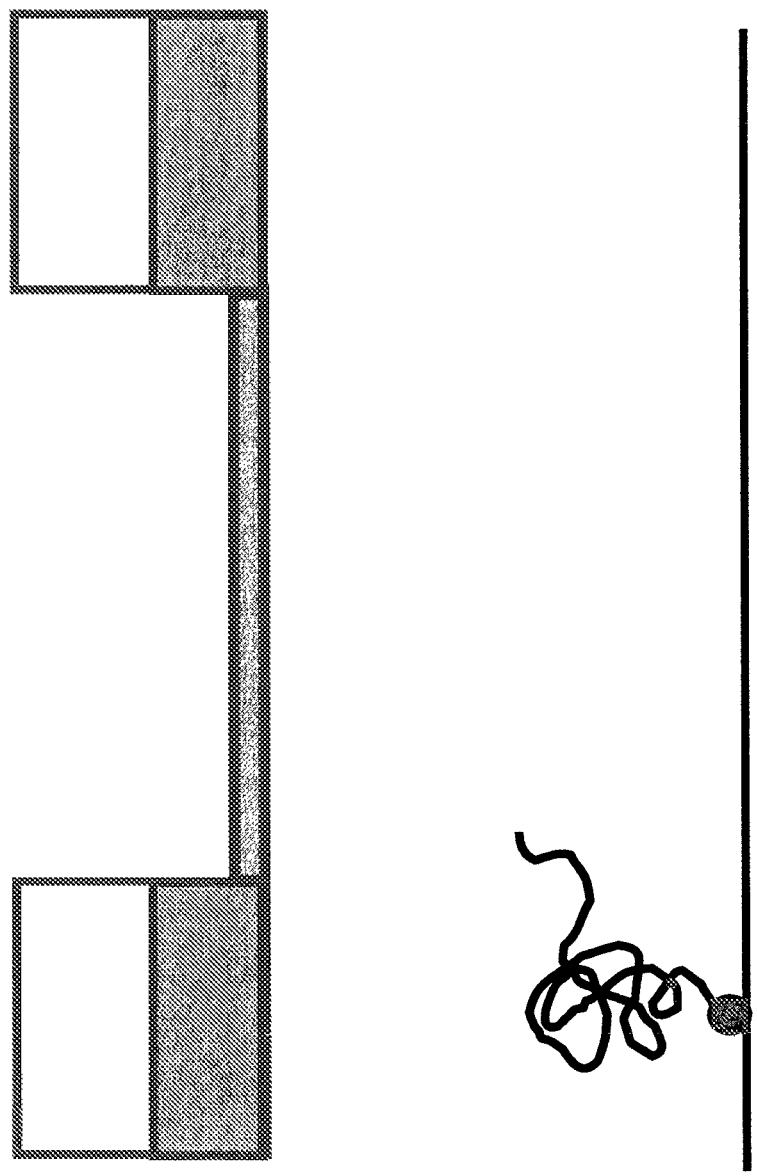
FIG. 15A-15C.
Figure 15B:
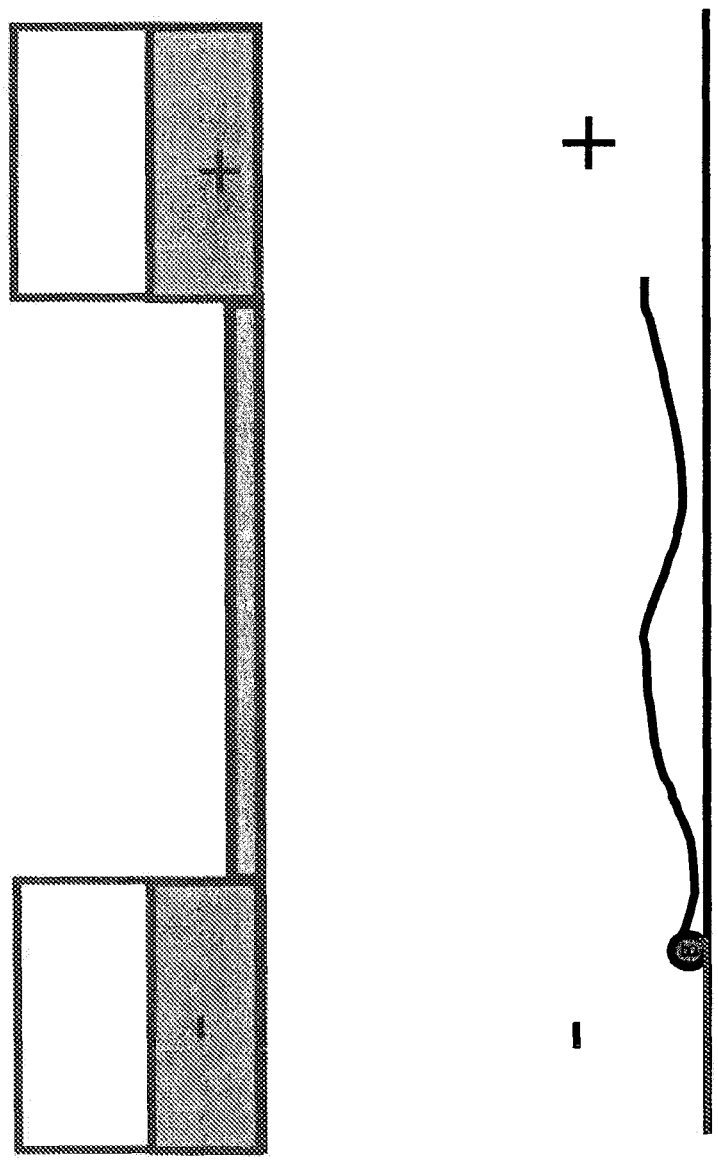
Figure 15C:
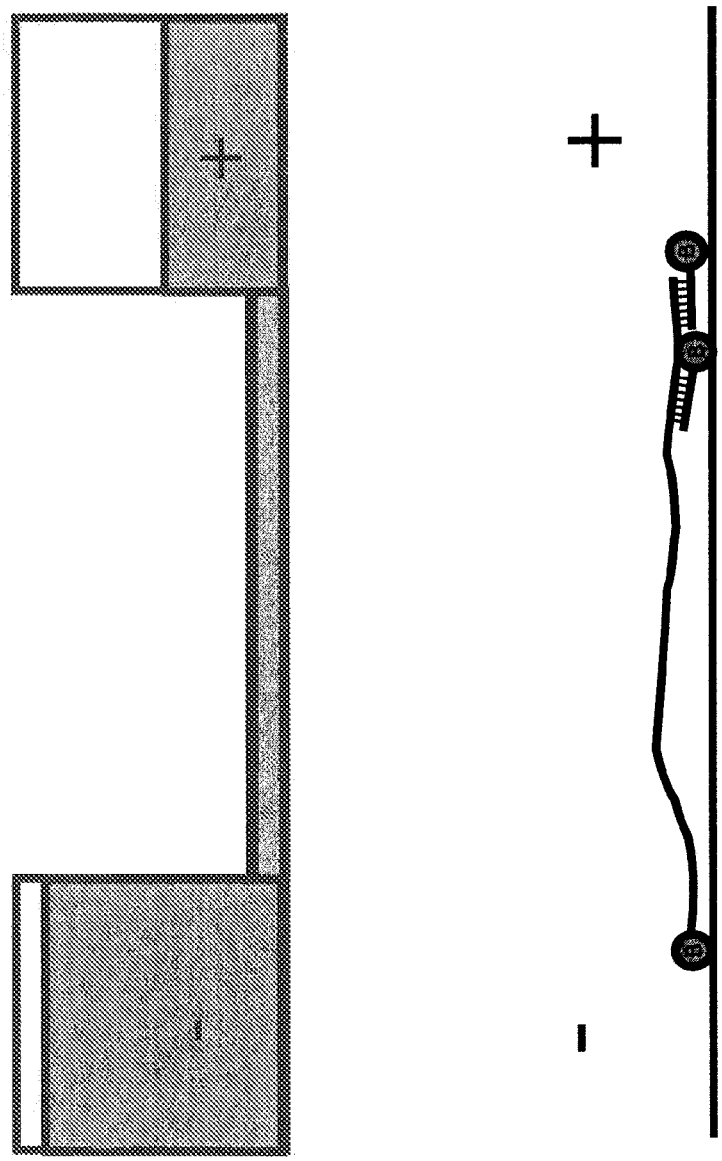
Figure 16:
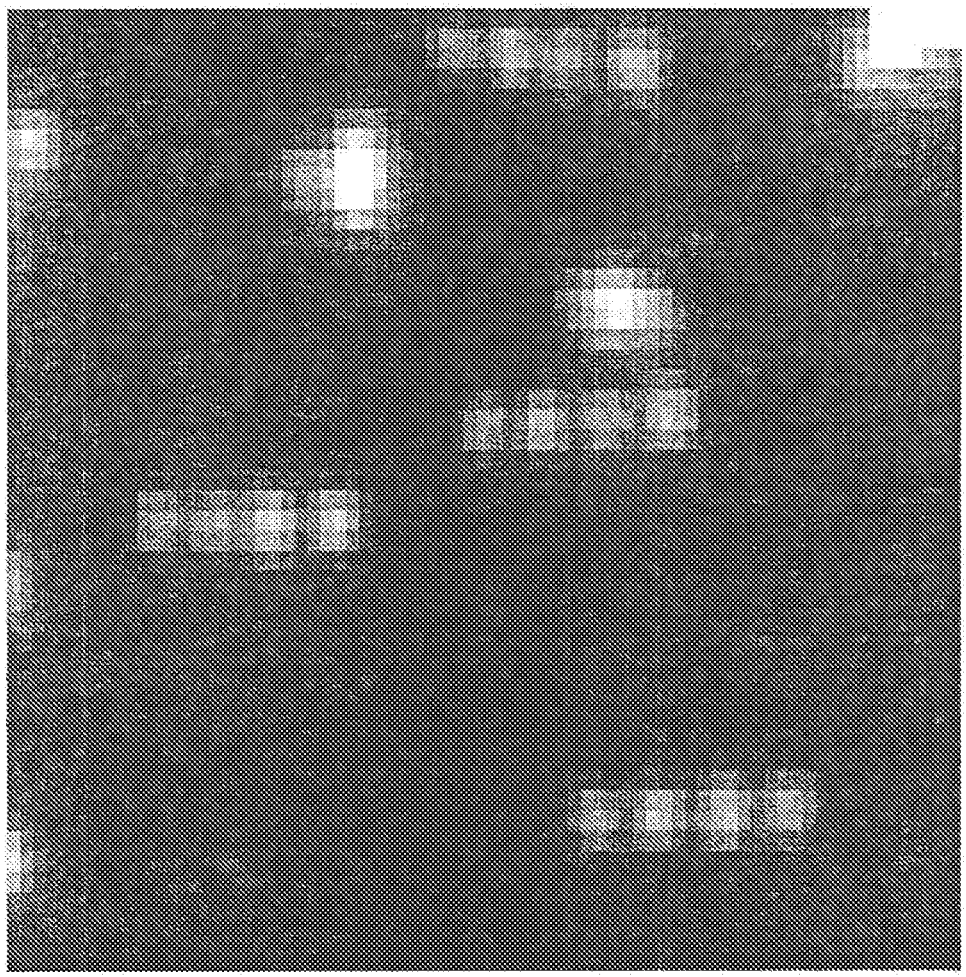
FIG. 16 provides an image of extended nanoreporters selectively immobilized by the methods of the present invention.

FIGS. 14A and 14B illustrate the selective immobilization of a nanoreporter according to methods of the present invention. In FIG. 14A, a first portion of the nanoreporter comprises binding moiety F1 that is capable of selectively binding a moiety on the illustrated substrate S. Binding moiety F1 can be, for instance, biotin, and substrate S can be coated with, for instance, avidin. The nanoreporter of FIG. 14A is extended by a force as described in the sections above. In FIG. 14B, the force is an electrical potential. While extended, the nanoreporter is contacted with molecules comprising binding moiety F2 that is capable of selectively binding a moiety on the illustrated substrate S. Binding moiety F2 can be, for instance, biotin, and substrate S can be coated with, for instance, avidin. Significantly, up to three molecules comprising F2 are capable of selectively binding to a second portion of the nanoreporter to selectively immobilize it in its extended state. As illustrated, the molecules comprise a second binding moiety that selectively binds a repeated binding moiety of the nanoreporter. The binding moieties can be, for instance, complementary nucleic acid sequences, as illustrated in FIG. 14B. The resulting nanoreporter is selectively immobilized in an extended state and should remain extended even when the force is removed. The selectively immobilized, extended nanoreporter can be used for any purpose apparent to those of skill in the art.

Immobilization of Two Portions of an Extended or Oriented Nanoreporter

In certain embodiments, the present invention provides methods for selective immobilization of a first portion and a second portion of a nanoreporter that is in an extended or oriented state. Significantly, according to these methods of the invention, the nanoreporter need not be immobilized prior to application of a force capable of extending or orienting the nanoreporter.

In these methods, the nanoreporter is extended or oriented, or both, by a force capable of extending or orienting the nanoreporter. Such forces are described in detail in the sections above. In particular embodiments, the force is a force capable of extending or orienting the nanoreporter while maintaining the nanoreporter in one location, i.e., a force capable of extending or orienting without substantially moving the nanoreporter. Exemplary forces include oscillating electromagnetic fields and oscillating hydrodynamic fields. In a particular embodiment, the force is an oscillating electrical field. Exemplary techniques for extending or orienting a nanoreporter in an oscillating electric field are described in Asbury et al., 2002, *Electrophoresis* 23(16):2658-66; Kabata et al., 1993, *Science* 262(5139):1561-3; and Asbury and van den Engh, 1998, *Biophys J.* 74:1024-30, the contents of which are hereby incorporated by reference in their entirety.

In the methods, the nanoreporter is immobilized at a first portion and at a second portion while extended or oriented. Both the first portion and the second portion can be immobilized non-selectively, both can be immobilized selectively, or one can be immobilized selectively and the other non-selectively. Techniques for immobilization of the first portion and second portion are described in detail in the sections above.

Substrate for Immobilization

In the methods of the invention, the substrate for immobilization can be any substrate capable of selectively binding the nanoreporter apparent to those of skill in the art. Further, in certain aspects, the present invention provides compositions comprising a selectively immobilized nanoreporter in an extended state. The compositions comprise a substrate, as described herein, having immobilized thereto a nanoreporter in an extended state. The nanoreporter can be, of course, immobilized according to a method of the invention.

The only requirement of the substrate is that it be capable of selectively binding the second portion of the nanoreporter as described above. Thus, the substrate can be a filter or a membrane, such as a nitrocellulose or nylon, glass, a polymer such as polyacrylamide, a gel such as agarose, dextran, cellulose, polystyrene, latex, or any other material known to those of skill in the art to which capture compounds can be immobilized. The substrate can be composed of a porous material such as acrylic, styrene methyl methacrylate copolymer and ethylene/acrylic acid.

The substrate can take on any form so long as the form does not prevent selective immobilization of the second portion of the nanoreporter. For instance, the substrate can have the form of a disk, slab, strip, bead, submicron particle, coated magnetic bead, gel pad, microtiter well, slide, membrane, frit or other form known to those of skill in the art. The substrate is optionally disposed within a housing, such as a chromatography column, spin column, syringe barrel, pipette, pipette tip, 96 or 384 well plate, microchannel, capillary, etc., that aids the flow of liquid over or through the substrate.

The nanoreporter can be immobilized on a single substrate or on a plurality of substrates. For instance, in certain embodiments, the first and second portions of nanoreporter are immobilized on the same substrate, as recognized by those of skill in the art. In certain embodiments, the first portion of the nanoreporter can be immobilized on a first substrate while the second portion of the nanoreporter can be immobilized on a second substrate, distinct from the first.

The substrate can be prepared according to any method apparent to those of skill in the art. For a review of the myriad techniques that can be used to activate exemplary substrates of the invention with a sufficient density of reactive groups, see *Wiley Encyclopedia of Packaging Technology*, 2d Ed., Brody & Marsh, Ed., "Surface Treatment," pp. 867-874, John Wiley & Sons (1997), and the references cited therein. Chemical methods suitable for generating amino groups on silicon oxide substrates are described in Atkinson & Smith, "Solid Phase Synthesis of Oligodeoxyribonucleotides by the Phosphite Triester Method," In: *Oligonucleotide Synthesis: A Practical Approach*, M. J. Gait, Ed., 1984, IRL Press, Oxford, particularly at pp. 45-49 (and the references cited therein); chemical methods suitable for generating hydroxyl groups on silicon oxide substrates are described in Pease et al., 1994, *Proc. Natl. Acad. Sci. USA* 91:5022-5026 (and the references cited therein); chemical methods for generating functional groups on polymers such as polystyrene, polyamides and grafted polystyrenes are described in Lloyd Williams et al., 1997, Chemical Approaches to the Synthesis of Peptides and Proteins, Chapter 2, CRC Press, Boca Raton, Fla. (and the references cited therein).

Exemplary useful substrates include surfaces coated with streptavidin, e.g., Accelr8 TB0200. Further useful substrates include surfaces coated with N-hydroxysuccinamide that are capable of reacting with a portion of a nanoreporter that comprises an amine. One such surface is OptArray-DNA (Accelr8). Additional useful surfaces are coated with aldehyde (e.g., Nexterion Slide AL, Schott) and surfaces coated with epoxy (e.g., Nexterion Slide E, Schott). Another useful surface is a biotinylated BSA coated surface useful for selective immobilization of a portion of a nanoreporter that comprises avidin or streptavidin.

Methods of Using Selectively Immobilized, Extended or Oriented Nanoreporters

In certain embodiments, the selectively immobilized, elongated nanoreporters can be used to create macromolecular barcodes for the purposes of separation and sequential detection of labels. These labels spaced along the molecule provide a unique code that can be read when the nanoreporter is extended and immobilized. Extension and selective immobilization can facilitate the decoding of the macromolecular barcode.

The selectively immobilized, elongated nanoreporters can be used in any context where detection or imaging of a nanoreporter might be useful. They can be used for diagnostic, prognostic therapeutic and screening purposes. For instance, they can be applied to the analysis of biomolecular samples obtained or derived from a patient so as to determine whether a diseased cell type is present in the sample and/or to stage the disease. They can be used to diagnose pathogen infections, for example infections by intracellular bacteria and viruses, by determining the presence and/or quantity of markers of bacterium or virus, respectively, in the sample. The compositions and methods of the invention can be used to quantitate target molecules whose abundance is indicative of a biological state or disease condition, for example, blood markers that are upregulated or downregulated as a result of a disease state. In addition, the compositions and methods of the invention can be used to provide prognostic information that assists in determining a course of treatment for a patient.

Kits Comprising Selectively Immobilized Extended or Oriented Nanoreporters

The invention further provides kits comprising one or more components of the invention. The kits can comprise, for example, a substrate according to the invention and one or more extended or oriented, or both, nanoreporters selectively immobilized on the substrate. The kits can be used for any purpose apparent to those of skill in the art, including those described above.

In certain embodiments, the present invention also provides kits useful for the extension and selective immobilization of nanoreporters. The kits can comprise a substrate for immobilization and one or more binding partners to facilitate extension or immobilization of a nanoreporter. The binding partners could, in certain embodiments, comprise a moiety useful for extension of the nanoreporter in an appropriate force. In certain embodiments, the binding partners could facilitate immobilization or selective immobilization of the nanoreporter to the surface. In further embodiments, the kit could comprise a nanoreporter for extension and immobilization. In further embodiments, the kit could comprise a device capable of extending the nanoreporter.

Detection of Nanoreporters

Nanoreporters are detected by any means available in the art that is capable of detecting the specific signals on a given nanoreporter. Where the nanoreporter is fluorescently labeled, suitable consideration of appropriate excitation sources may be investigated. Possible sources may include but are not limited to arc lamp, xenon lamp, lasers, light emitting diodes or some combination thereof. The appropriate excitation source is used in conjunction with an appropriate optical detection system, for example an inverted fluorescent microscope, an epi-fluorescent microscope or a confocal microscope. Preferably, a microscope is used that can allow for detection with enough spatial resolution to determine the sequence of the spots on the nanoreporter.

Microscope and Objective Lens Selection.

The major consideration regarding the microscope objective lens is with the optical resolution, which is determined by its numerical aperture (NA). Generally, the larger the NA, the better the optical resolution. The required NA is preferably at least 1.07 based on the relationship of $\delta=0.61\lambda/NA$ ($\delta$=optical resolution and $\lambda$=wavelength). The amount of light that is collected by an objective is determined by $NA^4/Mag^2$ (Mag=magnification of the objective). Therefore, in order to collect as much light as possible, objectives with high NA and low magnifications should be selected.

CCD Camera Selection and Image Capture Techniques.

When selecting a CCD camera, the first consideration is the pixel size, which partially determines the final resolution of the imaging system. Optimally the optical resolution should not be compromised by the CCD camera. For example, if the optical resolution is 210-300 nm, which corresponds to 12.6-18 µm on a CCD chip after a 60× magnification, in order to resolve and maintain the optical resolution there should be at least two pixels to sample each spot. Or the pixel size of the CCD chip should be at most 6.3-9 µm.

The second consideration is detection sensitivity which can be determined by many factors that include but are not limited to pixel size, quantum efficiency, readout noise and dark noise. To achieve high sensitivity, select a qualitative camera with big pixel size (which can give big collection area), high quantum efficiency and low noise. An exemplary camera with these criteria is the Orca-Ag camera from Hamamatsu Inc. The chip size is 1344×1024 pixels; when using the 60× objective, the field of view is 144×110 µm².

Computer Systems

The invention provides computer systems that may be used to computerize nanoreporter image collection, nanoreporter identification and/or decoding of the nanoreporter code. Specifically, the invention provides various computer systems comprising a processor and a memory coupled to the processor and encoding one or more programs. The computer systems can be connected to the microscopes employed in imaging the nanoreporter, allowing imaging, identification and decoding the nanoreporter, as well as storing the nanoreporter image and associated information, by a single apparatus. The one or more programs encoded by the memory cause the processor to perform the methods of the invention.

In still other embodiments, the invention provides computer program products for use in conjunction with a computer system (e.g., one of the above-described computer systems of the invention) having a processor and a memory connected to the processor. The computer program products of the invention comprise a computer readable storage medium having a computer program mechanism encoded or embedded thereon. The computer program mechanism can be loaded into the memory of the computer and cause the processor to execute the steps of the methods of the invention.

The methods described in the previous subsections can preferably be implemented by use of the following computer systems, and according to the following methods. An exemplary computer system suitable for implementation of the methods of this invention comprises internal components and being linked to external components. The internal components of this computer system include a processor element interconnected with main memory. For example, the computer system can be an Intel Pentium-based processor of 200 MHz or greater clock rate and with 32 MB or more of main memory.

The external components include mass storage. This mass storage can be one or more hard disks which are typically packaged together with the processor and memory. Such hard disks are typically of 1 GB or greater storage capacity. Other external components include user interface device, which can be a monitor and a keyboard, together with pointing device, which can be a "mouse", or other graphical input devices (not illustrated). Typically, the computer system is also linked to a network link, which can be part of an Ethernet link to other local computer systems, remote computer systems, or wide area communication networks, such as the Internet. This network link allows the computer system to share data and processing tasks with other computer systems.

Loaded into memory during operation of this system are several software components, which are both standard in the art and special to the instant invention. These software components collectively cause the computer system to function according to the methods of the invention. The software components are typically stored on mass storage. A first software component is an operating system, which is responsible for managing the computer system and its network interconnections. This operating system can be, for example, of the Microsoft Windows® family, such as Windows 95, Windows 2000, or Windows XP, or, alternatively, a Macintosh operating system, a Linux operating system or a Unix operating system. A second software component may include common languages and functions conveniently present in the system to assist programs implementing the methods specific to this invention. Languages that can be used to program the analytic methods of the invention include, for example, C, C++, JAVA, and, less preferably, FORTRAN, PASCAL, and BASIC. Another software component of the present invention comprises the analytic methods of this invention as programmed in a procedural language or symbolic package.

In an exemplary implementation, to practice the methods of the present invention, a nanoreporter code (i.e., a correlation between the order and nature of spots on a nanoreporter and the identity of a target molecule to which such a nanoreporter binds) is first loaded in the computer system. Next the user causes execution of analysis software which performs the steps of determining the presence and, optionally, quantity of nanoreporters with a given nanoreporter code.

The analytical systems of the invention also include computer program products that contain one or more of the above-described software components such that the software components may be loaded into the memory of a computer system. Specifically, a computer program product of the invention includes a computer readable storage medium having one or more computer program mechanisms embedded or encoded thereon in a computer readable format. The computer program mechanisms encoded, e.g., one or more of the analytical software components described above which can be loaded into the memory of a computer system and cause the processor of the computer system to execute the analytical methods of the present invention.

The computer program mechanisms or mechanisms are preferably stored or encoded on a computer readable storage medium. Exemplary computer readable storage media are discussed above and include, but are not limited to: a hard drive, which may be, e.g., an external or an internal hard drive of a computer system of the invention, or a removable hard drive; a floppy disk; a CD-ROM; or a tape such as a DAT tape. Other computer readable storage media will also be apparent to those skilled in the art that can be used in the computer program mechanisms of the present invention.

The present invention also provides databases useful for practicing the methods of the present invention. The databases may include reference nanoreporter codes for a large variety of target molecules. Preferably, such a database will be in an electronic form that can be loaded into a computer system. Such electronic forms include databases loaded into the main memory of a computer system used to implement the methods of this invention, or in the main memory of other computers linked by network connection, or embedded or encoded on mass storage media, or on removable storage media such as a CD-ROM or floppy disk.

Alternative systems and methods for implementing the methods of this invention are intended to be comprehended within the accompanying claims. In particular, the accompanying claims are intended to include the alternative program structures for implementing the methods of this invention that will be readily apparent to one of skill in the art.

Applications of Nanoreporter Technology

The compositions and methods of the invention can be used for diagnostic, prognostic therapeutic and screening purposes. The present invention provides the advantage that many different target molecules can be analyzed at one time from a single biomolecular sample using the methods of the invention. This allows, for example, for several diagnostic tests to be performed on one sample.

Diagnostic/Prognostic Methods

The present methods can be applied to the analysis of biomolecular samples obtained or derived from a patient so as to determine whether a diseased cell type is present in the sample and/or to stage the disease.

For example, a blood sample can be assayed according to any of the methods described herein to determine the presence and/or quantity of markers of a cancerous cell type in the sample, thereby diagnosing or staging the cancer.

Alternatively, the methods described herein can be used to diagnose pathogen infections, for example infections by intracellular bacteria and viruses, by determining the presence and/or quantity of markers of bacterium or virus, respectively, in the sample.

Thus, the target molecules detected using the compositions and methods of the invention can be either patient markers (such as a cancer marker) or markers of infection with a foreign agent, such as bacterial or viral markers.

Because of the quantitative nature of nanoreporters, the compositions and methods of the invention can be used to quantitate target molecules whose abundance is indicative of a biological state or disease condition, for example, blood markers that are upregulated or downregulated as a result of a disease state.

In addition, the compositions and methods of the invention can be used to provide prognostic information that assists in determining a course of treatment for a patient. For example, the amount of a particular marker for a tumor can be accurately quantified from even a small sample from a patient. For certain diseases like breast cancer, overexpression of certain genes, such as Her2-neu, indicate a more aggressive course of treatment will be needed.

Analysis of Pathology Samples

RNA extracted from formaldehyde- or paraformaldehyde-fixed paraffin-embedded tissue samples is typically poor in quality (fragmented) and low in yield. This makes gene expression analysis of low-expressing genes in histology samples or archival pathology tissues extremely difficult and often completely infeasible. The nanoreporter technology can fill this unmet need by allowing the analysis of very small quantities of low-quality total RNA.

To use nanoreporter technology in such an application, total RNA can be extracted from formaldehyde- or paraformaldehyde-fixed paraffin-embedded tissue samples (or similar) using commercially available kits such as RecoverAll Total Nucleic Acid Isolation Kit (Ambion) following manufacturer's protocols. RNA in such samples is frequently degraded to small fragments (200 to 500 nucleotides in length), and many paraffin-embedded histology samples only yield tens of nanograms of total RNA. Small amounts (5 to 100 ng) of this fragmented total RNA can be used directly as target material in a nanoreporter hybridization following the assay conditions described herein. As described in Example 6 in Section 11 below, nanoreporter analysis of approximately 3.3 ng cellular RNA permitted detection of transcripts present at approximately 0.5 copy/cell.

Screening Methods

The methods of the present invention can be used, inter alia, for determining the effect of a perturbation, including chemical compounds, mutations, temperature changes, growth hormones, growth factors, disease, or a change in culture conditions, on various target molecules, thereby identifying target molecules whose presence, absence or levels are indicative of particular biological states. In a preferred embodiment, the present invention is used to elucidate and discover components and pathways of disease states. For example, the comparison of quantities of target molecules present in a disease tissue with "normal" tissue allows the elucidation of important target molecules involved in the disease, thereby identifying targets for the discovery/screening of new drug candidates that can be used to treat disease.

5.17 Kits

The invention further provides kits comprising one or more components of the invention. The kits can contained pre-labeled nanoreporters, or unlabeled nanoreporters with one or more components for labeling the nanoreporters. Moreover, the nanoreporters provided in a kit may or may not have target-specific sequences pre-attached. In one embodiment, the target sequences are provided in the kit unattached to the nanoreporter scaffold.

The kit can include other reagents as well, for example, buffers for performing hybridization reactions, linkers, restriction endonucleases, and DNA ligases.

The kit also will include instructions for using the components of the kit, and/or for making and/or using the labeled nanoreporters.

EXAMPLE 1

Nanoreporter Manufacturing and Protocol

Herein is a step-by-step example of a method construction of a nanoreporter from various components.

It can be appreciated that various components can be constructed or added either at the same time, before or after other components. For example, annealing patch units or flaps to a scaffold can be done simultaneously or one after the other.

In this example the starting material is a circular M13mp18 viral vector. Using a single linear strand M13mp18, patch units are annealed to it to form a double stranded scaffold. Next, flaps are added, then a target-specific sequence is ligated. Meanwhile purification steps aid to filter out excess, unattached patch units and flaps. Construction of labeled nucleic acids (patches and/or flaps and/or other labeled oligonucleotides) that bind the nanoreporter are also described.

Upon attachment (e.g., via hybridization) of a target molecule, the nanoreporter is attached to a surface and stretched. Finally the nanoreporters are imaged by a camera.

Figure 4:
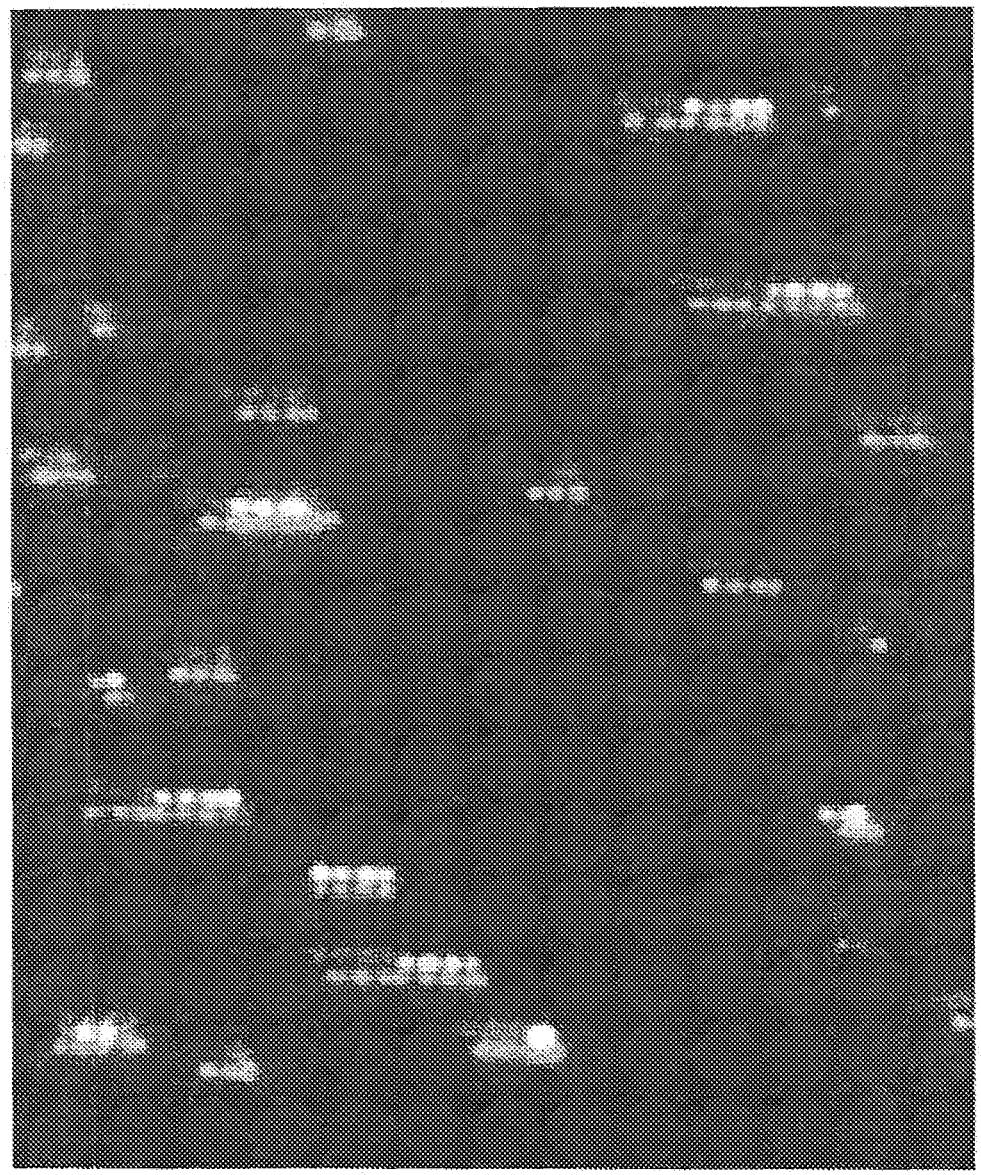
FIG. 4: Is an image of a dual nanoreporter hybridized to a target molecule. Here, both registers are labeled. The nanoreporters are labeled with three different colors, Alexa 488, Cy3 and Alexa 647 (labeled 1, 2 and 3, respectively). The left brackets show one probe of the dual nanoreporter and the right brackets show the other probe of the dual nanoreporter. Colors 1, 2 and 3 were each acquired in different channels and the first and second registers, seen as rows of spots, were shifted up by several pixels to be able to show each register individually.
Figure 8:
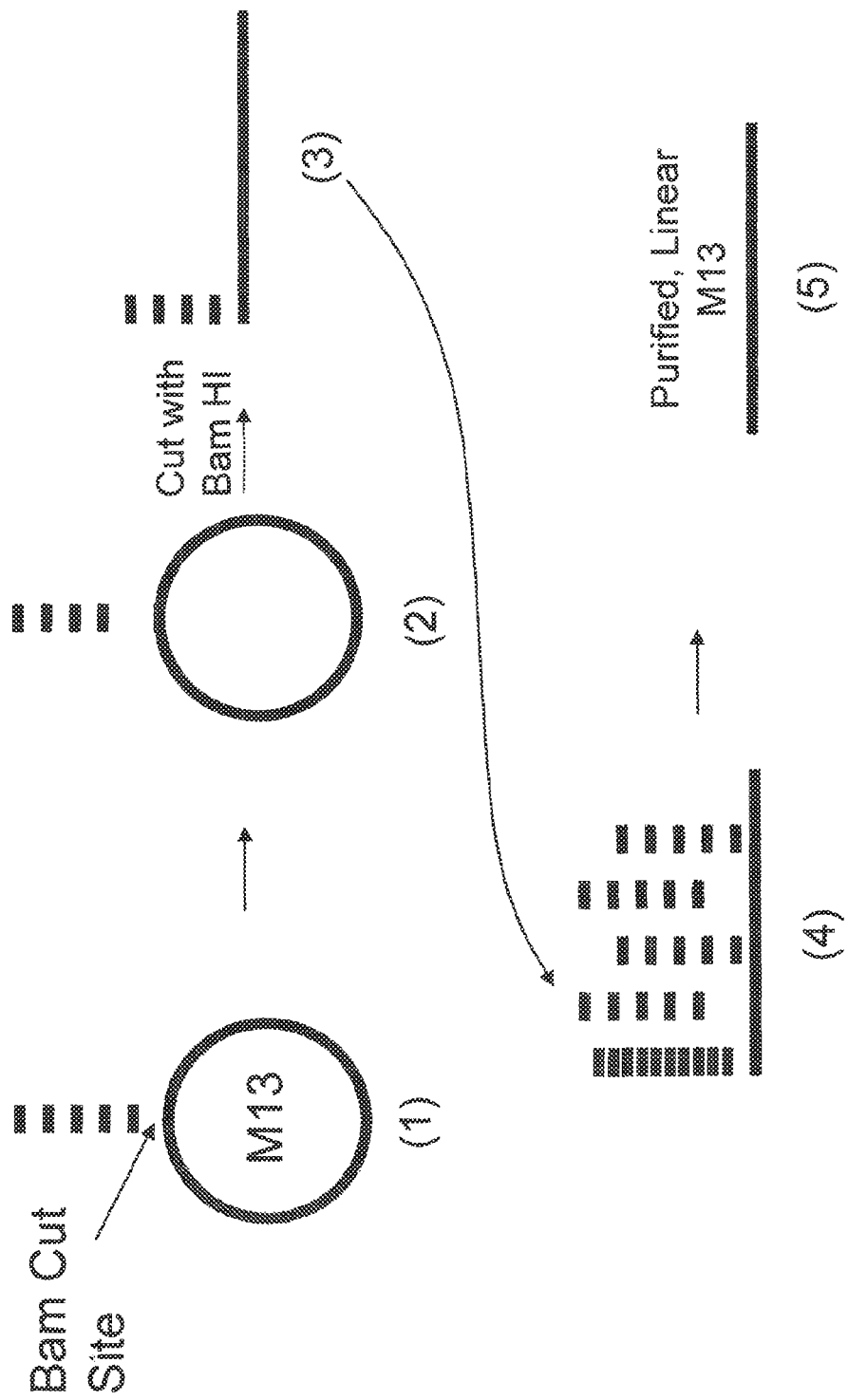
FIG. 8.
Figure 11A:
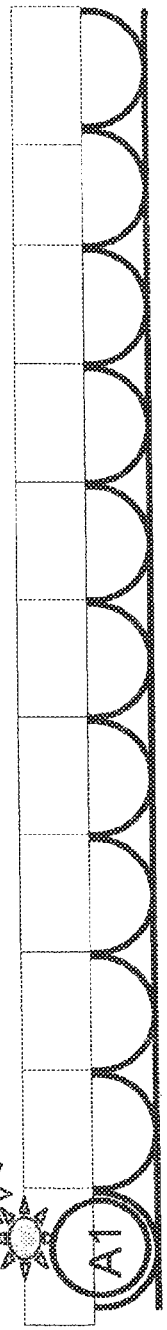
FIG. 11A-11B: Shows a labeled (nucleic acid-based) nanoreporter with an affinity tag, A1, at one end.
Figure 11B:
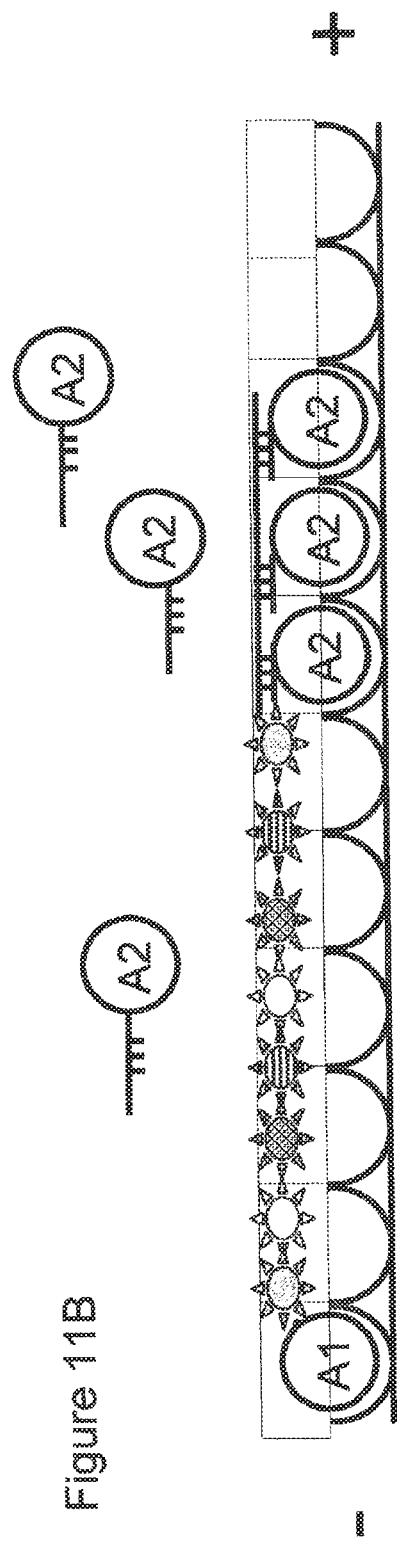

Nanoreporters were generated and successfully employed to detect target molecules using methods substantially as described in this example. An example of target detection using this method is shown in FIG. 4.

Scaffold Construction

The oligonucleotide scaffold sequence selected was analyzed using Vector NTI® software. First, a single stranded nucleic acid was made from linearizing a circular M13mp18 single stranded DNA, which was commercially purchased from New England Biolabs. The circular M13mp18 was digested with BamH1 enzyme to linearize it. Materials used consisted of M13mp18 vector (250 ng/μl), Patch_1L_BamH1.02 (10 μM dilution of a 100 μM stock), 10× BamH1 Buffer, BamH1 enzyme. Protocol for making 0.8 pmol total of linear M13mp18 involve the following steps. 1) preheat heating block to 37° C.; 2) in a 0.65 ml ependorff tube combine 40 μl of 250 ng/μl M13mp18 vector, 2 μl of 10 μM Patch_L_BamH1.02, and 5 μl of 10× BamH1 Buffer; 3) place the ependorff tube in the 37° C. heating block with foil over the top. Incubate the tube at 37° C. for 15 minutes to allow the patch unit to hybridize to the M13mp18 scaffold; 4) after 15 minutes add 2 μl of BamH1 enzyme and let the reaction digest at 37° C. for 30 minutes, after which add an additional 2 μl of BamH1 enzyme and let the reaction continue to digest for another 30 minutes at 37° C. (final volume of BamH1 enzyme is 8%); and 5) aliquot 10 μl into 0.65 ml ependorff tubes and store in freezer (final concentration of linear M13mp18 is 200 ng/μl).

Patch Unit Preparation of the Base Patch Pools (BPP).

Second, patch units are prepared in pools. Patch oligonucleotide sequences were selected for optimal length and desired homology/non-homology to M13mp18 strand and the human genomic sequence. Patches were commercially manufactured oligonucleotides (purchased from Integrated DNA technologies) either 60 or 65 nucleotide bases in length. 50 nucleotide bases of each patch oligonucleotide are complementary to the M13mp18 single stranded DNA, 10 nucleotide bases are complementary to an adjacent patch, and 5 nucleotide base pairs are complementary to a corresponding flap. The 10 nucleotide base match between patches forms a stem structure which stabilizes the structure and helps lift the flaps off the covered scaffold so they are more available to bind labeled oligonucleotides. Synthetic binding sites, the 5 nucleotide bases, on the patches for binding to the flaps make leveraging the power of a modular system possible.

The base patch pools contain nine patch units all corresponding to a specific letter grouping and position on the nanoreporter. For this example, there are four different fluorescent dyes (color) labeled A, B, C, and D and 8 different positions or regions where labeled nucleic acids can bind on a nanoreporter. For example, BPP A3 corresponds to all of the A patch units at position 3 (patch units 19-27) on the nanoreporter.

The nanoreporter positions are as follows:
Position 1: Patch units 1-9 (A or C)
Position 2: Patch units 10-18 (B or D)
Position 3: Patch units 19-27 (A or C)
Position 4: Patch units 28-36 (B or D)
Position 5: Patch units 37-45 (A or C)
Position 6: Patch units 46-54 (B or D)
Position 7: Patch units 55-63 (A or C)
Position 8: Patch units 64-72 (B or D)

Materials: right and left patches, pre-annealed to each other (each oligonucleotide is at a concentration of 10 μM). Materials for making 100 pmol of BPP 1: (In position 1, patch coordinate 1L is used for the BamH1 digest—this patch is not included in BPP 1): 10 μl each pre-annealed (10 μM/each) patch unit (coordinates 2-9), 5 μl [20 μM] Patch_1R (A or C). Final concentration of each patch is 1.18 pmol/μl. Materials for making 100 pmol of BPP 2-8: 10 μl each pre-annealed (10 μM/each) appropriate patch unit. There are 9 patch units added to each, or 90 μl total. Final concentration of each patch is 1.11 pmol/μl.

Below is a table of all the patch unit pools made for this example, with 8 positions or regions for dye-labeled nucleic acids to bind on the nanoreporter. Positions 1, 3, 5, and 7 can bind to nucleic acid labeled with dye A or dye C, and a positions 2, 4, 6, and 8 can bind to nucleic acid labeled with dye B or dye D.

TABLE 2 of resulting Basic Patch Pools (correspond to lables on tubes)

BPP-A1 [Pre-Paired, Color = A, Coordinates 1-9]
Patch_(1-9)R.A
Patch_(2-9)L
BPP-B2 [Pre-Paired, Color = B, Coordinates 10-18]
Patch_(10-18)R.B
Patch_(10-18)L
BPP-A3 [Pre-Paired, Color = A, Coordinates 19-27]
Patch_(19-27)R.A
Patch_(19-27)L
BPP-B4 [Pre-Paired, Color = B, Coordinates 28-36]
Patch_(28-36)R.B
Patch_(28-36)L TABLE 2-continued of resulting Basic Patch Pools (correspond to lables on tubes)

BPP-A5 [Pre-Paired, Color = A, Coordinates 37-45]
Patch_(37-45)R.A
Patch_(37-45)L
BPP-B6 [Pre-Paired, Color = B, Coordinates 46-54]
Patch_(46-54)R.B
Patch_(46-54)L
BPP-A7 [Pre-Paired, Color = A, Coordinates 55-63]
Patch_(55-63)R.A
Patch_(55-63)L
BPP-B8 [Pre-Paired, Color = B, Coordinates 64-72]
Patch_(64-72)R.B
Patch_(64-72)L
BPP-C1 [Pre-Paired, Color = C, Coordinates 1-9]
Patch_(1-9)R.C
Patch_(2-9)L
BPP-D2 [Pre-Paired, Color = D, Coordinates 10-18]
Patch_(10-18)R.D
Patch_(10-18)L
BPP-C3 [Pre-Paired, Color = C, Coordinates 19-27]
Patch_(19-27)R.C
Patch_(19-27)L
BPP-D4 [Pre-Paired, Color = D, Coordinates 28-36]
Patch_(28-36)R.D
Patch_(28-36)L
BPP-C5 [Pre-Paired, Color = C, Coordinates 37-45]
Patch_(37-45)R.C
Patch_(37-45)L
BPP-D6 [Pre-Paired, Color = D, Coordinates 46-54]
Patch_(46-54)R.D
Patch_(46-54)L
BPP-C7 [Pre-Paired, Color = C, Coordinates 55-63]
Patch_(55-63)R.C
Patch_(55-63)L
BPP-D8 [Pre-Paired, Color = D, Coordinates 64-72]
Patch_(64-72)R.D
Patch_(64-72)L Materials and Preparation for Annealing the Single Stranded Oligonucleotide with Patch Units for a Double Stranded Scaffold.

Third, patch units are prepared to be annealed to the single stranded linear M13mp18, covering the strand in order to make a double stranded oligonucleotide scaffold.

Conditions for annealing 60 and 65 nucleotide base patches to the M13mp18 need to occur at high salt concentrations so that binding will be very specific and patches will not anneal to an incorrect coordinate on the M13mp18 strand. For the annealing step, each patch unit is added at a 2:1 to 4:1 ratio with the single stranded M13mp18 sequence at 0.5 pmol total volume. Excess patches are removed before annealing flaps.

Materials used consisted of 20×SSC, linear M13mp18 (BamH1 digested at 0.08 pmol/µl or 200 ng/µl), appropriate base patch pools (BPP) (need 8 total at 1.11 pmol/µl—see above) and digital heat block set at 45° C. Annealing reaction make up is as follows. General guidelines: 2× each patch unit per M13mp18 molecule, pre-ligated flaps/patches (in position 1 or 8) added for purification later, and 5×SSC. Example (0.5 pmol of scaffold with F8 hook flaps) reaction consists of: 7.1 µl BamH1 Digested M13mp18 strand at 0.071 µM, 0.9 µl each new Base Patch Pools at 1.11 µM for first 7 positions: A1, B2, A3, B4, C5, B6 and A7:

1.7 µl A1 BPP (Pre-Annealed, 12/15; at 1.18 µM/each patch)

1.8 µl B2 BPP (Pre-Annealed, 12/15; at 1.11 µM/each patch)

1.8 µl A3 BPP (Pre-Annealed, 12/15; at 1.11 µM/each patch)

1.8 µl B4 BPP (Pre-Annealed, 12/15; at 1.11 µM/each patch)

1.8 µl C5 BPP (Pre-Annealed, 12/15; at 1.11 µM/each patch)

1.8 µl B6 BPP (Pre-Annealed, 12/15; at 1.11 µM/each patch)

1.8 µl A7 BPP (Pre-Annealed, 12/15; at 1.11 µM/each patch), 2.4 µl BPP-D8 (pool of the first seven patch units—coordinates 64, 65, 66, 67, 68, 69, and 70 at position 8—"D" specificity) with purification tags—F8 (FHF, which anneal to patch coordinates 71L, 71R, 72L, 72R, 73L making full split-flap/patch units that have "F" specificity for use as biotin linkers, at position F8) at 0.83 µM, and 7.3 µl 20×SSC. The final reaction volume will be 29.3 µl at 0.027 pmol/µl.

Anti-Bam oligonucleotide is also added to anneal to region in M13 that is complementary to the (missing) 1 L patch unit and to prevent recircularization of the M13 scaffold during ligation.

Annealing Patch Units to Single Stranded M13MP18 to Form a Double Stranded Scaffold.

The fourth step involves the protocol to anneal the patch units to the single stranded linear M13mp18, covering the strand in order to make a double stranded oligonucleotide scaffold, is performed in the following steps: 1) preheat heating block to 42° C., heat above reaction solution to 45° C. in small PCR (or strip) tube(s) with foil over top for 15 minutes, turn heat block to 65° C. and incubate for an additional 1 hour and 45 minutes and remove tubes, place on ice or freeze.

Purification of Nanoreporter Scaffold Using Biotin and Magnetic Beads with Streptavidin.

The fifth step occurs before attaching the flaps, where excess patch units that have not annealed to the M13mp18 strand are separated from the double stranded oligonucleotide scaffold. A purification tag with a 5 nucleotide base homologous region to some of the patch units' complementary 5 nucleotide base overhang is annealed to 'hook' the scaffold. Biotinylated oligonucleotides are annealed to the 'purification tag' and magnetic beads with streptavidin are used to capture the scaffold using the biotinylated oligonucleotides. Excess patch units are removed with the supernatant. The scaffold melts off of the magnetic beads into solution for recovery.

Anneal the D-Biotin Catchers to the Purification Tags

Anneal the D-Biotin catchers to the purification tags on the nanoreporter (making 2× to amount of D8-flap positions available in solution, which is 2× to M13, or 4× final): 0.5 pmol×25 hook oligonucleotide positions (5 multiplied by 5), 4× makes 50 pmols translates to 0.50 µl of 100 pmol/µl D-biotin, add 0.5 µl (D, E, F)—Biotin (at 100 µM) to sample, mix and incubate at room temperature for 30 minutes.

Purification Protocol to Wash Off Unattached Patch Units From Double Stranded Scaffold.

Anneal F-hook oligonucleotides in a 25 fold excess to nanoreporters in 5×SSC for 30 min at room temperature. Pipet 200 µl DynaBead MyOne Streptavidin™ bead solution into 1.5 ml tubes, place on magnet and remove supernatant. Wash twice with 5×SSC by resuspending and clearing with magnet as in step above. Add 80 µl of sample in 5×SSC (80 fmoles of sample in this example). Resuspend well, by placing on vortex for 15 minutes. Clear solution with magnet and transfer supernatant to fresh tubes for later gel analysis. While on magnet, wash pellets (do not resuspend) with 80 µl TE by pipeting over pellet three times with the same 80 µl volume originally added. Remove wash, place in freshly "washed" tubes for analysis. Heat up TE buffer to 45° C., add 80 µl to each pellet and resuspend. Place tubes on 45° C. heat block for 15 minutes, pipetting up/down once to insure beads remain suspended. Immediately clear product with magnet while warm and save. The majority of purified nanoreporters should be present in this product eluted at 45° C.

Annealing and Ligation of Flaps to Scaffold.

The sixth step involves split flap oligonucleotides which are annealed to the scaffold to make a 'covered scaffold.' Purification with magnetic beads is performed afterwards to remove excess split flaps. Ligation of the covered scaffold is done using T4 ligase to increase the stability of the structure. Only one type of flap is needed per fluorescent dye. Flaps are either 95 or 100 bases in length and have regions complementary to the patches, to labeled oligonucleotides and to each other. Each flap has 15 base repeating sequences for binding to labeled oligonucleotides. The repeat sequences are based on Lambda sequences that have been analyzed to remove any palindromes and hairpin structures.

Conditions for annealing the flaps are as follows. The sequence on the flaps that corresponds to the patch is 5 nucleotide base pairs long, and therefore the flaps anneal specifically to the patches even at high salt concentrations. The ratio of flaps to patches is 2:1. In order to increase stability at high temperatures, ligation of patches to each other and the flap to the patches may be carried out in the same reaction.

1) Quantify the purified scaffold using a spectrometer at A260 nm. Calculate the volume needed for appropriate amount of nanoreporter to prepare. For this example we used 110 ng or 0.023 pmol, reading at A260 nm shows 7.7 ng/µl, or 14.3 µl for 110 ng. 2) Setup ligation reaction as follows (volume will vary, depending on the purification and scale). Currently using 1.5× flaps to patches, calculate accordingly. For this example, there are four different fluorescent dyes (color) labeled A, B, C, and D and 8 different positions or regions where dye-labeled nucleic acids can bind on a nanoreporter. The number of positions for each color (in this case 1-4) multiply by 9 multiply by 1.5 moles of scaffold=moles of flaps to use.

For the nanoreporter with fluorescent dye in the sequence/positions [ABABCBAD]:

$ABABCBAD = A: 40.5 \times .023$ $= .93$ pmol; vol: .93 µl of $SF$ (split flap)-$AL$ at 1 µM .93 µl of $SF$-$AR$ at 1 µM B: $40.5 \times 0.23 = .93$ pmol; vol: .93 µl of $SF$-$BL$ at 1 µM .93 µl of $SF$-$BR$ at 1 µM C: $13.5 \times .023 = .31$ pmol; vol: .31 µl of $SF$-$CL$ at 1 µM .31 µl of $SF$-$CR$ at 1 µM D: $13.5 \times .023 = .31$ pmol; vol: .31 µl of $SF$-$DL$ at 1 µM .31 µl of $SF$-$DR$ at 1 µM Ligation reaction (25 µl total) consists of: Split Flaps (see above; 4.96 µl, or ~5 µl total), 14.3 µl of MODB-Scaffold at 0.0016 pmol/µl, 2.5 µl 10× T4 ligation Buffer, 2.2 µl NanoPure H₂O and 1 µl T4 ligase. Incubate tubes 5 minutes at 45° C. Move to 37° C. water bath, inc. for 5 minutes. Add 1 µl T4 ligase to samples. Incubate for additional 1 hour at 37° C. Freeze immediately, or heat at 75° C. for 5 minutes to kill T4 ligase.

Ligation of Target-Specific Sequences to Nanoreporters

The seventh step involves ligation of a target-specific sequence to the nanoreporter. A DNA target-specific sequence is designed to be complementary to the target molecule, which can be RNA (e.g., mRNA) or DNA (e.g., cDNA or genomic DNA). The target-specific sequence can be from 35, 60 or 70 nucleotide bases in length. The target-specific sequence can be ligated to the scaffold using a single stranded overhanging region on the covered scaffold. The scaffold with a single type of target-specific sequence can be manufactured separately and then mixed to form libraries.

Nanoreporter Construction

Addition of oligonucleotides to a nanoreporter can be done at any point during the construction of a nanoreporter. In certain aspects of the present invention, a labeled oligonucleotide is 15 nucleotide bases long. On the 5' end, a single fluorophore dye is attached. Oligonucleotides with a particular fluorophore dye will generally have the same sequence. These labeled oligonucleotides bind to the repeat sequences of the split flaps. Fluorophores best suited for this example include but are not limited to Alexa 488, cy3, Alexa 594, and Alexa 647. The 15 nucleotide base length holds the fluorophores far enough apart so that they cannot quench each other and ensure that the labeled nucleic acids will be stable (will not melt off complementary strand) at conditions in the visualization process. Labeled oligonucleotides are stable at 40° C. This short length also allows for packing a large number of fluorescent dyes onto the flaps. In certain aspects of the invention, labeled oligonucleotides are introduced during the target sample processing.

Attachment of Nanoreporters to Target Molecules

Nanoreporters can be attached to target molecules using any means known to one of skill in the art. In an exemplary embodiment, dual nanoreporters are hybridized to target molecules by mixing 250 pmols each of both the first probe and the second probe with 125 pmols of target. The total volume is adjusted to 4 µl and a final concentration of buffer of 5×SSC. This mixture is incubated in a covered PCR tube overnight at 42 degrees to allow hybridization to occur.

Surface Attachment

Once the nanoreporters are attached to both target molecule and corresponding labeled nucleic acids, i.e., nucleic acids attached to label monomers, they are attached to a surface and stretched to resolve the order of signals emitted by the label monomers and thus identify the target molecule. In this example, the nanoreporters are stretched to spatially resolve their fluorescent dye codes which correspond to a particular target molecule. The nanoreporters are stretched by attaching one end to a surface (in this example—a coverslip, see preparations below). Two methods for surface attachment may be used: A) streptavidin coated slides from Accelr8 Corporation with the nanoreporters being biotinylated and B) biotin coated slides with the nanoreporters having streptavidin. In buffer, the nanoreporters are brought into contact with the active surface and allowed to incubate for a period of time. The reaction is performed in flow cells which were made from PDMS molded in etched silicon wafers to make the channels. Metal tubing is used to core wells at the ends of the channels for buffer and sample insertion. Channel dimensions are 0.5 mm or 1 mm wide and 54 µm high. Once the sample has been loaded into the flow cell lane and incubated, the nanoreporters should be attached. Nanoreporters can be stretched either by applying a voltage or by removing the liquid with a receding meniscus leaving the strings stretched and dry.

Preparation of Surface and Assembly of Device

The binding surfaces (Accelr8 brand Streptavidin-OptiChem®, coated coverslips) are shipped in units of 5 surfaces per slide container, and each container is enclosed with a package of silica dessicant in a foil pouch. The pouches are stored at −20° C. until use.

To prepare the surface for binding, a pouch is first pulled from the freezer and allowed to come to room temperature over several minutes. If previously unopened, the pouch is then sliced along one edge to form a slit, and the container of surfaces is removed. Upon removal of the required surface, the container is replaced in the pouch with its dessicant, the slit is sealed closed with a strip of packaging tape, and the pouch is replaced in the freezer.

The surface is then lightly rinsed with a stream of Nanopure water (Barnstead Nanopure Diamond) and soaked for 10 minutes in 0.2 μm-filtered 1× PBS in a clean, slotted Coplin Jar. After soaking, the surface is dipped in Nanopure water and dried by blowing filtered nitrogen across the surface edge.

The PDMS device used to mate with the surface and provide localization of the sample is cleaned just before use by applying cellophane tape to the PDMS surface and then peeling away dust or other particles which may have become attached during storage. The binding side of the Accelr8 surface is laid face-up, and the clean PDMS structure is centered, channel side down, on the surface. PDMS adheres readily to coated glass, and no further attachment mechanism is necessary.

Sample Binding and Washing

The sample is bound to the surface by first applying a 5 μL drop of the sample (currently diluted in 100 mM sodium borate buffer, pH 9.8) in one well of the chosen lane. The drop should just touch the point at which the channel joins the well (some sample may wick into the channel at this point). The channel is filled, and binding is equalized throughout the channel, by pulling the droplet through the channel to the opposite well using a very weak vacuum (<2 kPa). The process is repeated for the other samples in their respective lanes. Excess fluid is then removed from the wells, the wells are taped to reduce evaporation, and the device is incubated at room temperature in the dark for 20 minutes.

After binding, the tape is removed, and the top well of each lane is filled with 100 μL of the borate buffer described above. About 20 μL of that buffer is pulled through the channels to the other wells using the vacuum, and the process is repeated once. All borate buffer is then removed from all wells, and the top well is filled with 1× TAE, pH 8.3. About 50 μL TAE is pulled through the channel, then all TAE is removed and the well is refilled. The process is repeated three times, for a total of about 150 μL of TAE rinse. Finally, all wells are filled with 100 μL 1× TAE.

Electrostretching

The bottom of the coverslip/PDMS device is spotted with immersion oil and placed on the microscope. Electrodes are inserted into the wells on opposite ends of the first PDMS channel (negative electrode in top well, positive in bottom). The first image of the channel will be taken close to the bottom well; the microscope stage is adjusted so that the area of interest is in focus.

Voltage (200 V) is then applied across the channel. Voltage is supplied by a DC power supply (Agilent E3630A) and amplified 100× through a home-built amplifier. After the current is applied, focus is readjusted, and the imaging process begins.

The electrostretching and imaging process is then repeated with the remaining channels. Image the bindings.

Light Source for the Fluorescent Dyes on the Nanoreporter

In using an arc lamp as a light source, the best fluorophore selection is the brightest types without leading to fluorescent overlap such as Alexa 488, Cy3, and Alexa 594. Weaker fluorescent dyes such as Alexa 647 and Cy5.5 may also be used.

Filters to Image the Fluorescent Dyes on the Nanoreporter

For the selected fluorophores Alexa 488, Cy3, Alexa 594 and Alexa 647 there may be an overlap between the Cy3 and Alexa 594. However, custom ordering an emission filter with a bandwidth of 572-600 nm minimizes the overlap.

Microscope and Objective Lens to Image the Nanoreporters

The microscope model used was the Nikon Eclipse TE2000E from Nikon Corporation using the inverted fluorescence imaging station which has 6 filter cassettes that allow the selection of fluorescent emission from multiple fluorescent dye candidates. For the selected dyes, the optical resolution required is about 400 nm for all the wavelengths (500-700 nm). The selected objective lens is the Nikon Plan Apo TIRF lens which has a NA of 1.45 and magnification of 60. The optical resolution is ~210-300 nm for different wavelengths.

EXAMPLE 2

Patch/Flap Nanoreporter Manufacturing Protocol

This example demonstrates another way of making a nanoreporter which consists of a single stranded linear M13mp18 viral DNA, oligonucleotide patch units and long flaps.

Nanoreporter label units were successfully generated using methods substantially as described in this example.

Pre-phosphorylated patch units and flaps are added together with the M13mp18 DNA vector and ligated together. After the ligation of the flaps to the patch units which are ligated to the M13mp18 DNA, the BamH1 enzyme is introduced to linearize the vector.

Prepare a batch of nanoreporters starting with 5 μg of M13mp18 as a scaffold. The hybridization may be scaled up accordingly to the desired amount. This process will take about 1-2 days to complete.

Materials:

| Qty | Item | Vendor |
| --- | --- | --- |
| 20 | 250 ug/μl M13mp18 viral ssDNA | New England Biolabs |
| 27 μl | 0.74 pmol/μl Oligonucleotide Patch Unit Mix | IDT |
| 8 μl | Long Flap Oligonucleotide A 100 pmol/μl | IDT |
| 8 μl | Long Flap Oligonucleotide B 100 pmol/μl | IDT |
| 0.5 μl | Flap patch Oligos at 100 pmol/μl from plates #529916 and #610591 | IDT |
| 31 μl | T4 Ligase 10x buffer | Fermentas |
| 19 μl | T4 Ligase | Fermentas |
| 15 μl | Optikinase 10x buffer | USB |
| 4.2 μl | 100 mM ATP | ANY |
| 5 μl | Optikinase Enzyme 10 units/μl | USB |
| 1 μl | BamH1 Oligonucleotide 10 pmol/μl | IDT |
| 20 μl | BamH1 10x buffer | Fermentas |
| 3 μl | BamH1 Enzyme 10 units/μl | Fermentas |

Preheat water bath to 37° C. and 55° C. before beginning protocol. Make sure buffers are all well mixed and thawed before using. A work plate should be available and labeled with the ordered oligos from IDT in plates #529916 and #610591. Take these two plates out and thaw at room temperature for 0.5-1 hours and spin down contents before removing the tape that covers the wells. Four separate reactions will be set up in 1.5 ml eppendorf tubes using specific oligonucleotides from these plates. To begin label these four separate tubes with roman numerals on their caps. Columns 5 and 6 A through H are for reaction I, Columns 7 and 8 A through H are for reaction ii are all found in plate #529916. Columns 1 and 2 are for reaction iv, and Columns 3 and 4 are for reaction iii.

Flap Ligations (Step A): Label four separate 1.5 ml tubes with roman numerals i through iv (mentioned above). Add the reagents below accordingly to each 50 µl reaction containing: 5 µl 10× ligase buffer, 0.5 µl/oligonucleotide from designated wells from plates #529916 and #610591, 4 µl Long Flap Oligo/reaction (A or B) for reactions I, ii and iv. 3 µl of LF for area iii, 29 H$_2$O for reactions I, ii and iv. 32 µl H$_2$O for reaction iii, and 4 µl T4 ligase. Preanneal oligos in this mix without the ligase at 37° C. for half an hour. Add ligase as last reagent and allow to ligate at room temperature for at least four hours. Product concentration is 1 pmol/flap/µl.

Flap Ligation Phosphorylation (Step B) Label four separate 1.5 ml tubes with roman numerals again, one through four with a P inside a circle to designate that the products are phosphorylated. Add the following reagents to the corresponding tube: 10 µl/Flap ligation reaction (take 10 µl/flap ligation reaction above), 2.5 µl Optikinase buffer, 0.5 µl 100 mM ATP, 11.5 µl H$_2$O, and 0.5 µl Optikinase enzyme. Incubate at 37° C. for 1 hour. Product concentration 0.4 pmol/flap/µl.

Oligonucleotide Patch Unit Phosphorylation (Step C) 27 µl Oligonucleotide Patch Unit mix 0.74 pmol/µl, 5 µl 10× buffer, 1 µl 100 mM ATP, 3 µl Optikinase enzyme, and 14 µl H$_2$O. Once reagents are all together gently mix the solution by flicking the tube a few times and spin down. Incubate at 37° C. for 1 hour.

Hybridization to M13mp18 scaffold (Step D) In a new 1.5 ml tube add the following reagents: 20 µl M13mp18 at 250 ng/µl, 27 µl Phosphorylated Oligonucleotide Patch Units 0.4 pmol/µl (Step C), 12.5 µl/Phosph. Flap Ligation (Step B) preheat at 55° C. for 5 minutes and put on ice, 11 µl 10× ligase buffer and heat entire mixture at 55° C. for 1 minute. Hybridize mixture at 37° C. for at least 4 hours.

Ligation (Step E) Spin down eppendorf contents. Add 1.2 µl 100 mM ATP and 3 µl T4 ligase. Gently mix contents by flicking the tube, then spin down.

BamH1 Digest (Step F): 1 µl of 10 pmol BamH1 oligo, 20 µl 10× BamH1 buffer and hybride at 37~1 hour. Adjust volume to 200 Add 3 µl BamH1 enzyme. Incubate at 37° C. for 1 hour.

First step: start by adding 20 µl of M13mp18 (NEB 250 µg/ml) to a clean 1.7 ml eppendorf tube. Take 5 µl of Phosphorylated Flap ligation reaction and preheat it at 70 for 2 minutes and immediately put on ice. Add the 5 µl of each Phosphorylated Flap Ligation reaction (1 pmol/flap/µl) to the tube and gently mix by pipetting a few times. Incubate the eppendorf tube at 37° C. for 1 hour.

Second step: put 13.5 µl. Oligonucleotide Patch Unit Mix (0.74 pmol/µl) and 1 µl of Acrydite Mix (10 pmol/µl) in a new eppendorf 1.7 ml eppendorf tube. Add 5 µl. 10× Optikinase buffer, 1 µl 100 mM ATP and 27.5 µl. H$_2$O. Mix gently by pipetting the solution. Add 2 µl Optikinase enzyme, gently mix by pipetting and incubate at 37° C. for 1 hr.

Third step: take the phosphorylated oligos rxn and add it entirely to the contents of the M13mp18+Flaps Hybridization. The reaction is mixed gently by pipetting and it is allowed to incubate at 30° C. for 1 hour. After the hybridization is complete adjust the ATP by adding 1 µl (100 ATP) to the reaction.

Fourth step: spin down contents in eppendorf tube and add 4 µl T4 Ligase enzyme (5 units/µl), mix gently by pipetting. Incubate at room temperature for at least four hours. Add 1 µl BamH1 oligonucleotide (10 pmol/µl) to hybridize at room temperature while ligation is taking place.

Fifth step: digest ligation reaction by adding 4 µl BamH1 enzyme (5 units/µl), mix gently by pipetting and incubate at 37° C. for 1 hour. Once the incubation period is over. Take an aliquot of 500 ng for QC.

Sixth step: treat with Psoralen, UV or DMPA light for 15 minutes.

Calculations include:

5 µg of M13=20 µl stock from New England Biolabs=2 pmols

Oligonucleotide mix: 180-34 flap areas–10 Acrydite modified Oligos=0.74 pmol/oligo 10 pmols/oligonucleotide=13.5 µl=1350 pmols Optikinase 1 unit converts 1 nmol of phosphate to ends—use excess. 4 µl of Optikinase was used.

M13mp18.

EXAMPLE 3

Protocol for Production of RNA Nanoreporters

Nanoreporters were generated and successfully employed to detect target molecules using methods substantially as described in this example. An example of target detection using such this method is shown in FIG. 6.

Scaffold Production

Single-stranded circular M13mp18 DNA (USB Corporation) is annealed to a 10-fold molar excess of an oligonucleotide complementary to the Bam HI recognition site (Bam Cutter oligo) and cut with Bam HI restriction enzyme to yield a linear single-stranded DNA backbone. An oligonucleotide complementary to the Bam Cutter oligonucleotide (anti-Bam oligonucleotide) is subsequently added in 50-fold excess to the Bam Cutter oligonucleotide to sequester free Bam Cutter oligonucleotide and thus prevent recircularization of the M13 during later steps.

The linear M13 molecule serves as a scaffold onto which RNA patches, or RNA segments, with incorporated fluorophores can be annealed.

PCR to Form Double-Stranded Positions on the M13 Scaffold

Ten sets of oligonucleotide primer pairs were designed to create 10 different regions along the M13 scaffold. Each pair contains one primer which has a T7 RNA polymerase promoter at the 5' end. Regions 2-7 are designed to be 900 bases (approximately 300 nm) long, as this is the approximate size of a diffraction-limited spot (the smallest spot that can be achieved with standard optics). Regions 1 and 8 have both long and short versions: the long versions cover the whole 900-base region, while the short versions cover only a portion of the 900-base region to allow a target-specific sequence to be ligated. Thus a target-specific sequence can be attached to either end. The ends can also be used for attachment of anchors or tags.

PCR is performed using Taq polymerase and 0.5 ng of double-stranded M13mp18 (USB Corporation) as a template. Reactions are cleaned up using a Qiaquick purification kit from Qiagen. Each PCR reaction yields a double-stranded fragment corresponding to one specific segment as illustrated below. These fragments are used as templates for the in vitro transcription of the RNA segments.

In Vitro transcription to produce dark RNA segments

Using the PCR products described above as double-stranded templates, RNA segments are generated using an in vitro transcription kit from Ambion (Megascript™ T7 kit).

The products of the transcription reactions are purified (including treatment with DNAse I to remove template) using a RNeasy Kit from Qiagen.

In Vitro Transcription to Produce RNA Segments Modified with Aminoallyl Groups

Using the PCR products described above as double-stranded templates, RNA segments for later dye-coupling are generated using an in vitro transcription kit from Ambion (MessageAmp aRNA kit). Aminoallyl-modified UTP nucleotides are incorporated into the RNA segments during transcription. The products of the transcription reactions are purified (including treatment with DNAse I to remove template) using a RNeasy Kit from Qiagen.

Dye Coupling of Aminoallyl RNA Segments to Produce Colored RNA Segments 20-100 µg of aminoallyl-modified RNA segment is coupled with NHS-ester dyes using Ambion Aminoallyl Labeling Kit. Dyes used include Alexa 488, Alexa 594 and Alexa 647 (Invitrogen/Molecular Probes) as well as Cy3 (Amersham).

Each segment is made separately in 4 colors so that each position on the scaffold can be filled with a segment in any of the four colors; thus different colors can be added at different positions to create many unique color combinations.

In this particular embodiment, adjacent segments must be of different colors or there may be dark segments interspersed so that each segment is detected as an individual 'spot'. Dark segments may be used as part of the nanoreporter code.

Assembly of the Label Molecule

Segments for each position are annealed in a 2:1 ratio of segment to M13 scaffold in 1× SSPE buffer at 70° C. for 2 hours.

An assembled nanoreporter with labeled RNA segments is depicted in FIG. 3A-3B. FIG. 3A depicts a nanoreporter in which only alternate "spots" (1, 3, 5 and 7) are labeled, and FIG. 3B depicts a nanoreporter in which every spot is labeled.

EXAMPLE 4

Detection of Target (S2) RNA and DNA Molecules Using an RNA Nanoreporter/Ghost Probe Combination Synthesis of Probe and Target Oligonucleotides S2 DNA target oligonucleotide was synthesized and purified by polyacrylamide gel electrophoresis (Integrated DNA Technologies). S2 RNA target molecules were generated by in vitro transcription of PCR products corresponding to region of cloned SARS coronavirus gene (Invitrogen) using an Ambion Megascript™ kit per manufacturer's instructions. The S2 ghost probe (FIG. 6A (i)) was complementary to a specific 50-base region of the S2 target sequence (S2-a) and was synthesized with a biotin-TEG monomer at the 5' end and purified by high performance liquid chromatograpy (Integrated DNA Technologies). A second oligonucleotide with 50 bps complementary to the S2 target (S2-b) plus 9 bp of an additional sequence used for ligation to the M13 scaffold (59 bp total) was synthesized and purified by HPLC (Integrated DNA Technologies). Note that S2-a and S2-b target regions were not overlapping.

Nanoreporter Synthesis

Oligonucleotide S2-b was ligated to the 5' end of linearized M13 [FIG. 6A (iii)], and the resulting product was purified away from residual unligated oligonucleotide by size-exclusion filtration through a YM100 filter (Millipore) per manufacturer's instructions. Amino-allyl-modified RNA segments complementary to M13 is positions 2, 4, 6, and 8 (SEQ ID NOs: ) (FIG. 1C) were generated from in vitro-transcription of DNA templates (PCR products) via the Ambion Megascript™ kit per manufacturer's instructions. The segments were then coupled to NHS-ester-modified Alexa 647 dye (Invitrogen) per Ambion's instructions (amino allyl MessageAmp™ II aRNA kit). RNA segments corresponding to positions 1, 3, 5, and 7 of the M13 scaffold (FIG. 1C) were generated as unmodified in vitro-transcribed RNAs from DNA templates as described above. Assembly of the nanoreporter was carried out by annealing 10 fmol/μl of each of the eight segments to 5 fmol/μl of the M13-S1-b scaffold for 2 hours at 70° C. in 1× SSPE buffer (150 mM sodium chloride, 10 mM sodium phosphate, 1 mM EDTA). The final product was a nanoreporter with 4 segments labeled with A647 (red) interspersed with dark segments.

Hybridization Conditions

Hybridization of nanoreporters and ghost probes to target were carried out under the following conditions: 5× SSPE (750 mM sodium chloride, 50 mM sodium phosphate, 5 mM disodium EDTA), 40 pM ghost probe (attachment oligonucleotide S2-a), 40 pM Nanoreporter S2-b, 100 ng/μl sheared salmon sperm DNA, 5× Denhardt's solution and 0.1% Tween. Final target concentrations were 20 pM S2 DNA target (FIG. 6B) and 1 pM S2 RNA target (FIG. 6C). No target was added to the negative control (FIG. 6D). The hybridization reaction was incubated at 65° C. for at least 16 h.

Hybridization reactions were diluted 1:2 with 100 mN Borate buffer solution (pH 9.8) and introduced into a flow cell channel and bound to a streptavidin-coated coverslip forming the bottom of the channel(Streptavidin-OptiChem® coverslips from Accelr8). Attachment to the slide by one end of the nanoreporter/target/ghost probe complex was achieved via interaction of the biotinylated ghost probe with the streptavidin surface. After rinsing the channel with additional borate buffer to remove excess reporters not bound to the surface, the was exchanged with 1× TAE (40 mM Tris-acetate, 1 mM EDTA) and a current of 200V was applied to stretch out the nanoreporter/target complexes during image capture.

Images were obtained using a Leica DMI 6000B microscope with a 63× oil immersion objective (1.4 NA), Xcite-120 light source (Exfo), customized filter sets (Chroma Technologies), an Orca-ER CCD camera (Hamamatsu) and Metamorph data acquisition software (Molecular Devices).

As predicted, when the correct target molecule S2 hybridizes [FIG. 6A (ii)] to both ghost probe [FIG. 6A (i), S2-a] and S2-b target-specific nanoreporter [FIG. 6A (iii)], the ghost probe/target/nanoreporter complex forms a single species that attaches to the slide and was visualized as 4 spots when exposed to 647 nm wavelength light (FIGS. 6B, 6C, and 6E). The amount of binding was dependent on the target concentration. There was no significant binding in absence of S2 target sequence (FIG. 6D).

EXAMPLE 5

Nanoreporter Comprising a Monovalent or Bivalent Antibody Fragment

Where a target molecule is a protein or polypeptide, a nanoreporter can be generated in which the nanoreporter scaffold is a nucleic acid and the target-specific sequence is a monovalent or bivalent antibody fragment.

Using routine methods, an antibody that recognizes a target molecule of interest is optionally digested with pepsin to generate $F(ab')_2$ fragments. The two parts of the antibody or the two $F(ab')_2$ fragments generated by the pepsin digestion are separated by mild reduction, for example with 2-mercaptoethylamine. This reduction separates either the antibody or the two $F(ab')_2$ fragments into two monovalent fragments with two sulfhydryl groups that can be functionalized.

A heterobifunctional crosslinking reagent (e.g., m-Maleimidobenzoyl-N-hydroxysuccinimide ester from Pierce Biotechnology Inc.) is used to attach a maleimide to an oligonucleotide with an amine modification (which can be ordered from many sources, such as Integrated DNA Technologies). The NHS on the cross-linking reagent is reacted with the amine on the oligonucleotides to produce a maleimide-conjugated oligonucleotide.

This maleimide conjugated oligonucleotide is then reacted with one of the sulfhydryl groups on the antibody fragment. Due to steric limitations, it is preferable that only one oligonucleotide be attached to each fragment.

This monovalent or bivalent antibody fragment attached to an oligonucleotide can then be hybridized to a complementary sequence on a nanoreporter scaffold, to generate a reporter probe in which the target-specific sequence is an antibody sequence. Such a reporter probe can be used alone to detect the target molecule, or in conjunction with a ghost probe or another reporter probe whose target-specific sequence is a monovalent or bivalent antibody or antibody fragment that binds to a different portion of the same target molecule.

EXAMPLE 6

Hybridization of 25 Cellular Genes to 100 NG of Placental Total RNA Using Nanostring Reporter System Detection and quantitation of 25 endogenous cellular genes was carried out in a single multiplexed hybridization reaction. In addition, three non-human control sequences were spiked into each reaction that corresponded to approximately 10, 100 and 300 copies per cell, respectively. A negative control hybridization was also performed in the absence of cellular RNA.

Hybridization Reaction

Each sample was hybridized in triplicate. Final concentrations of the hybridization reagents were as follows: 1.12 nM total Nanoreporters (28 individual Nanoreporters at 40 µM each), 1.12 nM total ghost probe (28 individual ghost probes), 5× SSPE (pH 7.5), 5× Denhardt's reagent, 100 ng/µl sheared salmon sperm DNA, 0.1% Tween 20, 150 fM S3 spike DNA, 50 fM S4 spike, and 5 fM S6 spike. The final concentration of total placental RNA was 33 ng/µl. No total placental RNA was added to the negative control hybridizations. The final volume of the reaction was 30 µl. Reagents were mixed and incubated at 65° C. in thermocycler block with heated lid for 20 hours.

| Master Mix | (1 Reaction) | (6 Reactions) |
|---|---|---|
| 1.8X hybridization mix* | 16.7 µl | 100 µl |
| 25 endogenous gene reporters (0.6 nM each) | 2 µl | 12 µl |
| 25 endogenous gene ghost probes (0.6 nM each) | 2 µl | 12 µl |
| Control reporters (0.6 nM each) | 2 µl | 12 µl |
| Control ghost probes (0.6 nM each) | 2 µl | 12 µl |
| 10X control target mix | 3 µl | 18 µl |
| H₂O | 1.3 µl | 8 µl |
| Total | 29 µl | 174 µl |

*Hybridization mix (9X SSPE, 9X Denhardt's reagent, 180 ng salmon sperm DNA, 0.18% Tween 20)

| | Reactions | | | | | |
|---|---|---|---|---|---|---|
| | 1 | 2 | 3 | 4 | 5 | 6 |
| Master mix | 29 µl | 29 µl | 29 µl | 29 µl | 29 µl | 29 µl |
| 100 ng/µl placental RNA | 1 µl | 1 µl | 1 µl | 0 µl | 0 µl | 0 µl |
| H₂O | 0 µl | 0 µl | 0 ul | 1 µl | 1 µl | 1 µl |
| Total Rxn volume | 30 µl | 30 µl | 30 µl | 30 µl | 30 µl | 30 µl |

Incubate reactions in thermocycler with heated lid overnight (18 hours).

Post-Hybridization Purification

Hybridization reactions were purified to remove unhybridized reporters using an oligonucleotide complimentary to ghost probe attached to magnetic beads (F-bead). Hybridization reactions were diluted 5 fold in 0.1% Tween 20 to bring the final salt concentration to 1× SSPE and the solution added to 30 µl of F-beads (prewashed 2 times in 150 µl of 1× SSPE/0.1% Tween 20). Hybridized complexes were allowed to bind to the beads at room temperature for 15 minutes with continuous rotation, washed once in 150 µl of 0.5× SSPE, and eluted in 25 µl of 0.1× SSPE for 15 minutes at 45° C.

Binding, Stretching, and Immobilization

The samples was prepared for binding by addition of 1 µl of 1/1000 dilution of 0.1 uM Tetraspec™ fluorescent microspheres (product # T7279, Molecular Probes) and 3 µl of 1M bis-tris propane (pH 9.0). Samples were loaded into a Nanostring fluidic device for attachment to Accelr8 Optichem® slide coated with streptavidin (product #TB0200). After loading, slide surface was washed once with 1× TAE and prepared for electrostretching by addition of 40 µl of TAE to each well. Attached complexes were stretched by applying 200V across the fluidic channel. After 1 minute the samples were immobilized in the stretched position by adding 60 µl of 500 mM of G-hook oligo solution to the well containing the negatively charged electrode while continuing to apply voltage for 5 minutes. After immobilization the TAE solution is removed and replaced with anti-photobleaching reagent for imaging.

Imaging

Slides were imaged on Nikon Eclipse TE2000E equipped with a metal halide light source (X-cite 120, Exfo Corporation) and a 60× oil immersion lens (1.4 NA Plan Apo VC, Nikon). For each field of view, 4 images at different excitation wavelengths (480, 545, 580 and 622) were acquired with an Orca Ag CCD camera (Hamamatsu) under control of Metamorph software (Universal Imaging Corporation). Images were processed with custom image processing software.

Data Analysis

Raw data were extracted from processed images using custom software. Data were normalized to the average counts for control spikes in each sample. To determine if a gene was "detected" by the system, the counts obtained for each gene from hybridizations containing RNA were compared to counts obtained in hybridizations without RNA using a Student's t-test. Genes with p values <0.05 were determined to be detected. After background subtraction, the concentrations of cellular mRNA were estimated from the linear regression of the spike controls. These concentrations were converted to copies per cell using the following assumptions: 1 cell contains 10 µg total RNA; each cell contains 300,000 mRNA molecules; final volume of the reaction is 304

Results and Conclusion

Table 3 below shows the results of the data analysis described above. These results show that using the nanoreporter technology described herein, it was possible to detect transcripts, such as CASP3, that are present at a concentration of less than 1 transcript/cell. Thus, the nanoreporter technology provides an exquisitely sensitive means of detecting and quantifying gene expression.

TABLE 3

Transcript Concentration and Abundances

| Gene | Avg counts* | error (counts) | concentration (fM) | error (conc.) | calculated copies/cell | error (copy/cell) | Detected/ Not Detected (p < 0.05) |
|---|---|---|---|---|---|---|---|
| GM2A | 149 | 17 | 3.39 | 0.39 | 6.12 | 0.07 | D |
| ATF4 | 68 | 2 | 1.55 | 0.06 | 2.80 | 0.01 | D |
| CTNNB1 | 792 | 50 | 17.95 | 1.19 | 32.44 | 0.22 | D |
| IRF1 | 221 | 20 | 5.01 | 0.47 | 9.05 | 0.09 | D |
| STAT5A | 120 | 11 | 2.72 | 0.25 | 4.91 | 0.05 | D |
| CREG1 | 409 | 17 | 9.28 | 0.44 | 16.76 | 0.08 | D |
| CASP3 | 13 | 1 | 0.30 | 0.03 | 0.54 | 0.00 | D |
| CCL20 | 2 | 1 | 0.04 | 0.03 | 0.07 | 0.01 | ND |
| NMI | 115 | 2 | 2.61 | 0.07 | 4.72 | 0.01 | D |
| XBP1 | 719 | 46 | 16.30 | 1.10 | 29.45 | 0.20 | D |
| PCGF4 | 75 | 18 | 1.70 | 0.40 | 3.08 | 0.07 | D |
| IFI27 | 747 | 41 | 16.94 | 1.00 | 30.61 | 0.18 | D |
| TAF7 | 185 | 11 | 4.19 | 0.26 | 7.57 | 0.05 | D |
| OAS3 | 74 | 9 | 1.68 | 0.20 | 3.03 | 0.04 | D |
| C2 | 850 | 49 | 19.28 | 1.19 | 34.83 | 0.21 | D |
| IL6 | 8 | 3 | 0.19 | 0.07 | 0.34 | 0.01 | D |
| MyD88 | 94 | 6 | 2.13 | 0.14 | 3.85 | 0.03 | D |
| HIF1A | 130 | 7 | 2.95 | 0.17 | 5.33 | 0.03 | D |
| APOA2 | −1 | 2 | −0.01 | −0.05 | −0.03 | −0.01 | ND |
| KISS | 6825 | 130 | 154.79 | 4.52 | 279.65 | 0.82 | D |
| ELK3 | 55 | 4 | 1.25 | 0.09 | 2.27 | 0.02 | D |
| CBF2 | 72 | 3 | 1.64 | 0.07 | 2.96 | 0.01 | D |
| IFI30 | 625 | 47 | 14.16 | 1.10 | 25.59 | 0.20 | D |
| RELB | 35 | 5 | 0.78 | 0.11 | 1.42 | 0.02 | D |
| CTCF | 103 | 3 | 2.35 | 0.09 | 4.24 | 0.02 | D |

*Normalized and background subtracted.

The hybridization methods described herein have been performed in single multiplexed reactions containing up to 120 different reporters with similar hybridization efficiencies and results.

EXAMPLE 7

Considerations Regarding Nanoreporter Hybridization Kinetics

Background

Solution hybridizations with a large excess of probe over target follow pseudo-first order kinetics. In this regime the speed of the reaction depends only on the probe concentration and not on the target concentration. For a two-probe, one-target strategy to provide accurate information on the concentration of a target in solution, the probes should both be present in excess of the target. The possible concentration range is preferably therefore bounded on the lower end by the concentration of the target. However, the useful concentration range for the nanoreporter technology described herein is practically bounded on the lower end by the amount of time needed to perform the hybridization.

Hybridization Kinetics

In preferred embodiments, target detection and quantification assays are performed in which the target (T) must hybridize to both a reporter probe (R) and a ghost probe (G) to be detected (for example by affinity selection and detection of complexes comprising only (R) and (G), which in turn only form complexes in the presence of (T)). Assuming that these reactions are irreversible, there are four possible elementary reactions that occur.

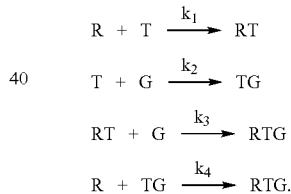

Because RT and TG are intermediate complexes of two out of the three species, these four reactions can be simplified to

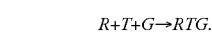

However, to quantitatively calculate the rate of production of RTG (the reporter-target-ghost probe complex), all four reactions must be considered. The differential equations describing the system are:

$$\frac{dC_G}{dt} = -k_2 C_G C_T - k_3 C_G C_{RT}$$

$$\frac{dC_G}{dt} = -k_1 C_R C_T - k_4 C_R C_{TG}$$

$$\frac{dC_T}{dt} = -k_2 C_G C_T - k_2 C_R C_T$$

$$\frac{dC_{TG}}{dt} = k_2 C_G C_T - k_4 C_R C_{TG}$$

$$\frac{dC_{RT}}{dt} = k_1 C_R C_T - k_3 C_G C_{RT}$$

$$\frac{dC_{RTG}}{dt} = k_4 C_R C_{TG} + k_3 C_G C_{RT}$$

where $C_R$, $C_T$, $C_G$, $C_{RT}$, $C_{TG}$, and $C_{RTG}$ are the concentrations of the various species, and $k_1$-$k_4$ are the kinetic constants for the four elementary reactions. Values for these kinetic constants when the probes and targets are complementary single-stranded molecules (i.e., when there is no purification tag on the ghost probe and no reporter) can be calculated from data available in the literature (Wetmur, *J. Annu. Rev. Biophys. Bioeng.* 1976.5:337-361).

$$k = k_N \frac{\sqrt{L}}{N} \frac{\alpha_{salt}}{\alpha_{ref}}$$

In the above equation, $k_N$ is the nucleation rate constant, L is the nucleic acid length (in base pairs), N is the nucleic acid complexity (equal to L for non-repetitive sequences) and $a_{salt}$ and $a_{ref}$ are corrections for salt concentration (Britten et al., 1974, *Methods in Enzymology* 29E:363-406). In the nanoreporter systems described herein, the kinetic constants will depend on the sizes of the attached ghost probe tags and reporter probe. Without being bound by any theory, it is the inventors' belief that the kinetic constants will have the same dependence on length that an elementary reaction has on the diffusion constants of the reactants.

$$k = k_N \frac{\sqrt{L}}{N} \frac{\alpha_{salt}}{\alpha_{ref}} \frac{D_1 + D_2}{2 D_{50}}$$

In the above equation $D_1$ and $D_2$ are the diffusion constants of the two reacting species (see the reactions above) and $D_{50}$ is the diffusion constant of a 50-mer single-stranded DNA molecule. Assuming a 100-base single-stranded target, 100-base single-stranded ghost probe, and 7200-base double stranded reporter, the relevant kinetic constants are $k_1 = 2.64 \times 10^5$ L/mol/s $k_2 = 6.55 \times 10^5$ L/mol/s $k_3 = 3.99 \times 10^5$ L/mol/s $k_4 = 1.91 \times 10^5$ L/mol/s Numerically solving the system of differential equations with these kinetic constants (assuming at least a 10-fold excess of probes over target) yields the prediction that 5 pM reporter and 5 pM ghost probe will drive hybridization to 10% of completion in an overnight reaction (16-18 hours). At concentrations lower than 5 pM, the amount of completely hybridized molecules is likely impractical to measure. Thus, in a preferred embodiment, the lower concentration of a nanoreporter component (ghost probe and/or reporter probe) is 5 pM.

Entanglement of Reporters

As probe concentrations increase, theory predicts that hybridization kinetics speed up without bound—the only limit being the solubility of the probes. However, the reporter probe can be very large compared to the target-specific sequence in the nanoreporter systems of the invention. Without being bound by any theory, the inventors believe that by its attachment to the reporter probe the kinetics of the target-specific sequence are altered from classical solution hybridization kinetics. Because the reporter probe is a large, polymeric molecule, it can have long-lived interactions (entanglements) with other nanoreporters when they come into contact. At low concentration the probability of two polymers becoming entangled is small, but as the concentration and/or size of a polymer in solution increases, these interactions become more and more common. In the extreme case of very long molecules at very high concentration the polymers form a permanent network, or gel, in solution. For solution hybridization to occur, a probe (e.g., a nanoreporter probe)/target pair must diffuse through solution until they contact one another and a hybridization nucleus forms. Classically, hybridization reactions are not diffusion limited because the translational diffusion of the molecules is faster than the nucleation of the hybridization (i.e., the probe and target diffuse together and interact many times before a nucleation occurs). In dilute solution its large size will slow the translational diffusion of the reporter probe, but may not significantly affect the kinetics. At some intermediate concentration, the reporter probes take up almost all of the space in the solution, effectively forming a permanently entangled gel, and can no longer diffuse in solution. However, the ghost probe and the targets are smaller molecules that are believed to still diffuse through the entangled reporter probes, allowing hybridization to take place (although possibly at a slower rate). The inventors also believe that at some higher concentration the reporter probe in solution will also hinder the movement of the ghost probe and the targets to the point that the reaction becomes diffusion limited. This concentration (which is not quantitatively known and depends upon the reporter probe structure, the ghost probe structure, and the target size) is the upper limit of the useful concentration range in the nanoreporter system, and can be empirically determined by one of skill in the art guided by the principles described herein.

Length Dependence of Kinetics

Since the limiting upper concentration for hybridization depends upon both the reporter structure and ghost probe structure (of which there are many possible variations), a theoretical framework to predict the permutations of useful concentration ranges is useful in the practice of the invention. Classical theory predicts that hybridization kinetics depend only on the size of the smaller probe. Theory would therefore predict that the size of the reporter will not play a role in the hybridization kinetics as long as both the target molecule and the ghost probe are significantly smaller. Theory then predicts that the rate of hybridization (for a constant target length) depends on $1/L^{1/2}$, where L is the length of the ghost probe, due to steric inhibition of hybridization. Consequently, the kinetics of hybridization will be faster with smaller ghost probes. As the ghost probe length increases, the hybridization rate should decrease as $1/L^{1/2}$. If a constant ghost probe length is assumed, then the range of reporter lengths and concentrations that will result in a measurable mount of hybridization events can be defined. Once a reporter size has been defined, then the approximate range of ghost probe sizes can be determined. This is an iterative process, but may give good starting points from which to gather data to generate detailed empirical guidelines, given that the theories that the inventors' rationale is based upon were generated from hybridization data in systems that do not employ a reporter probe.

Entanglement Threshold

A reporter probe is essentially a polymer in free solution, which behaves as a random coil. The volume occupied by a single reporter, $V_p$, can be calculated from polymer physics theories according to the Freely-Jointed Chain model (FJC, for a flexible polymer, such as single-stranded DNA or RNA) or the Worm-Like Chain model (WLC, for a stiff polymer such as double-stranded DNA or a reporter). For either model $$V_p = \frac{4}{3}\pi R_g^3$$

where $R_g$ is the radius of gyration. For the FJC $$R_g = b\left(\frac{N}{6}\right)^{0.6}$$

where b is the segment length and N is the number of segments in the chain. For the WLC $$R_g = \sqrt{\frac{1}{6}Nb^2 - \frac{b^2}{4} + \frac{b^2}{4N}\left(1 + \frac{1}{2N}(e^{-2N} - 1)\right)}$$

Figure 17:
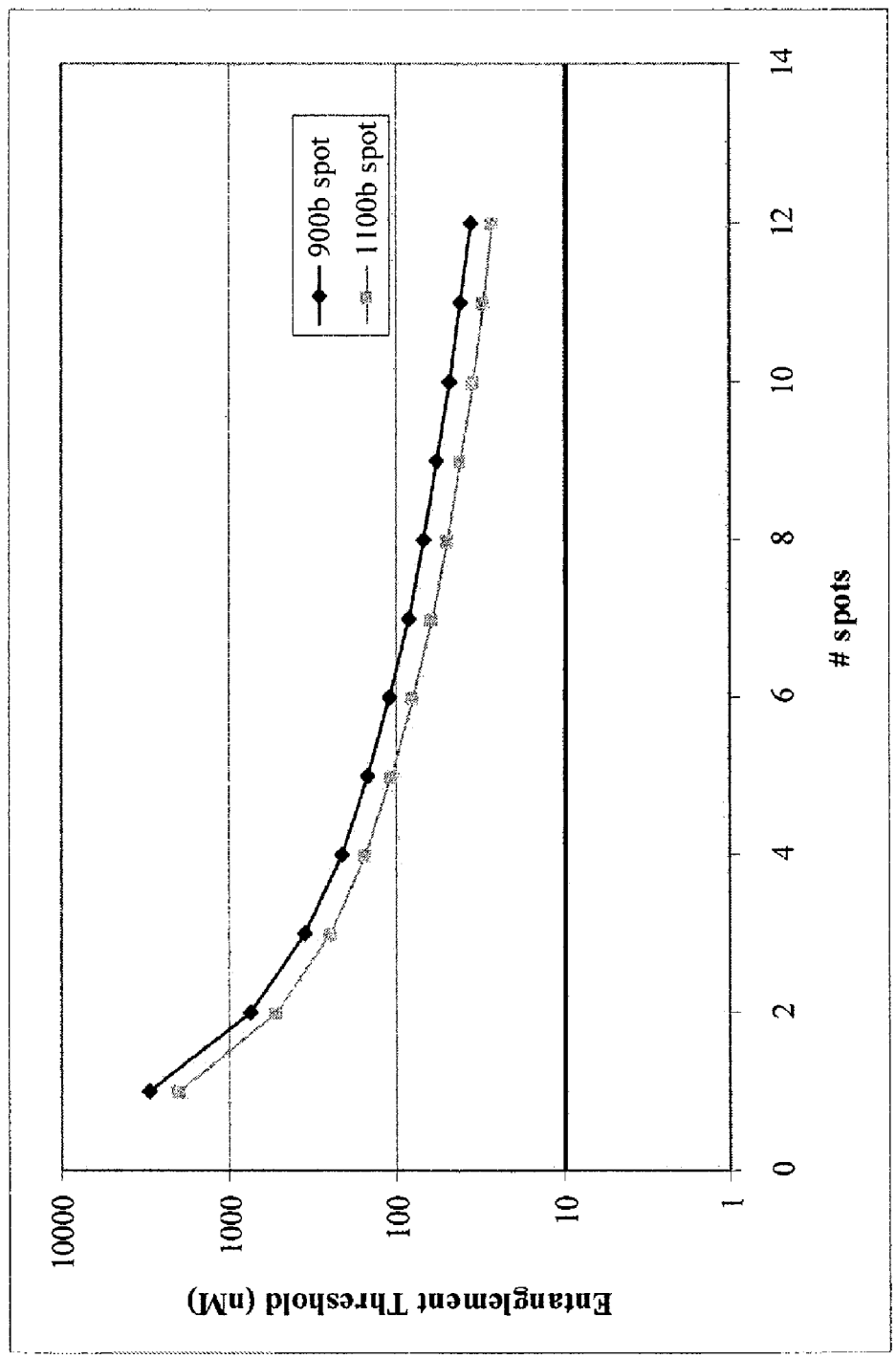
FIG. 17 depicts the relationship between the number of label attachment regions to the calculated entanglement threshold for nanoreporters for label attachment region sizes of 900 bp and 1100 bp
Figure 18:
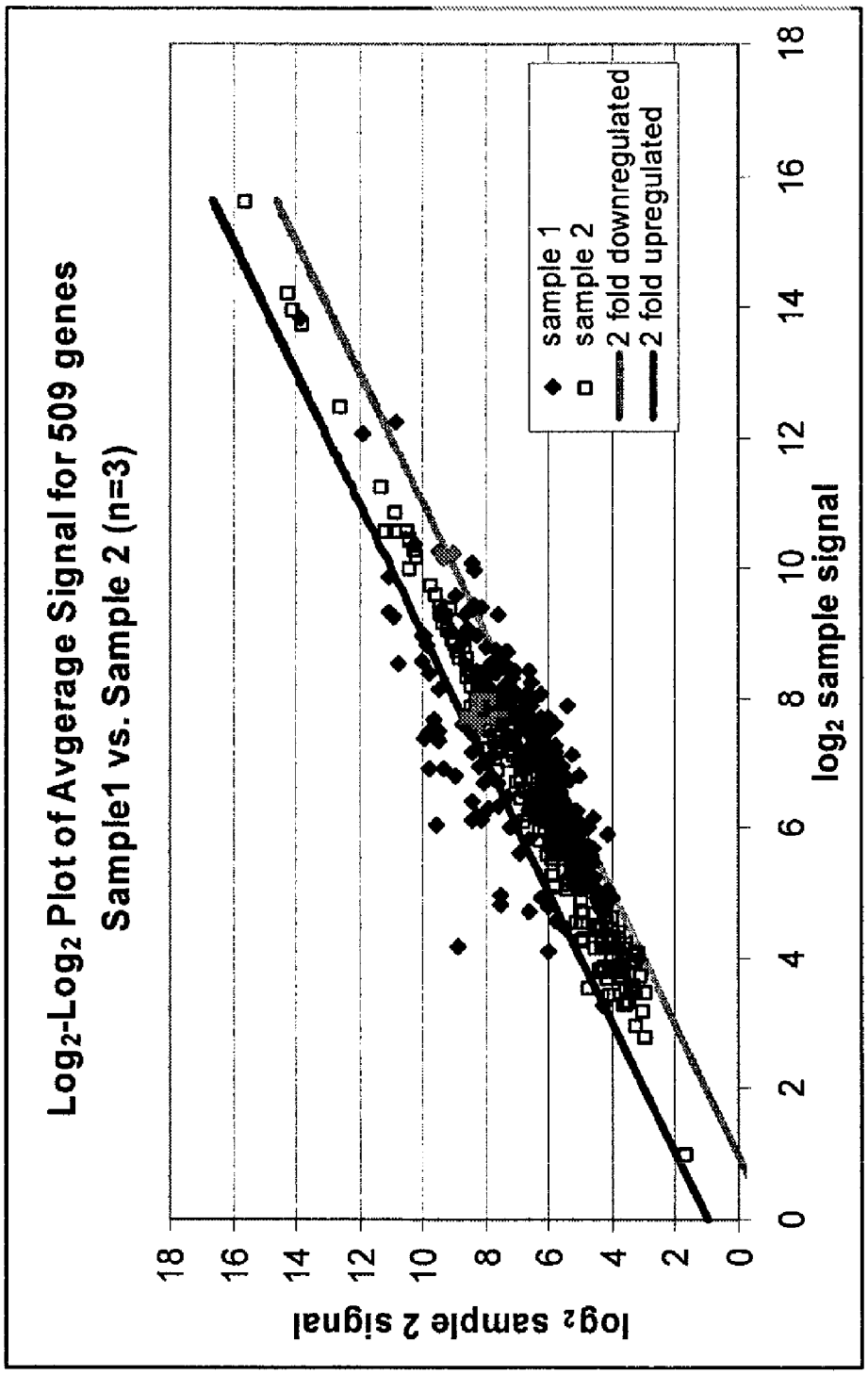
FIG. 18 is a scatter plot showing normalized and average $\log_2$ signal values from each positive sample (n=3) for all 509 genes whose expression was measured in a nanoreporter multiplex assay as described in Example 9 (Section 14) below.

The entanglement threshold concentration is defined as the concentration where the entire volume of the solution is occupied by the reporters.

$$C^* = \frac{3}{4\pi R_g^3 N_A}$$

where $N_A$ is Avogadro's number. Above this concentration it is assumed that the translational diffusion of the reporters is severely restricted. The entanglement threshold concentration varies with the reporter structure. As the reporter length increases, the entanglement threshold decreases (as $1/L^{1.5}$). From the equations above, the theoretical entanglement threshold for reporter probes with different spot sizes and different lengths can be calculated. The result of such calculations is shown in FIG. 17, which shows that for a 7200 bp RNA/DNA hybrid reporter probe with 8 label attachment regions of about 900 bp each, the entanglement threshold is about 70 nM.

If both the target and the ghost probe are much smaller than the reporters, then they will most likely be free to diffuse through the solution even at these high concentrations of reporters. Initial data indicates that hybridization kinetics do not slow appreciably up to a concentration of 80 nM with a 7200-bp reporter probe, a 100-base target, and a 100-base ghost probe.

Effect of Entanglement Threshold on Multiplexing

Assuming that the maximum concentration for reporters in a hybridization reaction is C*, then the concentration of each reporter (specific to a particular target) is equal to C*/M, where M is the multiplex of the reaction (number of different targets being addressed simultaneously). Conversely, the possible multiplex level for a particular reporter structure can be calculated from the lower limit of probe concentration ($C_p$ from kinetics~10 nM) and the entanglement threshold $$M = \frac{C^*}{C_p}$$

If the number of nanoreporter codes available does not depend on reporter probe size, then the multiplexing of the nanoreporter depends primarily on the reporter probe size and concentration (since it is much larger than the ghost probe). Because the ghost probe makes an insignificant contribution to entanglement during hybridization, it is the inventors' belief that the concentration of the ghost probe can be increased far above the concentration of the reporter probe. In Table 4 below, the maximum total ghost probe concentration ([G]) is set to 1000 nM for all reporter concentrations. This difference in concentration of ghost probe and reporter probe is an adjustable parameter. Preliminary experiments show that in a multiplex hybridization reaction with a 7200 bp reporter and 100 b ghost, 40 pM of each reporter probe and 200 pM of each ghost probe results in near complete hybridization in an overnight reaction.

Optimal Size and Concentration Ranges

Below in Table 4 is a summary of the optimal useful size and concentration ranges of the ghost probe and reporter probe at different multiplexing as approximated by the above theories. It is the inventors' belief that ghost probes up to about 200 bases will be practical for most applications

TABLE 4

Optimal size and concentration ranges of reporter probe, ghost probe and target, as well as multiplicity of probes, in the nanoreporter systems of the invention.

| Reporter Length (bp) | Ghost Length (b) | Minimum [R] (pM) | Minimum [G] (pM) | Maximum [R] (nM) | Maximum [G] (nM) | Max Multiplex |
|---|---|---|---|---|---|---|
| 2000 | 100 | 5 | 5 | 603 | 1000 | 114417 |
| 2000 | 50 | 4 | 4 | 603 | 1000 | 161811 |
| 2000 | 200 | 7 | 7 | 603 | 1000 | 80905 |
| 3000 | 100 | 6 | 6 | 292 | 1000 | 45182 |
| 3000 | 50 | 5 | 5 | 292 | 1000 | 63897 |
| 3000 | 200 | 9 | 9 | 292 | 1000 | 31948 |
| 4000 | 100 | 7 | 7 | 178 | 1000 | 23912 |
| 4000 | 50 | 5 | 5 | 178 | 1000 | 33817 |
| 4000 | 200 | 11 | 11 | 178 | 1000 | 16908 |
| 5000 | 100 | 8 | 8 | 123 | 1000 | 14746 |
| 5000 | 50 | 6 | 6 | 123 | 1000 | 20854 |
| 5000 | 200 | 12 | 12 | 123 | 1000 | 10427 |
| 6000 | 100 | 9 | 9 | 91 | 1000 | 9988 |
| 6000 | 50 | 6 | 6 | 91 | 1000 | 14125 |

TABLE 4-continued

Optimal size and concentration ranges of reporter probe, ghost probe and target, as well as multiplicity of probes, in the nanoreporter systems of the invention.

| Reporter Length (bp) | Ghost Length (b) | Minimum [R] (pM) | Minimum [G] (pM) | Maximum [R] (nM) | Maximum [G] (nM) | Max Multiplex |
|---|---|---|---|---|---|---|
| 6000 | 200 | 13 | 13 | 91 | 1000 | 7062 |
| 7200 | 100 | 10 | 10 | 68 | 1000 | 6792 |
| 7200 | 50 | 7 | 10 | 68 | 1000 | 6792 |
| 7200 | 200 | 14 | 10 | 68 | 1000 | 6792 |
| 8000 | 100 | 11 | 11 | 57 | 1000 | 5444 |
| 8000 | 50 | 7 | 7 | 57 | 1000 | 7699 |
| 8000 | 200 | 15 | 15 | 57 | 1000 | 3850 |
| 10000 | 100 | 12 | 12 | 40 | 1000 | 3419 |
| 10000 | 50 | 8 | 8 | 40 | 1000 | 4835 |
| 10000 | 200 | 17 | 17 | 40 | 1000 | 2417 |

EXAMPLE 8

Exemplary Embodiments for Dual Nanoreporter ASSEMBLY

This section describes an embodiment for assembly of a dual nanoreporter in which one probe is a ghost probe and the other probe is a reporter probe comprising color RNA segments assembled on an M13 backbone. The ghost probe is attached to a biotinylated F-hook and the reporter probe is attached to a biotinylated G-hook. The dual nanoreporter is hybridized to a biomolecular sample to detect and quantify a target molecule. The steps below do not have to be performed in the order presented. Moreover, each particular step represents a specific embodiment that may be combined with embodiments other than those presented below.

Preparation of the M13 Scaffold

Single-stranded circular M13mp18 DNA (USB Corporation) is annealed to a 5-fold molar excess of an oligonucleotide complementary to the BamH1 recognition site (Bam Cutter oligo) and cut with Bam H1 restriction enzyme to yield a linear single-stranded DNA backbone. An oligonucleotide complementary to the Bam Cutter oligonucleotide (anti-Bam oligonucleotide) is subsequently added in 50-fold excess to sequester free Bam Cutter oligonucleotide and thus prevent recircularization of the M13 during later steps.

The linear M13 molecule serves as a scaffold onto which RNA patches, or RNA segments, with incorporated fluorophores can be annealed.

Attachment of a Target-Specific Sequence to the Scaffold

An oligonucleotide comprising a sequence (of, e.g., 30-70 nucleotides) complementary to the target nucleic acid of interest, plus 9 bp of additional sequence used for ligation to the M13 scaffold, is generated and ligated to the 3' end of the linearized M13 scaffold.

Attachment of G-Tags to the Scaffold

A G-tag (e.g., an oligonucleotide having the sequence 5'-AACATCACACAGACC AACATCACACAGACC AACATCACACAGACC AACATCACACAGACC AGCCCTTTG-3' (SEQ ID NO: 2), which includes 4 copies of the complement of the G-hook 5'-GGTCTGTGTGATGTT-3' (SEQ ID NO: 3), followed by 9 bases of ligator sequence, and which is complementary to the G-hook) is attached to the 5' end of the linearized single-stranded M13 backbone to allow for (1) purification of the reporter following ligation and/or annealing of segments; and (2) immobilization of the reporter once it is "stretched" on a solid surface. The sequence of the ligator for attaching G-tag to the 5' end of single-stranded M13 which has been linearized at the BamH1 site can be 5'-CTCTAGAGGATCCAAAGGGCT-3' (SEQ ID NO: 4).

The ligation reaction can be performed according to the following protocol to produce approximately 80 pmol of G-tag/M13 ligation product:

Materials:
  [100 µM] anti-G4 tag oligo
  [100 µM] anti-G4 tag ligator oligo
  [80 nM] Linear single-stranded M13
  [10× T4 DNA Ligase Buffer (Fermentas)
  T4 DNA Ligase (Fermentas)
  20×SSC (Ambion)
  DEPC H$_2$O (Ambion)

Method:
  1. Pre-anneal the G-tag and ligator:
    25 uM 2:1 G/Glig in 1×SSC
    20 µl [100 uM] G-tag Ligator
    40 µl [100 uM] G-tag
    4 µl 20×SSC
    16 µl A DEPC H$_2$O
    *Anneal on the MJ Thermocycler
    95° C., 3 min; 72° C., 30 sec, −1° C./cycle, x 68 cycles; hold at 4° C.
  2. Ligate the G-tag to the linear M13:
    64 nM M13-G4 in 1× Lig Buffer
    1000 µl [80 nM] Linear M13
    80 µl [25 uM] 2:1 G/Glig in 1×SSC
    124 µl 10× T4 DNA Ligase Buffer
    40 µl T4 DNA Ligase
    *Ligate in an aluminum heat block covered with foil at 37° C. for 2 hr then at 65° C. for 15 minutes to inactivate the enzyme.

Preparation of RNA Segments

Ten sets of oligonucleotide primer pairs are designed to create 10 different regions along the M13 scaffold. Each pair contains one primer which has a T7 RNA polymerase promoter at the 5' end. Regions 2-7 are designed to be 900 bases (approximately 300 nm) long, as this is the approximate size of a diffraction-limited spot (the smallest spot that can be achieved with standard optics). Regions 1 and 8 have both long and short versions: the long versions cover the whole 900-base region, while the short versions cover only a portion of the 900-base region to allow a target-specific sequence to be ligated. Thus a target-specific sequence can be attached to either end. The ends can also be used for attachment of anchors or tags.

PCR is performed using Taq polymerase and 0.5 ng of double-stranded M13mp18 (USB Corporation) as a template. Reactions are cleaned up using a Qiaquick purification kit from Qiagen. Each PCR reaction yields a double-stranded fragment corresponding to one specific segment as illustrated below. These fragments are used as templates for the in vitro transcription of the RNA segments.

Using the PCR products described above as double-stranded templates, RNA segments are generated using an in vitro transcription kit from Ambion (Megascript™ T7 kit). The products of the transcription reactions are purified (including treatment with DNAse Ito remove template) using a RNeasy Kit from Qiagen.

Labeling of the RNA Segments

Using the PCR products described above as double-stranded templates, RNA segments for later dye-coupling are generated using an in vitro transcription kit from Ambion (MessageAmp aRNA kit). Aminoallyl-modified UTP nucleotides are incorporated into the RNA segments during transcription. The products of the transcription reactions are purified (including treatment with DNAse Ito remove template) using a RNeasy Kit from Qiagen.

20-100 µg of aminoallyl-modified RNA segment is coupled with NHS-ester dyes using Ambion Aminoallyl Labeling Kit. Dyes used include Alexa 488, Alexa 594 and Alexa 647 (Invitrogen/Molecular Probes) as well as Cy3 (Amersham).

Each segment is made separately in 4 colors so that each position on the scaffold can be filled with a segment in any of the four colors; thus different colors can be added at different positions to create many unique color combinations.

In this particular embodiment, adjacent segments are of different colors or there may be dark segments interspersed so that each segment is detected as an individual 'spot'. Dark segments may be used as part of the nanoreporter code.

Annealing of the RNA Segments to the Scaffold

Segments for each position are annealed in a 2:1 ratio of segment to M13 scaffold in 1× SSPE buffer at 70° C. for 2 hours. An assembled nanoreporter with labeled RNA segments is depicted in FIG. 3A-3B. FIG. 3A depicts a nanoreporter in which only alternate "spots" (1, 3, 5 and 7) are labeled, and FIG. 3B depicts a nanoreporter in which every spot is labeled.

Preparation of the Ghost Probe

One or more oligonucleotides comprising sequences (of, e.g., 30-70 nucleotides) complementary to different regions of the target nucleic acid(s) of interest than those to which the target-specific sequences of the reporter probe are complementary, are generated. Optionally, F-tags for F-hook attachment are ligated to the 5' end of the ghost probe using a ligator oligonucleotide that is complementary to a short sequence on the 3' end of the F-hook as well as a short sequence on the 5' end of the ghost probe. The sequences that are complementary to the ligator oligonucleotide are not part of the F-hook sequence or the probe sequence, but are additional nucleotides added to those oligos in order to facilitate ligation.

Attachment of F-Tags to the Ghost Probe

An F-tag (e.g., an oligonucleotide having the sequence 5'-GATGGAGAC GTCTATCATCACAGC GTCTATCAT-CACAGC-biotin -3' (SEQ ID NO: 5), which includes 2 copies of the complement of the F-hook 5'-GCTGTGATGATA-GAC-3' (SEQ ID NO: 6), followed by 9 bases of ligator sequence and is complementary to the F-hook) is attached to the 3' end of the ghost probe to allow for (1) purification of the ghost-probe-target-reporter hybridization complex; and (2) attachment of the hybridization complex on the slide via the biotin moiety. The sequence of the ligator for attaching F-tag to the 3' end of the ghost probe can be 5'-GTCTCCATCTTC-CGACAG-3' (SEQ ID NO: 7).

Materials:
100 uM F-biotin tag
100 uM F ghost probe ligator
Fermentas 10× T4 DNA Ligase Buffer
1 uM ghost probes
Fermentas T4 DNA Ligase Method:
1. Pre-anneal the hook and ligator:
5 uM F-biotin tag/ligator mix
5 µl [100 uM] F-biotin tag
5 µl [100 uM] F-ghost probe ligator
10 µl 10× T4 DNA Ligase Buffer
80 µl DEPC H$_2$O
Anneal on the MJ Thermocycler (95° C., 3 min; 72° C., 30 sec, −1° C./cycle×68 cycles; hold at 4° C.).

2. Set up the following ghost probe ligation:
300 nM anti-F2-biotin-GP
6.0 µl [1 uM] Ghost Probe
4.8 µl [5 uM] anti-F2-biotin tag/ligator mix
1.52 µl 10× T4 DNA Ligase Buffer
3.68 µl DEPC H$_2$O
4.0 µl T4 DNA Ligase
Ligate on the MJ Thermocycler (37° C., 18 hr; 65° C., 15 minutes; hold at 4° C.)

3. QC the ligation on a 15% Novex TBE-Urea gel:
Prepare the following loading solutions:

| Ligation | Neg Control-Ghost Probe |
| --- | --- |
| 3.33 µl [300 nM] ligation | 1 µl [1 uM] ghost probe |
| 1.67 µl DEPC H$_2$O | 0.33 µl 10X T4 DNA Ligase Buffer |
| 5 µl 2X Loading Buffer | 3.67 µl DEPC H$_2$O |
|  | 5 µl 2X Loading Buffer |

Neg Control-F-Biotin Tag/Ligator Mix
2 µl [0.5 uM] F-biotin tag/ligator mix
0.33 µl 10× T4 DNA Ligase Buffer
2.67 µl DEPC H$_2$O
5 µl 2× Loading Buffer
50 bp Oligo Ladder
4 µl Ladder
6 µl 2× loading buffer
Run of a 15% Novex TBE-Urea gel at 180V for 50 minutes.
Stain with SYBR® Gold for 30 minutes.

Alternative Embodiments

Rather than covalently coupling biotin to the single-stranded F-tag, the biotinylation of the ghost probe can also be accomplished by annealing a biotinylated oligonucleotide (DNA or RNA) with a sequence complementary to the common portion of the ghost probe. Such a sequence could be the F sequence itself, or another sequence which is added to the ghost probe in addition to the F sequence. If such an additional sequence is added, it could be from 10-100 bases long, from 1-10 copies, with the preferred configuration being a single copy from 50-100 bases long.

Biotinylation of Target mRNA

There are a number of commercially available kits available for the direct labeling of an mRNA sample including Label IT® µArray™$^{Biotin}$Mirus #MIR 8010) and Biotin-Chem-Link (Roche (1 812 149). Following manufacturer's procedures biotin labeled mRNA is added to the hybridization reaction as described in Section 3d (below) with the following modifications: Since most protocols suggest the use of poly A+ mRNA, the amount of RNA used could be reduced below the 100 ng total RNA in a typical hybridization to 10 ng and possibly 1 ng. No ghost probe should be added to this reaction. F bead post-hybridization purification is no longer required. G-bead post-hybridization purification should be used to remove unhybridized biotinylated mRNA that might compete for binding to the slide. Depending on the amount of RNA used, this may or may not be required. Alternatively, total RNA could be biotinylated without the need for purification of the poly A+ fraction. In this case, the original amount of total RNA should be used (100 ng). The use of total RNA might require modifications of the manufacturer's protocol to increase labeling efficiency.

An alternative approach would be to enzymatically generate biotinylated 1st strand cDNA or biotinylated amplified RNA (aRNA) using commercially available kits and use these in place of total or mRNA. This approach would require a redesign of the reporter probes to be in the sense orientation. Both ghost probe and F-bead post-hybridization reactions would be omitted while G-bead purification would remain for removal of non-hybridized RNA.

Hybridization of Dual Nanoreporter to Target

Many hybridization conditions are sufficient for achieving gene expression data. To shorten hybridization times while maintaining reasonable hybridization efficiency, several parameters can be altered: i) increasing ghost probe and reporter concentrations, ii) fragmenting of total RNA to average size range of 200-500 bp while lowering the pH of hybridization to 6.5, iii) using more total RNA in same hybridization volume, iv) lowering hybridization volume to approximately 10 µl. Blocking reagents such as Denhardt's and ssDNA can be removed without deleterious effects on hybridization efficiency or cross hybridization to mRNAs from different species.

The following protocol has been performed successfully with multiplexing from 1 to >500 nanoreporters with ghost probes (an example demonstrating a nanoreporter assay utilizing 25 nanoreporters is described in Example 6 above, and another example demonstrating a nanoreporter assay utilizing 509 nanoreporters is described in Example 9 below). The final concentration of all nanoreporters varies depending on 1) the concentration of each reporter and 2) the number of genes being multiplexed.

Typical total nanoreporter concentrations range from 40 pM (1 gene @ 40 pM) to 20 nM (500 genes @40 pM). Ghost probe concentrations also vary from 200 pM (1 gene @ 200 pM) to 100 nM (500 genes @ 200 pM). The example that follows describes a single multiplexed hybridization containing approximately 500 endogenous genes with positive and negative controls. Add, 11.1 µl of 2.7× hybridization mix [13.5× SSPE pH 7.5 (USB #75890), 0.27 µg/µl sheared salmon sperm DNA (Sigma #D-7656), 0.27% Tween 20 (Sigma #P-1379), and 13.5× Denhardt's reagent (Sigma D-2532)], 5 µl of gene Nanoreporter mix (0.24 nM each or 123 nM total, includes 509 endogenous genes and 8 hybridization controls), 4.6 µl 513 gene ghost probe mix (1.3 nM each or 667 nM total, includes 509 endogenous genes and 8 hybridization controls), 1 µl of purification control reporter mix (0.5 pM), 1 µl of total cellular RNA (100 ng/ul), 1 µl of 30× spike target mix (1.5 nM-3 fM) and 6.3 µl of DEPC treated water (Ambion #9922) to a 0.2 ml thin wall tube (final volume 30 µl).

Final concentration of hybridization reagents should be 5× SSPE, 0.1% Tween 20, 100 ng/µl sheared salmon sperm DNA, 5× Denhardt's reagent, 40 pM each Nanoreporter (~20 nM total), 200 pM each ghost probe (~100 nM total) and 33 ng/µl of total cellular RNA. Control spike targets typically vary in range from 50 fM down to 0.1 fM in a single reaction. All reagents are most preferably free of all nuclease activity. For optimal results, all reagents should be free of nuclease activity.

Mix reagents well and incubate in temperature block with heated lid for 20 hours. After hybridization purify the nanoreporters with affinity reagents for both the ghost probe and the reporter probe.

Alternative Embodiment: Hybridization Protocol for Without SSDNA and Denhardt'S Reagent This protocol has been performed successfully with multiplexing from 1-500 nanoreporters and ghost probes. Removal of ssDNA and Denhardt's reagent from hybridizations performed with human reagents (Nanoreporters and ghost probes) had no effect on cross hybridization with mouse total RNA when compared to a hybridization containing ssDNA and Denhardt's. In addition, removal of ssDNA and Denhardt's does not result in an increased background signal (based on negative hybridization controls). Finally, there is no significant loss (or gain) of signal for endogenous genes hybridized in the presence or absence of ssDNA and Denhardt's (509 genes, $R^2$ value=0.998).

Alternative Embodiment: Hybridization Conditions for Fragmented Cellular MRNA

Fragmentation of cellular RNA has been achieved by both thermal and cation catalyzed protocols. These protocols were designed to obtain fragment lengths between 100 and 700 bp (on average). Thermal fragmentation: Dilute total RNA sample to 200 ng/µl in RNAse free water. Heat sample to 95° C. in temperature block with heated lid.

Stop fragmentation by placing sample on ice. Use immediately or store at −80° C. until use. Fragmentation via cation catalyzed reaction modified from manufacturer's protocol (Ambion). Bring volume of RNA sample up to 9 µl with RNAse free water. Final concentration of total RNA should be between 0.2 and 2 µg/ml. Add 1 µl of 10× fragmentation buffer (Ambion 10× fragmentation buffer). Incubate at 70° C. for 5 minutes in temperature block. Longer times will result in smaller fragment size on average. Stop reaction by addition of 1 µl 200 mM EDTA. Use immediately or store at −80° C. until use.

Fragmented RNA samples are hybridized as described herein except for the following modifications: i) pH of SSPE is reduced to 6.5 and ii) the time of reaction is reduced to 6 hours (for hybridization reactions in which reporter probe and ghost probe concentrations are 200 pM).

Purification of Nanoreporter-Target Complexes

Post-hybridization purification is preferred when the total reporter probe concentration is above 1 nM. Purification significantly decreases non-specific binding and increases specific binding efficiency to the slide at higher reporter and ghost probe concentrations. In the example provided above, a single F-bead purification is described (purifies hybridized complexes from the ghost-probe end). As described in Example 9 below, optimal results at high ghost probe concentrations (>5 nM total) are obtained via a subsequent G-bead purification which purifies the hybridization complexes from the 5' end of the reporter effectively removing excess non-hybridized ghost probes. The preferred order of purification is F-bead, then G-bead but the order can be reversed and the protocols optimized accordingly. The exact sequences used in these affinity purifications can likely be changed and optimized in alternative embodiments of the technology. These affinity purification steps and reagents are currently nucleic acid based but could theoretically be any sort of binding pairs that exhibit specific binding to one another and can be released by chemical treatment or alteration of binding conditions such that the interaction is disrupted and released. For example, an antibody/antigen pair, a protein/metal interaction, or ligand/receptor interaction, etc.

One example of purification is provided below.

After hybridization is complete, the salt of a hybridization sample (30 μl, starting at 5× SSPE=825 mM Na$^+$) is adjusted to a final concentration of approximately 1× SSPE. The diluted sample is added to 30 μl F-hook MyOne Dynabeads (F-MODB) and bound for 15 minutes at room temperature while rotating. The beads are sequestered with a magnet and the supernatant removed. The beads are washed twice with 150 μl 10.1× SSPE+0.1% Tween at room temperature for 15 minutes with rotation and discarded. The purified reporters are eluted in 30 μl 0.1× SSPE at 45° C. for 15 minutes with rotation. At this point the hybridized reporters are purified from the contaminating un-hybridized reporters. The elution still contains contaminating un-hybridized ghost probes which will compete with the reporters for biotin-binding sites on the streptavidin coated slide. The 30 μl is added to 130 μl of 1× SSPE+0.1% Tween to increase salt concentration. The sample (150 μl) is then loaded onto 30 μl of G-MODB and bound for 15 min at room temperature. The supernatant is discarded and the beads washed with 150 μl 0.1× SSPE+0.1% Tween at room temperature for 15 minutes with rotation. The wash is discarded and the fully purified reporters eluted with 25 μl 0.1× SSPE at 45° C. for 15 minutes with rotation. At this point only targets molecules that are hybridized to both a ghost probe (containing the anti-F sequence) and a reporter (containing the anti-G sequence) will remain in solution.

Immobilization and Stretching and Imaging of Nanoreporter-Target Complexes

Attachment to the slide and immobilization of the stretched complex may be achieved via a biotin-streptavidin interaction. In alternative embodiments, immobilization and stretching are achieved with other interaction pairs provided one of the two could be immobilized on the slide and the other attached to either the ghost probe or the reporter. Stretching does not have to be achieved via electrophoresis but can be done mechanically. The addition of bis-tris propane to the sample before binding is not required. The technology is not limited to the use of particular label monomers exemplified herein as long as the different label monomers can be separated by image processing.

One example of an immobilization and stretching protocol is provided below.

After purification, the hybridization products are loaded directly into an open well of a microfluidic device. The liquid is pulled into a microfluidic channel by capillary action where the hybridized molecules bind to the streptavidin-coated slide through the biotinylated ghost probe. The microfluidic device then intermittently tilts along the axis perpendicular to the length of the channels in alternating directions in order to force the reaction mixture to repeatedly pass through the channel and increase the binding efficiency.

After binding the hybridization reaction, the channel is washed with 1× TAE for 5 minutes by tilting the device at an angle. Fresh TAE is then added to each well to a level sufficient to contact platinum electrodes which are inserted in the wells (30 microliters in our current geometry). An electrical potential of 200V is then applied between the two wells connected by the microfluidic channel, stretching the reporters. After one minute of pre-electrophoresis to remove any remaining contaminating un-bound reporter molecules in the channel, a solution of 0.5 μM G-hooks in 1× TAE is added to the cathodic well (60 microliters of this solution). The electrical potential draws the G-hooks through the channel toward the anodic well. As they pass through the channel, the hooks hybridize with the free G-tag sequences on the free-end of the reporters which are bound to the surface and stretched. The streptavidin on the surface then binds the biotin on the G-hook and immobilizes the free end. When the potential is removed, the reporters remain stretched for imaging.

EXAMPLE 9

Hybridization of 509 Cellular Genes to 100NG Total RNA from A549 Cells Using Nanostring Reporter System Hybridization Reaction Detection of 509 endogenous cellular genes was carried out in single multiplexed hybridization reaction. Eight non-human control sequences were spiked into each reaction that corresponded to approximately 0.1, 0.5, 1, 5, 10, 50, and 100 copies per cell as well as two reporters with no target (negative controls). There were also 4 reporters added that served as positive (3) and negative (1) controls for the post-hybridization purification process. A set of negative control hybridization was also performed containing the entire Nanostring reporter library but lacking cellular RNA.

Each sample was hybridized in triplicate. Final concentrations of the hybridization reagents were as follows: 20.8 nM total Nanoreporters (521 individual Nanoreporters at 40 pM each), 103 nM total ghost probe (517 individual ghost probes @ 200 pM each), 5× SSPE (pH 7.5), 5× Denhardt's reagent, 100 ng/ul sheared salmon sperm DNA, 0.1% Tween 20, 50 fM S11 spike target DNA, 10 fM S10 spike target DNA, 5 fM S9 spike target DNA, 1 fM S8 spike target DNA, 0.5 fM S7 spike target DNA, 0.1 fM S6 spike target DNA. S3 and S4 were added as negative controls. RNA was obtained from A549 lung epithelial cells under two different conditions. The final concentration of total RNA per hybridization was 33 ng/ul. No total RNA was added to the negative control hybridizations. The final volume of the reaction was 30 ul. Reagents were mixed and incubated at 65° C. in thermocycler block with heated lid for 20 hours.

| Master mix | (1 Reaction) | (9.3 reactions) |
|---|---|---|
| 2.7X hybridization mix* | 11.1 μl | 103.2 μl |
| 513 endogenous gene reporters (0.24 nM each) | 5 μl | 46.5 μl |
| 5 513 endogenous gene ghost probes (1.3 nM each) | 4.6 μl | 42.9 μl |
| Purification Control reporters (0.6 nM each) | 1 μl | 9.3 μl |
| 30X control target mix | 1 μl | 9.3 μl |
| Total | 22.7 μl | 211.2 μl |

*Hybridization mix (13.5X SSPE, 13.5X Denhardt's reagent, 270 ng salmon sperm DNA, 0.27% Tween 20)

|  | Reactions | | | | | | | | |
| --- | --- | --- | --- | --- | --- | --- | --- | --- | --- |
|  | 1 | 2 | 3 | 4 | 5 | 6 | 7 | 8 | 9 |
| Master mix | 22.7 | 22.7 | 22.7 | 22.7 | 22.7 | 22.7 | 22.7 | 22.7 | 22.7 |
| 48.5 ng/µl RNA #1 | 2.1 | 2.1 | 2.1 | 0 | 0 | 0 | 0 | 0 | 0 |
| 48.4 ng/µl RNA #2 | 0 | 0 | 0 | 2.1 | 2.1 | 2.1 | 0 | 0 | 0 |
| H$_2$O | 5.2 | 5.2 | 5.2 | 5.2 | 5.2 | 5.2 | 7.3 | 7.3 | 7.3 |
| Total Rxn volume | 30 µl | 30 µl | 30 µl | 30 µl | 30 µl | 30 µl | 30 µl | 30 µl | 30 µl |

Incubate reactions in thermocycler with heated lid overnight (20 hours).

Post-Hybridization Purification

Hybridization reactions were purified to remove unhybridized reporters using an oligonucleotide complimentary to ghost probe attached to magnetic beads (F-bead). Hybridization reactions were diluted 5 fold in 0.1% Tween-20/TE to bring the final salt concentration to 1× SSPE. The diluted hybridization solution was then added to 100 ul of F-beads (in 0.1% Tween-20) and allowed to bind to the beads at room temperature for 30 min with continuous rotation. The beads were then washed three times in 150 ul of 0.1× SSPE/0.1% Tween-20 and eluted in 100 ul of 0.1×SSPE/0.1% Tween-20 for 15 min at 45° C.

After F-bead elution, samples were purified from the opposite end of the hybridized complex using G-beads. Elutions were brought to a final concentration of 1× SSPE by the addition of 50 ul of 3× SSPE/0.1% Tween-20 and bound to 30ul of G-beads (in 0.1% Tween-20) for 15 min at room temperature with rotation. Beads were then washed as above and eluted in 30 ul of 0.1× SSPE/Tween-20 and prepared for binding as described below.

Binding, Stretching, and Immobilization

The samples were prepared for binding by addition of 1 ul of 1/5000 dilution of 0.1 uM Tetraspec™ fluorescent microspheres (product # T7279, Molecular Probes). Samples were loaded into a Nanostring fluidic device and attached to Accelr8 Optichem® slide coated with streptavidin (product #TB0200) by tilting the device 45 deg for 15 min and repeated a total of 4 times. After loading, slide surface was washed once with 90 ul of 1× TAE. After wash buffer is removed the sample is prepared for electrostretching by addition of 40 ul of TAE to each well. Attached complexes were stretched by applying 200V across the fluidic channel. After 1 minute the samples were immobilized in the stretched position by adding 60 ul of 500 nM of G-hook oligo solution to the well containing the negatively charged electrode while continuing to apply voltage for 5 minutes. After immobilization the TAE solution is removed and replaced with anti-photobleaching reagent for imaging.

Imaging

Slides were imaged on Nikon Eclipse TE2000E equipped with a metal halide light source (X-cite 120, Exfo Corporation) and a 60× oil immersion lens (1.4 NA Plan Apo VC, Nikon). For each field of view, 4 images at different excitation wavelengths (480, 545, 580 and 622) were acquired with an Orca Ag CCD camera (Hamamatsu) under control of either Metamorph (Universal Imaging Corporation) or custom software. Images were processed with custom image processing software.

Data Analysis

Raw data was extracted from processed images using custom software. Data was normalized to the average counts for control spikes in each sample. To determine if a gene was "detected" by the system, the counts obtained for each gene from hybridizations containing RNA were compared to average counts of the two negative controls using a Student's t-test. The number of genes detected was 441 (87%) and 445 (88%) in sample #1 and #2, respectively. A scatter plot (Figure shows normalized and average log$_2$ signal values from each positive sample (n=3) for all 509 genes. The genes that were significantly different in the two samples were identified by a T-test of signal values in sample #2 against sample #1. In the graph below, the solid lines indicate the 2-fold upregulated threshold (black line) and 2-fold downregulated threshold (gray line) relative to sample #1. Genes with significant fold changes (p-value <0.05) are shown in solid black diamonds. Genes whose fold change p-values were above this threshold are shown in open black squares.

EXAMPLE 10

Detection of Small Spots

As mentioned above, the label attachment regions of a nanoreporter scaffold region have a length anywhere from 10 nm to 10,000 nm, but preferably corresponds closely to the smallest spot that can be detected with standard optics, which is about 300 nm. Spots of different color (spectrally distinguishable) are spatially resolvable at closer spacing than spots of the same color. It is possible to fit one, two, three or four spots of different colors between two spots of the same color, and yet spectrally and spatially resolve all the spots. It is also possible to significantly reduce the distance between two spots of the same color.

The limits of spatial resolution, i.e., differentiating closely spaced spots of the same color, are often thought of as hard limits, i.e., the Rayleigh Criteria (Inoue, S., Spring, Video Microscopy (Plenum Press, 1997), p 30). There are many techniques to drive beyond these limits that involve different imaging and/or image processing techniques. On the imaging side, structured illumination is one method to resolve spots of the same color that are spaced closer together. 50 nm has been demonstrated but, in theory, resolution with structured illumination is unlimited (Gustafsson, 2005, Proc. Nat'l. Acad. Sci. U.S.A. 102:13081-13086). On the image processing side, mixture modeling is an effective technique to push beyond commonly accepted limits (Thomann et al., 2002, J. Microsc. 211:230-248). The combination of these techniques allows for drastically smaller nanoreporters with smaller spots, corresponding to label attachment regions of less than 50 nm.

These smaller spot spacings could allow for drastically shorter and more stable reporters, a larger number of codes, as well as a higher degree of multiplexing before the entanglement threshold is passed (for an explanation of entanglement thresholds, see Example 9 (described in Section 14) above.

The tradeoff of making the spots much smaller and the reporters much shorter would be decreased signal and slower scan times. However, other technical advances, such as

EXAMPLE 11

Figure 22A:
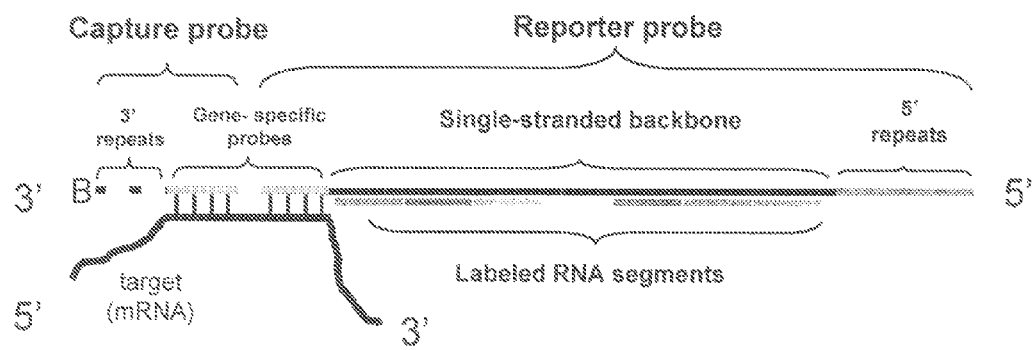
FIG. 22A-22C provides a schematic representation of the hybridized complex (not to scale).
Figure 22B:
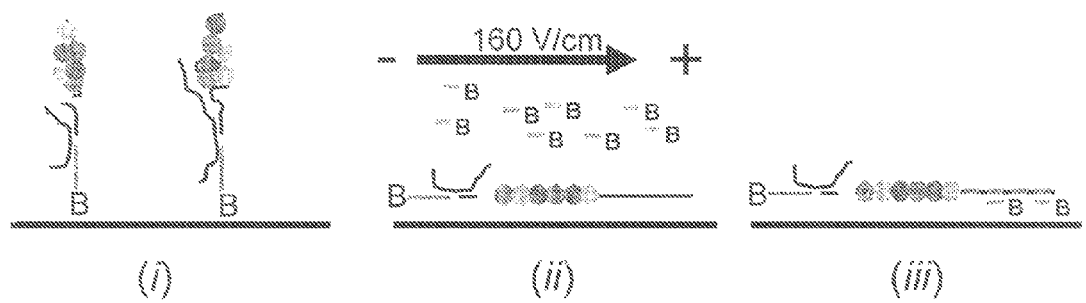

Comparison of nCounter Gene Expression System with Microarrays and Taqman® PCR In one embodiment, the present invention provides a novel technology to capture and count specific nucleic acid molecules in a complex mixture. This system can be used to detect any type of nucleic acid in solution and, with appropriate recognition probes, can be modified to detect other biological molecules as well. In this Example, we focused on mRNA expression profiling. In brief, a multiplexed probe library was made with two sequence-specific probes for each gene of interest. The first probe, which we refer to as a capture probe (FIG. 22a), contained a 35 to 50 base sequence complementary to a particular target mRNA plus a short common sequence coupled to an affinity tag such as biotin. The second probe, which we refer to as the reporter probe, contained a second 35 to 50 base sequence complementary to the target mRNA that was coupled to a color-coded tag that provides the detection signal. The tag consisted of a single-stranded DNA molecule, which we refer to as the backbone, annealed to a series of complementary in vitro transcribed RNA segments each labeled with a specific fluorophore (FIG. 22a). The linear order of these differently-colored RNA segments created a unique code for each gene of interest.

Figure 22C:
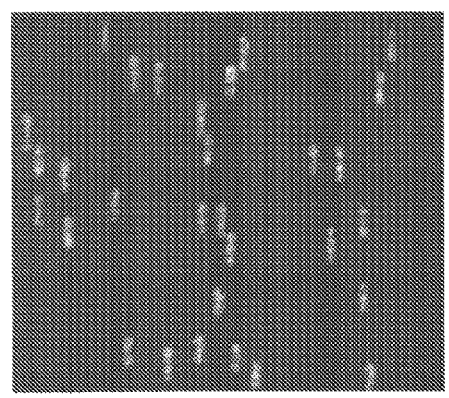

To detect transcripts, unique pairs of capture and reporter probes were constructed for each gene of interest. All probes were mixed together with total RNA in a single hybridization reaction that proceeds in solution. Hybridization results in the formation of tripartite structures, each comprised of a target mRNA bound to its specific reporter and capture probes (FIG. 22a). Unhybridized reporter and capture probes were removed via affinity-purification, and the remaining complexes were washed across a surface that was coated with the appropriate capture reagent (e.g. streptavidin). After capture on the surface, an electric field was applied to the solution which extended and oriented each complex in the same direction. The complexes were then immobilized in an elongated state (FIG. 22b), and imaged (FIG. 22c). Each target molecule of interest was identified by the color code generated by the ordered fluorescent segments present on the reporter probe. The level of expression was measured by counting the number of codes for each mRNA.

In this work, we demonstrated the linearity, reproducibility, and sensitivity of the nCounter system of the present invention and demonstrated that fold-change measurements of significantly regulated genes correlated well with microarrays, and even better with real-time PCR. In addition, we showed that the nCounter system can detect low abundance mRNAs that are declared "Absent" by DNA microarrays. The validity of this detection was confirmed for a subset of genes using real-time PCR. These results demonstrate the advantages of the methods and systems of the present invention and demonstrate that they can fill an immediate niche in the expression analysis of hundreds of genes across many samples. Applications include translational medical studies, research involving gene regulatory systems, diagnostic fingerprinting, and validation of high-throughput gene expression experiments.

nCounter Gene Expression System Overview

The basis of the nCounter system is the unique code assigned to each gene to be assayed. As outlined below under Methods, we used 7 positions (visualized as "spots") and 4 colors. The 4 colors were chosen to minimize spectral overlap during imaging. The number of positions was based on a combination of factors that include the length of the DNA backbone, the minimum spot size that can be resolved under current imaging conditions, flexibility in code selection for modestly-sized gene sets (i.e. <1000 genes) and the number of potential codes for future versions of the system ($4^7$=16,384 if all possible combinations of codes are used). The total number of codes required for the experiments described below was 524 (15 controls and 509 genes) or roughly 3% of the available codes in a seven-spot system.

Specific reporter and capture probes were synthesized in 96-well plates using a semi-automated process (see Methods). Briefly, gene-specific probes were ligated to reporter backbones, and each ligated backbone was annealed to a unique pool of seven dye-coupled RNA segments corresponding to a single code. The reporter probes were then pooled and purified using a common sequence at the end of each backbone (the 5'-repeat sequence, see FIG. 22a) to remove excess probe oligonucleotides and dye-coupled RNA segments. Capture probes were made by ligating a second sequence-specific oligonucleotide for each gene to a universal sequence containing biotin (see FIG. 22a). After ligation, the capture probes were also pooled and affinity-purified using the universal sequence to remove the excess unligated gene-specific oligonucleotides. Reporter and capture probes were combined into a single "library" and used as a single reagent in subsequent hybridizations.

The expression levels of all selected mRNAs was measured in a single multiplexed hybridization reaction. The sample was combined with the probe library, and hybridization occurred in solution. After hybridization, the tripartite hybridized complexes (FIG. 22a) were purified in a two-step procedure using magnetic beads linked to oligonucleotides complementary to universal sequences present on the capture and reporter probes (see Methods). This dual purification process allowed the hybridization reaction to be driven to completion with a large excess of gene-specific probes, as they were ultimately removed and thus did not interfere with binding and imaging of the sample. All post hybridization steps were handled robotically on a custom liquid-handling robot (Prep Station, NanoString Technologies). The Prep Station can process 12 samples in 2.5 hours for a total of 48 assays per instrument in 10 hours.

Purified reactions were deposited by the Prep Station into individual flow cells of a sample cartridge, bound to a streptavidin-coated surface via the capture probe, electrophoresed to elongate the reporter probes, and immobilized (see FIG. 22). After processing, the sample cartridge was transferred to a fully automated imaging and data collection device (Digital Analyzer, NanoString Technlogies). The expression level of a gene was measured by imaging each sample in 4 colors and counting the number of times the code for that gene is detected. For each sample, over 600 fields-of-view (FOV) were imaged (1376×1024 pixels) representing approximately 10 mm² of the binding surface. Typical imaging density was 100-200 counted reporters per field of view depending on the degree of multiplexing, the amount of RNA, and overall gene expression levels. However the system is capable of operating at densities 5-10 fold higher. The Digital Analyzer can accommodate up to 6 cartridges at once and current scan times for 600 FOV were 4 hours per sample cartridge. Unattended, it can process 72 samples in 24-hours per instrument.

Image processing and code counting was performed (see Methods). To minimize false positives, a reporter must meet stringent criteria concerning the number, size, brightness and spacing of the spots to ensure that the code is interpreted correctly. Reporters that did not meet all of these criteria were discarded. Using these criteria, approximately 20% of the detected molecules were counted. No parity schemes or error correction were employed in the current system. Data was output in simple spreadsheet format listing the number of counts per gene per sample.

Experimental Design

To demonstrate the utility of the NanoString nCounter system, we performed a series of experiments in which the expression levels of 509 genes were assayed with NanoString's nCounter system. 347 of these genes were selected from previous microarray studies of poliovirus (PV)-infected A549 cells and the remaining 162 genes were a selection of previously-designed probes added to bring the multiplex total to over 500. Additional experiments with other probe libraries were performed with commercially-available RNAs and total RNA isolated from developing sea urchin embryos. We compared the nCounter results to those obtained with the Affymetrix GeneChip® system and with real-time PCR measuring the same total RNA samples.

Figure 26A:
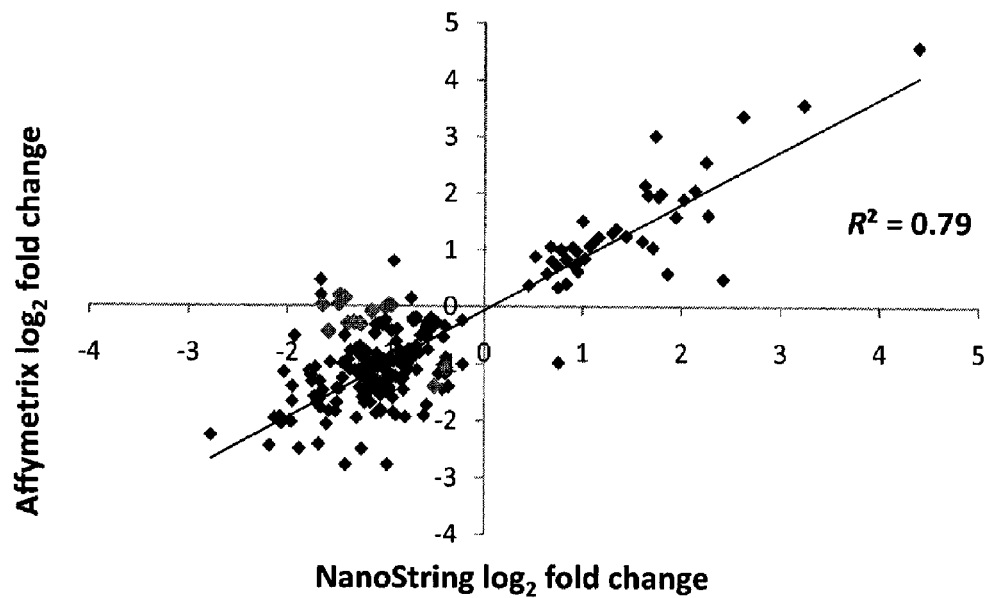
FIG. 26A-26C provides comparison plots of NanoString nCounter to Affymetrix GeneChip® and Applied BioSystemsTaqMan® platforms.
Figure 26B:
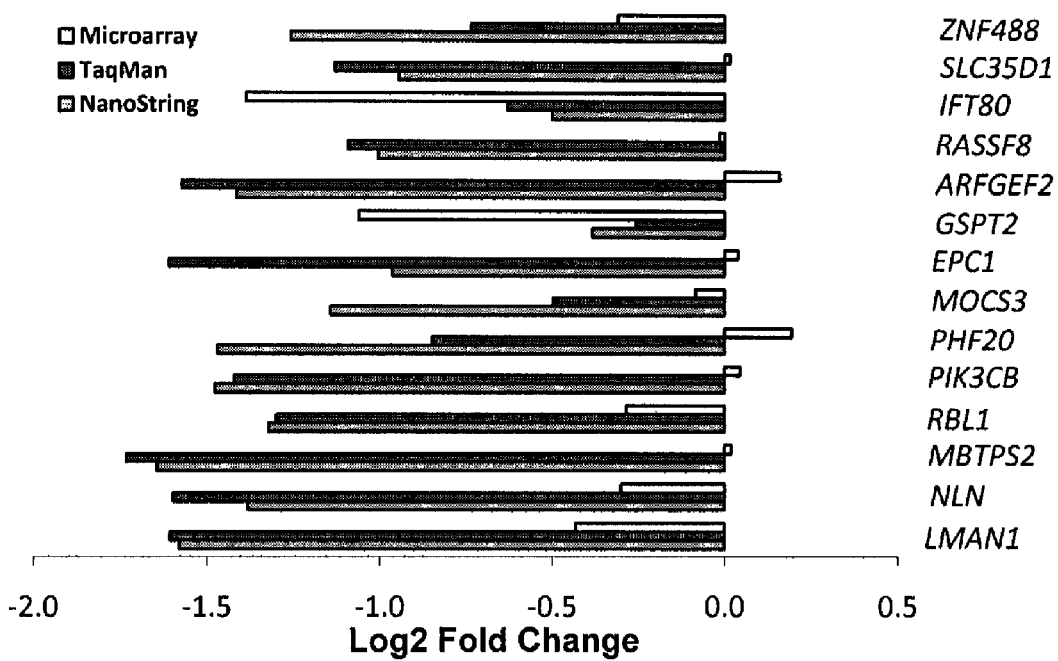

Table 5 summarizes the results obtained using a set of 14 genes tested on all three platforms. They are listed by RefSeq Accession numbers, Probeset ID, and TaqMan® ID. Signal levels for both samples in all three platforms are shown with standard deviations in parentheses. Values shown correspond to normalized counts for the nCounter system, RMA normalized intensity for Affymetrix's GeneChip®, and cycle threshold (Ct) for ABI TaqMan® assay. Detected (D) and Undetected (U) calls are based on platform-specific criteria. For the Affymetrix platform, a gene was only considered undetected if all 3 replicates for each sample were called "Absent" by the MAS 5 algorithm. All genes were detected by the TaqMan® assay based on a cutoff of less than 35 cycles. Fold-change comparisons are shown in FIG. 26b.

Methods

Cell Culture; Infection; and RNA Isolation

A549 cells, a human lung epithelial cell line, were purchased from ATCC. Poliovirus (PV) stocks were the kind gift of Kurt Gustin's laboratory (University of Idaho). Sub-confluent A549 cells were either mock-infected or infected with PV at a multiplicity of infection of 50. Virus was adsorbed for 30 minutes at 32° C. in PBS supplemented with 10 mM $MgCl_2$ and 10 mM $CaCl_2$. Following adsorption, residual virus was removed and DMEM with 10% FBS, 2 mM L-Glutamine and Penicillin-Streptomycin was added. After 5 hours of infection, the total RNA was extracted using Qiagen RNeasy mini-spin columns according to the manufacturer's protocols. Two independent mock- and PV-infections were performed. Following RNA isolation, the RNA from the replicates was pooled to create one sample of RNA from PV-infected cells and another from mock-infected cells. Aliquots of these two RNAs were used in all subsequent microarray, real-time PCR and nCounter analyses.

Control Target Preparation

Targets for spike-in controls consisted of 100-base HPLC purified oligonucleotides that were complementary to the spike-in reporter and capture probes. These and all other oligonucleotides were purchased from Integrated DNA Technologies. They were generated to specific 100-base regions of the following non-human sequences and arbitrarily named A-H [spikes A, E and F, (accession number AY058658.1); spikes B-D, (accession number AY058560.1), and spikes G and H, accession number DQ412624)].

Generation of Fluorescent RNA Segments

To prepare the RNA segments for reporter probe synthesis, PCR fragments for each segment were generated using primers specific to M13 and containing either T7, T3 or SP6 RNA polymerase promoters. RNA transcripts were in vitro tran-

TABLE 5

Comparison of signal levels and detected/undetected calls for 14 genes on the nCounter, GeneChip and TaqMan platforms.

| | | | | NanoString | | | Affymetrix | | | TaqMan | | |
|---|---|---|---|---|---|---|---|---|---|---|---|---|
| Accession# | Gene Name | Affymetrix Probeset ID | TaqMan ID | Mock signal | PV signal | Mock/PV Detection | Mock signal | PV signal | Mock/PV Detection | Mock Ct | PV Ct | Mock/PV Detection |
| NM_005570 | LMAN1 | 203293_s_at | Hs00194366_m1 | 669 (63) | 224 (10) | D/D | 61 (11) | 45 (9) | D/U | 25.5 (0.17) | 27.2 (0.11) | D/D |
| NM_020726 | NLN | 225943_at | Hs00252959_m1 | 428 (78) | 164 (10) | D/D | 545 (54) | 443 (47) | D/D | 25.7 (0.03) | 27.4 (0.09) | D/D |
| NM_015884 | MBTPS2 | 206473_at | Hs00210639_m1 | 347 (37) | 111 (9) | D/D | 48 (3) | 48 (8) | U/U | 26.7 (0.04) | 28.5 (0.09) | D/D |
| NM_002895 | RBL1 | 1555004_a_at | Hs00161234_m1 | 270 (39) | 108 (7) | D/D | 62 (8) | 51 (3) | D/D | 27.4 (0.05) | 28.8 (0.10) | D/D |
| NM_006219 | PIK3CB | 217620_s_at | Hs00178872_m1 | 204 (31) | 73 (9) | D/D | 23 (0) | 24 (3) | U/U | 28.0 (0.07) | 29.5 (0.15) | D/D |
| NM_016436 | PHF20 | 209423_s_at | Hs00363134_m1 | 195 (19) | 70 (8) | D/D | 47 (4) | 54 (9) | U/U | 27.9 (0.02) | 28.8 (0.05) | D/D |
| NM_014484 | MOCS3 | 206141_at | Hs00819330_s1 | 183 (6) | 83 (9) | D/D | 42 (2) | 40 (2) | D/U | 28.5 (0.15) | 29.1 (0.30) | D/D |
| NM_025209 | EPC1 | 223875_s_at | Hs00228677_m1 | 111 (22) | 57 (6) | D/D | 30 (1) | 31 (2) | U/U | 27.2 (0.07) | 28.9 (0.07) | D/D |
| NM_018094 | GSPT2 | 205541_s_at | Hs00250696_s1 | 100 (43) | 76 (3) | D/D | 214 (12) | 102 (18) | D/D | 30.3 (0.22) | 30.7 (0.04) | D/D |
| NM_006420 | ARFGEF2 | 215931_s_at | Hs00197455_m1 | 77 (2) | 29 (1) | D/D | 42 (5) | 47 (6) | U/U | 26.6 (0.12) | 28.3 (0.23) | D/D |
| NM_007211 | RASSF8 | 207754_at | Hs00200537_m1 | 62 (13) | 31 (7) | D/D | 37 (2) | 37 (2) | D/U | 27.3 (0.05) | 28.5 (0.09) | D/D |
| NM_020800 | IFT80 | 226098_at | Hs00398803_m1 | 41 (6) | 29 (5) | D/D | 321 (15) | 123 (22) | D/D | 29.0 (0.06) | 29.8 (0.41) | D/D |
| NM_015139 | SLC35D1 | 209713_s_at | Hs00209446_m1 | 38 (1) | 20 (3) | D/D | 42 (7) | 43 (0) | D/U | 27.8 (0.03) | 29.1 (0.16) | D/D |
| NM_153034 | ZNF488 | 229901_at | Hs00399237_m1 | 31 (8) | 13 (4) | D/U | 114 (7) | 92 (15) | D/D | 29.1 (0.09) | 30.0 (0.80) | D/D | scribed from these templates using the Megascript™ kit (Ambion) in the presence of 50% amino-allyl UTP (Sigma). Each of the seven resulting amino-allyl labeled RNA transcripts was coupled to one of 4 NHS-ester fluorophores [ALEXA Fluor® 488, ALEXA Fluor™ 594, ALEXA Fluor™ 647 (Invitrogen) or Cy3 (GE Healthcare)].

TaqMan® real-time PCR Data

Genes which showed discordant levels of expression between the NanoString and microarray systems were selected based on the following criteria: 1) genes had to be significantly differentially expressed in one platform (greater than 2-fold, P-value <0.05) and not in the other platform (less than 1.5-fold, P-value >0.05); 2) both the Affymetrix and NanoString probe sets had to map to the same RefSeq mRNA; and 3) an inventoried ABI TaqMan® probe set had to be available. For each sample, 4μg of total RNA was reverse-transcribed using random hexamers in a final volume of 40μl. The reactions were diluted to 200μl in TE and then 5μl, equivalent to 100 ng of total RNA, was used in each real-time PCR reaction. All assays were performed in triplicate. The data were normalized to Beta-glucuronidase (GUS).

NanoString Reporter Preparation

NanoString reporters consisted of linearized single-stranded M13 DNA, referred to as backbone, annealed to fluorescently-labeled, in vitro transcribed RNA segments. Using standard molecular biology protocols, circular single-stranded M13 (United States Biological) was linearized, and an oligonucleotide containing four 15-base repeats, referred to as the 5'-repeat, was ligated on to the 5' end of the backbone. Using a Hamilton STAR liquid-handling robot, a master mix containing a universal oligonucleotide that served as a ligation "bridge" plus ligase buffer was added to individual wells of 96-well plates containing normalized (10 μM) gene-specific oligonucleotide probes (35-50 bases). After a short incubation at 37° C. to anneal the probe oligonucleotide to the complementary portion of the bridge oligonucleotide, ligation was initialized by addition of another master mix containing the equivalent of 1.2 pmoles of M13 backbone per well, additional ligation buffer, and T4 ligase. Plates were incubated at 37° C. in a 96-well thermocycler for 2 h. The efficiency of the ligation reactions was assessed by cutting the backbone approximately 600 bases away from the ligation site using short oligonucleotides to generate double-stranded restriction sites, and analyzing the size of the resulting fragments by PAGE. Ligation reactions were desalted via centrifugation through G-50 Sephadex columns in a 96-well format.

Each gene-specific backbone was assigned a unique code consisting of an ordered series of differently-colored RNA segments annealed to the backbone. Sets of seven approximately 900-base fluorescently-labeled RNA transcripts complementary to distinct sequences on the backbone were created in 96-well plates using a Hamilton STAR robot. Each well received a unique combination of RNA segments that, when annealed to the M13 backbone and visualized in linear sequence, resulted in a unique code. Plates containing RNA segment pools were mixed with probe-ligated M13 backbones in a 2:1 molar ratio. Annealing of segments to the backbone was performed in individual wells of a 96-well PCR plate. At the same time, one unlabeled RNA segment was also annealed to each reporter to cover the remaining single-stranded region of the backbone, leaving only the probe at one end and the 5'-repeat at the other as single-stranded DNA. The rest of the reporter is a double-stranded DNA/RNA hybrid. To remove excess RNA transcripts and unligated probes, the reporters were then pooled and affinity-purified over magnetic beads (Dynal, Invitrogen) coupled to oligonucleotides complementary to the 5'-repeat sequence on the 5' end of each backbone. The final reporter molecules had seven labeled regions in a linear sequence each of which resulted in a ~300 nm spot when imaged by an epi-fluorescent microscope under the conditions described below.

Nanostring Capture Probe Preparation

The capture probe consisted of a 35- to 50-base gene-specific sequence attached to a capture-oligonucleotide comprised of two 15-base repeats, referred to as 3'-repeats, linked to a biotin molecule. In a process similar to reporter probe synthesis, normalized gene-specific oliogonucleotides were annealed to a short universal "bridge" oligonucleotide in ligation buffer. A master mix containing the 3'-repeat oligonucleotide, additional ligation buffer, and T4 ligase was added. The 3'-repeat oligonucleotide was present in 4-fold excess. Ligation reactions were performed in 96-well plates in a thermocycler for 2 h at 37° C. The efficiency of each ligation was assessed by PAGE. After ligation there are 3 potential species of molecules in the reaction: the 3'-repeat ligated to the gene-specific probe (the "capture probe" in FIG. 22), the excess unligated 3'-repeat, and any residual unligated probe oligonucleotide if the reaction did not go to completion. Excess free probe is the only species that negatively affects the hybridization results as it competes for target with the fully-ligated capture probe. Therefore, after ligation the capture probes were pooled and purified over magnetic beads coupled to an oligonucleotide complementary to the 3'-repeat to remove free probe oligonucleotide. A later post-hybridization purification step removed excess unligated 3'-repeat oligonucleotide (see the anti-5'-repeat post-hybridization purification, below).

Probe Design and Selection

Potential pairs of 50-base probes were chosen by first screening 100-base target regions of the mRNA to eliminate long direct and inverted repeats, high GC content, and long poly-C stretches (due to the difficulty in synthesizing poly-G sequences in probe oligonucleotides). The refined list of target regions was then screened for cross-hybridization using NCBI BLAST[13] (version 2.2.14) to align them against the Human RefSeq mRNA database[1] (Hs: release 17). These 100-base target BLAST alignments were used to filter out targets that resulted in either 50-base probe having greater than 85% identity or stretches greater than 15 contiguous bases complementary to any non-target mRNA. The cross-hybridization cutoffs were chosen based on prior 50-base hybridization and probe design studies.[14,15] Probes were then screened for inter- and intra-reporter and capture probe interactions and selected for probe pairs with calculated melting temperatures ($T_m$) between 78-83° C., with an ideal target of 80.5° C. In the last stage of selection, probes that met all requirements but had a calculated $T_n$, greater than 83° C. were dynamically trimmed until the $T_m$ was calculated to be less than or equal to 83° C. with a minimum-length cutoff of 35 bases. Final probe-pair selection was based on a score calculated from cross-hybridization and $T_m$, screens, with preference given to probes which did not need to be trimmed to meet $T_m$ requirements.

Nanostring Reporter Gene Libraries

The reporter library for the A549 cell study contained probes to 509 human genes. The majority of these genes (347) were selected based on previous microarray studies on PV infected A549 cells (unpublished) using the Limma package in Bioconductor[16] to identify genes with a false detection rate of less than 0.05. The remaining 162 genes were collected from a variety of other studies; they have no particular biological relevance to the PV study, but were added to evaluate the ability of the nCounter assay to multiplex more than 500 genes. The list of 509 RefSeq mRNAs was based on the current human genome organization (HUGO) gene name associated with the list of Affymetrix probe set IDs. Note that not all of the target regions for the Affymetrix probe sets overlap completely with the RefSeq mRNAs. The reporter library for the MAQC-consortium study contained probes to 35 human genes that were selected based on the RefSeq gene list published in the MAQC consortium study.[2] The probe library for the *Strongylocentrotus purpuratus* study contained probes to 55 *S. purpuratus* genes including polyubiquitin, which was used for nolinalization purposes, and seven probes to *Homo sapiens* genes, which were used as the negative controls. The analysis described in this paper only includes the 21 *S. purpuratus* genes for which there was comparable real-time PCR data available. All libraries described also contained 8 non-human control probe pairs (spike-ins) and multiple control reporters that did not contain gene-specific probes, but were used to assess purification and binding efficiencies.

Hybridization Reactions

Detection of cellular transcripts was carried out in multiplexed hybridization reactions. Each sample was hybridized in triplicate with final concentrations of the hybridization reagents as follows: 200 pM each capture probe, 40 pM each reporter probe, 5× SSPE (pH 7.5), 5× Denhardt's reagent (Sigma), 100 ng/µl sheared salmon sperm DNA (Sigma), and 0.1% Tween-20. Each 30 µl hybridization reaction also contained 100 ng total RNA at a final concentration of 3.3 ng/µl. In addition, 6 positive and 2 negative control probe-pairs to non-human sequences were added to each reaction. Final concentrations of the 100-base control targets were 50 fM spike A target, 10 fM spike B target, 5 fM spike C target, 1 fM spike D target, 0.5 fM spike E target, and 0.1 fM spike F target. No target was added for spikes G and H (negative controls). Reagents were mixed and incubated at 65° C. in a thermocycler block with a heated lid for 20 hours.

Post-Hybridization Purification

To remove unhybridized reporters, reactions were purified over magnetic beads (Invitrogen) coupled to oligonucleotides complementary to the 3'-repeat sequence contained on every capture probe. Reactions were first diluted to 1× SSPE in 0.1% Tween-20/TE and allowed to bind to beads at 22.5° C. for 30 minutes with continuous rotation. The beads were washed three times in 150 µl of 0.1× SSPE/0.1% Tween-20 and the hybridized complexes eluted in 100 µl of 0.1× SSPE/ 0.1% Tween-20 for 15 minutes at 45° C. After elution, samples were purified a second time to remove excess capture probes by binding to magnetic beads coupled to oligonucleotides complementary to the 5'-repeat sequence contained on every reporter probe. The elutions from the anti-3'-repeat beads were brought to a final concentration of 1× SSPE by addition of 50 µl of 3× SSPE/0.1% Tween-20 and bound for 15 minutes at 22.5° C. with rotation. Beads were washed as above and eluted in 300 of 0.1× SSPE/0.1% Tween-20 at 45° C. The doubly-purified samples were then prepared for capture as described below.

Nanostring Reporter Capture, Stretching, and Imaging

One microliter of 1/5000 dilution of a 0.1% solids solution of a custom-formulation of Tetraspeck fluorescent microspheres (Invitrogen) was added to each sample. Samples were loaded into a NanoString fluidic device made by lamination of laser-machined cast acrylic with a coverslip coated with streptavidin (Optichem®, Accelr8 Technology Corporation) using a laser-cut double-sided adhesive layer (Fralock) to generate 30 µm deep microfluidic channels. The samples were driven through the channel by hydrostatic pressure and bound specifically by the biotinylated 3' end of the capture probe. After capture, the surface was washed once with 90 µl of 1× TAE and prepared for stretching by the addition of 40 µl of TAE to each well. Reporter probes were stretched and aligned by applying 160V/cm for 1 minute along the fluidic channel. Stretched reporters were then immobilized to the surface by addition of 60 µl of a 500 nM solution of a biotinylated oligonucleotide complementary to the 5'-repeats present on the 5' end of all reporter probes. The current remained on for 5 minutes, throughout the immobilization process. After immobilization, the TAE solution was removed and replaced with a custom formulation of the anti-photobleaching reagent SlowFade (Invitrogen) for imaging.

Slides were imaged on a Nikon Eclipse TE2000E equipped with Perfect Focus, a 1.4 NA Plan Apo VC 60× oil-immersion lens (Nikon), an X-cite 120 metal halide light source (Exfo Corporation), an automated H117 stage (Prior Scientific), and a SmartShutter (Sutter Instrument). For each field of view, 4 images at different excitation wavelengths (480, 545, 580 and 622) were acquired with an Orca Ag CCD camera (Hamamatsu) under control of either Metamorph (Universal Imaging Corporation) or custom software.

Image Processing

Image processing was performed on 4 images (one for each wavelength) on a FOV-by-FOV basis. The custom algorithm treats each FOV as a fundamental block in which the following basic steps are performed: 1) spot identification, 2) image registration, 3) spatial clustering to produce strings, and 4) string classification.

In the first step of the algorithm, spots were identified. The background intensity level of each channel was computed and used to threshold the image into signal and background, where signal regions are the result of a specific wavelength of light observed as a point spread function (PSF). The signal mask was segmented using a custom Watershed algorithm. The segmented regions were then labeled, parameterized, and filtered to remove non-PSF spots. The remaining spots were centrally archived for use in registration and reporter calling.

Image registration was performed on each FOV based on archived spots that correspond to fluorescent beads (fiducials) that were bound to the imaging surface (see NanoString reporter capture, stretching, and imaging). The archived spots were cross-referenced to identify inter-channel clusters of spots that meet fiducial requirements (interchannel intensity thresholds and ratios). Clusters that met requirements were archived as fiducials. The final list of fiducials represented the spatial transforms that occurred between channels during image acquisition. Spatial offsets were as large as 5-6 pixels. The spatial transform was solved for using the observed fiducial centroids and their pre transform (assumed) coincident centroids ($X_2=X_1*T$). The inverse transform was then applied to all identified spots to restore their original centroids.

After spot identification and image registration, spots were assembled into "strings" via clustering. At this point, each string was filtered to remove any spots attributed to bleed-though signal. The filtered strings were then classified as reporters or non-reporters. To be classified as a reporter the string must contain the correct number of spots, meet specific spot-to-spot spacing thresholds (1.2-2.9 pixels), and meet acceptable linearity and orientation requirements. Clusters that were classified as reporters were then counted and summed for each gene over all FOVs.

Nanostring Data Normalization and Analysis

To account for slight differences in hybridization and purification efficiency, data was normalized to the average counts for all control spikes in each sample. To determine if a gene was "detected" by the NanoString system, the triplicate measurements obtained for each experimental gene were compared to triplicate measurements for the two negative controls. For a gene to be categorized as detected, the average counts for the experimental gene had to be greater than the average counts for the 2 negative controls, and the Student's T-test P-value had to be less than 0.05. For the *S. purpuratus* study, the data were normalized to the polyubiquitin gene and detected genes were determined by a Student's T-test against the 7 human negatives.

Production of Affymetrix Array Data

Aliquots of the same RNA samples analyzed by the NanoString nCounter system were also analyzed by microarray. In brief, triplicate samples of 100 ng of total RNA were analyzed on Human U133 Plus 2 arrays. Since 1-2 µg of total RNA is typically required for the standard Affymetrix single amplification protocol, the RNA expression data was produced following the manufacturer's standard protocol using the GeneChip® Two-Cycle Target Labeling kit (Affymetrix part #900494). Hybridization, washing and staining were carried out using the manufacturer's standard protocols. Data was normalized using RMA. Affymetrix "presence/absence" calls were obtained by independently processing the data with MAS 5.0 algorithm. The array and NanoString data have been made public via the Array Express database (E-MEXP-1072).[17] For data in FIG. 25, an Affymetrix probe set was declared detected if any one of the 3 replicates was called "present" or "marginal".

TaqMan® real-time PCR Data

Genes which showed discordant levels of expression between the NanoString and microarray systems were selected based on the following criteria: 1) genes had to be significantly differentially expressed in one platform (greater than 2-fold, P-value<0.05) and not in the other platform (less than 1.5-fold, P-value>0.05); 2) both the Affymetrix and NanoString probe sets had to map to the same RefSeq mRNA; and 3) an inventoried ABI TaqMan® probe set had to be available. For each sample, 4 µg of total RNA was reverse-transcribed using random hexamers in a final volume of 40 µl. The reactions were diluted to 200 µl in TE and then 5 µl, equivalent to 100 ng of total RNA, was used in each real-time PCR reaction. All assays were performed in triplicate. The data were normalized to Beta-glucuronidase (GUS).

MAQC comparisons

A library of 35 RefSeq mRNAs that were also listed in the MAQC TaqMan® real-time PCR data set[2] was used to analyze differential gene expression between the two commercially-available reference RNAs, Human Reference total RNA (Stratagene) and Human Brain Reference total RNA (Ambion). As described in the original study[2], genes that were not detected in all samples for both the NanoString and TaqMan® platforms were removed from further analysis. STAT5A was removed from the NanoString data due to a known cross-hybridization issue with STAT5B. Fold-change correlation of NanoString results with MAQC TaqMan® real-time PCR data for the remaining 27 genes was determined by plotting the $\log_2$ ratio of normalized signal values (Human Reference RNA versus Human Brain Reference RNA) and calculating the linear correlation coefficient for that plot.

SYBR®Green Real-Time PCR Methods

S. purpuratus total RNA isolation, cDNA synthesis and real-time PCR was carried out as described.[6,18] Twenty-one S. purpuratus genes were assayed by quantitative real-time PCR. All genes were assayed in quadruplicate.

Nanostring nCounter Gene Expression System Performance

Hybridization reactions were performed in triplicate with total RNA samples isolated from mock- and PV-infected A549 cells. Each reaction contained 100 ng of total RNA plus reporter and capture probes for 509 human mRNAs contained in the RefSeq database.[1] In addition, 6 pairs of positive and 2 pairs of negative control reporter and capture probes were included in every reaction. The spike-in controls produced a standard concentration curve for every hybridization reaction and were used to normalize the data for slight differences in hybridization, purification and capture efficiencies.

Figure 23A:
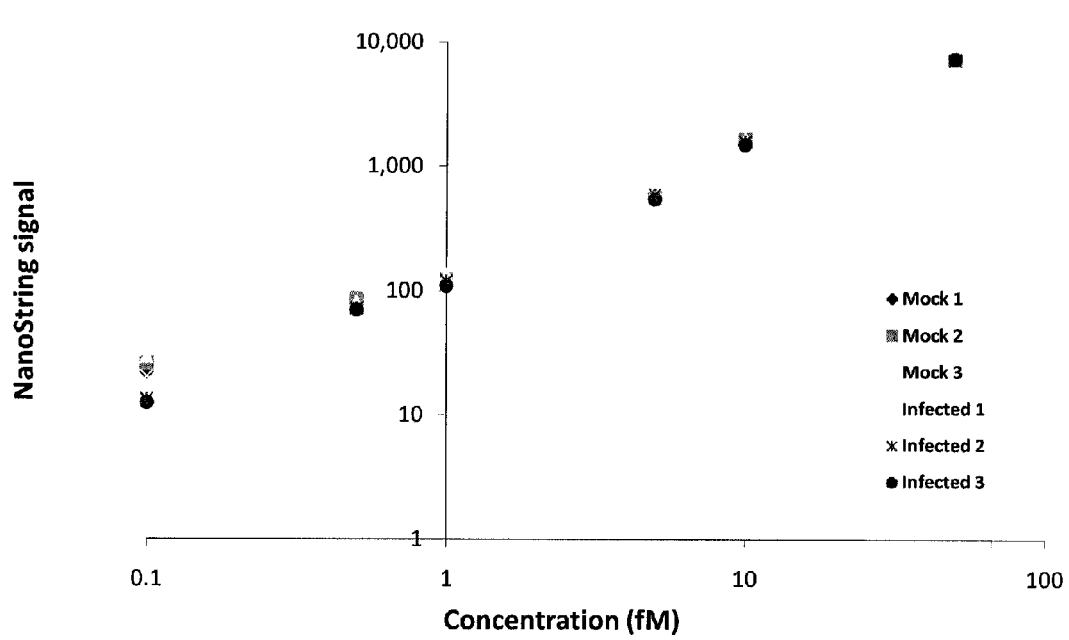
FIG. 23A-23B demonstrates the linearity and reproducibility of the NanoString spike-in controls. Non-human DNA oligonucleotide targets were spiked into each sample at concentrations of 0.1, 0.5, 1, 5, 10 and 50 fM. No target was added for the two negative control probe pairs.
Figure 23B:
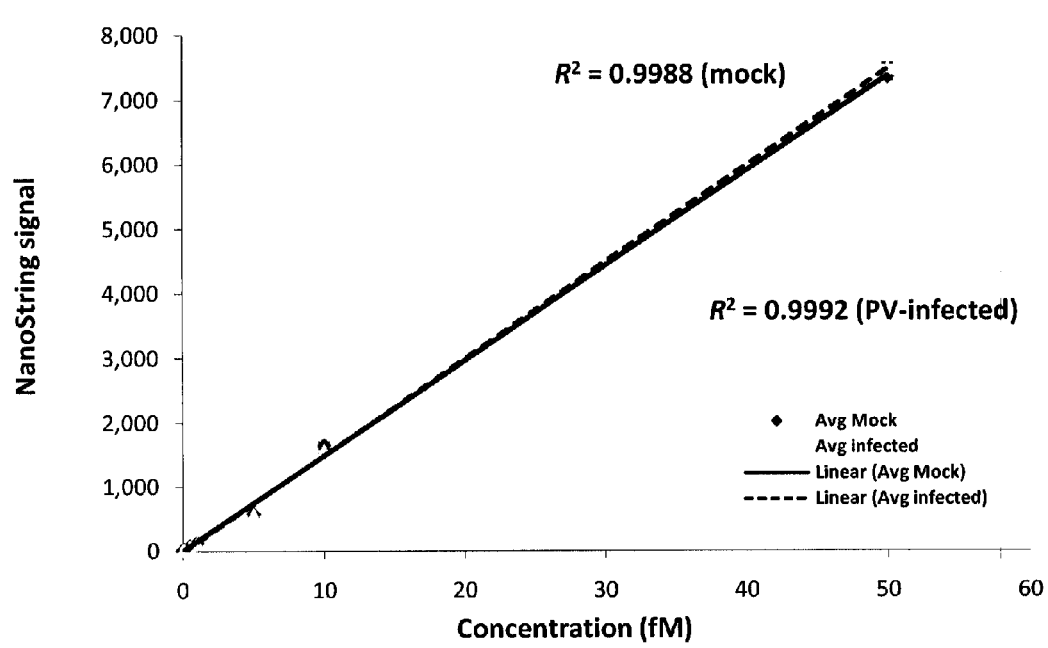

We first examined the linearity, dynamic range, and reproducibility of the six positive controls. FIG. 23*a* shows the results of the control measurements from each hybridization reaction with RNA from mock- and PV-infected cells (n=6). The control signal values (counts) for each replicate were very reproducible between 0.5 fM and 50 fM as indicated by overlapping points on the log-log plot. The assay was also highly linear over 2.5 logs of concentration with linear regression correlation coefficients of counts vs. concentration at $\geq 0.998$ (FIG. 23*b*).

We then examined the sampling efficiency and the lower limit of detection. The sampling efficiency of the system was estimated by dividing the number of counts for a spike-in target by the theoretical number of molecules of that target in the reaction. For example, there were a total of approximately 1800 molecules of the 0.1 fM spike-in target in each reaction. The average measurement for this target in the mock sample was 25 counts, resulting in a sampling efficiency of approximately 1%. The limit of detection of the assay was determined by comparing the counts for the positive control at the lowest concentration to the counts of the negative controls using a Student's T-Test (see Methods). The lowest concentration of controls detected in the context of the 500-plex hybridization reaction was between 0.1 fM and 0.5 fM in a total volume of 30 W containing 100 ng of total RNA. Background signal for the two negative controls averaged 14.4+/−6.5 and 10.2+/−3.5 for the mock and PV-infected cells, respectively. Assuming 10 pg of total RNA/cell (i.e. 10,000 cells in 100 ng), the limit of detection corresponds to between 0.2 to 1 molecules of control target per cell.

Figure 24A:
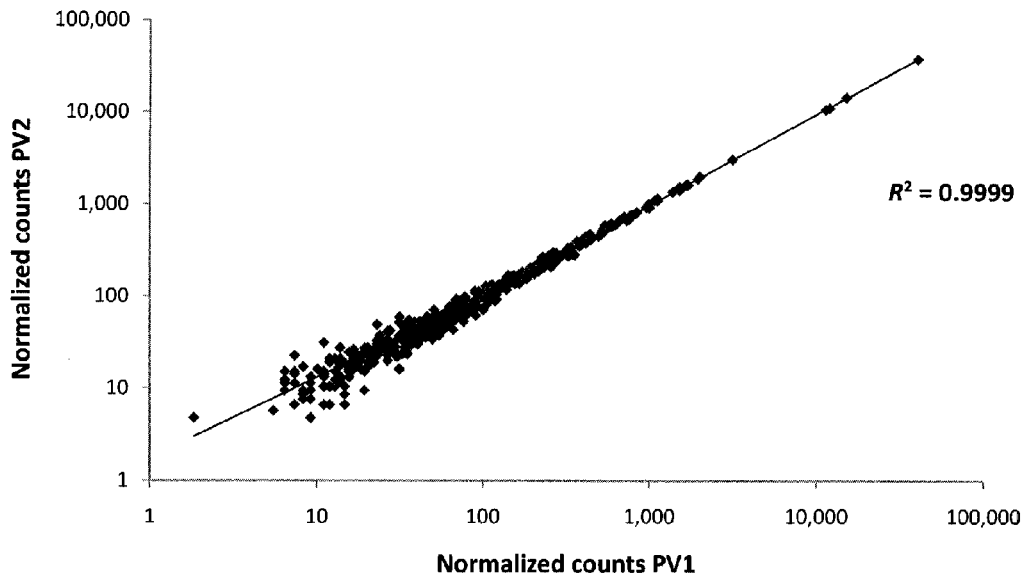
FIG. 24A-24B depicts the reproducibility and differential gene expression plots for 509 genes on the NanoString nCounter platform.

The reproducibility of the nCounter system in measuring the 509 mRNAs was also examined. In FIG. 24*a*, the normalized counts for all 509 genes from two independent hybridizations of RNA from PV-infected cells (technical replicates) are shown on a log-log scale. The data demonstrate that the NanoString system is reproducible: a linear fit to the data results in a correlation coefficient of 0.9999. The average correlation coefficient of each pair-wise combination of replicate assays was 0.9995+/−0.0004. This was slightly higher than that obtained from the same analysis of genes on the DNA microarray (average correlation coefficient=0.9934+/−0.0059). In addition, FIG. 24*a* shows that endogenous genes were detected with signals ranging from about 25 counts to over 50,000 counts, which suggests that the dynamic range of the system is larger than the 2.5 logs tested with the positive spike-in controls.

Figure 24B:
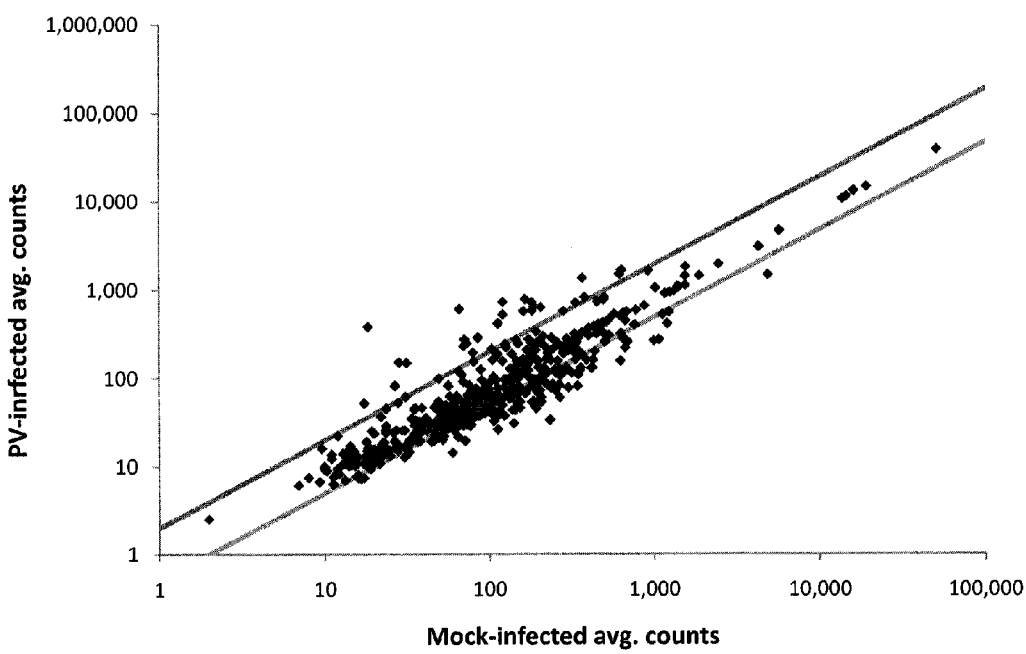

An important feature of any gene expression technology is determining the relative difference in gene expression between two or more samples. We measured change in expression levels for the 509 genes in the reporter library between mock- and PV-infected cells. The results are plotted in FIG. 24*b* (n=3). Using cutoff criteria of a 2-fold change in expression with a P-value of 0.05 or below, there were 28 genes that were induced and 115 genes that were repressed by PV infection as indicated by the upper and lower lines in FIG. 24*b*. These results demonstrate the nCounter system can be used to measure gene expression of more than 500 genes in a single assay and identify those genes that change significantly between samples.

Comparisons Between Nanostring and Microarrays

We compared the ability of the NanoString system to detect and measure the level of endogenous transcripts against microarrays; using the widely-used Affymetrix GeneChip® system as a representative microarray platform. As described above, nCounter assays were performed directly on 100 ng of total RNA without amplification. The same samples and amount of RNA were also analyzed with Affymetrix U133Plus2 arrays, using the two-cycle amplification/labeling protocol recommended by the manufacturer.

In order to determine how the nCounter system compares in sensitivity to microarrays, we examined the number of genes detected in each platform. Of the 509 genes assayed, there were 60 for which there was no acceptable corresponding Affymetrix Probe ID (based on Supplementary Table 2 of Shi et al.[2]). For the remaining 449 genes, we examined how many were called detected by each platform. The NanoString system uses a Student's T-Test of the replicate values for each gene compared to 2 negative controls (n=6) to determine the presence or absence of each gene, whereas the Affymetrix MAS 5.0 algorithm is based on the relationship between the Perfect Match and Mismatch probe sets. The average percentage of detected transcripts in both samples was higher in the NanoString assay than in the DNA microarray assay (88.4% vs. 82.6%; FIGS. 4a and 4b, respectively), and the boundary between detected and undetected calls was more distinct. The accuracy of the NanoString detection calls for several genes was further validated in TaqMan assays (Table 5).

The correlation of fold-change measurements for genes that change significantly in both the NanoString and Affymetrix platforms was assessed. After normalization and preprocessing of data (see Methods), the mean $\log_2$ fold-change between PV-infected and mock-infected samples was calculated for both platforms. A Student's T-Test for differential expression was performed between the samples. A threshold P-value of 0.05 without multiple testing correction was used to identify significantly regulated genes. This analysis resulted in 4 classes of genes: those that are determined to be regulated by both platforms (202 genes), by NanoString only (55 genes), or by microarray only (78 genes), and those that are not found to be regulated by either platform (114 genes). A plot of $\log_2$ ratios for all 449 genes with their significance in each platform is available in FIG. 27. FIG. 26a (♦) shows a comparison of $\log_2$ ratios for the 202 genes that were found to be significantly regulated in both the NanoString and microarray assays. The two platforms agree well for these 202 genes; only 4 are found to be regulated in opposite directions (dark diamonds in the upper left and lower right quadrants of FIG. 26a). The correlation coefficient of a linear fit to $\log_2$ ratios between the assays was 0.788. This correlation coefficient is similar to previous results comparing different array platforms, as well as comparisons with other quantitative measurement technologies such as real-time PCR[2-4] suggesting the results can be extrapolated to other microarray platforms.

Taqman® Analysis of Selected Genes

As mentioned above, there were a number a genes in which the measured $\log_2$ fold-change was significant in one platform but not the other. We selected a subset of 14 of these genes for further analysis by TaqMan® real-time PCR. Selection criteria are described in Methods. Twelve genes were determined to be differentially expressed by the NanoString assay and two by the microarray assay. TaqMan® real-time PCR was performed using RNA from the same master stock of mock- and PV-infected samples, and $\log_2$ fold changes were calculated. Overall, the NanoString assay showed much higher concordance with the TaqMan® assay than did the DNA microarray assay (FIG. 26b). Nine of the 12 genes met the same fold change criteria by real-time PCR and the other 3 showed similar trends but had slightly higher p-value (ZNF488) or missed the 2-fold cutoff criteria (MOCS3 and PHF20). In contrast, neither of the two genes determined to be regulated by the Affymetrix system alone (GSPT2 and IFT80) were validated by the TaqMan® assay.

Using the same set of 14 genes, we also compared the sensitivity of each platform by its ability to detect each gene in the two samples (Table 5). All 14 genes were detected in both samples by real-time PCR in less than 35 cycles. The results were similar for the NanoString system, with 13 of the 14 samples being detected in both samples and 1 gene (ZNF488) detected in mock-infected but not the PV-infected sample. In contrast, 6 genes were declared absent in both samples by microarrays and another 3 genes were declared absent in PV-infected cells. Hence, in these experiments the sensitivity of the NanoString system was superior to that of microarrays and similar to that of real-time PCR.

Comparison of nCounter System with MAQC Data Set

Recently, a series of studies performed by members of the MAQC consortium utilized commercially-available reference RNA samples to compare the performance of different microarray platforms[2, 4] as well as several quantitative gene expression technologies,[5] using TaqMan real-time PCR as the benchmark technology.

Figure 26C:
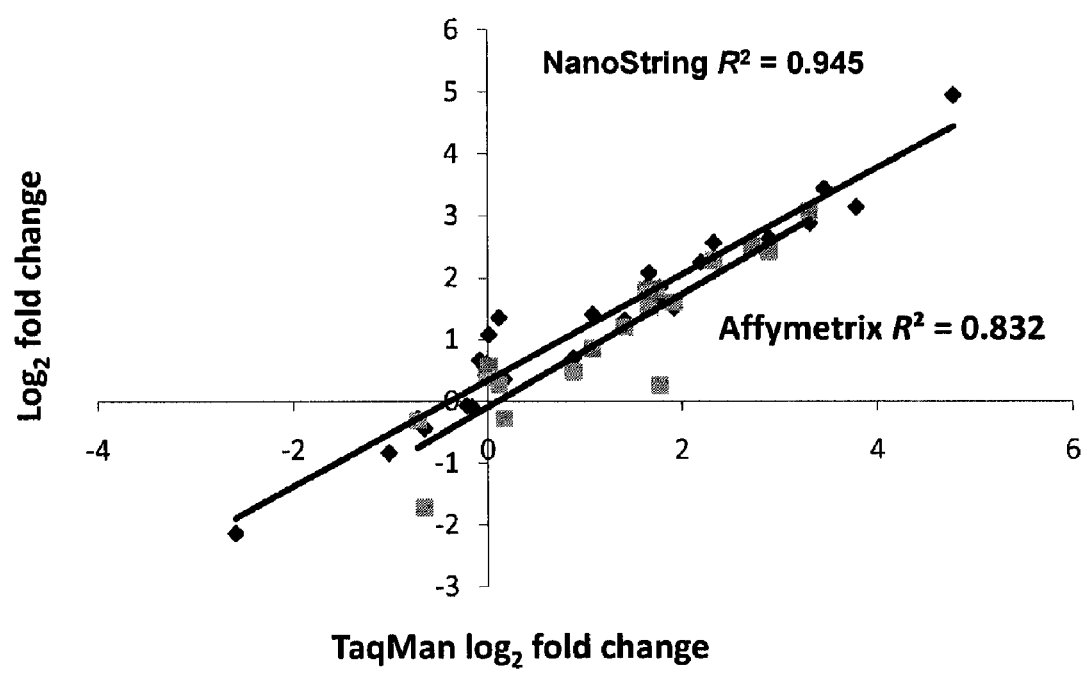

An nCounter probe library was constructed that was specific for 35 RefSeq mRNAs that overlapped with the MAQC gene set. The library was hybridized to Human Reference RNA and Human Brain Reference RNA samples used by the MAQC consortium to determine $\log_2$ fold-change values. After eliminating genes declared absent in either sample by either the nCounter or the TaqMan data (as described in Shi et al.[2]), we compared the $\log_2$ fold-change values for the remaining 27 genes. As FIG. 26c shows, there was excellent correlation between the NanoString and TaqMan platforms ($R^2=0.945$). A similar analysis of Affymetrix microarray data (site 1, Affymetrix Inc.[2]) from the same study revealed a significantly lower correlation of $R^2=0.832$ for the 18 genes that met the same criteria (FIG. 26c).

Comparison of nCounter System and Sybr®Green Real-Time PCR

In order to further demonstrate the sensitivity, accuracy, and dynamic range of the nCounter system, we compared it to real-time PCR in a different biological system. Total RNA was isolated from sea urchin embryos at seven time points of development (egg-70h) and either analyzed directly with the nCounter system or converted into cDNA and analyzed by real-time PCR. The transcript levels of 21 genes were examined at each time point. For the nCounter assay, all genes were combined in one library and analyzed in a multiplexed reaction. Each hybridization was performed in triplicate on 100 ng of total RNA (21 assays). For real-time PCR, each gene was assayed individually in quadruplicate for each time point from 2.8 ng of starting material (588 assays). For both assays, the data was normalized to ubiquitin[6].

Figure 28:
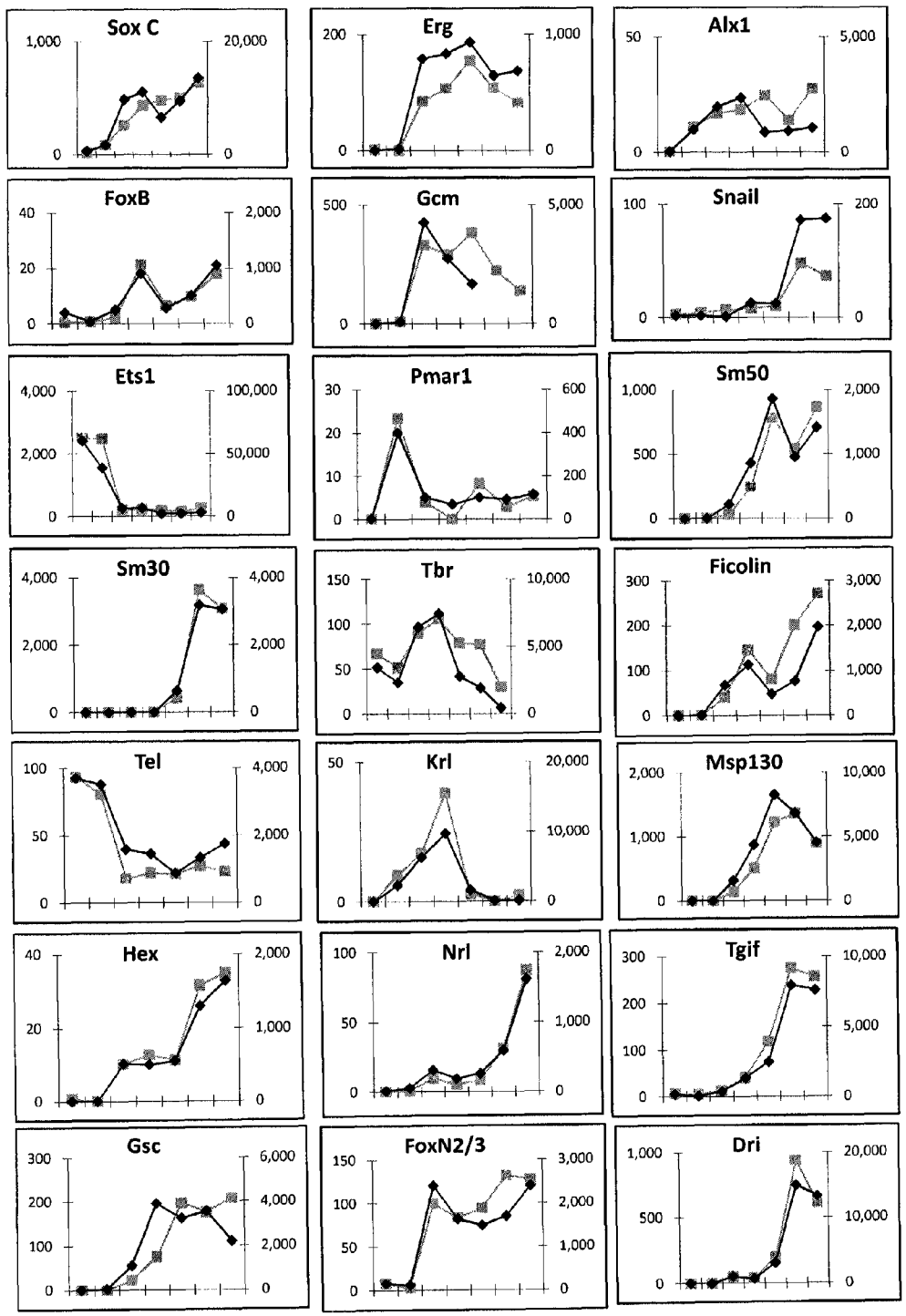
FIG. 28 shows the correlation between nCounter and real-time PCR. Individual line plots for 21 genes across 7 time points are shown. The normalized counts obtained from the NanoString system are shown ( ) on the left-hand y-axis scale. Quantitative real-time PCR results in copies/embryo are shown ( ) on the right-hand y-axis. The 7 time points (x-axis) were 0h (egg), 9.3h, 18h, 24h, 33h, 48h, and 70h. All data has been normalized to the expression levels of the polyubiquitin gene. Real-time PCR data is shown in copies/embryo and the NanoString data is shown in normalized counts. A quantitative comparison of the nCounter system and real-time PCR (not shown) revealed that estimates of the transcript number for some genes are similar in the two systems, whereas others disagree. The discrepancies are likely to reflect differences in the two platforms. The nCounter system is based on solution-hybridization kinetics, directly measures mRNA transcripts, and uses a standard curve in each reaction to estimate transcript number. In contrast, real-time PCR involves a reverse transcription step followed by amplification of a portion of the cDNA with specific primers, and transcript copy number is calculated relative to polyubiquitin expression levels.

A remarkable correlation in the relative expression patterns was observed between nCounter and real-time PCR data across the time course for all 21 genes (FIG. 28). The correlation was consistent for genes that were expressed at both low (e.g. Snail, Pmar 1) and high (e.g. Est, Dri) transcript levels per embryo as well as those whose expression levels changed over 3 logs during the timecourse (e.g. Tgif, Msp130). These results confirm that the nCoutner system is capable of producing real-time PCR quality data without enzymatic or signal amplification.

Discussion

As demonstrated above, the gene expression analysis system described herein (nCounter) is extremely sensitive (0.1-0.5 fM detection limit), reproducible (replicates averaging $R^2$ of 0.999 over a 3-log dynamic range), and simple to use. We have demonstrated that the nCounter system is capable of a high degree of multiplexing, measuring over 500 genes in a single reaction starting with just 100 ng of total RNA sample. The overall performance of the nCounter Gene Expression System correlated well with both microarrays ($R^2$=0.79 over 202 genes) and real-time PCR($R^2$=0.95 in MAQC) in head-to-head comparisons with the same total RNA samples. In addition, our data indicates that the nCounter gene expression system is more sensitive than microarrays and similar in sensitivity and accuracy to real-time PCR (Table 5).

The nCounter system has distinct advantages not found in the major existing gene expression technologies. First, the sample RNA is measured directly without amplification or cloning. Thus, no gene-specific or 3' biases are introduced, and the levels of each transcript within a sample can be established by counting the number of molecules of each sequence type and calculating concentration with reference to internal standards. In contrast, in real-time PCR transcript concentration is calculated from the number of enzymatic steps required to attain a threshold level of product. Secondly, both the probe and target are in solution rather than bound to a surface. The reaction is driven to completion (data not shown), allowing for a higher level of sensitivity than microarrays across many target genes with lower amounts of starting material. Thirdly, NanoString's technology provides a digital readout of the amount of transcript in a sample. A pure digital readout of transcript counts is linear across a large dynamic range, exhibits less background noise and is less ambiguous for downstream analysis than technologies that use analog signals. Finally, the time, effort, and sample requirements of the nCounter system are more scalable than real-time PCR or microarrays. For example, to measure 500 genes using 2 ng of RNA per real-time PCR reaction in triplicate, one would need 3 ng of total RNA and 1500 reactions whereas the same experiment could be performed using the nCounter system with 300 ng of total RNA in 3 reactions.

There are many applications for a technology that is capable of highly-multiplexed measurement of gene expression from relatively low amounts of starting material, particularly one which can detect transcripts of low abundance. For example, estimates of mRNA expression levels in both mouse and human cells suggest that the vast majority of the genes in the transcriptome are expressed at or below 20 transcripts per cell.[7,8] Currently, real-time PCR is the most widely accepted platform for measuring low-abundance messages. We have shown the nCounter system yields remarkable similar results. Another potential application of the technology is to measure expression profiles in clinical settings. Several studies have used expression arrays to identify a set of genes whose expression pattern or "signature" can serve as a clinical diagnostic or prognostic indicator. Classic examples of such studies include the AML/ALL work of Golub et al.[9] and the breast cancer classification studies of van't Veer et al.[10,11] After identifying a set of predictive genes via full genome arrays, one would like to validate their expression profile on a large number of patients and ultimately develop a diagnostic assay (see Simon[12] for a recent review). Typically these clinical signatures involve more than 30, but fewer than 500, genes. The nCounter system is ideally suited for profiling such clinically-relevant signatures, particularly from small samples with limited amounts of RNA such as tissue biopsies, microdissected or laser-captured samples, and cells sorted by flow cytometry. Preliminary work using the nCounter system directly on cell lysates looks promising, and has the potential to reduce further the amount of sample and sample handling needed.

References Cited

1. Pruitt, K. D., Tatusova, T. & Maglott, D. R. NCBI Reference Sequence (RefSeq): a curated non-redundant sequence database of genomes, transcripts and proteins. *Nucleic Acids Res* 33, D501-504 (2005).
2. Shi, L. et al. The MicroArray Quality Control (MAQC) project shows inter- and intraplatform reproducibility of gene expression measurements. *Nat Biotechnol* 24, 1151-1161 (2006).
3. Kuo, W. P. et al. A sequence-oriented comparison of gene expression measurements across different hybridization-based technologies. *Nat Biotechnol* 24, 832-840 (2006).
4. Patterson, T. A. et al. Performance comparison of one-color and two-color platforms within the MicroArray Quality Control (MAQC) project. *Nat Biotechnol* 24, 1140-1150 (2006).
5. Canales, R. D. et al. Evaluation of DNA microarray results with quantitative gene expression platforms. *Nat Biotechnol* 24, 1115-1122 (2006).
6. Oliveri, P., Carrick, D. M. & Davidson, E. H. A regulatory gene network that directs micromere specification in the sea urchin embryo. *Dev Biol* 246, 209-228 (2002).
7. Hastie, N. D. & Bishop, J. O. The expression of three abundance classes of messenger RNA in mouse tissues. *Cell* 9, 761-774 (1976).
8. Velculescu, V. E. et al. Analysis of human transcriptomes. Nat Genet. 23, 387-388 (1999).
9. Golub, T. R. et al. Molecular Classification of Cancer: Class Discovery and Class Prediction by Gene Expression Monitoring. *Science* 286, 531-537 (1999).
10. van't Veer, L. J. et al. Gene expression profiling predicts clinical outcome of breast cancer. *Nature* 415, 530-536 (2002).
11. van de Vijver, M. J. et al. A gene-expression signature as a predictor of survival in breast cancer. *N Engl J Med* 347, 1999-2009 (2002).
12. Simon, R. Roadmap for developing and validating therapeutically relevant genomic classifiers. *J Clin Oncol* 23, 7332-7341 (2005).
13. Altschul, S. F., Gish, W., Miller, W., Myers, E. W. & Lipman, D. J. Basic local alignment search tool. *J Mol Biol* 215, 403-410 (1990).
14. Kane, M. D. et al. Assessment of the sensitivity and specificity of oligonucleotide (50mer) microarrays. *Nucleic Acids Res* 28, 4552-4557 (2000).
15. Li, X., He, Z. & Zhou, J. Selection of optimal oligonucleotide probes for microarrays using multiple criteria, global alignment and parameter estimation. *Nucleic Acids Res* 33, 6114-6123 (2005).
16. Gentleman, R. C. et al. Bioconductor: open software development for computational biology and bioinformatics. *Genome Biol* 5, R80 (2004).
17. Brazma, A. et al. ArrayExpress—a public repository for microarray gene expression data at the EBI. *Nucleic Acids Res* 31, 68-71 (2003).
18. Rast, J. P. et al. Recovery of developmentally defined gene sets from high-density cDNA macroarrays. *Dev Biol* 228, 270-286 (2000).

The present invention can be implemented as a computer program product that comprises a computer program mechanism embedded in a computer readable storage medium. For instance, the computer program product could contain the program modules shown in FIG. 19. These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The program modules in the computer program product can also be distributed electronically, via the Internet or otherwise, by transmission of a computer data signal (in which the software modules are embedded) either digitally or on a carrier wave.

Many modifications and variations of this invention can be made without departing from its spirit and scope, as will be apparent to those skilled in the art. For instance, data storage module 44, label identification module 50, and probe identification module 54 can be combined into a single program, can each be a separate program, or could, in fact, be dispersed in multiple (e.g., three or more) programs. The specific embodiments described herein are offered by way of example only, and the invention is to be limited only by the terms of the appended claims, along with the full scope of equivalents to which such claims are entitled.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

What is claimed is:

1. A method comprising the steps of:
   (a) generating candidate target-specific nucleotide sequences that are reverse complements of a target mRNA sequence;
   (b) dividing each target-specific nucleotide sequence into two nucleotide sequences of equal length consisting of a 5' sequence and a 3' sequence, thereby generating a first pool of adjacent target-specific sequence pairs;
   (c) deleting from said first pool one or more adjacent target-specific sequence pairs if either sequence of the sequence pair meets any of the following criteria: (i) contains inverted repeats of greater than 7 consecutive nucleotides; (ii) contains direct repeats of greater than 9 consecutive nucleotides; (iii) contains a GC content outside a range of 30-70%; (iv) contains contiguous stretches of C residues of greater than 3 nucleotides in length; and (v) has a melting temperatures outside a first melting temperature range of 70-90° C.; thereby generating a second pool of adjacent target-specific sequence pairs;
   (d) deleting from said second pool one or more adjacent target-specific sequence pairs if either sequence of the sequence pair has a cross-hybridization potential to non-specific sequences that is 85% or greater, thereby generating a third pool of adjacent target-specific sequence pairs;

(e) deleting from said third pool one or more adjacent target-specific sequence pairs if either sequence of the sequence pair has a melting temperature outside a second melting temperature range of 78-83° C., thereby generating a fourth pool of adjacent target-specific sequence pairs;

(f) generating a fifth pool of adjacent target-specific sequence pairs, said fifth pool comprising the adjacent target-specific sequence pairs deleted from said third pool;

(g) determining the melting temperature of each sequence of the adjacent target-specific sequence pairs of said fifth pool;

wherein if both sequences in an adjacent target-specific probe pair have a melting temperature below the second melting temperature range of 78-83° C., said adjacent target-specific probe pair is deleted from the fifth pool;

wherein if one or both sequences in an adjacent target-specific probe pair have a melting temperature above the second melting temperature range of 78-83° C., one or both sequences are trimmed until one or both of said sequences are within the second melting temperature, thereby generating a sixth pool of adjacent target-specific sequence pairs;

wherein if one sequence in an adjacent target-specific probe pair has a melting temperature below the second melting temperature range of 78-83° C., and the other sequence in said pair is within or above the second melting temperature, said sequence with the low melting temperature is extended until said sequence is within the second melting temperature, thereby generating a seventh pool of adjacent target-specific sequence pairs;

(h) selecting and producing one or more adjacent target-specific sequence pairs from said fourth, sixth and seventh pools for use as a probe pair hybridizable to a target mRNA, thereby producing adjacent target-specific probe pairs;

(i) hybridizing at least one probe of each said one or more adjacent target-specific probe pairs, selected and produced in step (h), to at least a first label attachment region, comprising a DNA sequence having a regularly repeated base every about 4 to about 25 bases, and comprising a RNA molecule having a regularly repeated base every about 4 to about 25 bases which is hybridized to the DNA sequence, to which RNA molecule are attached at said regularly repeated base one or more label monomers that emit light constituting at least a first signal; and, (j) contacting an adjacent target specific probe pair from step (i) with a target mRNA under conditions sufficient to permit hybridization of said adjacent target specific probe pair and said target mRNA.

2. The method of claim 1, which further comprises the step of outputting to a user interface device, a computer readable storage medium, or a local or remote computer system, or displaying, one or more of the adjacent target-specific sequence pairs in said fourth pool.

3. The method of claim 1, wherein steps (a) through (j) are repeated to produce a plurality of adjacent target-specific probe pairs, wherein each adjacent target-specific probe pair is hybridizable to a different target mRNA sequence.

4. The method of claim 1, wherein the length of the candidate target-specific nucleotide sequences is selected from the range of 70 to 120 nucleotides.

5. The method of claim 1, wherein the predetermined range of GC content of step (c)(iii) is 40-70%.

6. The method of claim 1, wherein the target mRNA is an alternatively spliced mRNA.

7. The method of claim 1, wherein said 5' sequence of adjacent target-specific sequence pair is trimmed from the 5' end.

8. The method of claim 1, wherein said 3' sequence of adjacent target-specific sequence pair is trimmed from the 3' end.

9. The method of claim 1, wherein said 5' sequence of adjacent target-specific sequence pair is extended from the 5' end.

10. The method of claim 1, wherein said of the 3' sequence of adjacent target-specific sequence pair is extended from the 3' end.

* * * * *

UNITED STATES PATENT AND TRADEMARK OFFICE
CERTIFICATE OF CORRECTION

| | | |
|---|---|---|
| PATENT NO. | : 8,415,102 B2 | Page 1 of 1 |
| APPLICATION NO. | : 12/100990 | |
| DATED | : April 9, 2013 | |
| INVENTOR(S) | : Gary K. Geiss et al. | |

It is certified that error appears in the above-identified patent and that said Letters Patent is hereby corrected as shown below:

On the Title Page:

(75) Inventors: "Eric Davidson" should read -- Eric H. Davidson --.

(74) Attorney, Agent, or Firm: "Mintz Levin Cohn Ferris Glovsky and Popep, P.C." should read -- Mintz Levin Cohn Ferris Glovsky and Popeo, P.C. --.

In the Claims:

In claim 10, at column 120, line 40, the phrase "of the" following "wherein said" should be deleted.

Signed and Sealed this
Twenty-eighth Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,415,102 B2  
APPLICATION NO. : 12/100990  
DATED : April 9, 2013  
INVENTOR(S) : Gary K. Geiss et al.

Page 1 of 1

It is certified that error appears in the above-identified patent and that said Letters Patent is hereby corrected as shown below:

On the Title Page:

Item (75) Inventors: Should read

-- Gary K. Geiss, Seattle, WA (US)

Tim Dahl, Seattle, WA (US)

Eric H. Davidson, Pasadena, CA (US)

Philippa J. Webster, Seattle, WA (US) --.

Signed and Sealed this
Seventeenth Day of May, 2016

Michelle K. Lee
*Director of the United States Patent and Trademark Office*

SEQUENCE LISTING

```
<160> NUMBER OF SEQ ID NOS: 7

<210> SEQ ID NO 1
<211> LENGTH: 900
<212> TYPE: DNA
<213> ORGANISM: Artificial Sequence
<220> FEATURE:
<223> OTHER INFORMATION: Label Attachment Region

<400> SEQUENCE: 1
gagctcggga gatggcgagc tggaagcatc agaaagtagg aagatgacaa aatagggcca      60
tagaagcatg aagaactgaa cgcatgagac aataggaagc tacgccacta gggacctgag     120
aagctgagcg gctcagcggg tccgagcgtc aaaaaataaa agagtgaaac aatagacgaa     180
tgacgcggta aaaccatcca gaagtaaacg ggtacaaaca tacagagata gccacctgga     240
ccaataggca cgtacaaacg tacaagcctg gcgcgatgag gcaatccaca cgtgcagagc     300
tggaacaatg gaaagatgca agaataaacc gataccggga tcgagggctc agcgaataaa     360
gcagtcaaca actggaaaga tccacacata ccggcgtaac cgagtccaaa catacagacc     420
tgcaagactc gcgacatggg acggtaaaac catccgaccg taaaccggta accaggtagc     480
cgggtaaaaa catagcaggg tggagacctc agaacgtaaa gacgtccaag ggtcgccgga     540
tagcgaacta cgcgcatcgc ccaatgggcc aatcaacaga taaacgagta gaaaagtcag     600
aaaataagaa actaacgaaa tacgagggtc caaggatgca agactgaggc cctaaggaga     660
taaggaaata ggccgatgca gacctgaaac gatgcaccga tccgacggta aaagactaga     720
cacgtagccg gatcagggcc tgggaggctg gaaccgtgag cacatagcaa agtcgcagcg     780
tcggcagatg cgccggtaaa aaagtagagg catgaccgga tgggcaaata gcgacgtaca     840
gcagtgaagc actaaaagca tccaagggta ggagactagg cgcctcgacg ggtaggtacc     900

<210> SEQ ID NO 2
<211> LENGTH: 69
<212> TYPE: DNA
<213> ORGANISM: Artificial Sequence
<220> FEATURE:
<223> OTHER INFORMATION: G-tag

<400> SEQUENCE: 2
aacatcacac agaccaacat cacacagacc aacatcacac agaccaacat cacacagacc      60
agcccttctg                                                              69
```

-continued

```
<210> SEQ ID NO 3
<211> LENGTH: 15
<212> TYPE: DNA
<213> ORGANISM: Artificial Sequence
<220> FEATURE:
<223> OTHER INFORMATION: G-hook

<400> SEQUENCE: 3
ggtctgtgtg atgtt                                                      15

<210> SEQ ID NO 4
<211> LENGTH: 21
<212> TYPE: DNA
<213> ORGANISM: Artificial Sequence
<220> FEATURE:
<223> OTHER INFORMATION: Ligator sequence

<400> SEQUENCE: 4
ctctagagga tccaaagggc t                                               21

<210> SEQ ID NO 5
<211> LENGTH: 39
<212> TYPE: DNA
<213> ORGANISM: Artificial Sequence
<220> FEATURE:
<223> OTHER INFORMATION: F-tag
<220> FEATURE:
<221> NAME/KEY: modified_base
<222> LOCATION: (39)..(39)
<223> OTHER INFORMATION: wherein c is attached to biotin

<400> SEQUENCE: 5
gatggagacg tctatcatca cagcgtctat catcacagc                            39

<210> SEQ ID NO 6
<211> LENGTH: 15
<212> TYPE: DNA
<213> ORGANISM: Artificial Sequence
<220> FEATURE:
<223> OTHER INFORMATION: F-hook

<400> SEQUENCE: 6
gctgtgatga tagac                                                      15

<210> SEQ ID NO 7
<211> LENGTH: 18
<212> TYPE: DNA
<213> ORGANISM: Artificial Sequence
<220> FEATURE:
<223> OTHER INFORMATION: Ligator sequence

<400> SEQUENCE: 7
gtctccatct tccgacag                                                   18
```